United States Patent
Wagman et al.

(10) Patent No.: US 8,445,476 B2
(45) Date of Patent: May 21, 2013

(54) CARBACEPHEM β-LACTAM ANTIBIOTICS

(75) Inventors: Allan S. Wagman, Belmont, CA (US);
Heinz E. Moser, San Mateo, CA (US)

(73) Assignee: Achaogen, Inc., South San Francisco, CA (US)

( * ) Notice: Subject to any disclaimer, the term of this patent is extended or adjusted under 35 U.S.C. 154(b) by 448 days.

(21) Appl. No.: 12/764,503

(22) Filed: Apr. 21, 2010

(65) Prior Publication Data
US 2010/0267686 A1    Oct. 21, 2010

Related U.S. Application Data

(63) Continuation of application No. PCT/US2008/081150, filed on Oct. 24, 2008.

(60) Provisional application No. 60/982,697, filed on Oct. 25, 2007, provisional application No. 60/982,695, filed on Oct. 25, 2007.

(51) Int. Cl.
| | |
|---|---|
| C07D 463/22 | (2006.01) |
| A61K 31/4353 | (2006.01) |
| A61P 31/04 | (2006.01) |
| C07D 417/12 | (2006.01) |
| C07D 401/12 | (2006.01) |
| C07D 401/14 | (2006.01) |

(52) U.S. Cl.
USPC ...... 514/210.04; 540/205; 548/128; 548/194; 546/256; 546/261

(58) Field of Classification Search
USPC ........................ 514/210.04; 540/205
See application file for complete search history.

(56) References Cited

U.S. PATENT DOCUMENTS

| | | | | |
|---|---|---|---|---|
| 4,470,983 | A | 9/1984 | Blumbach et al. | 424/246 |
| 4,537,886 | A | 8/1985 | Taylor et al. | 514/193 |
| 4,640,919 | A | 2/1987 | Mochida et al. | 514/241 |
| 4,788,185 | A | 11/1988 | Miyake et al. | 514/205 |
| 4,826,834 | A | 5/1989 | Yoshimura et al. | 514/207 |
| 4,855,418 | A | 8/1989 | Cook et al. | 540/205 |
| 5,077,287 | A | 12/1991 | Ternansky | 514/210 |
| 5,158,946 | A | 10/1992 | Gasson et al. | 514/202 |
| 5,362,724 | A | 11/1994 | Kubota et al. | 514/210 |
| 5,538,964 | A | 7/1996 | Cama et al. | 514/210 |
| 5,565,445 | A | 10/1996 | Cama et al. | 514/210 |
| 5,688,786 | A | 11/1997 | Christensen et al. | 514/210 |
| 5,716,948 | A | 2/1998 | Burton et al. | 514/210 |
| 5,939,410 | A | 8/1999 | Angehrn et al. | 514/210 |
| 6,504,025 | B2 | 1/2003 | Hebeisen et al. | 540/222 |
| 6,599,893 | B2 * | 7/2003 | Glinka | 514/206 |
| 6,723,716 | B1 | 4/2004 | Hecker et al. | 514/203 |
| 7,109,190 | B2 | 9/2006 | Glinka et al. | 514/210.04 |
| 2002/0019381 | A1 | 2/2002 | Hebeisen et al. | 514/202 |
| 2005/0004095 | A1 | 1/2005 | Glinka et al. | 514/204 |
| 2008/0146535 | A1 | 6/2008 | Glinka et al. | 514/210.08 |
| 2011/0224186 | A1 * | 9/2011 | Wagman et al. | 514/210.04 |

FOREIGN PATENT DOCUMENTS

| | | |
|---|---|---|
| CA | 2 408 941 C | 1/2009 |
| CN | 1763046 A | 4/2006 |
| EP | 0 034 760 B1 | 9/1981 |
| EP | 0 112 481 A1 | 7/1984 |

(Continued)

OTHER PUBLICATIONS

Andes et al., "Pharmacodynamics of the New Fluoroquinolone Gatifloxacin in Murine Thigh and Lung Infection Models," *Antimicrobial Agents and Chemotherapy* 46(6):1665-1670, Jun. 2002.

Appelbaum et al., "Recently approved and investigational antibiotics for treatment of severe infections caused by Gram-positive bacteria," *Current Opinion in Microbiology* 8:510-517, 2005.

Bassetti et al., "Gram-positive bacterial resistance: Future treatment options," *Current Opinion in Investigational Drugs* 4(8):944-952, 2003.

Blaszczak et al., "Comparative Reactivity of 1-Carba-1-dethiacephalosporins with Cephalosporins," *J. Med. Chem.* 33:1656-1662, 1990.

(Continued)

*Primary Examiner* — Mark Berch

(57) ABSTRACT

Carbacephem β-lactam antibiotics having the following chemical structures (I) and (II) are disclosed:

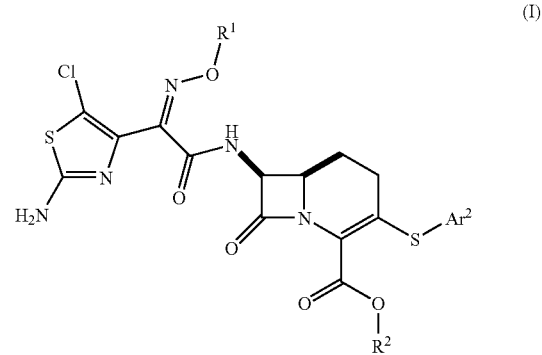

(I)

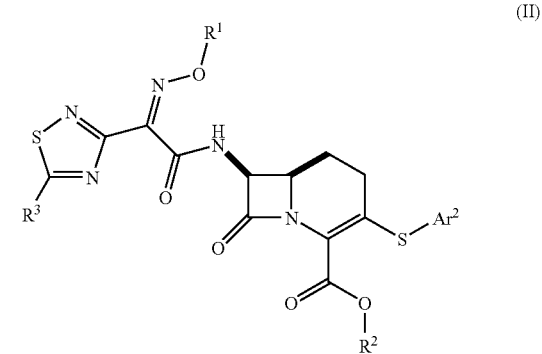

(II)

including stereoisomers, pharmaceutically acceptable salts, esters and prodrugs thereof, wherein $Ar^2$, $R^1$, $R^2$ and $R^3$ are as defined herein. The compounds are useful for the treatment of bacterial infections, in particular those caused by methicillin-resistant *Staphylococcus* spp.

20 Claims, 2 Drawing Sheets

FOREIGN PATENT DOCUMENTS

| | | |
|---|---|---|
| EP | 0 154 253 A1 | 9/1985 |
| EP | 0 182 301 B1 | 5/1986 |
| EP | 0 324 562 A1 | 7/1989 |
| EP | 0 831 093 A1 | 3/1998 |
| EP | 0 849 269 A1 | 6/1998 |
| EP | 1 435 357 A2 | 7/2004 |
| EP | 1 289 998 B1 | 3/2005 |
| GB | 2 271 564 A | 4/1994 |
| JP | 62-267228 A | 11/1987 |
| JP | 2003-535059 A | 11/2003 |
| WO | 99/64049 A1 | 12/1999 |
| WO | WO 01/90111 A1 | 11/2001 |
| WO | WO 2004/098500 A2 | 11/2004 |
| WO | WO 2005/100330 A1 | 10/2005 |
| WO | WO 2005/100367 A1 | 10/2005 |
| WO | WO 2009/055696 A1 | 4/2009 |
| WO | WO 2010/030810 A1 | 3/2010 |
| WO | WO 2010/030811 A2 | 3/2010 |
| WO | WO 2010/123997 A1 | 10/2010 |
| WO | WO 2010123997 A1 * | 10/2010 |

OTHER PUBLICATIONS

Bodurow et al., "An Enantioselective Synthesis of Loracarbef (LY163892/KT3777)," *Tetrahedron Letters* 30(18):2321-2324, 1989.

Comber et al., "Comparative Effects of Amoxycillin and Ampicillin in the Treatment of Experimental Mouse Infections," *Antimicrobial Agents and Chemotherapy* 7(2):179-185, 1975.

Cook et al., "Palladium-Catalyzed Chemistry of β-Lactam Vinyl Triflates: Coupling with Organostannanes and Alkoxycarbonylation," *J. Org. Chem.* 54:5828-5830, 1989.

Cooper et al., "The carbacephems," *Exp. Opin. Invest. Drugs* 3(8):831-848, 1994.

Cooper, "Novel β-lactam structures—the carbacephems," *The Chemistry of β-Lactams* ed. Page, Blackie Academic & Professional, New York, NY, pp. 275-305, 1992.

Craig et al., "In Vivo Activity of BP-102, a New Carbacephem, Against Methicillin-Susceptible and Resistant Strains of *Staphylococcus aureus* (MSSA and MRSA) in the Thighs of Neutropenic Mice," F 1166, *Interscience Conference on Antimicrobial Agents and Chemotherapy*, Washington, D.C., Dec. 16-19, 2005.

Crowell et al., "3-Sulfonyl-1-carba-1-dethiacephems," *J. Med. Chem.* 32:2436-2442, 1989.

Diederen et al., "The emergence of infections with community-associated methicillin resistant *Staphylococcus aureus*," *Journal of Infection* 52:157-168, 2006.

Elston, "Community-acquired methicillin-resistant *Staphylococcus aureus*," *J. Am. Acad. Dermatol.* 56:1-16, 2007.

Evans et al., "The Asymmetric Synthesis of β-Lactam Antibiotics—I. Application of Chiral Oxazolidones in the Staudinger Reaction," *Tetrahedron Letters* 26(32):3783-3876, 1985.

Evans et al., "The Asymmetric Synthesis of β-Lactam Antibiotics—II. The First Enantioselective Synthesis of the Carbacephalosporin Nucleus," *Tetrahedron Letters* 26(32):3787-3790, 1985.

Farina et al., "Palladium Catalysis in Cephalosporin Chemistry: A Versatile New Approach to 3-Substituted Cephems," *Tetrahedron Letters* 29(47):6043-6046, 1988.

Furuya et al., "Antimicrobial-resistant bacteria in the community setting," *Nature* 4:36-45, Jan. 2006.

Glinka, "Novel cephalosporins for the treatment of MRSA infections," *Current Opinion in Investigational Drugs* 3(2):206-217, 2002.

Glinka et al., "SAR Studies of Anti-MRSA Non-zwitterionic 3-Heteroarylthiocephems," *The Journal of Antibiotics* 53(10):1045-1052, Oct. 2000.

Glinka et al., "Relationships Between Structure, Antibacterial Activity, Serum Stability, Pharmacokinetics, and Efficacy in 3-(Heteroarylthio)cephems. Discovery of RWJ-333441 (MC-04,546)," *Bioorganic & Medicinal Chemistry* 11:591-600, 2003.

Goldstein et al., "Antimicrobial Activity of MDL 63,246, a New Semisynthetic Glycopeptide Antibiotic," *Antimicrobial Agents and Chemotherapy* 39(7):1580-1588, Jul. 1995.

Griffith et al., "Pharmacodynamics of Levofloxacin against *Pseudomonas aeruginosa* with Reduced Susceptibility Due to Different Efflux Pumps: Do Elevated MICs Always Predict Reduced in Vivo Efficacy?," *Antimicrobial Agents and Chemotherapy* 50(5):1628-1632, May 2006.

Griffith et al., "Preclinical Pharmacokinetics and Serum Protein Binding of BP-102 and other Members of a Novel Series of Carbacephems Active Against Resistant Gram-positive Bacteria," F 1458, *Interscience Conference on Antimicrobial Agents and Chemotherapy*, Washington, D.C., Dec. 16-19, 2005.

Grundmann et al., "Emergence and resurgence of meticillin-resistant *Staphylococcus aureus* as a public-health threat," *Lancet* 368:874-885, Sep. 2, 2006.

Guzzo et al., "Catalytic, Asymmetric Synthesis of the Carbacephem Framework," *J. Org. Chem.* 59:4862-4867, 1994.

Hanaki et al., "The Synthesis of 7-Substituted-3-dinitrostyryl Cephalosporins and Their Ability for Detecting Extended Spectrum β-Lactamases (ESBLs)," *J. Antibiotics* 58(1):69-73, 2005.

Hatanaka et al., "A Simple Synthesis of (±)-1-Carbacephem Derivatives," *Tetrahedron Letters* 24(44):4837-4838, 1983.

Hecker et al., "Discovery of RWJ-54428 (MC-02,479), a New Cephalosporin Active Against Resistant Gram-positive Bacteria," *The Journal of Antibiotics* 53(11):1272-1281, Nov. 2000.

Hecker et al., "Prodrugs of Cephalosporin RWJ-333441 (MC-04,546) with Improved Aqueous Solubility," *Antimicrobial Agents and Chemotherapy* 47(6):2043-2046, Jun. 2003.

Hornback et al., "3-(thiazol-4-yl)-1-Carba-1-Dethiacephalosporins: Synthesis and in Vitro Activity," *American Chemical Society National Meeting*, Abstract 153, Washington, D.C., 1990.

International Preliminary Report on Patentability, for PCT/US2008/081150, mailed Apr. 27, 2010, 8 pages.

International Preliminary Report on Patentability, for PCT/US2004/013054, mailed Nov. 4, 2005, 6 pages.

International Search Report, for PCT/US2008/081150, mailed Jan. 30, 2009, 3 pages.

International Search Report, for PCT/US2004/013054, mailed Apr. 5, 2005, 2 pages.

International Search Report, for PCT/US2009/056555, mailed Jun. 15, 2010, 7 pages.

International Search Report, for PCT/US2009/056554, mailed Jan. 13, 2010, 4 pages.

Jackson et al., "Synthesis of Carbacephem Antibiotics: Synthesis Via Dieckmann Reaction Using Phenyl Esters to Direct the Regioselectivity of the Cyclization," *Tetrahedron Letters* 31(44):6317-6320, 1990.

Jackson et al., "Enantioselective Syntheses of 1-Carbacephalosporins from Chemoenzymically Derived β-Hydroxy-α-Amino Acids: Applications to the Total Synthesis of Carbacephem Antibiotic Loracarbef," *Tetrahedron* 56:5667-5677, 2000.

Kim et al., "Cephalosporins with the Dichlorophenyl Group at C-7 Position and Pyrimidines at C-3 Position Exhibiting Potent Activity against Gram-positive Strains," *The Journal of Antibiotics* 57(7):468-472, Jul. 2004.

Kluytmans-VandenBergh et al., "Community-acquired methicillin-resistant *Staphylococcus aureus*: current perspectives," *Clin. Microbiol. Infect.* 12(Suppl. 1):9-15, 2006.

Kollef et al., "Methicillin-resistant *Staphylococcus aureus*: a new community-acquired pathogen?," *Current Opinion in Infectious Diseases* 19:161-168, 2006.

Liu et al., "Synthesis of Balofloxacin," *Chinese Journal of Pharmaceuticals* 35(7):388-390, 2004.

Lotz et al., "Diastereoselective Synthesis of the Carbacephem Framework," *J. Org. Chem.* 58:618-625, 1993.

Lowy, "Antimicrobial resistance: the example of *Staphylococcus aureus*," *The Journal of Clinical Investigation* 111(9):1265-1273, May 2003.

Maltezou et al., "Community-acquired methicillin-resistant *Staphylococcus aureus* infections," *International Journal of Antimicrobial Agents* 27:87-96, 2006.

Misiek et al., "Microbiological Properties of a New Cephalosporin, BL-S 339: 7-(Phenylacetimidoyl-aminoacetamido)-3-(2-Methyl-1,3

,4-Thiadiazol-5-Ylthiomethyl)Ceph-3-em-4-Carboxylic Acid," *Antimicrobial Agents and Chemotherapy* 3(1):40-48, Jan. 1973.

Misner et al., "Enantioselective synthesis of the carbacephem antibiotic loracarbef via Mitsunobu and Dieckmann cyclization from an unnatural amino acid," *Tetrahedron Letters* 44:5991-5993, 2003.

Mochida et al., "Synthesis and Antibacterial Activity of Novel 3-Substituted Carbacephems," *The Journal of Antibiotics* 42(2):283-292, 1989.

Moosavi-Movahedi et al., "Design, Synthesis, and Antibacterial Activity of Novel Carbacephems," *Letters in Drug Design & Discovery* 3:91-97, 2006.

Neyer et al., "A Novel Dieckmann-Type Cyclization, the Final Step of the Synthesis of a Carbacephem Derivative," *Synthesis* 1991(9):743-744, Sep. 1991.

O'Shea et al., "Physicochemical Properties of Antibacterial Compounds: Implications for Drug Discovery," *Journal of Medicinal Chemistry* 51(10):2871-3049, May 22, 2008.

Rice, "Antimicrobial Resistance in Gram-Positive Bacteria," *The American Journal of Medicine* 119(6A):S11-S19, 2006.

Rosiello et al., "Rapid and Accurate Determination of the Median Lethal Dose ($LD_{50}$) and Its Error With a Small Computer," *Journal of Toxicology and Environmental Health* 3:797-809, 1977.

Sabol et al., "Community-Associated Methicillin-Resistant *Staphylococcus aureus*: New Bug, Old Drugs," *The Annals of Pharmacotherapy* 40:1125-1133, Jun. 2006.

Ternansky et al., "Discovery and Structure-Activity Relationship of a Series of 1-Carba-1-dethiacephems Exhibiting Activity against Methicillin-Resistant *Staphylococcus aureus*," *J. Med. Chem.* 36:1971-1976, 1993.

Ternansky et al., "Synthesis and Anaerobic Activity of Novel 1-Carba-1-dethiacephalosporins," *J. Med. Chem.* 36:2332-2334, 1993.

Written Opinion of the International Searching Authority, for PCT/US2008/081150, mailed Jan. 30, 2009, 7 pages.

Written Opinion of the International Searching Authority, for PCT/US2004/13054, mailed Apr. 5, 2005, 5 pages.

Written Opinion of the International Searching Authority, for PCT/US2009/056555, mailed Jun. 15, 2010, 14 pages.

Written Opinion of the International Searching Authority, for PCT/US2009/056554, mailed Jan. 13, 2010, 11 pages.

International Search Report, mailed Aug. 9, 2010, for PCT/US2010/031904 (6 pages).

Written Opinion of the International Searching Authority, mailed Aug. 9, 2010, for PCT/US2010/031904 (11 pages).

International Preliminary Report on Patentability for PCT/US2009/056554, mailed Mar. 15, 2011, 12 pages.

International Preliminary Report on Patentability for PCT/US2009/056555, mailed Mar. 15, 2011, 15 pages.

\* cited by examiner

CARBACEPHEM β-LACTAM ANTIBIOTICS

CROSS-REFERENCE TO RELATED APPLICATIONS

This application is a continuation of International PCT Patent Application No. PCT/US2008/081150, filed Oct. 24, 2008, now pending, which claims the benefit under 35 U.S.C. §119(e) of U.S. Provisional Patent Application Nos. 60/982,695 filed Oct. 25, 2007 and 60/982,697 filed Oct. 25, 2007. The foregoing applications are incorporated herein by reference in their entireties.

BACKGROUND

1. Field

The present invention relates to novel carbacephem β-lactam antibiotics, and the use of such compounds to treat bacterial infections, in particular, infections caused by bacterial species resistant to conventional β-lactams.

2. Description of the Related Art

Over the past three decades a variety of antibiotics have become available for clinical use. One class of antibiotics that has seen remarkable growth is the β-lactams, over 70 of which have entered clinical use since 1965. Unfortunately, the widespread use of these antibiotics has resulted in an alarming increase in the number of resistant strains, especially among clinically important bacteria such as the genera *Salmonella, Enterobacteriaceae, Pseudomonas* and *Staphylococcus*.

Bacterial resistance to cephalosporins occurs primarily through three mechanisms: (a) destruction of the antibiotic by β-lactamases; (b) decreased penetration due to changes in bacterial outer membrane composition; and (c) alteration of penicillin-binding proteins (PBPs) resulting in interference with β-lactam binding. The latter pathway is especially important, as the binding of β-lactams to PBPs is essential for inhibiting peptidoglycan biosynthesis (peptidoglycan is a required bacterial cell-wall component). Certain Gram-positive bacteria such as methicillin-resistant *Staphylococcus aureus* ("MRSA") and various genus *Enterococcus* bacteria are highly resistant to β-lactam antibiotics. The resistance of MRSA is due to the presence of a PBP called PBP2a, which binds very poorly to β-lactam antibiotics. The options for treating infections caused by MRSA are limited and there is a need for new antibiotics with activity against these strains.

In recent years, a novel family of β-lactam antibiotics, the carbacephems (1), has been sporadically touted as having promise against MRSAs and other resistant species. In compound (1), $R_1$ and $R_2$ are generally described as aromatic and heteroaromatic entities, and $R_3$ has generally been reported as an optionally substituted alkyl group.

However, one problem with the carbacephem compounds developed thus far is that researchers investigating the family have been unable to achieve an acceptable balance between MRSA potency and serum protein binding. That is, MRSA activity was demonstrated relatively early on to correlate with lipophilicity; the more lipophilic the carbacephem, the greater its potency. Unfortunately, the greater the lipophilicity of the compound, the greater is its tendency toward high protein binding. Protein binding reduces the concentration of free drug circulating in blood. Lower circulating free drug concentrations typically result in less efficacious beta-lactams. Lack of oral bioavailability is another issue facing MRSA active beta-lactams. Historically, cephalosporins were both poorly absorbed by oral dosing and suffered from hydrolytic degradation, due to chemical instability, in the acidic environment of the stomach. Carbacephems offer an advantage for treating community-acquired MRSA which is most conveniently treated by oral antibiotics. Since carbacephems, due to their molecular structure, are intrinsically more stable to the gastric environment, this class of beta-lactam has a much greater potential for development as an oral agent.

Despite the above, carbacephems remain an intriguing approach to dealing with MRSA and other resistant bacterial species. What is needed, however, is a novel class of carbacephems that achieves the requisite balance of MRSA potency, protein binding and oral availability. The present invention addresses this need and provides further related advantages.

BRIEF SUMMARY

In brief, the present invention is directed to novel carbacephem β-lactam antibiotics, including stereoisomers, pharmaceutically acceptable salts, esters and prodrugs thereof, and the use of such compounds to treat bacterial infections, in particular, infections caused by bacterial species resistant to conventional β-lactams, such as MRSA.

In one embodiment, a compound is provided having the following structure (I):

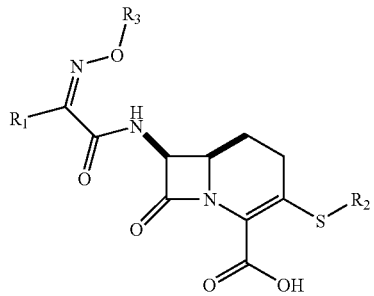

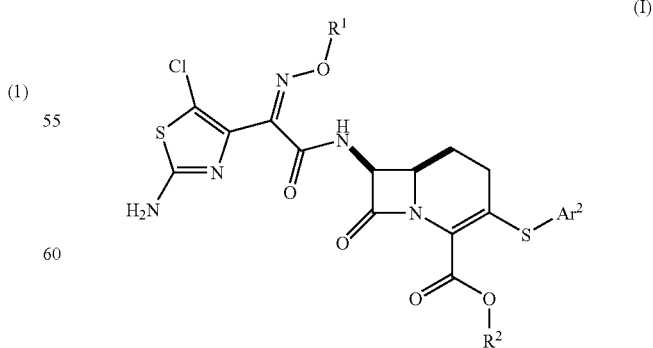

or a stereoisomer, pharmaceutically acceptable salt, ester, or prodrug thereof, wherein:

R¹ is selected from hydrogen, optionally substituted alkyl, optionally substituted alkenyl, optionally substituted alkynyl, optionally substituted alkoxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl and —C(=O)R$^{1a}$, wherein:
R$^{1a}$ is selected from hydrogen, optionally substituted alkyl, optionally substituted alkenyl, optionally substituted alkynyl, optionally substituted alkoxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl and optionally substituted heteroarylalkyl;

R² is selected from hydrogen, optionally substituted alkyl, optionally substituted alkenyl, optionally substituted alkynyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl and optionally substituted heteroarylalkyl;

Ar² is a heteroaryl having 5 ring atoms selected from:

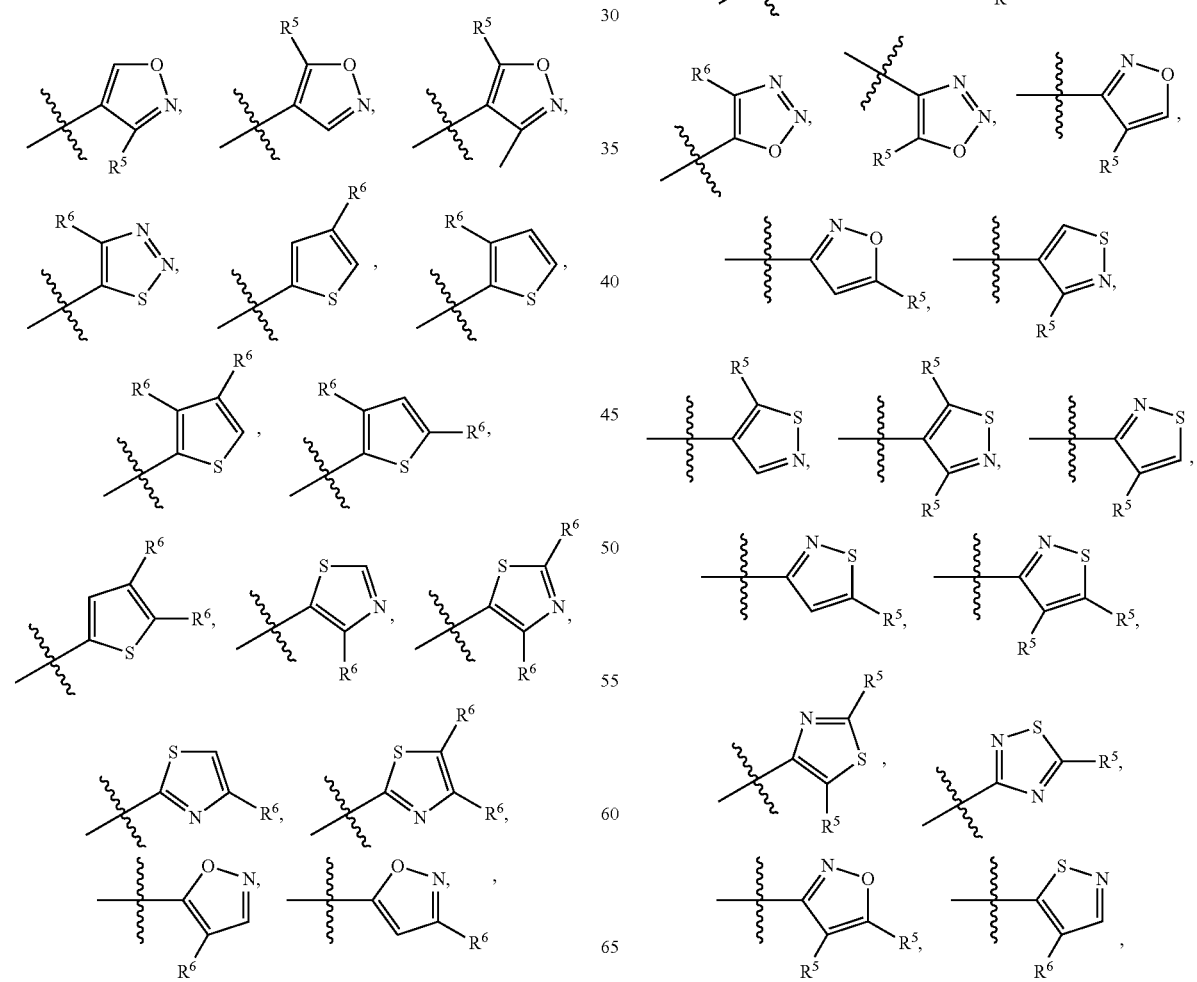

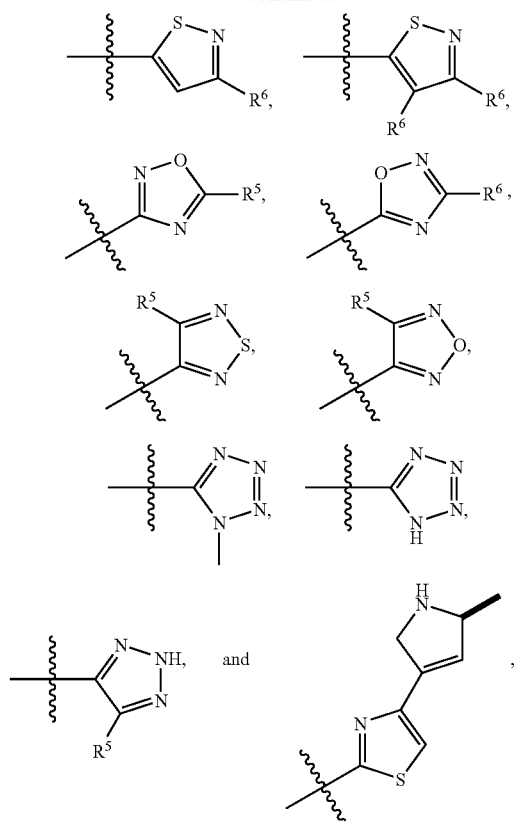
Ar² is a heteroaryl having 6 ring atoms selected from:
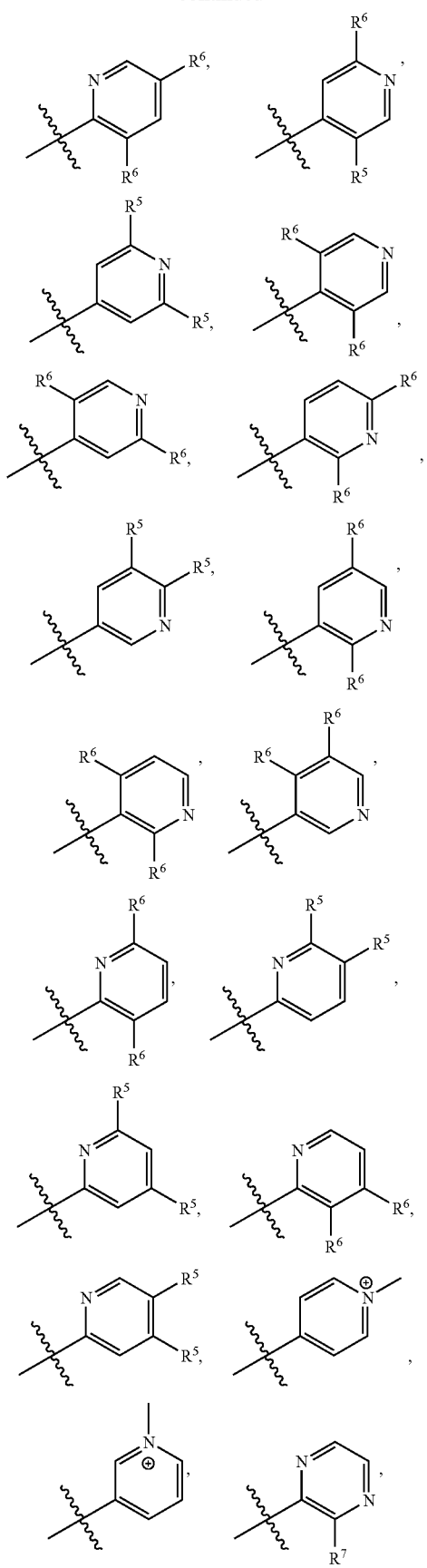

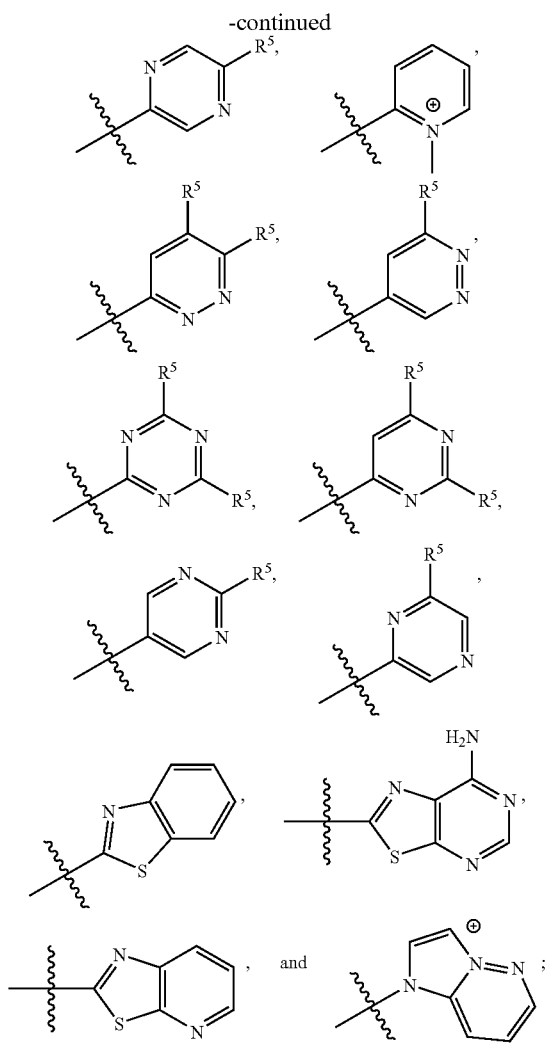

R⁵ is selected from hydrogen, chloro, bromo, fluoro, iodo, cyano, optionally substituted alkyl, optionally substituted alkenyl, optionally substituted alkynyl, optionally substituted cycloalkyl, optionally substituted heterocyclyl, —SO$_2$R$^{5a}$, —SR$^{5a}$, —C(=O)R$^{5a}$, —C(=O)NR$^{5a}$R$^{5b}$, —NR$^{5a}$R$^{5b}$ and —OR$^{5a}$, wherein:

R$^{5a}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl; and R$^{5b}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl, or R$^{5a}$ and R$^{5b}$, together with the N atom to which they are attached, form an optionally substituted heterocyclyl or an optionally substituted heteroaryl;

R⁶ is selected from chloro, bromo, fluoro, iodo, cyano, optionally substituted alkyl, optionally substituted alkenyl, optionally substituted alkynyl, optionally substituted cycloalkyl, optionally substituted heterocyclyl, —SO$_2$R$^{6a}$, —SR$^{6a}$, —C(=O)R$^{6a}$, —C(=O)NR$^{6a}$R$^{6b}$, —NR$^{6a}$NR$^{6b}$ and —OR$^{6a}$, wherein:

R$^{6a}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl; and R$^{6b}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl, or R$^{6a}$ and R$^{6b}$, together with the N atom to which they are attached, form an optionally substituted heterocyclyl or an optionally substituted heteroaryl; and R⁷ is selected from hydrogen, chloro, bromo, fluoro, iodo, cyano, optionally substituted alkyl, optionally substituted alkenyl, optionally substituted alkynyl, optionally substituted cycloalkyl, optionally substituted heterocyclyl, —SO$_2$R$^{7a}$, —SR$^{7a}$, —C(=O)R$^{7a}$, —C(=O)NR$^{7a}$R$^{7b}$, —NR$^{7a}$R$^{7b}$ and —OR$^{7a}$, wherein:

R$^{7a}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl; and R$^{7b}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl, or R$^{7a}$ and R$^{7b}$, together with the N atom to which they are attached, form an optionally substituted heterocyclyl or an optionally substituted heteroaryl, and R⁷ is not —CH$_2$S(CH$_2$)$_2$NH$_2$.

In another embodiment, a compound is provided having the following structure (II):

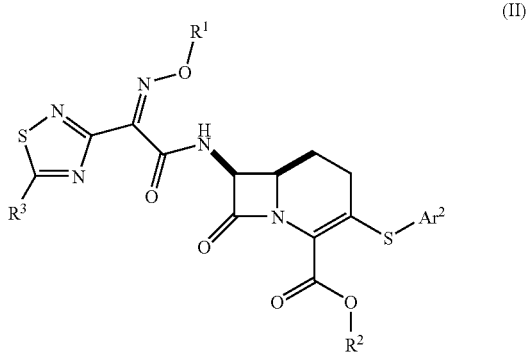

or a stereoisomer, pharmaceutically acceptable salt, ester, or prodrug thereof, wherein:

R¹ is selected from hydrogen, optionally substituted alkyl, optionally substituted alkenyl, optionally substituted alkynyl, optionally substituted alkoxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl and —C(=O)R$^{1a}$, wherein:

R$^{1a}$ is selected from hydrogen, optionally substituted alkyl, optionally substituted alkenyl, optionally substituted alkynyl, optionally substituted alkoxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl and optionally substituted heteroarylalkyl;

R$^2$ is selected from hydrogen, optionally substituted alkyl, optionally substituted alkenyl, optionally substituted alkynyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl and optionally substituted heteroarylalkyl;

R$^3$ is selected from hydrogen, chloro, bromo, fluoro, iodo, cyano, optionally substituted alkyl, optionally substituted alkenyl, optionally substituted alkynyl, optionally substituted cycloalkyl, optionally substituted aryl, optionally substituted heterocyclyl, optionally substituted heteroaryl, —SO$_2$R$^{3a}$, —SOR$^{3a}$, —SR$^{3a}$, —C(=O)R$^{3a}$, —C(=O)NR$^{3a}$R$^{3b}$, —NR$^{3a}$R$^{3b}$ and —OR$^{3a}$, wherein:

R$^{3a}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl; and R$^{3b}$ is selected from hydrogen, optionally substituted alkyl, optionally substituted alkenyl, optionally substituted alkynyl, optionally substituted cycloalkyl, optionally substituted aryl, optionally substituted heterocyclyl, optionally substituted heteroaryl and an amino acid, or R$^{3a}$ and R$^{3b}$, together with the N atom to which they are attached, form an optionally substituted heterocyclyl or an optionally substituted heteroaryl; and Ar$^2$ is optionally substituted monocyclic aryl or optionally substituted monocyclic heteroaryl, wherein Ar$^2$ is not substituted with optionally substituted aryl or optionally substituted heteroaryl.

In other embodiments, a pharmaceutical composition is provided comprising a compound having structure (I) or structure (II), or a stereoisomer, pharmaceutically acceptable salt, ester or prodrug thereof, and a pharmaceutically acceptable carrier, diluent or excipient.

In other embodiments, a method of using a compound having structure (I) or structure (II) in therapy is provided. In particular, the present invention provides a method of treating a bacterial infection is provided comprising administering a pharmaceutically effective amount of a compound having structure (I) or structure (II), or a stereoisomer, pharmaceutically acceptable salt, ester or prodrug thereof, to a mammal in need thereof. In certain embodiments, the bacterial infection may be caused by a β-lactam antibiotic-resistant bacterium, such as a methicillin-resistant genus *Staphylococcus* bacterium.

In other embodiments, a compound is provided having one of the following structures:

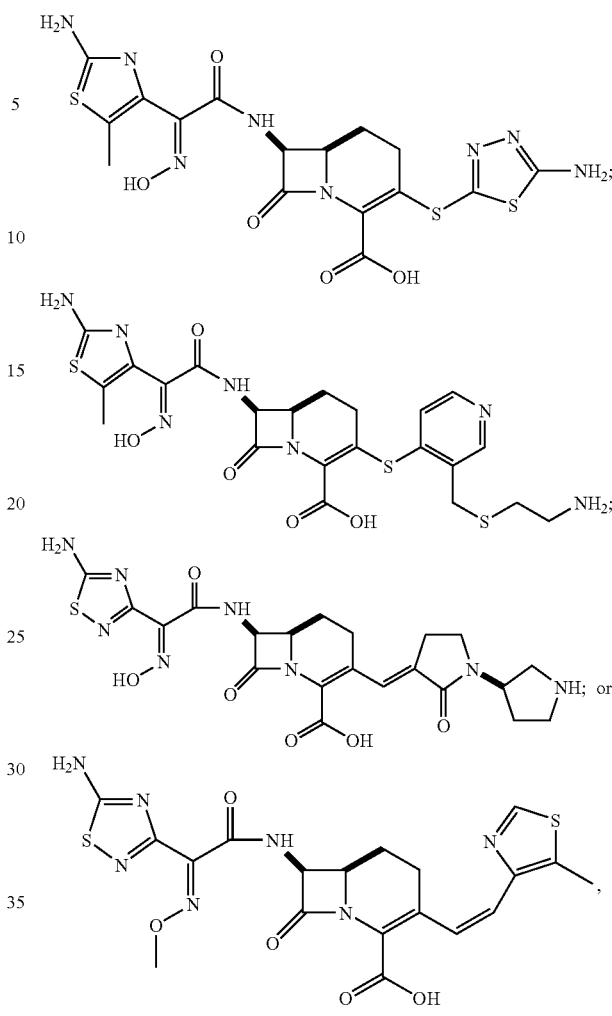

or a stereoisomer, pharmaceutically acceptable salt, ester, or prodrug thereof.

In other embodiments, a pharmaceutical composition is provided comprising a compound having one of the foregoing four structures, or a stereoisomer, pharmaceutically acceptable salt, ester or prodrug thereof, and a pharmaceutically acceptable carrier, diluent or excipient.

In other embodiments, a method of using a compound having one of the foregoing four structures in therapy is provided. In particular, the present invention provides a method of treating a bacterial infection is provided comprising administering a pharmaceutically effective amount of a compound having one of the foregoing four structures, or a stereoisomer, pharmaceutically acceptable salt, ester or prodrug thereof, to a mammal in need thereof. In certain embodiments, the bacterial infection may be caused by a β-lactam antibiotic-resistant bacterium, such as a methicillin-resistant genus *Staphylococcus* bacterium.

These and other aspects of the invention will be evident upon reference to the following detailed description.

DETAILED DESCRIPTION

Figure 1:
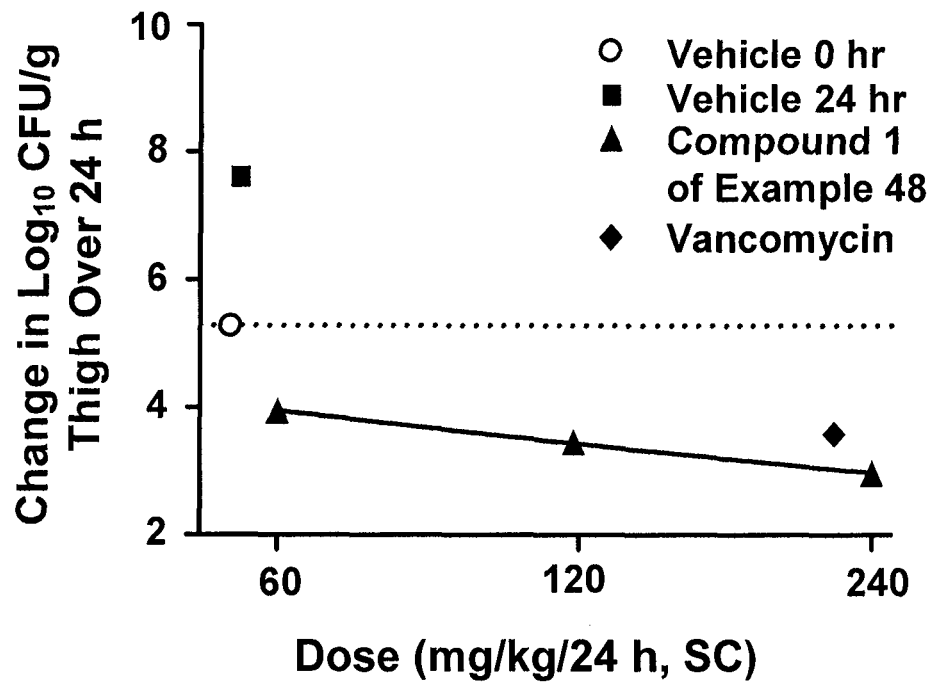
FIG. 1 shows the efficacy of Compound 1 of Example 48 dosed in a neutropenic mouse thigh infection model with a MRSA strain (ATCC 33591).

In the following description, certain specific details are set forth in order to provide a thorough understanding of various embodiments of the invention. However, one skilled in the art will understand that the invention may be practiced without these details.

Unless the context requires otherwise, throughout the specification and claims which follow, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in the specification and appended claims, unless specified to the contrary, the following terms have the meaning indicated:

"Amino" refers to the —$NH_2$ radical.

"Cyano" refers to the —CN radical.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Alkyl" refers to a straight or branched hydrocarbon chain radical consisting solely of carbon and hydrogen atoms, containing no unsaturation, having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group may be optionally substituted.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted.

"Alkynyl" refers to a straight or branched hydrocarbon chain radical group comprising solely of carbon and hydrogen atoms, containing at least one triple bond, optionally containing at least one double bond, having from two to twelve carbon atoms, preferably two to eight carbon atoms and which is attached to the rest of the molecule by a single bond, for example, ethynyl, propynyl, butynyl, pentynyl, hexynyl, and the like. Unless stated otherwise specifically in the specification, an alkynyl group may be optionally substituted.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain may be optionally substituted.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, e.g., propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, an alkynylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Alkoxyalkyl" refers to a radical of the formula —$R_b$—O—$R_a$ where $R_b$ is an alkylene chain as defined above and $R_a$ is an alkyl radical as defined above. The oxygen atom may be bonded to any carbon in the alkylene chain and in the alkyl radical. Unless stated otherwise specifically in the specification, an alkoxyalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Aralkenyl" refers to a radical of the formula —$R_d$-$R_c$ where $R_d$ is an alkenylene chain as defined above and $R_c$ is one or more aryl radicals as defined above. Unless stated otherwise specifically in the specification, an aralkenyl group may be optionally substituted.

"Aralkynyl" refers to a radical of the formula —$R_e R_c$ where $R_e$ is an alkynylene chain as defined above and $R_c$ is one or more aryl radicals as defined above. Unless stated otherwise specifically in the specification, an aralkynyl group may be optionally substituted.

"Aryloxy" refers to a radical of the formula —$OR_b$ where $R_b$ is an aryl group as defined above. Unless stated otherwise specifically in the specification, an aryloxy group may be optionally substituted.

"Aralkyloxy" refers to a radical of the formula —$OR_b$ where $R_b$ is an aralkyl group as defined above. Unless stated otherwise specifically in the specification, an aralkyloxy group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —$R_b R_g$ where $R_b$ is an alkylene chain as defined above and $R_g$ is a cycloalkyl radical as defined above. Unless stated otherwise specifically in the specification, a cycloalkylalkyl group may be optionally substituted.

"Cycloalkylalkenyl" refers to a radical of the formula —$R_d R_g$ where $R_d$ is an alkenylene chain as defined above and $R_g$ is a cycloalkyl radical as defined above. Unless stated otherwise specifically in the specification, a cycloalkylalkenyl group may be optionally substituted.

"Cycloalkylalkynyl" refers to a radical of the formula —$R_e R_g$ where $R_d$ is an alkynylene radical as defined above and $R_g$ is a cycloalkyl radical as defined above. Unless stated otherwise specifically in the specification, a cycloalkylalkynyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. Unless stated otherwise specifically in the specification, a haloalkyl group may be optionally substituted.

"Haloalkenyl" refers to an alkenyl radical, as defined above, that is substituted by one or more halo radicals, as defined above. Unless stated otherwise specifically in the specification, a haloalkenyl group may be optionally substituted.

"Haloalkynyl" refers to an alkynyl radical, as defined above, that is substituted by one or more halo radicals, as defined above. Unless stated otherwise specifically in the specification, a haloalkynyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_b R_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heterocyclylalkenyl" refers to a radical of the formula —$R_d R_h$ where $R_d$ is an alkenylene chain as defined above and $R_h$ is a heterocyclyl radical as defined above, and if the heterocyclyl is a nitrogen-containing heterocyclyl, the heterocyclyl may be attached to the alkenylene chain at the nitrogen atom. Unless stated otherwise specifically in the specification, a heterocyclylalkenyl group may be optionally substituted.

"Heterocyclylalkynyl" refers to a radical of the formula —$R_e R_h$ where $R_e$ is an alkynylene chain as defined above and $R_h$ is a heterocyclyl radical as defined above, and if the heterocyclyl is a nitrogen-containing heterocyclyl, the heterocyclyl may be attached to the alkynyl radical at the nitrogen atom. Unless stated otherwise specifically in the specification, a heterocyclylalkynyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrrolyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_b R_i$, where $R_b$ is an alkylene chain as defined above and $R_i$ is a heteroaryl radical as defined above. Unless stated otherwise specifically in the specification, a heteroarylalkyl group may be optionally substituted.

"Heteroarylalkenyl" refers to a radical of the formula —$R_d R_i$, where $R_d$ is an alkenylene chain as defined above and $R_i$ is a heteroaryl radical as defined above. Unless stated otherwise specifically in the specification, a heteroarylalkenyl group may be optionally substituted.

"Heteroarylalkynyl" refers to a radical of the formula —$R_e R^i$, where $R_e$ is an alkynylene chain as defined above and $R_i$ is a heteroaryl radical as defined above. Unless stated otherwise specifically in the specification, a heteroarylalkynyl group may be optionally substituted.

"Hydroxyalkyl" refers to an alkyl radical, as defined above, substituted by one or more hydroxy groups.

The term "substituted" used herein means any of the above groups (i.e., alkyl, alkenyl, alkynyl, alkylene, alkenylene, alkynylene, alkoxy, alkoxyalkyl, aryl, aralkyl, aralkenyl, aralkynyl, aryloxy, aralkyloxy, cycloalkyl, cycloalkylalkyl, cycloalkylalkenyl, cycloalkylalkynyl, haloalkyl, haloalkenyl, haloalkynyl, heterocyclyl, N-heterocyclyl, heterocyclylalkyl, heterocyclylalkenyl, heterocyclylalkynyl, heteroaryl, N-heteroaryl, heteroarylalkyl, heteroarylalkenyl and/or heteroarylalkynyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diary lamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more bonds are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. "Substituted" further means any of the above groups in which one or more bonds are replaced by a bond to an amino, cyano, hydroxyl, imino, nitro, oxo, thioxo, halo, hydroxyalkyl, alkyl, alkenyl, alkynyl, alkylene, alkenylene, alkynylene, alkoxy, alkoxyalkyl, aryl, aralkyl, aralkenyl, aralkynyl, aryloxy, aralkyloxy, cycloalkyl, cycloalkylalkyl, cycloalkylalkenyl, cycloalkylalkynyl, haloalkyl, haloalkenyl, haloalkynyl, heterocyclyl, N-heterocyclyl, heterocyclylalkyl, heterocyclylalkenyl, heterocyclylalkynyl, heteroaryl, N-heteroaryl, heteroarylalkyl, heteroarylalkenyl and/or heteroarylalkynyl group. In addition, the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like. More specifically, example of prodrugs include (in addition to the prodrugs of structures (I-B) and (II-B) described below), but are not limited to, compounds of structure (I) or (II) wherein $R^1$ is alkyl (such as, for example, methyl) and $R^1$ is bonded to an ester group (such as, for example, —OC(=O)CH$_3$ or —OC(=O)C(CH$_3$)$_2$).

The invention disclosed herein is also meant to encompass all pharmaceutically acceptable compounds of a structure disclosed herein being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action on the sodium channels, or binding affinity to pharmacologically important site of action on the sodium channels. Certain isotopically-labelled compounds of a structure disclosed herein, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of a structure disclosed herein can generally be prepared by conventional techniques known to those skilled in the art or by processes analogous to those as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising contacting a compound of this invention with a mammal for a period of time sufficient to yield a metabolic product thereof. Such products are typically are identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefore.

"Effective amount" or "therapeutically effective amount" refers to that amount of a compound of the invention which, when administered to a mammal, preferably a human, is sufficient to effect treatment, as defined below, of a bacterial infection in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

"MIC", which stands for minimum inhibitory concentration, refers to that concentration, in µg/mL, of a compound of this invention that inhibits the growth and/or proliferation of a strain of bacteria by at least 80% compared to an untreated control.

"MRSA" refers to methicillin-resistant *Staphylococcus aureus*.

"Bacterial infection" refers to the establishment of a sufficient population of a pathogenic bacteria in a patient to have a deleterious effect on the health and well-being of the patient and/or to give rise to discernable symptoms associated with the particular bacteria.

"β-lactam resistant bacterium" refers to bacterium against which a β-lactam antibiotic has a minimum inhibitory concentration (MIC) greater than 8 µg/mL.

As noted above, in one embodiment of the present invention, compounds having antibacterial activity are provided, the compounds having the following structure (I):

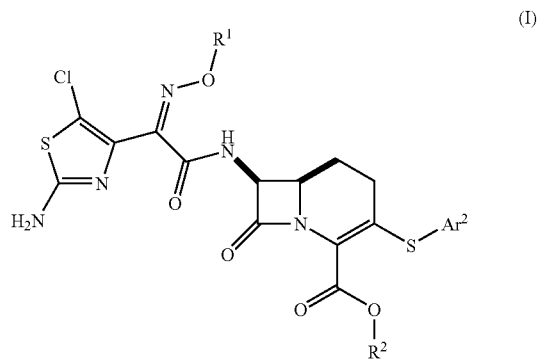

(I)

or a stereoisomer, pharmaceutically acceptable salt, ester, or prodrug thereof, wherein:

$R^1$ is selected from hydrogen, optionally substituted alkyl, optionally substituted alkenyl, optionally substituted alkynyl, optionally substituted alkoxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl and —C(=O)$R^{1a}$, wherein:

$R^{1a}$ is selected from hydrogen, optionally substituted alkyl, optionally substituted alkenyl, optionally substituted alkynyl, optionally substituted alkoxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl and optionally substituted heteroarylalkyl;

$R^2$ is selected from hydrogen, optionally substituted alkyl, optionally substituted alkenyl, optionally substituted alkynyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl and optionally substituted heteroarylalkyl;

Ar² is a heteroaryl having 5 ring atoms selected from:
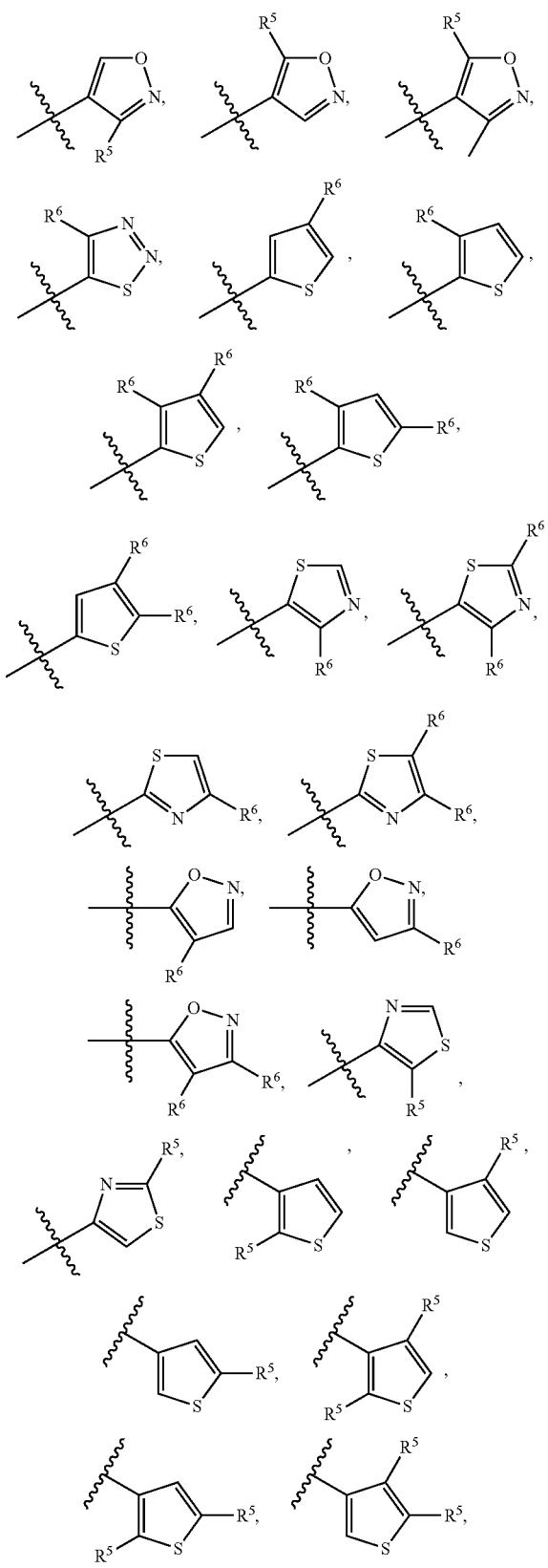
-continued
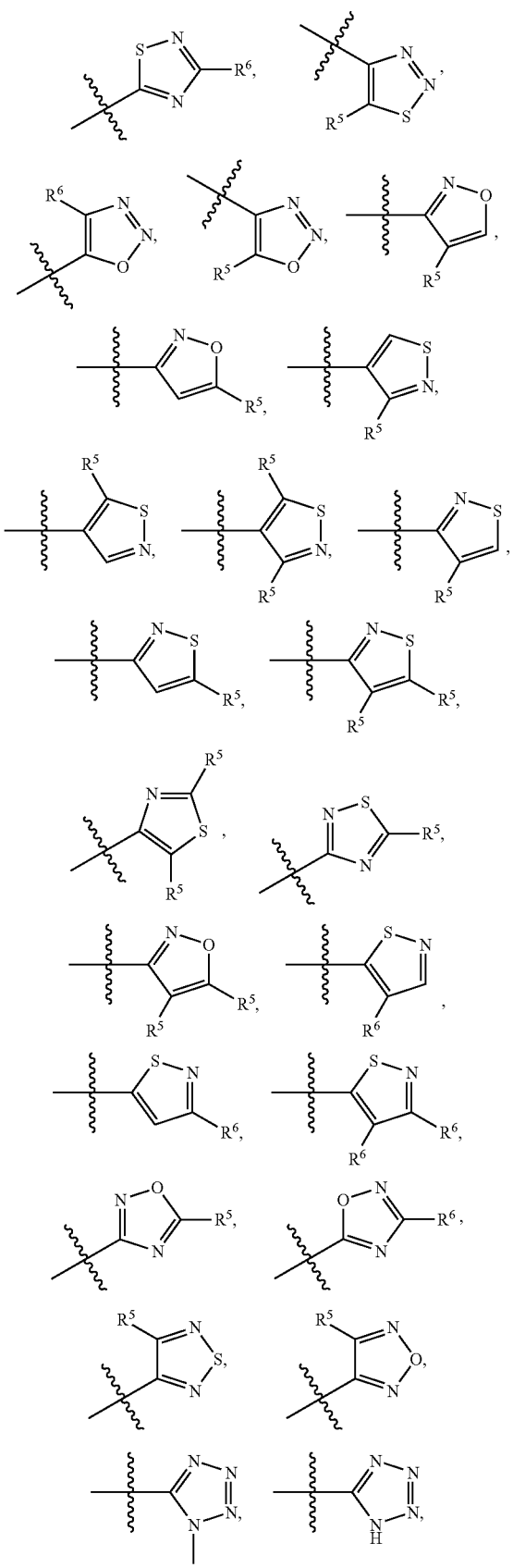

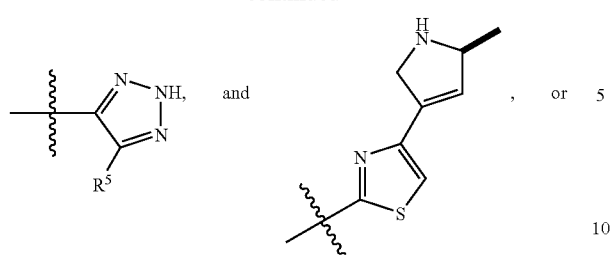
Ar² is a heteroaryl having 6 ring atoms selected from:
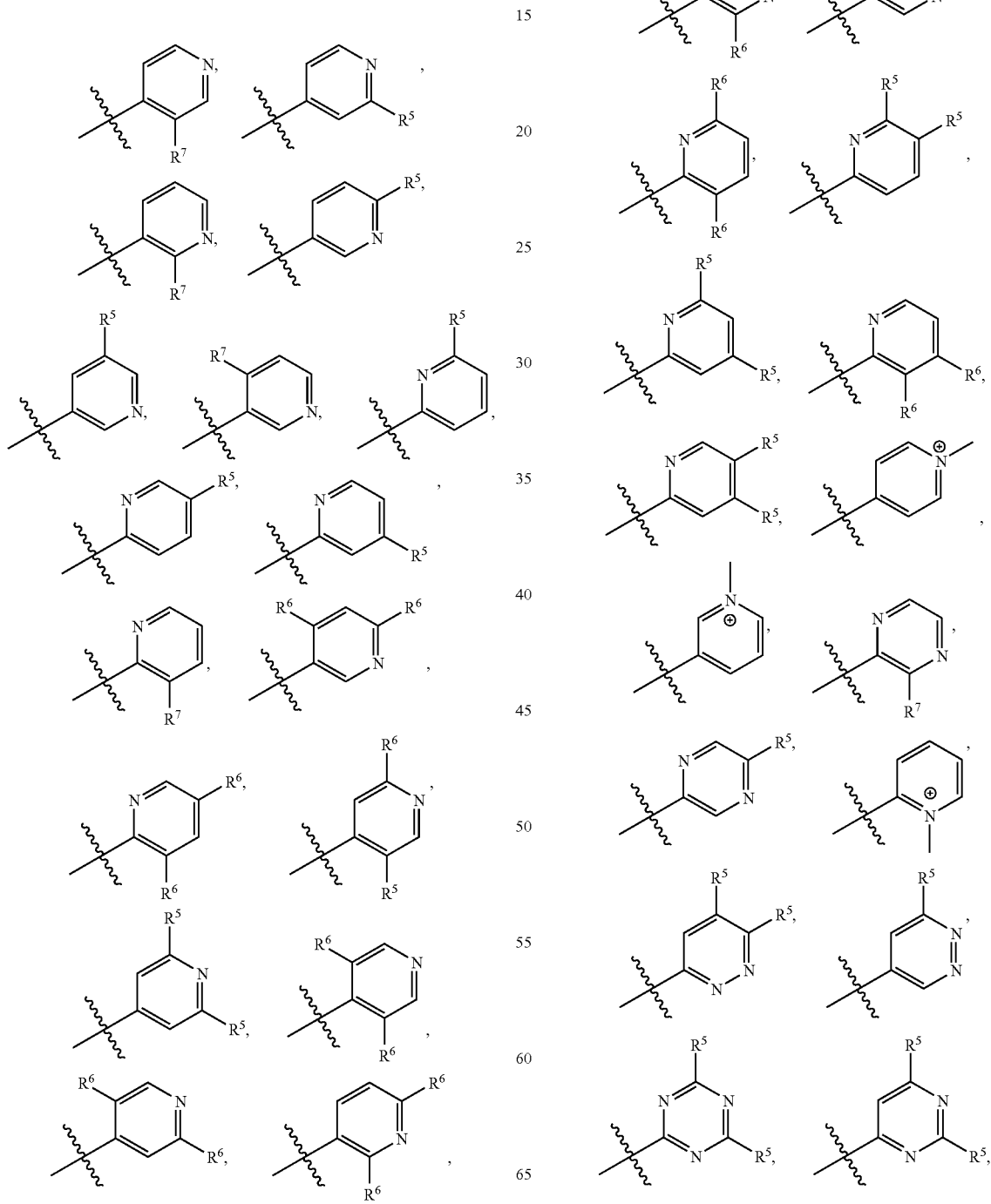

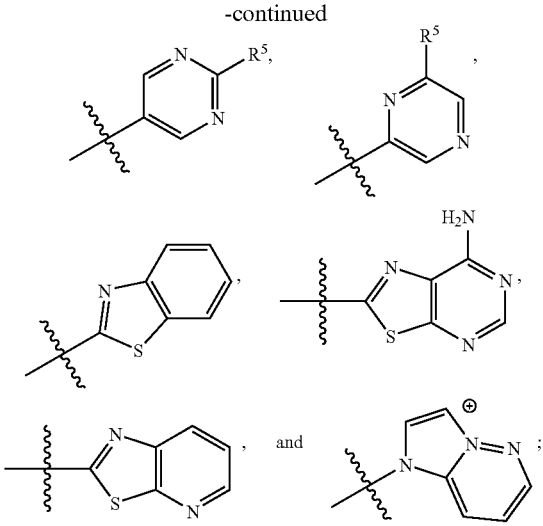

$R^5$ is selected from hydrogen, chloro, bromo, fluoro, iodo, cyano, optionally substituted alkyl, optionally substituted alkenyl, optionally substituted alkynyl, optionally substituted cycloalkyl, optionally substituted heterocyclyl, —SO$_2$R$^{5a}$, —SR$^{5a}$, —C(=O)R$^{5a}$, —C(=O)NR$^{5a}$R$^{5b}$, —NR$^{5a}$R$^{5b}$ and —OR$^{5a}$, wherein:
R$^{5a}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl; and R$^{5b}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl, or R$^{5a}$ and R$^{5b}$, together with the N atom to which they are attached, form an optionally substituted heterocyclyl or an optionally substituted heteroaryl;

R$^6$ is selected from chloro, bromo, fluoro, iodo, cyano, optionally substituted alkyl, optionally substituted alkenyl, optionally substituted alkynyl, optionally substituted cycloalkyl, optionally substituted heterocyclyl, —SO$_2$R$^{6a}$, —SR$^{6a}$, —C(=O)R$^{6a}$, —C(=O)NR$^{6a}$R$^{6b}$, —NR$^{6a}$R$^{6b}$ and —OR$^{6a}$, C(=O)R$^{6a}$, —C(=O)NR$^{6a}$R$^{6b}$, —NR$^{6a}$R$^{6b}$ and —OR$^{6a}$, wherein:
R$^{6a}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl; and R$^{6b}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl, or R$^{6a}$ and R$^{6b}$, together with the N atom to which they are attached, form an optionally substituted heterocyclyl or an optionally substituted heteroaryl; and R$^7$ is selected from hydrogen, chloro, bromo, fluoro, iodo, cyano, optionally substituted alkyl, optionally substituted alkenyl, optionally substituted alkynyl, optionally substituted cycloalkyl, optionally substituted heterocyclyl, —SO$_2$R$^{7a}$, —SR$^{7a}$, —C(=O)R$^{7a}$, —C(=O)NR$^{7a}$R$^{7b}$, —NR$^{7a}$R$^{7b}$ and —OR$^{7a}$, wherein:
R$^{7a}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl; and R$^{7b}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl, or R$^{7a}$ and R$^{7b}$, together with the N atom to which they are attached, form an optionally substituted heterocyclyl or an optionally substituted heteroaryl, and R$^7$ is not —CH$_2$S(CH$_2$)$_2$NH$_2$.

In further embodiments, R$^1$ is hydrogen.

In other further embodiments, R$^1$ is alkyl and is selected from methyl, ethyl, n-propyl, iso-propyl, n-butyl, tert-butyl, iso-butyl and sec-butyl.

In other further embodiments, R$^1$ is substituted alkyl and is optionally substituted haloalkyl. For example, in certain embodiments, R$^1$ is selected from —CH$_2$CH$_2$Cl, —CH$_2$CH$_2$F, —CH$_2$CHF$_2$, —CH$_2$CF$_3$, —CHFCH$_2$F, —CHFCHF$_2$, —CHFCF$_3$, —CH$_2$F, —CHF$_2$, —CF$_3$ and —CH$_2$CH$_2$CH$_2$F.

In other further embodiments, R$^1$ is substituted alkyl and is optionally substituted alkoxyalkyl or optionally substituted hydroxyalkyl. For example, in certain embodiments, R$^1$ is —CH$_2$CH$_2$OH, —CH$_2$CH$_2$OMe or —CH$_2$CH$_2$OCF$_3$.

In other further embodiments, R$^1$ is substituted alkyl and is —CH$_2$CH$_2$SMe, —CH$_2$CH$_2$SO$_2$Me, —CH$_2$CH$_2$NMe$_3$, —CH$_2$CH$_2$NMe$_2$ or —CH$_2$CN.

In other further embodiments, R$^1$ is alkenyl and is —CH$_2$CH=CH$_2$.

In other further embodiments, R$^1$ is substituted alkenyl and is optionally substituted haloalkenyl. For example, in certain embodiments, R$^1$ is —CH$_2$CH=CCl$_2$ or —CH$_2$CH=CF$_2$.

In other further embodiments, R$^1$ is cycloalkyl and is selected from cyclopropyl, cyclobutyl, cyclopentyl, cyclopentenyl, cyclohexyl, and cyclohexenyl.

In further embodiments, R$^2$ is hydrogen.

In other further embodiments, R$^2$ is alkyl and is selected from methyl, ethyl, n-propyl, iso-propyl, n-butyl, tert-butyl, iso-butyl and sec-butyl.

In other further embodiments, R$^2$ is substituted alkyl and is selected from haloalkyl, —(CH$_2$)$_n$OR$^{2a}$, —(CH$_2$)$_n$N(R$^{2a}$)$_2$, —(CH$_2$)$_n$N(R$^{2a}$)$_3$, —(CH$_2$)$_n$SOR$^{2a}$, —(CH$_2$)$_n$SO$_2$R$^{2a}$ and —(CH$_2$)$_n$CN; n is 1 or 2; and each R$^{2a}$ is independently optionally substituted alkyl. For example, in certain embodiments, R$^2$ is selected from —CH$_2$F, —CH$_2$CN, —CH$_2$CH$_2$F, —CH$_2$CHF$_2$, —CH$_2$CF$_3$, —CH$_2$CH$_2$OCH$_3$, —CH$_2$CH$_2$OCF$_3$, —CH$_2$CH$_2$SO$_2$CH$_3$, —CH$_2$CH$_2$CN, —CH$_2$CH$_2$N(CH$_3$)$_3$ and —CH$_2$CH$_2$N(CH$_3$)$_2$.

In other further embodiments, R$^2$ is cycloalkyl and is selected from cyclopropyl, cyclobutyl, cyclopentyl and cyclohexyl.

In other further embodiments, R$^2$ is aryl and is phenyl.

In other further embodiments, R$^2$ is substituted aryl and is substituted phenyl.

In other further embodiments, R$^2$ is heteroaryl and is a 6-membered ring comprising at least one N atom.

In other further embodiments, the compound is a pharmaceutically acceptable salt of structure (I) having the following structure (I-A):

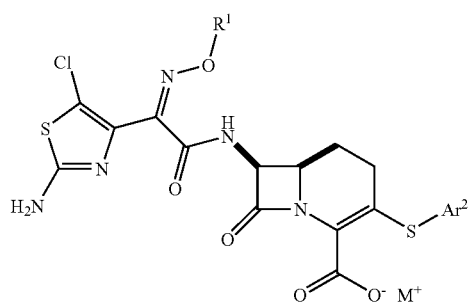
(I-A)
wherein M is an alkali metal atom.
In other further embodiments, the compound is a prodrug of structure (I) having the following structure (I-B):
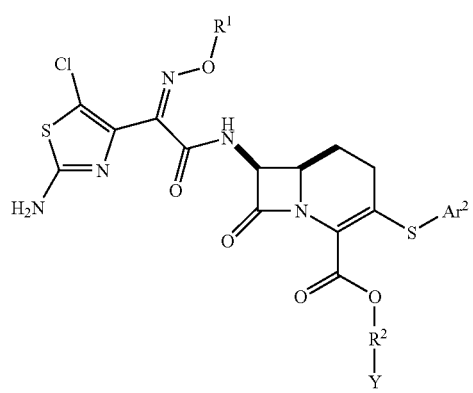
(I-B)
wherein $R^2$ and Y, taken together, are selected from:
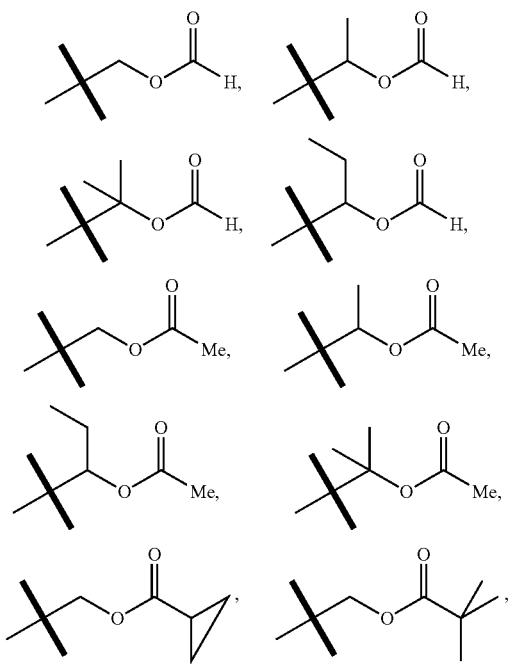
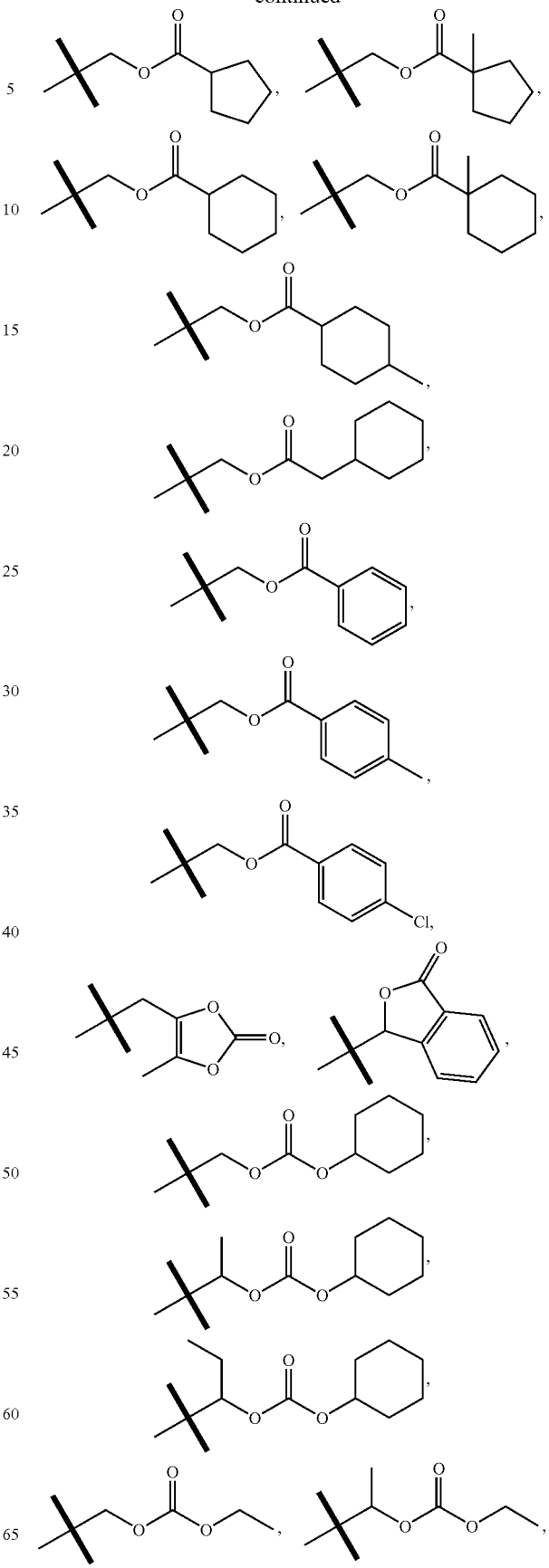

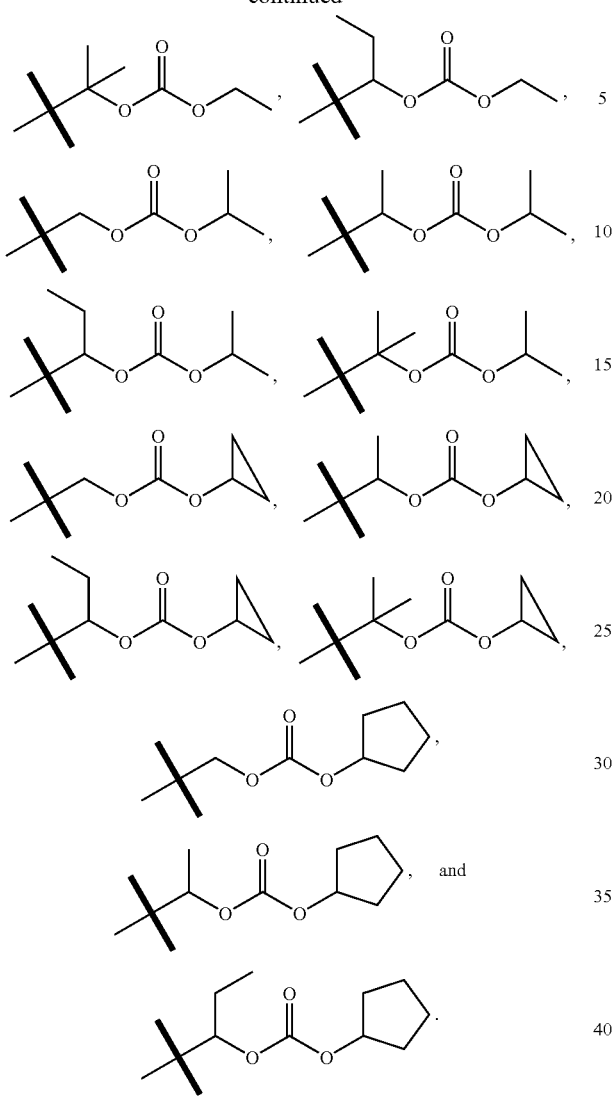
In other further embodiments, the compound is a prodrug of structure (I) having the following structure (I-B):
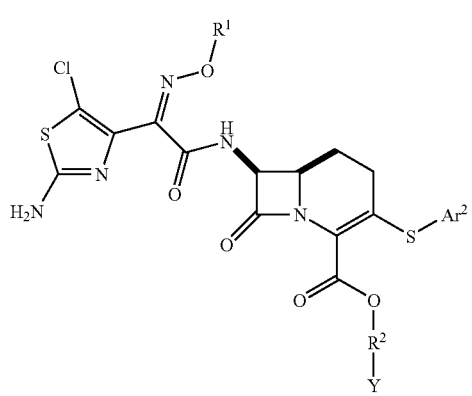
(I-B)
wherein $R^2$ and Y, taken together, are selected from:
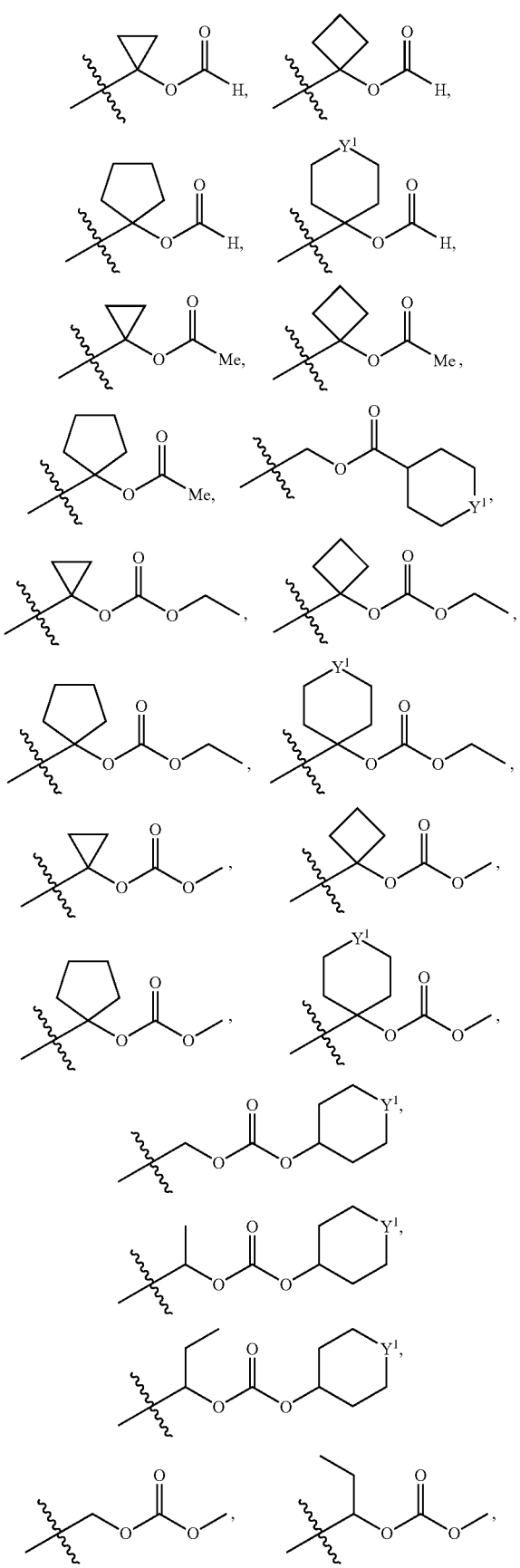

-continued

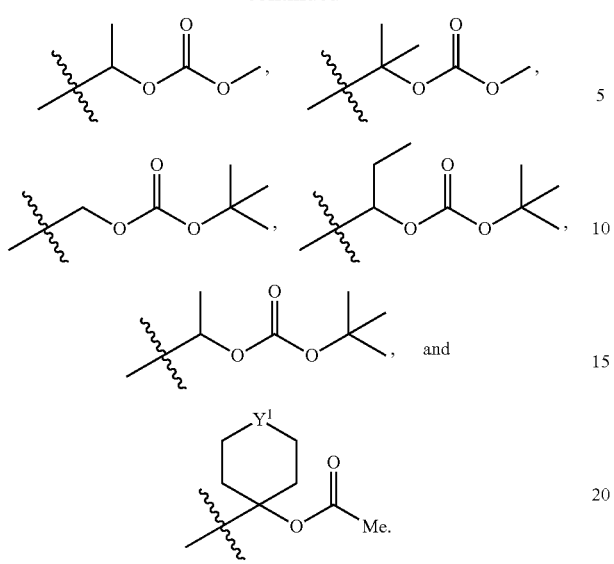

wherein $Y^1$ is —$CH_2$—, —O—, —S—, —$SO_2$—, —NH—, —$NCH_3$—, —$NCH_2CH_3$—, —$NCH_2CH_2CH_3$— or —$NCH_2CF_3$—.

In other further embodiments, $R^5$ is selected from hydrogen, chloro, fluoro, bromo, iodo, cyano, —$CH_3$, —$CF_3$, —$SO_2CH_3$, —$SCH_3$, —$OCH_3$, —$OCF_3$, —$NH_2$, —$NHCH_3$, —$N(CH_3)_2$, —$NHCH_2CH_3$, —$N(CH_2CH_3)_2$, —$NHCH(CH_3)_2$, -continued

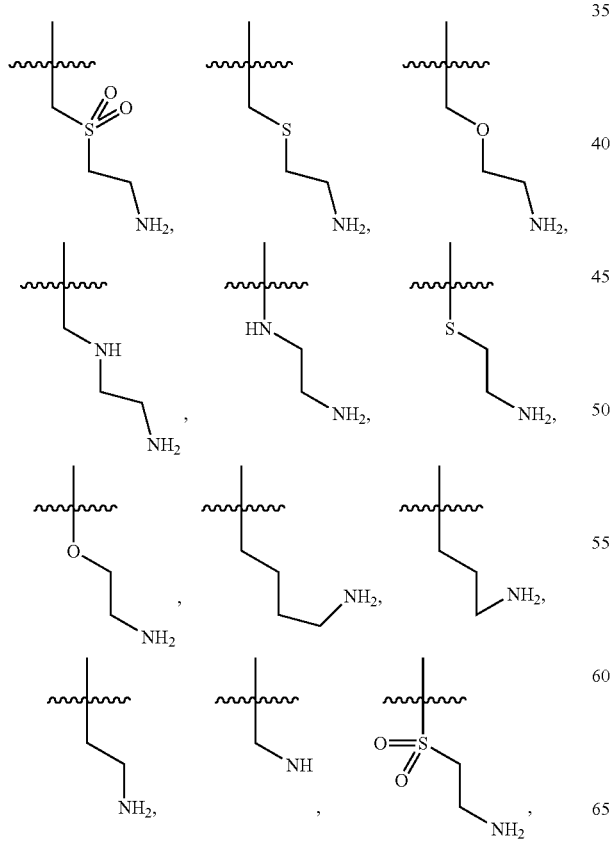

In other further embodiments, $R^6$ is selected from chloro, fluoro, bromo, iodo, cyano, —$CH_3$, —$CF_3$, —$SO_2CH_3$, —$SCH_3$, —$OCH_3$, —$OCF_3$, —$NH_2$, —$NHCH_3$, —$N(CH_3)_2$, —$NHCH_2CH_3$, —$N(CH_2CH_3)_2$, —$NHCH(CH_3)_2$,

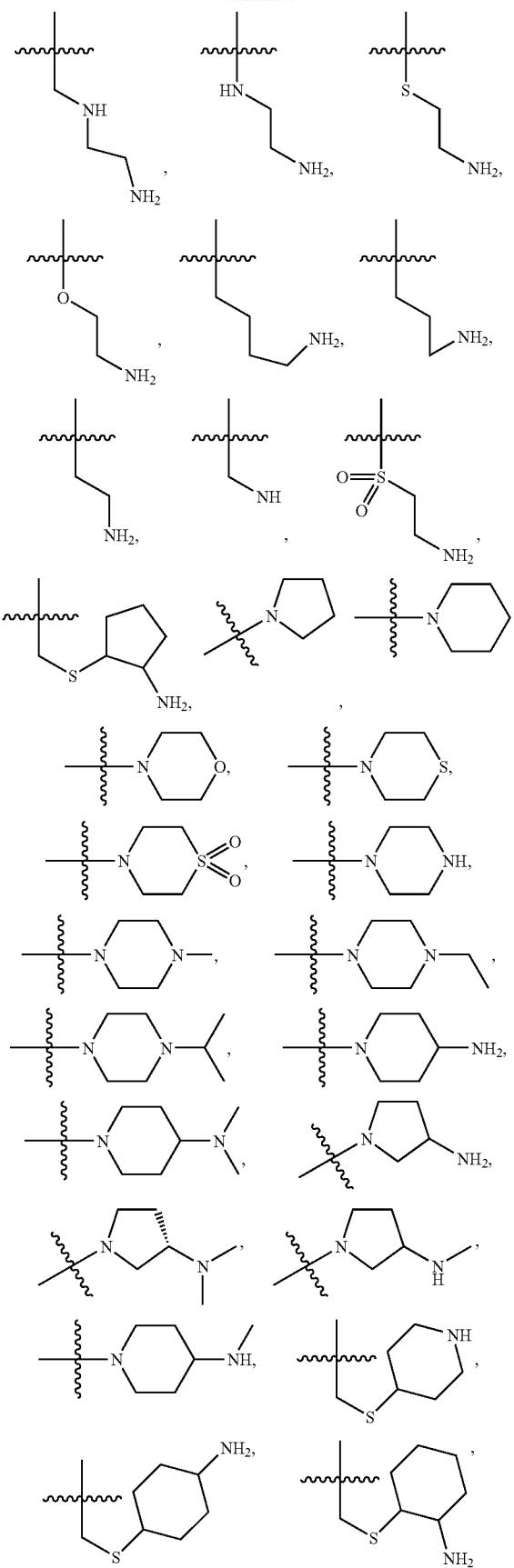
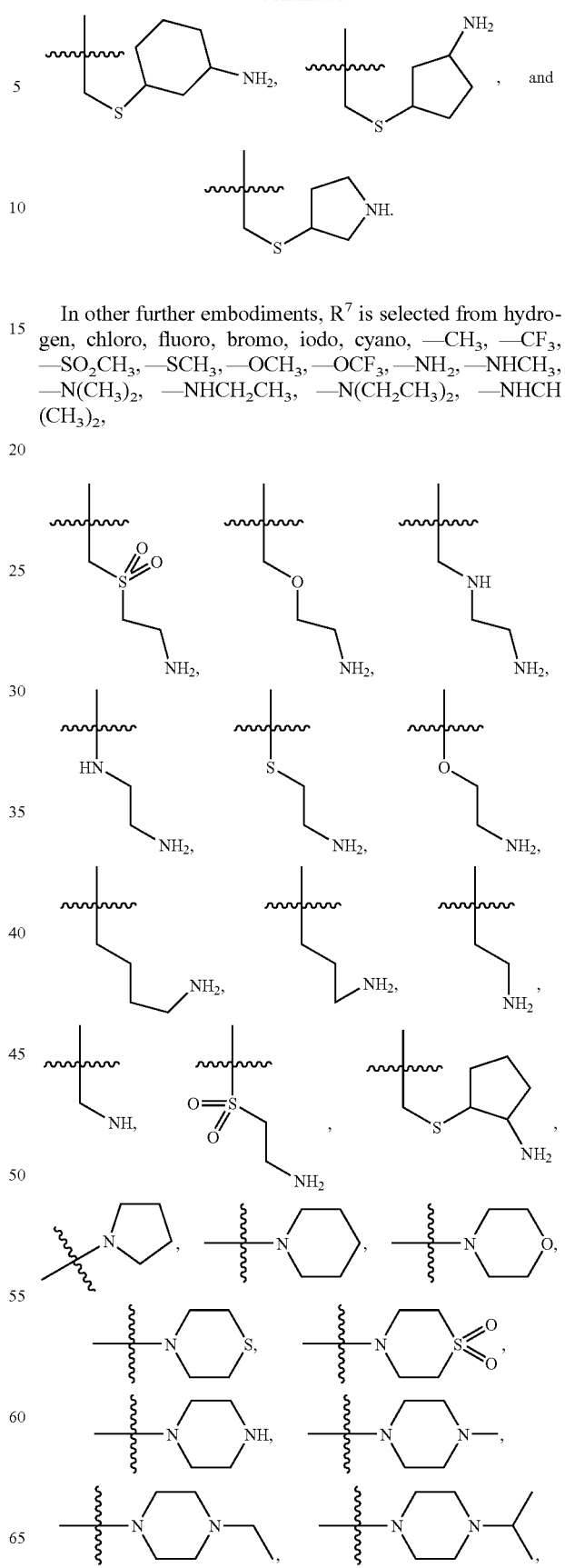
In other further embodiments, $R^7$ is selected from hydrogen, chloro, fluoro, bromo, iodo, cyano, —$CH_3$, —$CF_3$, —$SO_2CH_3$, —$SCH_3$, —$OCH_3$, —$OCF_3$, —$NH_2$, —$NHCH_3$, —$N(CH_3)_2$, —$NHCH_2CH_3$, —$N(CH_2CH_3)_2$, —$NHCH(CH_3)_2$,

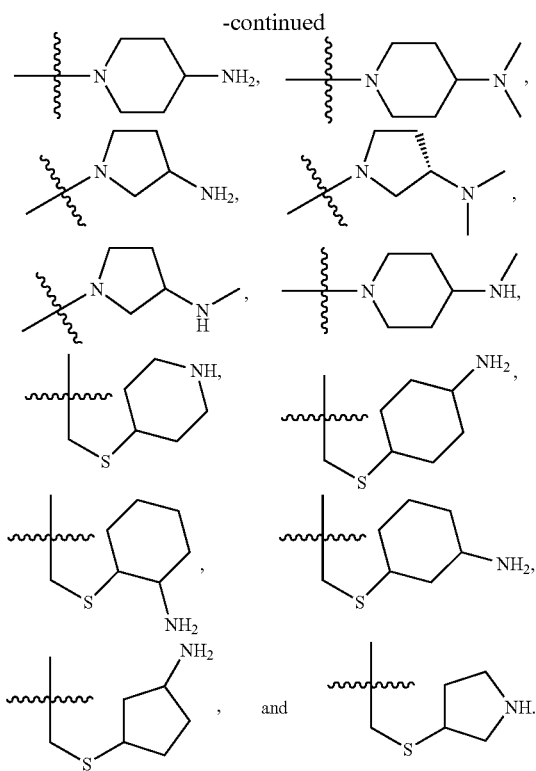

As also noted above, in another embodiment of the present invention, compounds having antibacterial activity are provided, the compounds having the following structure (II):

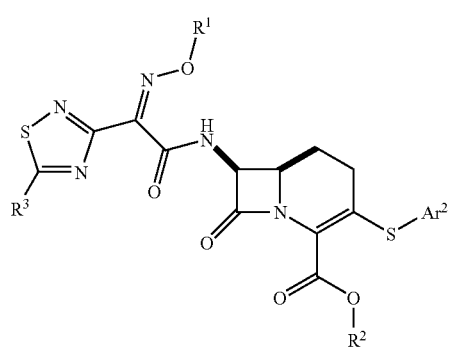

or a stereoisomer, pharmaceutically acceptable salt, ester, or prodrug thereof,
wherein:
$R^1$ is selected from hydrogen, optionally substituted alkyl, optionally substituted alkenyl, optionally substituted alkynyl, optionally substituted alkoxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl and —C(=O)$R^{1a}$,
wherein:
$R^{1a}$ is selected from hydrogen, optionally substituted alkyl, optionally substituted alkenyl, optionally substituted alkynyl, optionally substituted alkoxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl and optionally substituted heteroarylalkyl;

$R^2$ is selected from hydrogen, optionally substituted alkyl, optionally substituted alkenyl, optionally substituted alkynyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl and optionally substituted heteroarylalkyl;

$R^3$ is selected from hydrogen, chloro, bromo, fluoro, iodo, cyano, optionally substituted alkyl, optionally substituted alkenyl, optionally substituted alkynyl, optionally substituted cycloalkyl, optionally substituted aryl, optionally substituted heterocyclyl, optionally substituted heteroaryl, —SO$_2$R$^{3a}$, —SOR$^{3a}$, —SR$^{3a}$, —C(=O)R$^{3a}$, —C(=O)NR$^{3a}$R$^{3b}$, —NR$^{3a}$R$^{3b}$ and —OR$^{3a}$, wherein:

$R^{3a}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl; and $R^{3b}$ is selected from hydrogen, optionally substituted alkyl, optionally substituted alkenyl, optionally substituted alkynyl, optionally substituted cycloalkyl, optionally substituted aryl, optionally substituted heterocyclyl, optionally substituted heteroaryl and an amino acid,
or $R^{1a}$ and $R^{3b}$, together with the N atom to which they are attached, form an optionally substituted heterocyclyl or an optionally substituted heteroaryl; and $Ar^2$ is optionally substituted monocyclic aryl or optionally substituted monocyclic heteroaryl, wherein $Ar^2$ is not substituted with optionally substituted aryl or optionally substituted heteroaryl.

In further embodiments, $R^1$ is hydrogen.
In other further embodiments, $R^1$ is alkyl and is selected from methyl, ethyl, n-propyl, iso-propyl, n-butyl, tert-butyl, iso-butyl and sec-butyl.
In other further embodiments, $R^1$ is substituted alkyl and is optionally substituted haloalkyl. For example, in certain embodiments, $R^1$ is selected from —CH$_2$CH$_2$Cl, —CH$_2$CH$_2$F, —CH$_2$CHF$_2$, —CH$_2$CF$_3$, —CHFCH$_2$F, —CHFCHF$_2$, —CHFCF$_3$, —CH$_2$F, —CHF$_2$, —CF$_3$ and —CH$_2$CH$_2$F.
In other further embodiments, $R^1$ is substituted alkyl and is optionally substituted alkoxyalkyl or optionally substituted hydroxyalkyl. For example, in certain embodiments, $R^1$ is —CH$_2$CH$_2$OH, —CH$_2$CH$_2$OMe or —CH$_2$CH$_2$OCF$_3$.
In other further embodiments, $R^1$ is substituted alkyl and is —CH$_2$CH$_2$SMe, —CH$_2$CH$_2$SO$_2$Me, —CH$_2$CH$_2$NMe$_3$, —CH$_2$CH$_2$NMe$_2$ or —CH$_2$CN.
In other further embodiments, $R^1$ is alkenyl and is —CH$_2$CH=CH$_2$.
In other further embodiments, $R^1$ is substituted alkenyl and is optionally substituted haloalkenyl. For example, in certain embodiments, $R^1$ is —CH$_2$CH=CCl$_2$ or —CH$_2$CH=CF$_2$.
In other further embodiments, $R^1$ is cycloalkyl and is selected from cyclopropyl, cyclobutyl, cyclopentyl, cyclopentenyl, cyclohexyl, and cyclohexenyl.
In further embodiments, $R^2$ is hydrogen.
In other further embodiments, $R^2$ is alkyl and is selected from methyl, ethyl, n-propyl, iso-propyl, n-butyl, tert-butyl, iso-butyl and sec-butyl.
In other further embodiments, $R^2$ is substituted alkyl and is selected from haloalkyl, —(CH$_2$)$_n$OR$^{2a}$, —(CH$_2$)$_n$N(R$^{2a}$)$_2$, —(CH$_2$)$_n$N(R$^{2a}$)$_3$, —(CH$_2$)$_n$SOR$^{2a}$, —(CH$_2$)$_n$SO$_2$R$^{2a}$ and —(CH$_2$)$_n$CN; n is 1 or 2; and each R$^{2a}$ is independently optionally substituted alkyl. For example, in certain embodiments, R$^2$ is selected from —CH$_2$F, —CH$_2$CN, —CH$_2$CH$_2$F, —CH$_2$CHF$_2$, —CH$_2$CF$_3$, —CH$_2$CH$_2$OCH$_3$, —CH$_2$CH$_2$OCF$_3$, —CH$_2$CH$_2$SO$_2$CH$_3$, —CH$_2$CH$_2$CN, —CH$_2$CH$_2$N(CH$_3$)$_3$ and —CH$_2$CH$_2$N(CH$_3$)$_2$.

In other further embodiments, R$^2$ is cycloalkyl and is selected from cyclopropyl, cyclobutyl, cyclopentyl and cyclohexyl.

In other further embodiments, R$^2$ is aryl and is phenyl.

In other further embodiments, R$^2$ is substituted aryl and is substituted phenyl.

In other further embodiments, R$^2$ is heteroaryl and is a 6-membered ring comprising at least one N atom.

In other further embodiments, the compound is a pharmaceutically acceptable salt of structure (II) having the following structure (II-A):

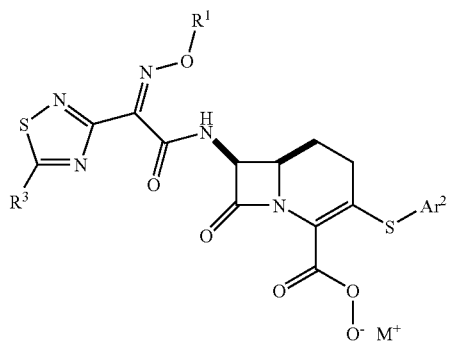

(II-A)

wherein M is an alkali metal atom.

In other further embodiments, the compound is a prodrug of structure (II) having the following structure (II-B):

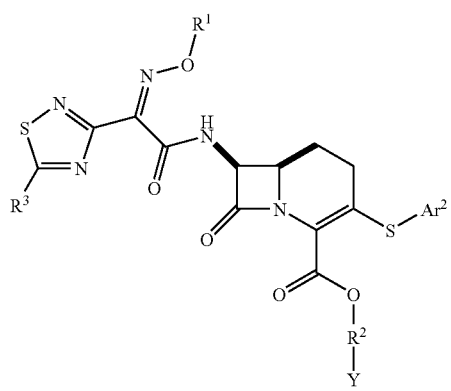

(II-B)

wherein R$^2$ and Y, taken together, are selected from:

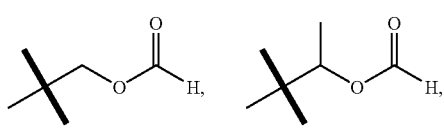

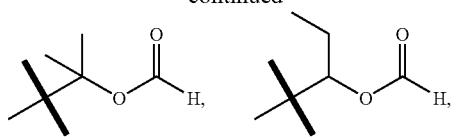

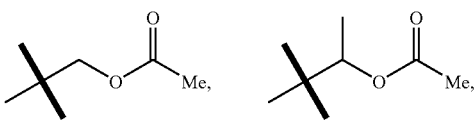

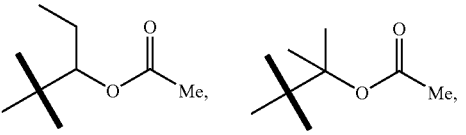

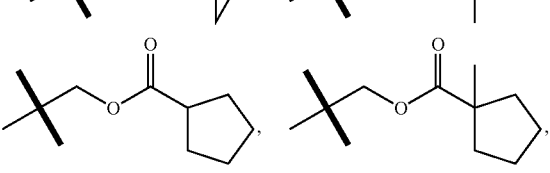

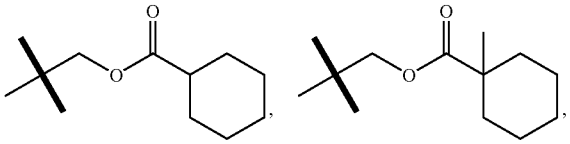

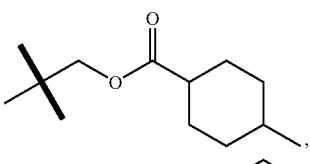

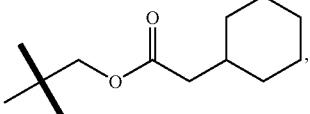

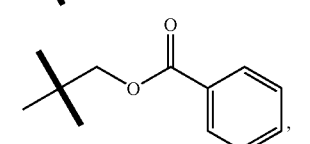

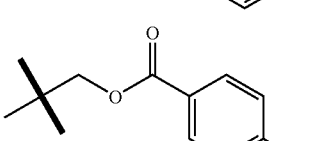

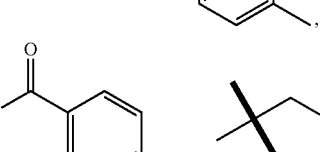

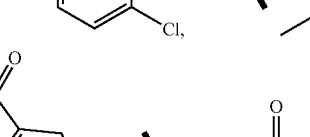

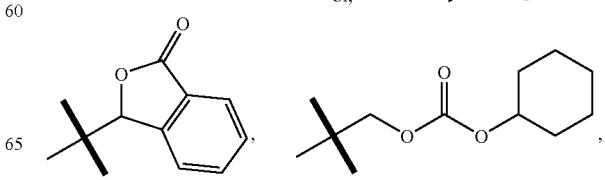

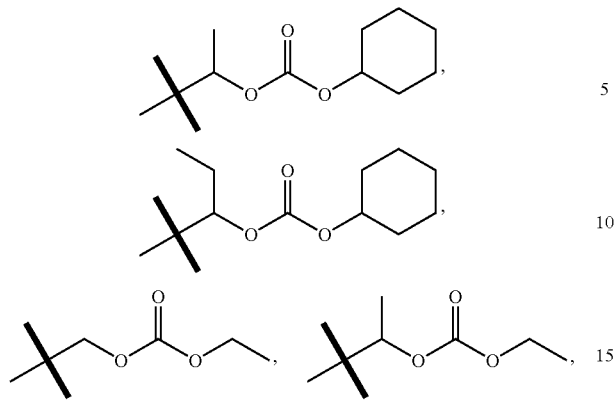
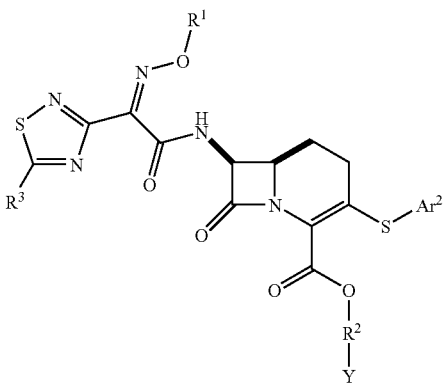
wherein $R^2$ and Y, taken together, are selected from:
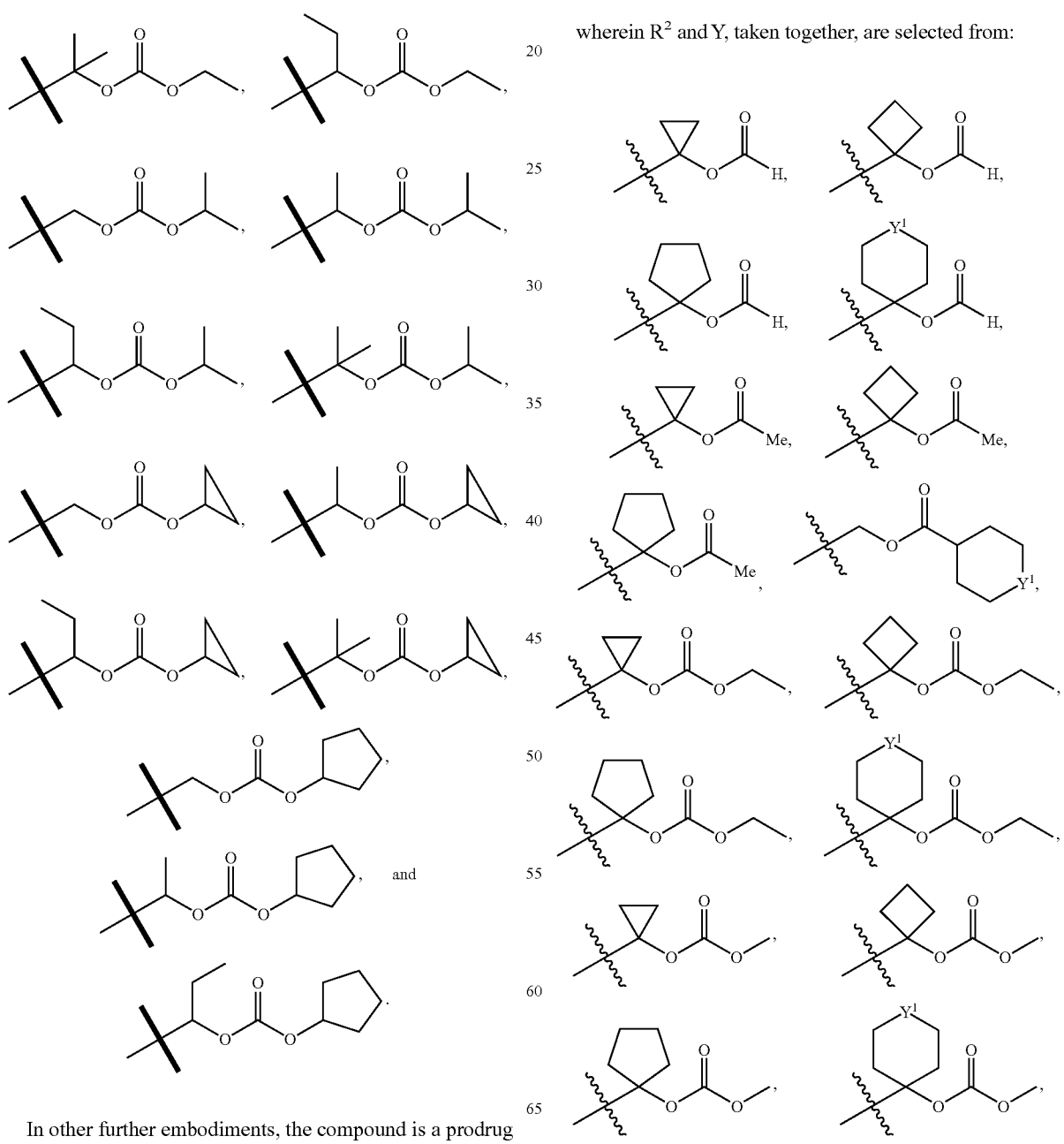
In other further embodiments, the compound is a prodrug of structure (II) having the following structure (II-B):

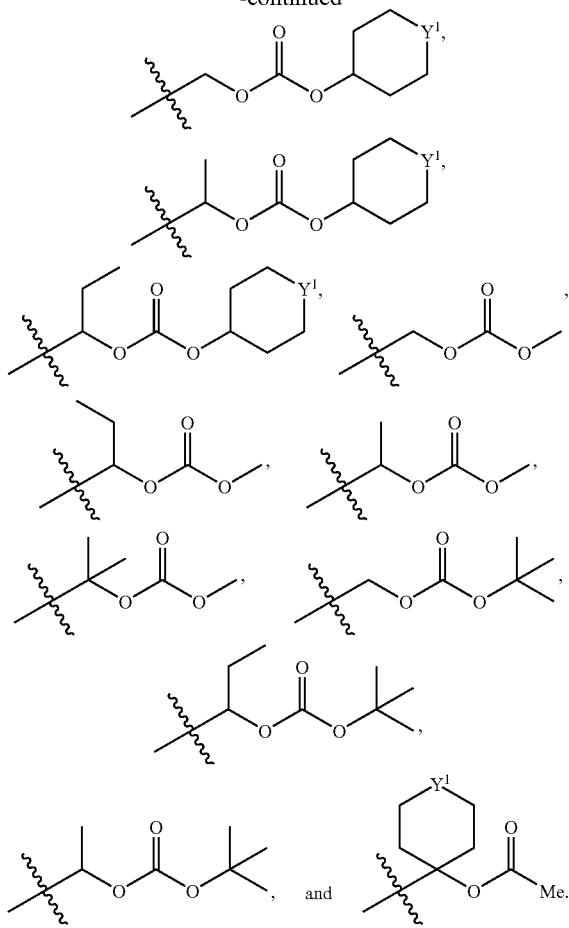

wherein $Y^1$ is —$CH_2$—, —O—, —S—, —$SO_2$—, —NH—, —$NCH_3$—, —$NCH_2CH_3$—, —$NCH_2CH_2CH_3$— or —$NCH_2CF_3$—.

In other further embodiments, $R^3$ is hydrogen.

In other further embodiments, $R^3$ is —$NR^{3a}R^{3b}$. For example, in certain embodiments, $R^3$ is —$NH_2$.

In other further embodiments, $R^3$ is —$OR^{3a}$ and $R^{3a}$ is optionally substituted alkyl. For example, in certain embodiments, $R^{3a}$ is —$CH_3$ or —$CF_3$.

In other further embodiments, $R^3$ is substituted alkyl and is optionally substituted haloalkyl. For example, in certain embodiments, $R^3$ is —$CF_3$.

In other further embodiments, $Ar^2$ is selected from:

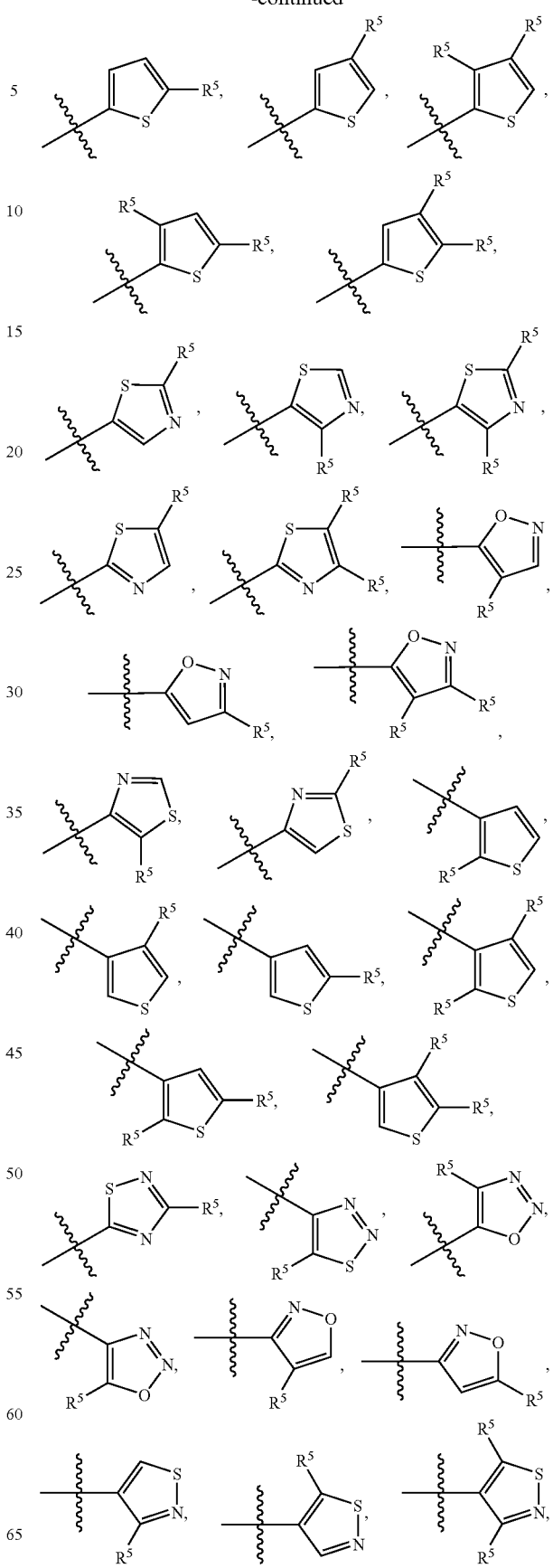

-continued

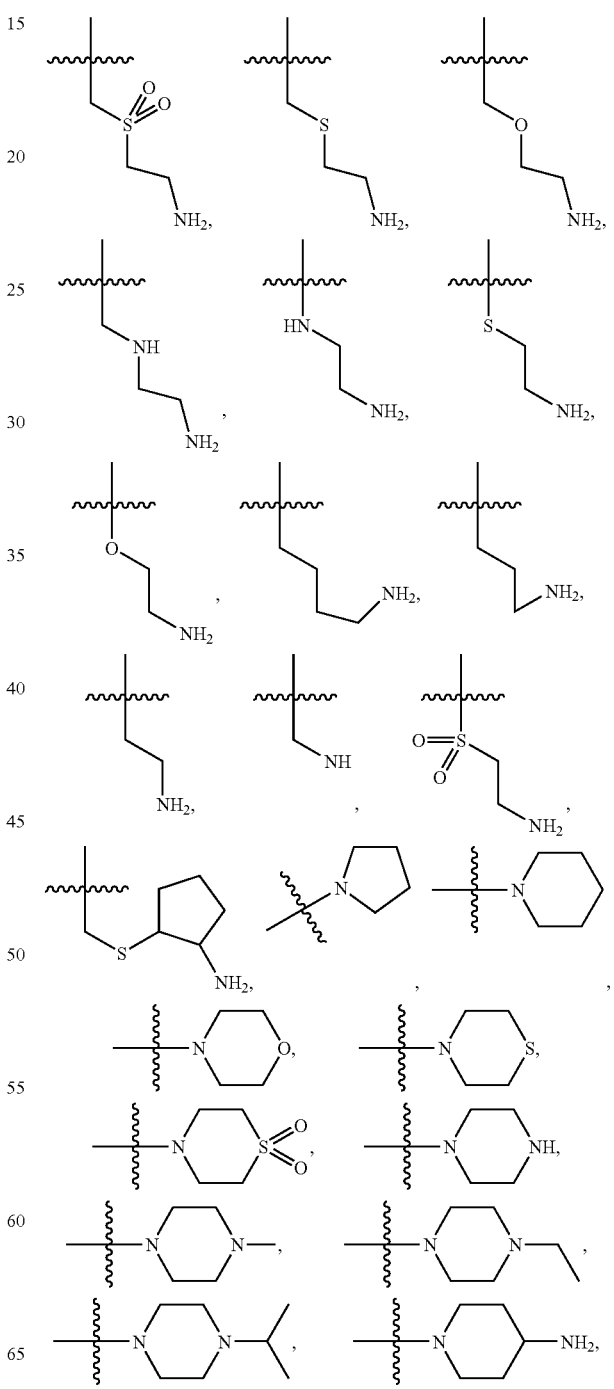

wherein R⁵ is selected from hydrogen, chloro, bromo, fluoro, iodo, cyano, optionally substituted alkyl, optionally substituted alkenyl, optionally substituted alkynyl, optionally substituted cycloalkyl, optionally substituted heterocyclyl, —SO₂R⁵ᵃ, —SR⁵ᵃ, —C(=O)R⁵ᵃ, —C(=O)NR⁵ᵃR⁵ᵇ, —NR⁵ᵃR⁵ᵇ and —OR⁵ᵃ, wherein:
R⁵ᵃ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl; and
R⁵ᵇ is selected from hydrogen, optionally substituted alkyl, optionally substituted alkenyl, optionally sub- stituted alkynyl, optionally substituted cycloalkyl, optionally substituted aryl, optionally substituted heterocyclyl and optionally substituted heteroaryl, or R⁵ᵃ and R⁵ᵇ, together with the N atom to which they are attached, form an optionally substituted heterocyclyl or an optionally substituted heteroaryl.

For example, in certain embodiments, R⁵ is selected from hydrogen, chloro, fluoro, bromo, iodo, cyano, —CH₃, —CF₃, —SO₂CH₃, —SCH₃, —OCH₃, —OCF₃, —NH₂, —NHCH₃, —N(CH₃)₂, —NHCH₂CH₃, —N(CH₂CH₃)₂, —NHCH(CH₃)₂,

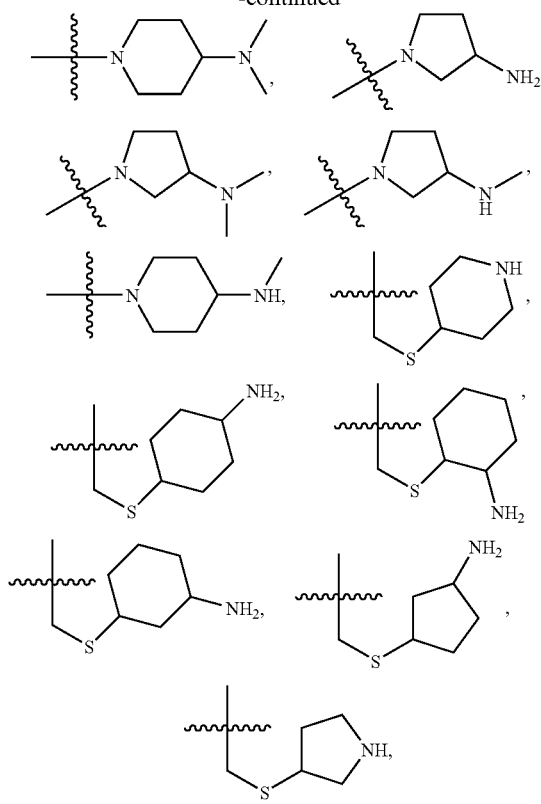
In other further embodiments, Ar² is selected from:
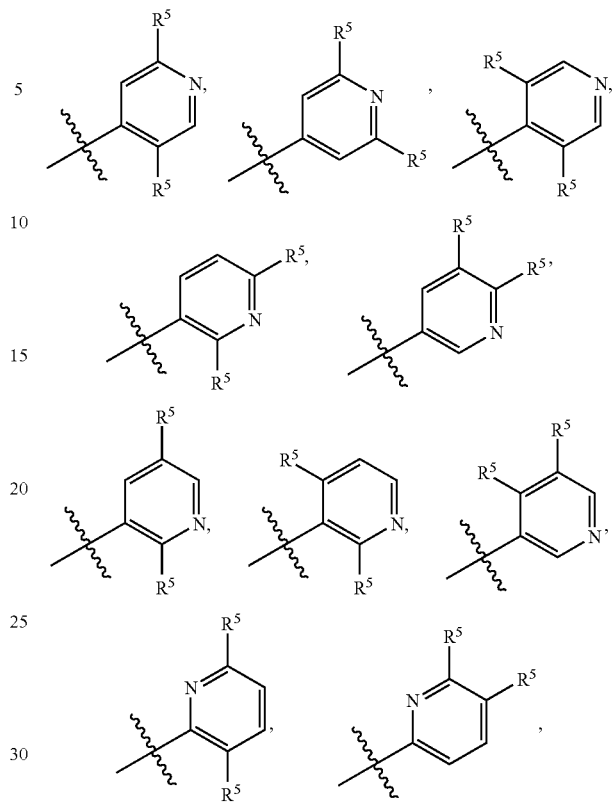
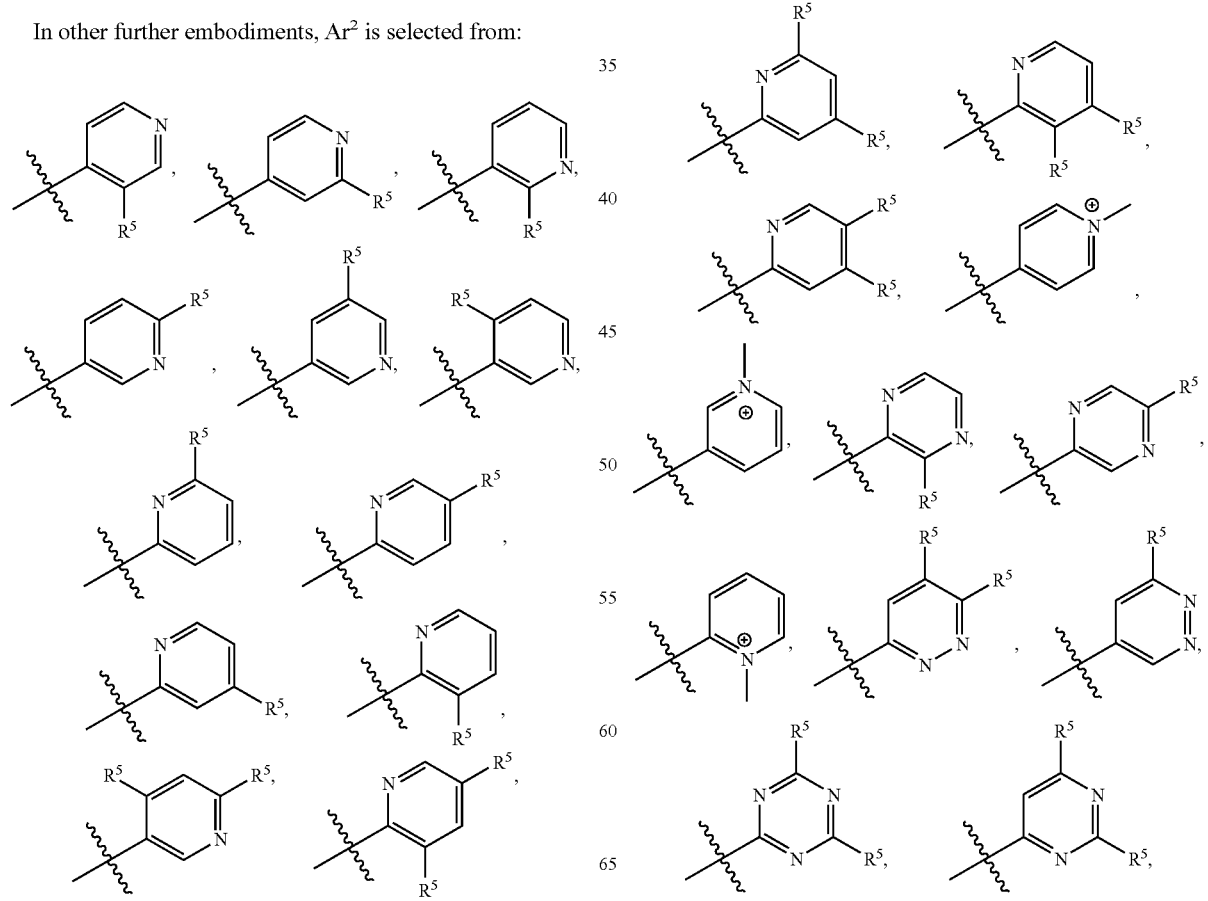

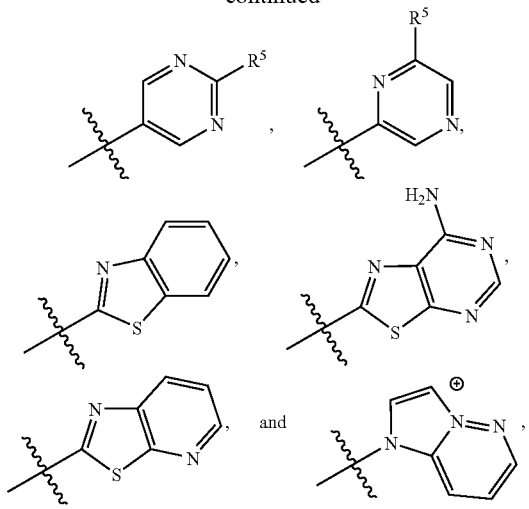

wherein R[5] is selected from hydrogen, chloro, bromo, fluoro, iodo, cyano, optionally substituted alkyl, optionally substituted alkenyl, optionally substituted alkynyl, optionally substituted cycloalkyl, optionally substituted heterocyclyl, —SO$_2$R[5a], —SR[5a], —C(=O)R[5a], —C(=O)NR[5a]R[5b], —NR[5a]R[5b] and —OR[5a], wherein:
R[5a] is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl; and R[5b] is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl, or R[5a] and R[5b], together with the N atom to which they are attached, form an optionally substituted heterocyclyl or an optionally substituted heteroaryl.

For example, in certain embodiments, R[5] is selected from hydrogen, chloro, fluoro, bromo, iodo, cyano, —CH$_3$, —CF$_3$, —SO$_2$CH$_3$, —SCH$_3$, —OCH$_3$, —OCF$_3$, —NH$_2$, —NHCH$_3$, —N(CH$_3$)$_2$, —NHCH$_2$CH$_3$, —N(CH$_2$CH$_3$)$_2$, —NHCH(CH$_3$)$_2$,

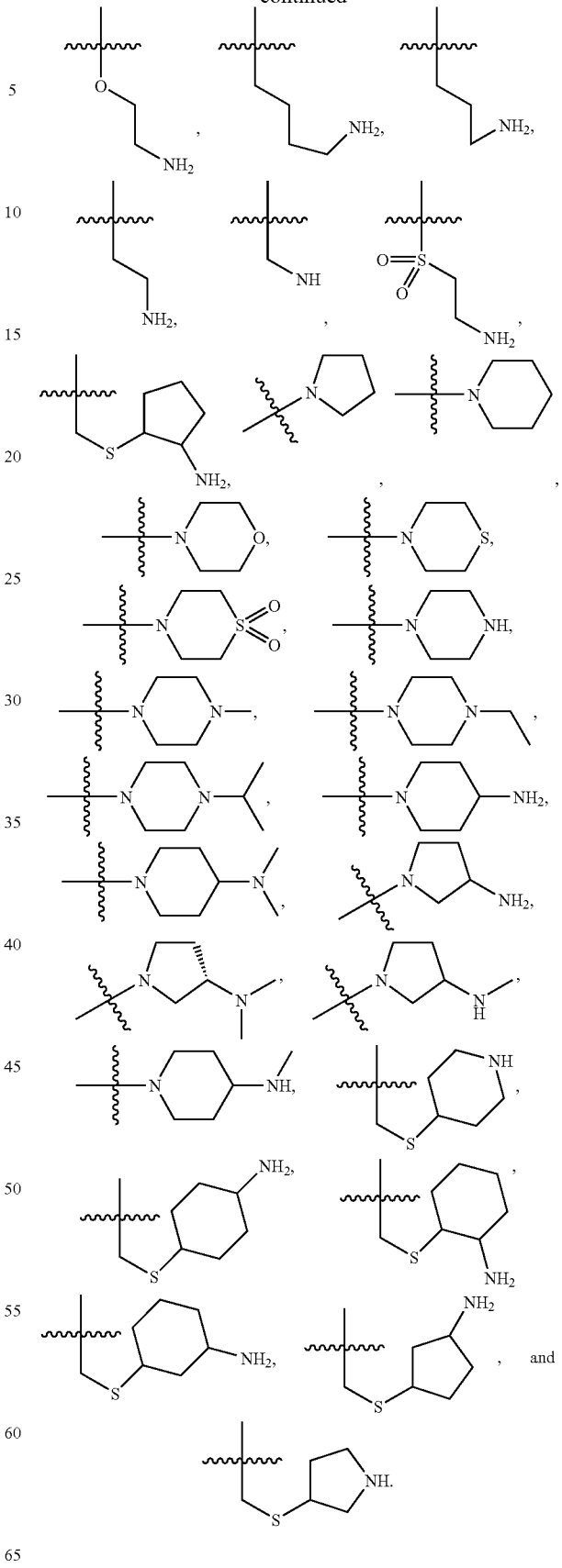

It is understood that any embodiment of the compounds of a structure disclosed herein, as set forth above, and any specific substituent set forth herein for an Ar², R¹, R² and R³ group in the compounds of a structure disclosed herein, as set forth above, may be independently combined with other embodiments and/or substituents of compounds of a structure disclosed herein to form embodiments of the inventions not specifically set forth above. In addition, in the event that a list of substituents is listed for any particular substituent group in a particular embodiment and/or claim, it is understood that each individual substituent may be deleted from the particular embodiment and/or claim and that the remaining list of substituents will be considered to be within the scope of the invention.

For example, in one embodiment of compounds of structure (I), R¹ and R² are hydrogen, and the compounds have the following structure:

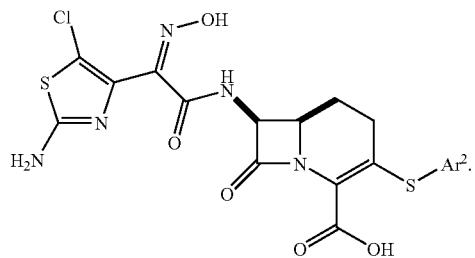

In another embodiment of compounds of structure (I), R¹ is alkyl (such as, for example, methyl) and R² is hydrogen, and the compounds have the following structure:

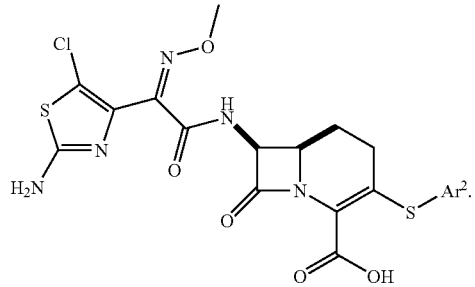

Similarly, in one embodiment of compounds of structure (II), R¹ and R² are hydrogen, and the compounds have the following structure:

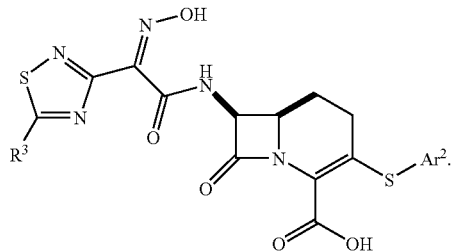

Again, similarly, in another embodiment of compounds of structure (II), R¹ is alkyl (such as, for example, methyl) and R² is hydrogen, and the compounds have the following structure:

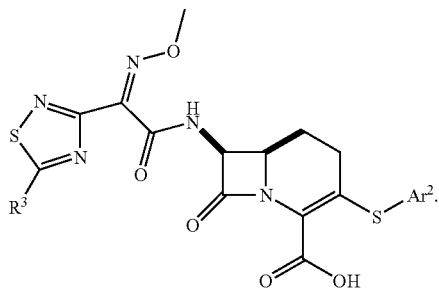

As a further example, in further embodiments of the foregoing embodiments of compounds of structure (II), R³ is —NH₂, and the compounds have one of the following 2 structures:

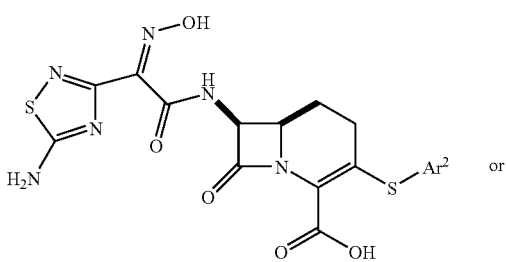

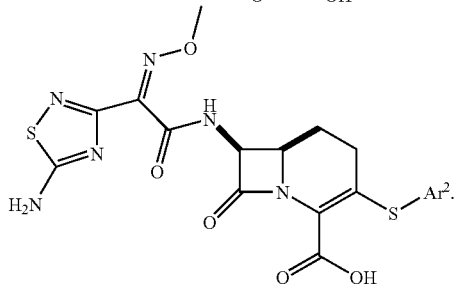

As a further example, in another embodiment of compounds of structure (I), Ar² is a heteroaryl having 6 ring atoms selected from:

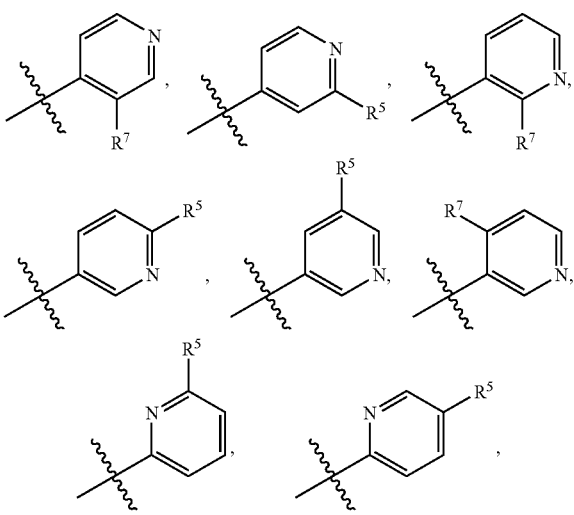

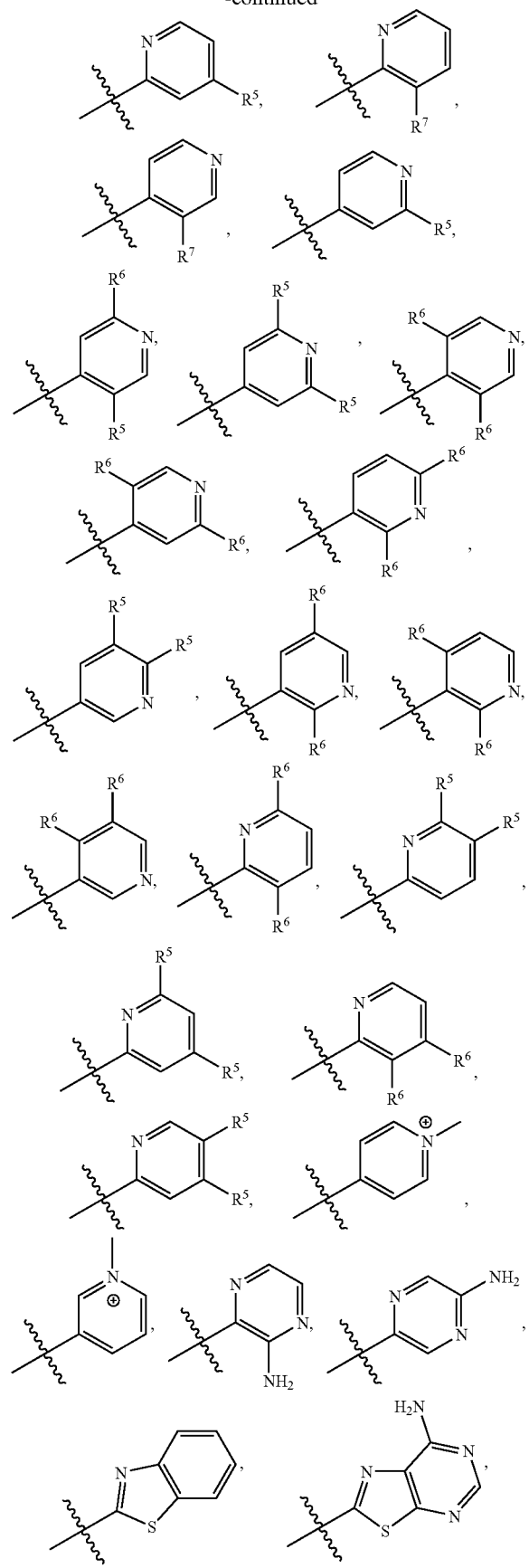
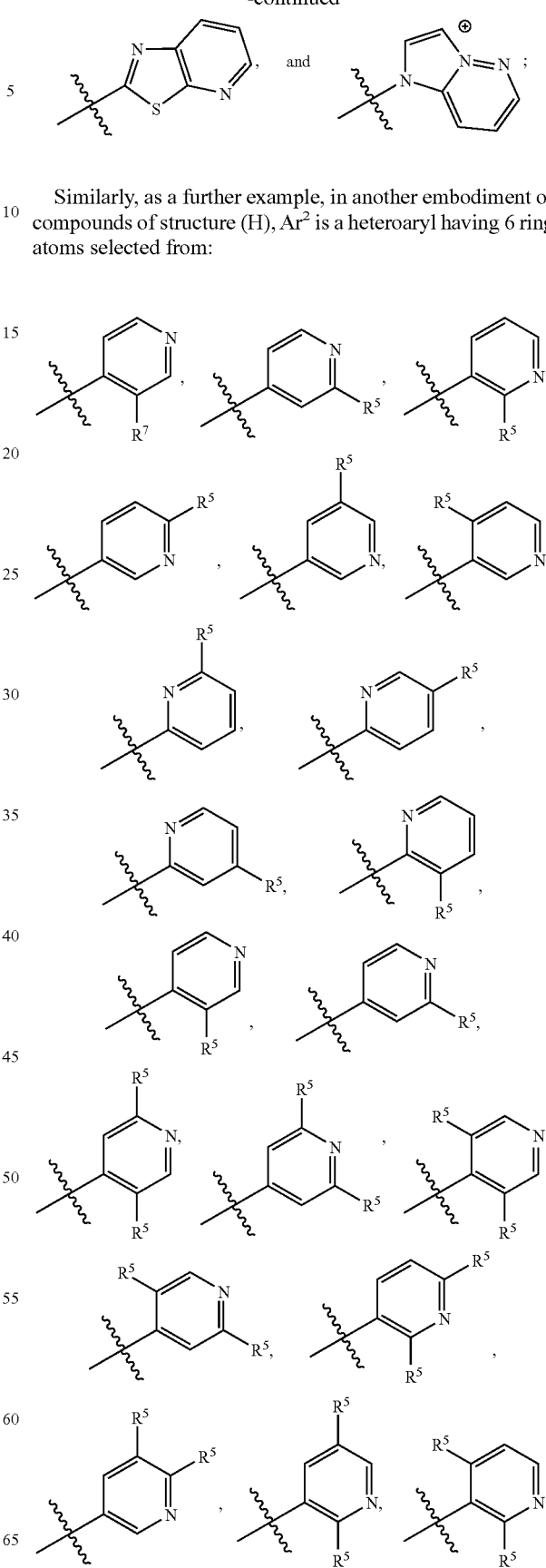
Similarly, as a further example, in another embodiment of compounds of structure (H), Ar² is a heteroaryl having 6 ring atoms selected from:

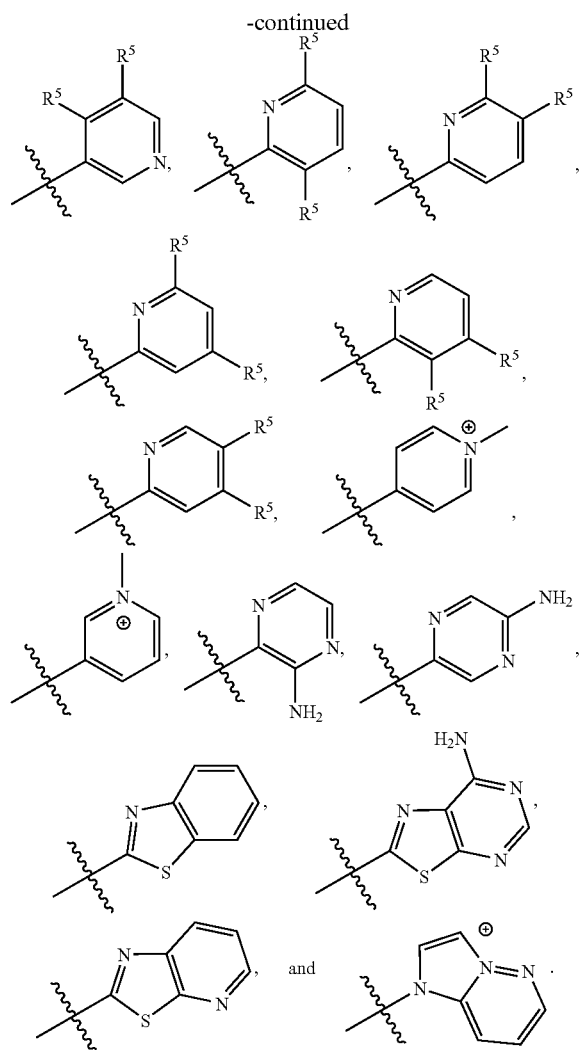

It is further understood that in the present description, combinations of substituents and/or variables of the depicted formulae are permissible only if such combinations result in stable compounds.

For the purposes of administration, the compounds of the present invention may be administered as a raw chemical or may be formulated as pharmaceutical compositions. Pharmaceutical compositions of the present invention comprise a compound of a structure disclosed herein and a pharmaceutically acceptable carrier, diluent or excipient. The compound of a structure disclosed herein is present in the composition in an amount which is effective to treat a particular disease or condition of interest—that is, in an amount sufficient to treat a bacterial infection, and preferably with acceptable toxicity to the patient. The antibacterial activity of compounds of a structure disclosed herein can be determined by one skilled in the art, for example, as described below. Appropriate concentrations and dosages can be readily determined by one skilled in the art.

The compounds of the present invention possess antibacterial activity against a wide spectrum of Gram-positive and Gram-negative bacteria, as well as enterobacteria and anaerobes. Representative susceptible organisms generally include those Gram-positive and Gram-negative, aerobic and anaerobic organisms whose growth can be inhibited by the compounds of the invention such as *Staphylococcus, Lactobacillus, Streptococcus, Sarcina, Escherichia, Enterobacter, Klebsiella, Pseudomonas, Acinetobacter, Proteus, Campylobacter, Citrobacter, Nisseria, Baccillus, Bacteroides, Peptococcus, Clostridium, Salmonella, Shigella, Serratia, Haemophilus, Brucella* and other organisms. In particular, the compounds of the present invention possess antibacterial activity against bacterial species resistant to conventional β-lactams, such as MRSA.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primojel®, corn starch and the like; lubricants such as magnesium stearate or Sterotex®; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

The following Examples illustrate various methods to make compounds of this invention, i.e., compounds having a structure disclosed herein, such as a compound of structure (I) or structure (II):

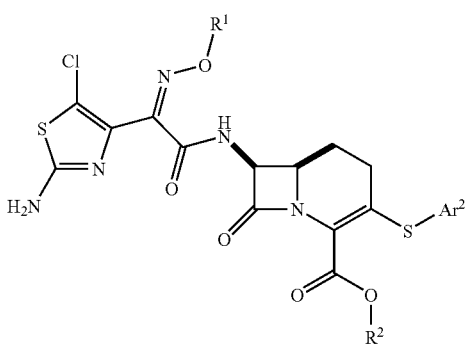

(I)

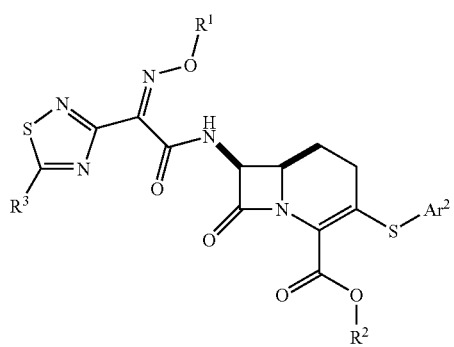

(II)

where Ar², R¹, R² and R³ are described above. It is understood that one skilled in the art would be able to make these compounds by similar methods or by methods known to one skilled in the art. See, e.g., U.S. Pat. No. 5,077,287; Appelbaum, P. C., et al., *Current Opinion in Microbiology*, 2005, 8: 510-517; Bassetti, M., et al., *Current Opinion in Investigational Drugs*, 2003, 4(8): 944-952; Cooper, R. D. G, et al., *Exp. Opin. Invest. Drugs*, 1994, 3(8): 831-848; Elston, D. M., *J. Am. Acad. Dermatol.*, 2007, 56(1): 1-16; Furuya, et al., *Nature*, 2006, 4: 36-45; Glinka, T. W., *Current Opinion in Investigational Drugs*, 2002, 3(2): 206-217; Glinka, T. W., et al., *J. Antibiotics*, 2000, 53(10): 1045-1052; Glinka, T. W., et al., *Bioorganic & Medicinal Chemistry*, 2003, 11: 591-600; Guzzo, P. R., et al., *J. Org. Chem.*, 1994, 59(17): 4862-4867; Hecker, S. J., et al., *J. Antibiotics*, 2000, 53(11): 1272-1281; Hecker, S. J., et al., *Antimicrobial Agents and Chemotherapy*, 2003, 47(6): 2043-2046; Jackson, B. G., et al., *Tetrahedron Letters*, 1990, 31(44): 6317-6320; Jackson, B. G., *Tetrahedron Letters*, 2000, 56: 5667-5677; Lotz, B. T., et al., *J. Org. Chem.*, 1993, 58(3): 618-625; Lowy, et al., *J. Clinical Investigation*, 2003, 111(9): 1265-1273; Misner, J. W., et al., *Tetrahedron Letters*, 2003, 44: 5991-5993; Mochida, K., et al., *J. Antibiotics*, 1989, 42(2): 283-292; and Rice, L. B., *Am. J. Medicine*, 2006, 119(6A): S11-S19. It is also understood that one skilled in the art would be able to make in a similar manner as described below other compounds of a structure disclosed herein not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described herein.

It will be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

The following Examples are provided for purposes of illustration, not limitation.

EXAMPLES

Example 1

Generation of the Chiral Carbacephem Core

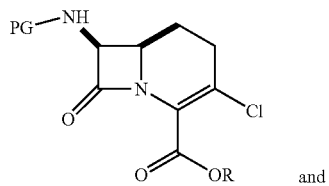

and

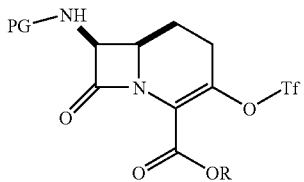

(6R,7S)-7-protected amino-3-chloro (or triflate)-8-oxo-1-azabicyclo[4.2.0]oct-2-ene-2-carboxylate Esters

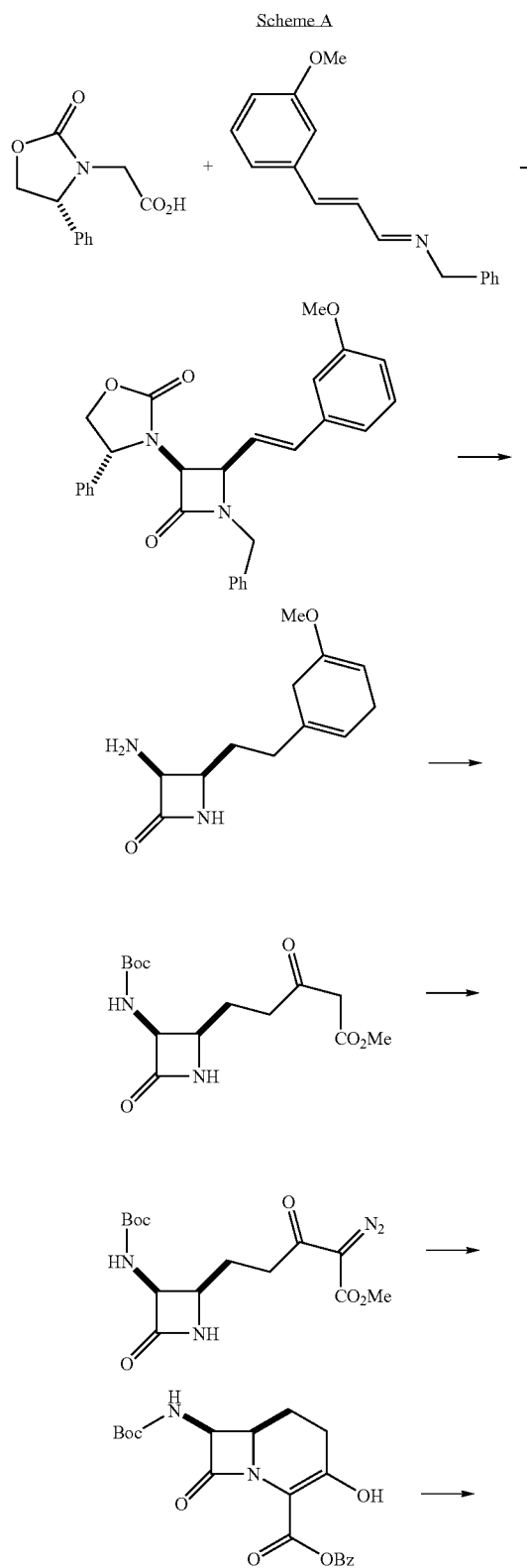

Scheme A

The final compound in the Evans scheme can be converted to several important carbacephem intermediates with selective protecting group manipulations. The 3-pos triflate can be displaced by nucleopliles to give sulfur linked groups, see, e.g., Ternansky, R. J., et al., *J. Med. Chem.,* 1993, 36: 1971-1976 and Hatanaka, M. et al., *Tetrahedron Letters,* 1983, 24(44): 4837-4838. The triflate can also be converted to an alkene by Stille reaction to give double bond linked groups at the 3-position. The Boc can be removed for coupling to an acid at the 7-position. See, e.g., Evans, D. A., et al., *Tetrahedron Letters,* 1985: 3783-3787 and Evans, D. A., et al., *Tetrahedron Letters,* 1985: 3787-3790.

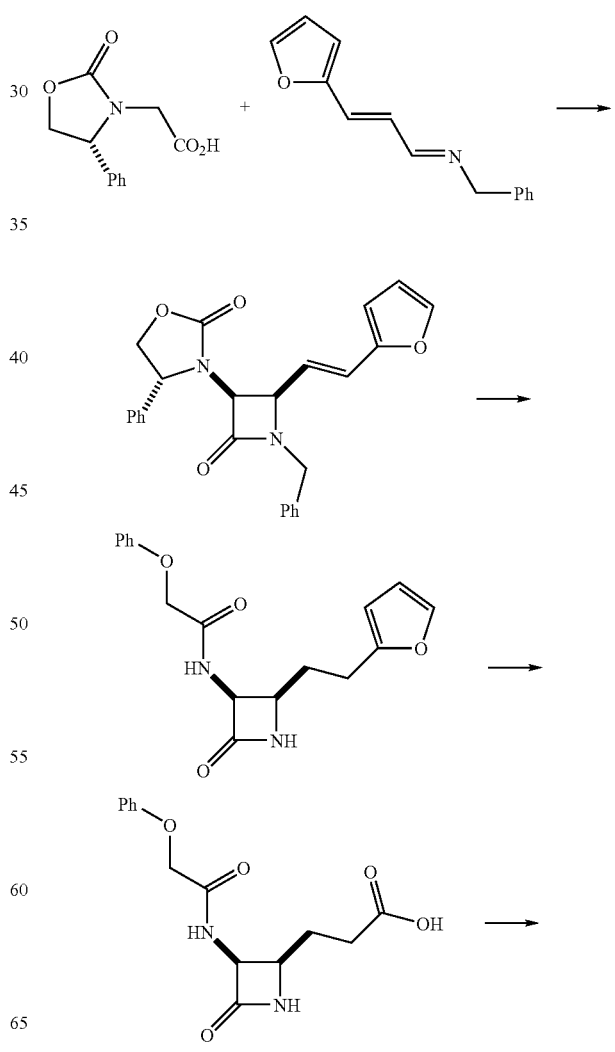

Scheme B

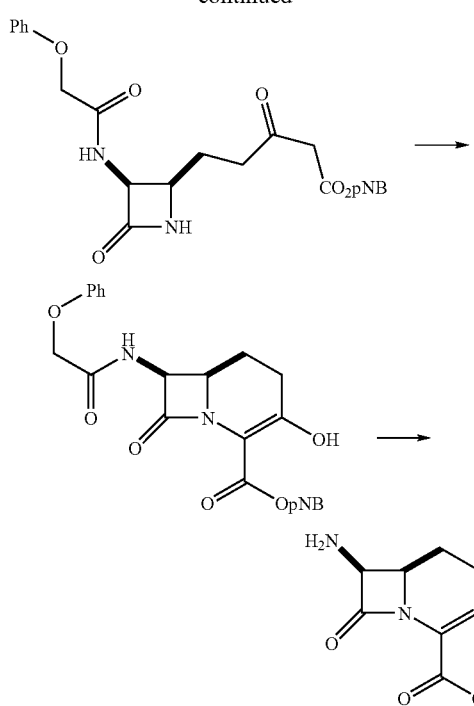

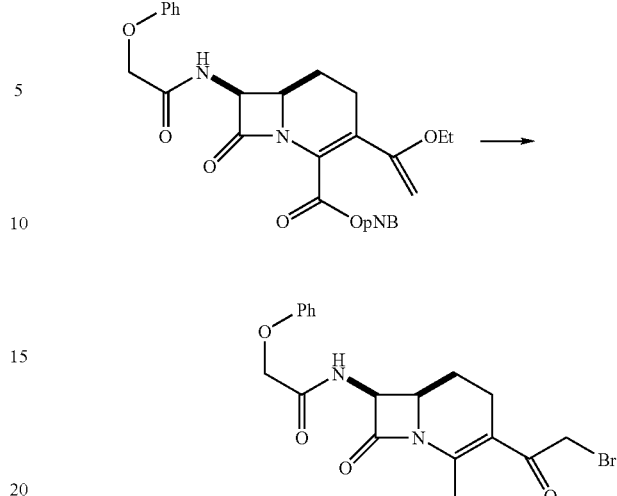

See, e.g., Hornback, W. J., *American Chemical Society National Meeting*, Abstract 153, Washington, 1990.

The Bodurow method gives the needed intermediate for the schemes below for 3-position S-linked analogues. The Bz protected ester can be converted to the free acid by hydrogenation or saponification. See, e.g., Bodurow, C. C, et al., *Tetrahedron Letters*, 1989: 2321-2324.

Example 2

Stille Coupling from the 7-Position Triflate and Transformation to the Bromomethyl Ketone Example 3

Carbonylation from the 7-Position Triflate

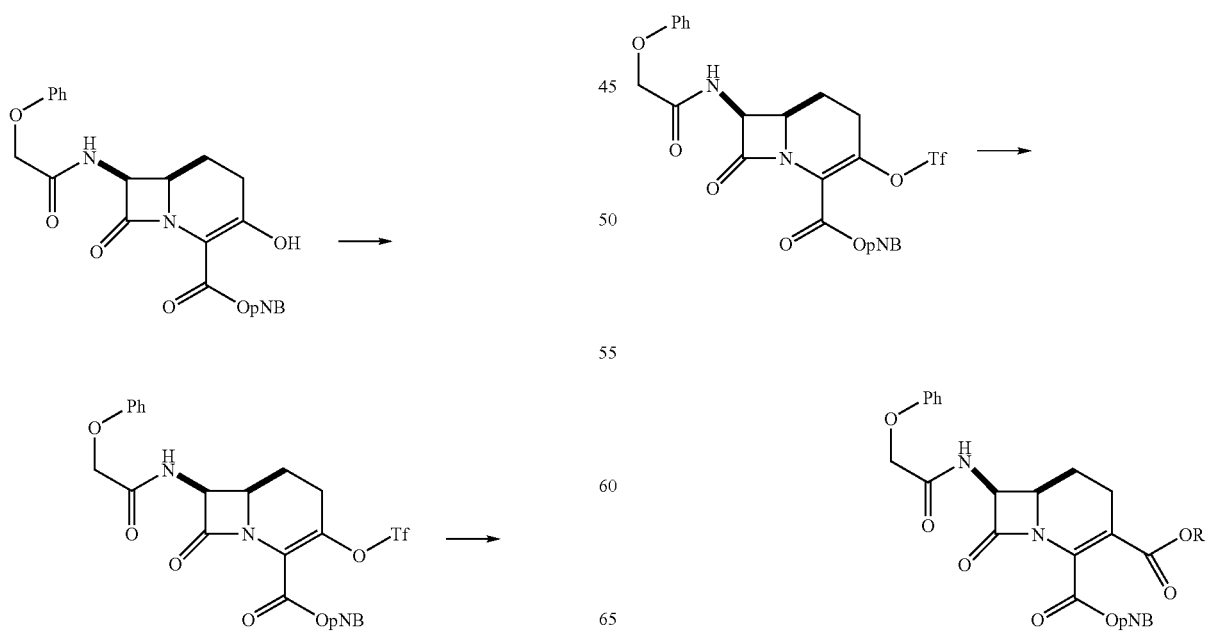

G. K. Cook, W. J. Hornback, C. L, Jordan, J. H, McDonald III and J. E. Munroe, *J. Org. Chem.*, 1989, 54: 5828-5830.

Example 4

Conversion of 7-Position Triflate to Carboxylic Acid, Vinyl, Aldehyde and Methylene-Linked Heterocycles Scheme A

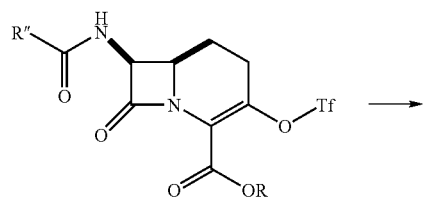

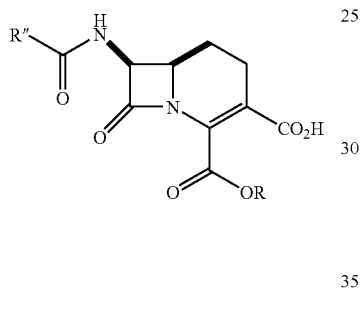

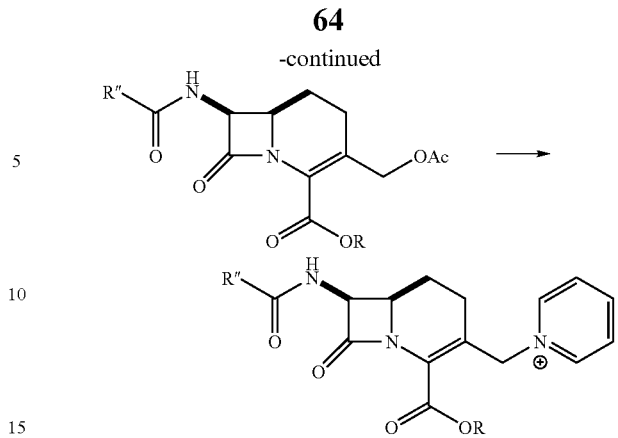

See, e.g., Blaszczak, L. C., et al., *J. Med. Chem.*, 1990, 33(6): 1656-62.

Example 5

Coupling at 7-Position

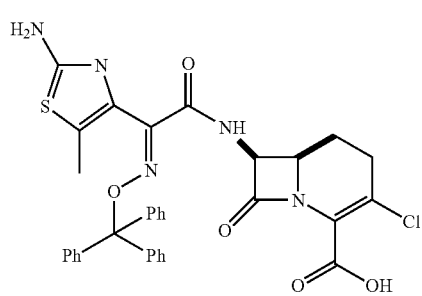

Scheme B

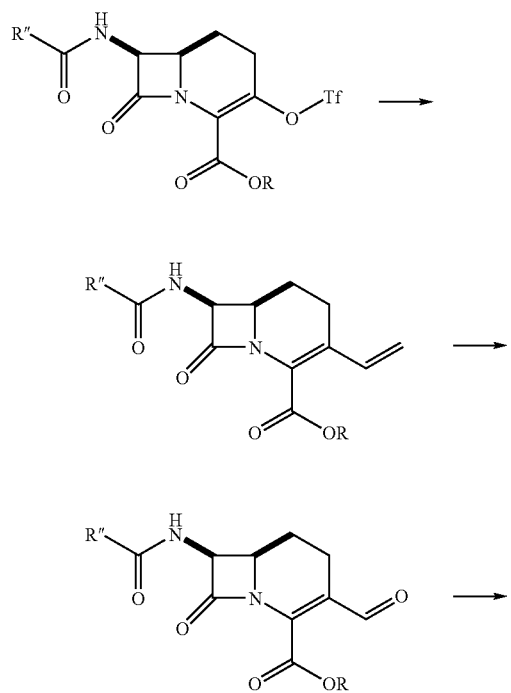

(7R)-7-[(Z)-2-(2-amino-5-methylthiazol-4-yl)-2-(triphenylmethoxyimino]acetamido]-3-chloro-8-oxo-1-aza-bicyclo[4.2.0]oct-2-ene-2-carboxylate Triethyl Amine Salt To a solution of bis-(2-benzothiazolyl)-disulfide (0.013 mol) in dichloromethane (100 mL) was added triphenylphosphine (0.013 mol). The mixture was stirred for 15 minutes after which (Z)-2-(2-amino-5-methylthiazol4-yl)-2-(triphenylmethoxyimino)acetic acid (0.010 mol) was added. The mixture was stirred for 1 hour and was cooled to 0° C. In a separate flask, (7R)-7-amino-3-chloro-8-oxo-1-aza-bicyclo[4.2.0]oct-2-ene-2-carboxylic acid trifluoroacetic acid salt (0.008 mol) was suspended in dichloromethane (50 mL) and triethylamine (4.0 g, 0.04 mol) was added. The suspension was stirred for 0.5 hour at room temperature and then was transferred to the flask containing the activated ester of 7-[(Z)-2-(2-amino-thiazolyl-4)-2-trityloxyimino]carboxylic acid. The resulting clear solution was allowed to warm to room temperature and was stirred for 48 hours. The reaction mixture was washed twice with 100 mL portions of water, and the organic layer was separated, dried over anhydrous MgSO$_4$, filtered and concentrated to approximately 50 mL. The oily residue was treated with diethyl ether (250 mL), and the solid was filtered and dried giving crude product. HPLC analysis indicated that it contained approximately 0.004 mol of the desired compound 1 as the triethylamine salt.

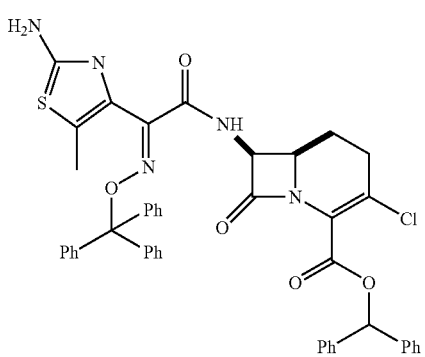

(7R)-7-[(Z)-2-(2-amino-5-methylthiazol-4-yl)-2-(triphenylmethoxyimino)acetamido]-3-chloro-8-oxo-1-aza-bicyclo[4.2.0]oct-2-ene-2-carboxylate diphenylmethyl ester The crude (7R)-7-[(Z)-2-(2-amino-5-methylthiazol-4-yl)-2-triphenyl methoxyimino]-acetamido]-3-chloro-a-oxo-1-aza-bicyclo[4.2.0]oct-2-ene-2-carboxylic acid triethylamine salt (0.004 mol) was dissolved in dichloromethane (200 mL) and was washed twice with 50% $NaPO_4H_2O$ and then with water. The organic layer was dried over anhydrous $MgSO_4$, filtered and treated with diphenyldiazomethane solution in dichloromethane (40 mL of 0.5 mol/L solution, 0.02 mol), followed by stirring at room temperature for 1 hour. The reaction mixture was concentrated to dryness and the residue was dissolved in ethyl acetate (20 mL). The ethyl acetate solution was then chromatographed on silica gel (200 g). Nonpolar byproducts were eluted with ethyl acetate:hexane (1:6), and the product with ethyl:acetate:hexane (1:1). After evaporation, the title ester was obtained. HPLC indicated that it contained approximately 0.004 mol of the desired product 2.

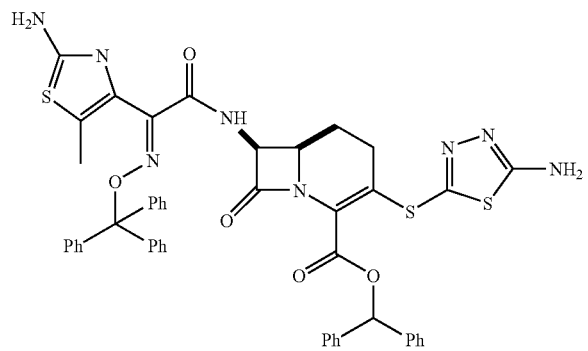

(7R)-7-[(Z)-2-(2-amino-5-methylthiazol-4-yl)-2-(triphenylmethoxyimino)acetamido]-3-[5-amino-1,3,4-thiadiazol-2-ylthio]-8-oxo-1-aza-bicyclo[4.2.0]oct-2-ene-2-carboxylate diphenylmethyl Ester To a solution of 5-amino-1,3,4-thiadiazole-2-thiol (0.0045 mol) in dimethylformamide (25 mL) was added potassium carbonate (1.0 g, 0.0076 mol). The mixture was stirred for 1 hour at room temperature after which (7R)-7-[(Z)-2-(2-amino-5-methylthiazol-4-yl)-2-(triphenylmethoxyimino)acetamido]-3-chloro-8-oxo-1-aza-bicyclo[4:2.0]oct-2-ene-2-carboxylate diphenylmethyl ester (0.0039 mol) was added. Stirring was continued for 18 hours. The mixture was partitioned between ethyl acetate (50 mL) and water (50 mL). The organic layer was separated, washed with water (30 mL), dried over anhydrous $MgSO_4$ and the solvent was removed with a rotary evaporator. The resultant thick oil was treated with diethyl ether (50 mL) and the solid which formed was filtered and dried to give ca. 0.0028 mol of crude product 3.

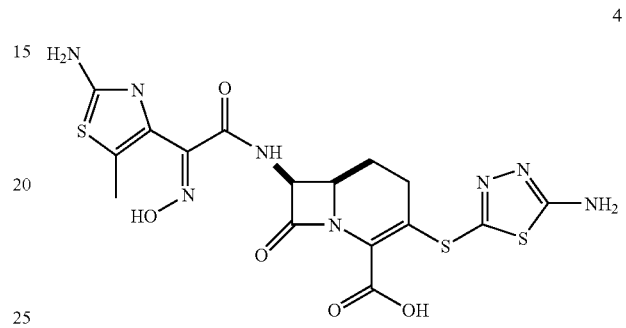

(7R)-7-[(Z) 2-(2-amino-5-methylthiazol-4-yl)-2-(hydroxyimino)acetamido]-3-[5-amino-1,3,4-thiadiazol-2-ylthio]-8-oxo-1-aza-bicyclo[4.2.0]oct-2-ene-2-carboxylic acid A solution of trifluoroacetic acid (10 mL), triethylsilane (5 mL) and dichloromethane (10 mL) was cooled to 0° C. and (7R)-7-[(Z)-2-(2-amino-5-methylthiazol-4-yl)-2-(triphenylmethoxyimino)acetamido]-3-[5-amino-1,3,4thiadiazol-2-ylthio]-8-oxo-1-aza-bicyclo[4.2.0]oct-2-ene-2-carboxylate diphenylmethyl ester from the previous step (ca. 0.0028 mol) was added in portions. The reaction mixture was stirred for 3 hours at 0° C., allowed to warm up to room temperature and evaporated to dryness. The residue was treated with diethyl ether (50 mL) and the solid that formed was filtered and dried to give crude product. The crude product was purified with Diaion® HP-20 resin initially with water elution until the pH was neutral, after which the product was eluted with acetonitrile:water 80:20. The solvent was evaporated to give the ca. 0.0013 mol of the title compound 4.

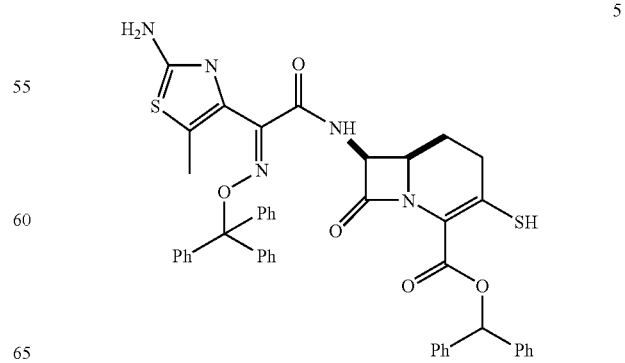

(7R)-7-[(Z)-2-(2-amino-5-methylthiazol-4-yl)-2-(triphenylmethoxyimino)acetamido]-3-mercapto-8-oxo-1-aza-bicyclo[4.2.0]oct-2-ene-2-carboxylate diphenylmethyl Ester A solution of (7R)-7-[(Z)-2-(2-amino-5-methylthiazol-4-yl)-2-(triphenyl methoxyimino]-acetamido]-3-chloro-8-oxo-1-aza-bicyclo[4.2.0]oct-2-ene2-carboxylate diphenylmethyl ester (0.0036 mol) in dimethylformamide (40 mL) was cooled to −20° C. and a solution of ammonium sulfide in water (20%, 5.7 mL) was added drop-wise. The mixture was stirred at −20° C. for 4 hours and then was poured into pH 3 phosphate buffer (100 mL). The resulting solid was filtered, washed with water and dried to afford the crude title compound 5 (ca. 0.0036 mol).

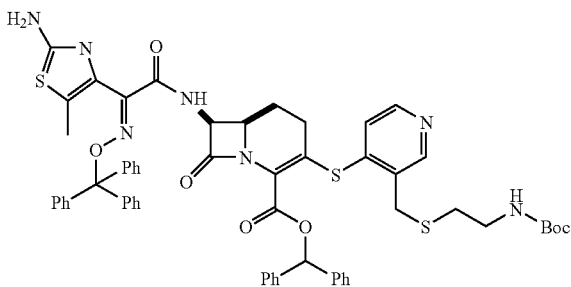

6

(7R)-7-((Z)-2-(2-amino-5-methylthiazol-4-yl)-2-(triphenylmethoxyimino)acetamido]-3-(3-(N-tert-butoxycarbonylaminoethylthiomethyl)pyrid-4-ylthio]8-oxo-1-aza-bicyclo[4.2.0]oct-2-ene-2-carboxylate diphenylmethyl Ester To a solution of (7R)-7-[(Z)-2-(2-amino-5-methylthiazol-4-yl)-2-(triphenyl methoxyimino]-acetamido]-3-mercapto-8-oxo-1-aza-bicyclo[4.2.0]oct-2ene-2-carboxylate diphenylmethyl ester (0.0036 mol) in dimethylformamide (30 mL) was added 3-(N-tert-butoxycarbonylaminoethylthiomethyl)-4-chloropyridine (1.3 g, 0.0043 mol) at room temperature. After stirring overnight, the reaction mixture was treated with water (200 mL), and the solid that formed was filtered and dried to afford the crude title compound 6 (ca. 0.0027 mol).

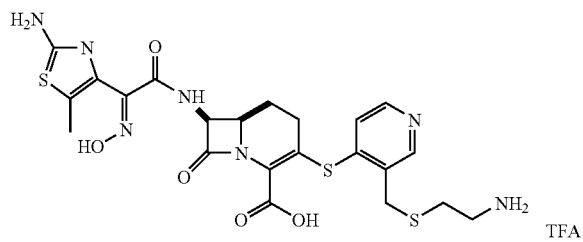

7

(7R)-7-[(Z)-2-(2-amino-5-methylthiazol-4-yl)-2-(hydroxyimino)acetamido]-3-[3(aminoethylthiomethyl)pyrid-4-ylthio]-8-oxo-1-aza-bicyclo[4.2.0]oct-2-ene-2-carboxylate Trifluoroacetic Acid Salt A solution of trifluoroacetic acid (10 mL), triethylsilane (5 mL) and dichloromethane (10 mL) was cooled to 0° C. and (7R)-7-[(Z)-2-(2-amino-5-methylthiazol-4-yl)-2-(triphenyl-methoxyimino]acetamido]-3-[3-(N-tertbutoxycarbonylaminoethylthiomethyl)-pyrid-4-ylthio]-8-oxo-1-aza-bicyclo[4.2.0]oct2-ene-2-carboxylate diphenyl methyl ester (ca. 0.0027 mol) was added in portions. The reaction mixture was stirred at 0° C. for 6 hours, was allowed to warm to room temp. and was evaporated to dryness. The residue was treated with diethyl ether (50 mL), and the solid that formed was filtered and dried to give crude product. The crude product was purified with Diaion® HP-20 resin with water elution until the pH was neutral, and thereafter with acetonitrile:water 80:20, to give the product 7 (ca. 0.0002 mol).

Example 6

Ceftobiprole Style Methylene Linker at 7-Position

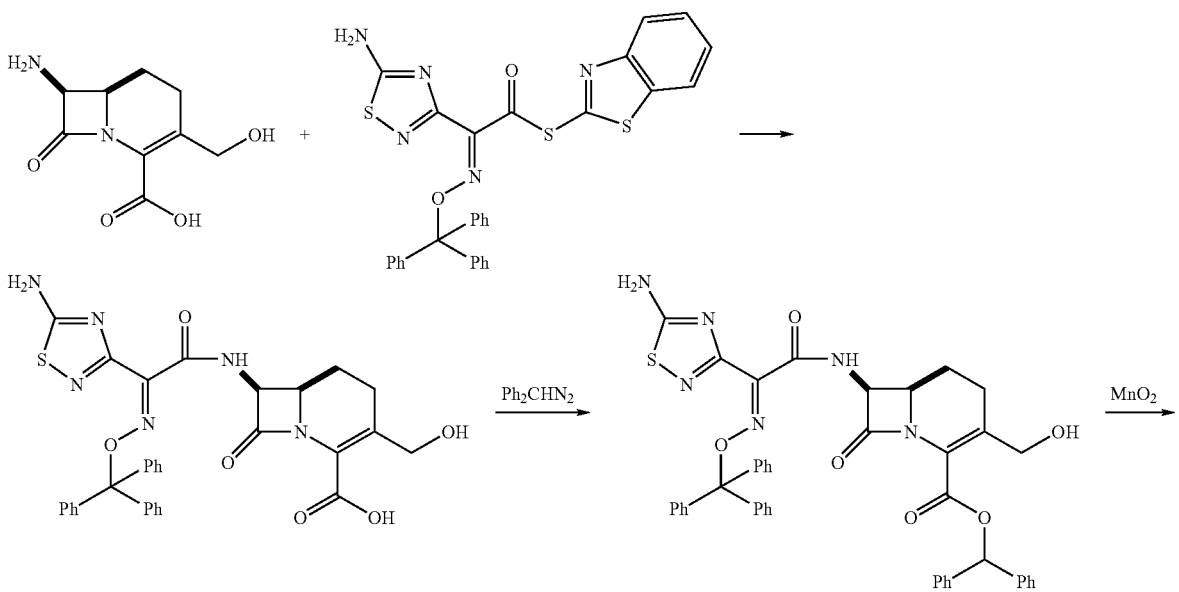

-continued

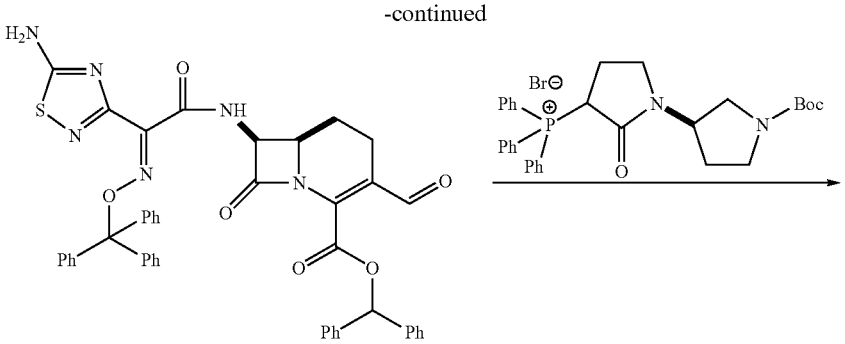

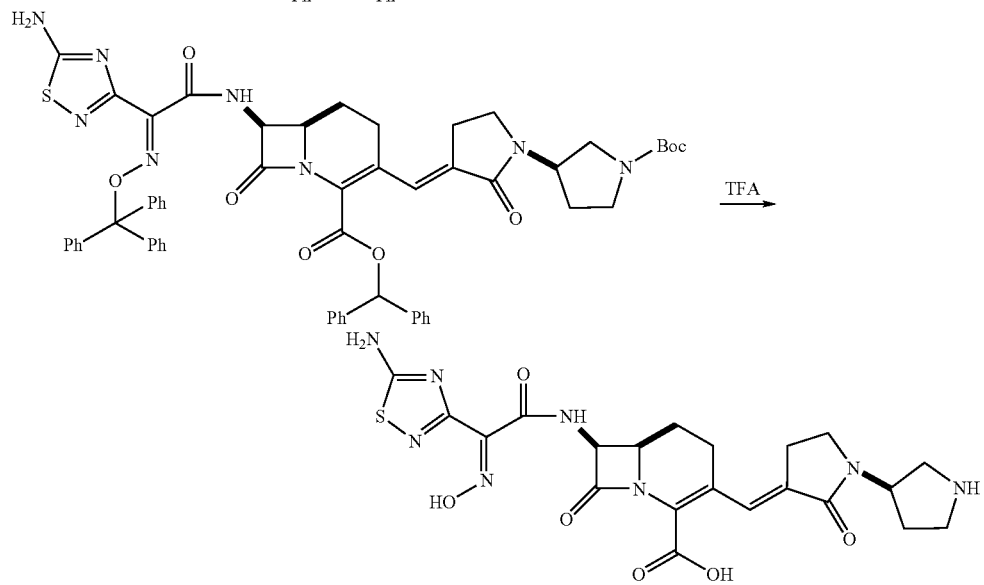

The procedures used to produce ceftobiprole can be applied to carbacephem compounds. See, e.g., Canadian Patent No. 2408941, European Patent Nos. 1 289 998 and 1 435 357, Japanese Patent No. 2003535059, U.S. Patent Application No. 2002/019381, U.S. Pat. No. 6,504,025 and International PCT Application Publication No. WO 01/90111.

Example 7

Preparation of Alkylene Linked Groups at 7-Position

Scheme A

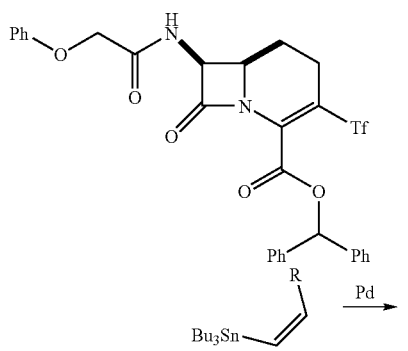

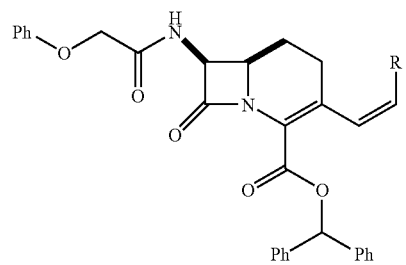

See, e.g., U.S. Pat. No. 4,855,418 and Farina, V., et al, *Tetrahedron Letters,* 1988, 29(47): 6043-6.

Scheme B

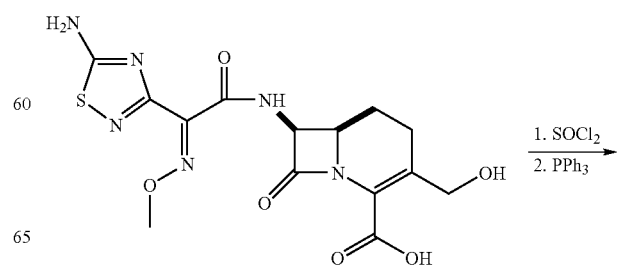

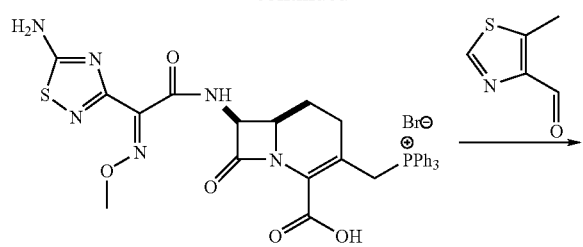

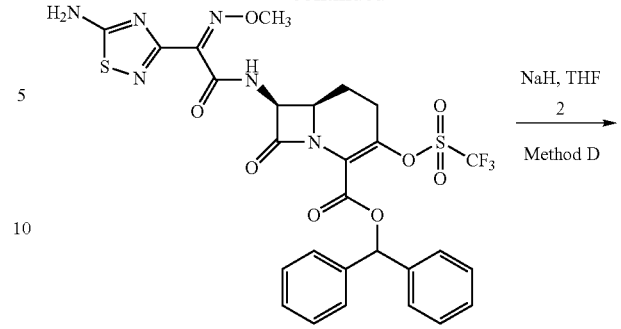

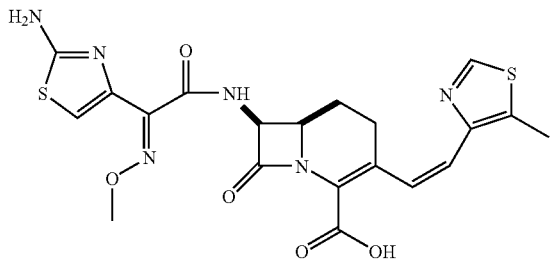

See, e.g., Chinese Patent No. 1763046; Xiao, T. Z., et al., *Chinese J. Pharmaceuticals,* 2004, 35(7): 388-390; Kim, G. T., et al., J. Antibiotics, 2004, 57(7): 468-472; International PCT Application Publication No. WO 2005/100330; International PCT Application Publication No. WO 2005/100367; and Hanaki, H., et al., *J. Antibiotics,* 2005, 58(1): 69-73.

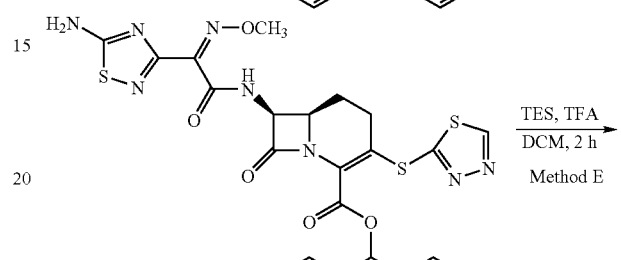

Example 8

Methods A, B, C, D and E

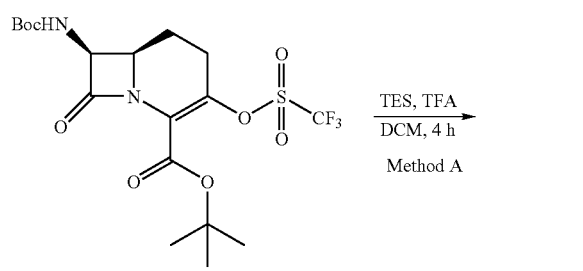

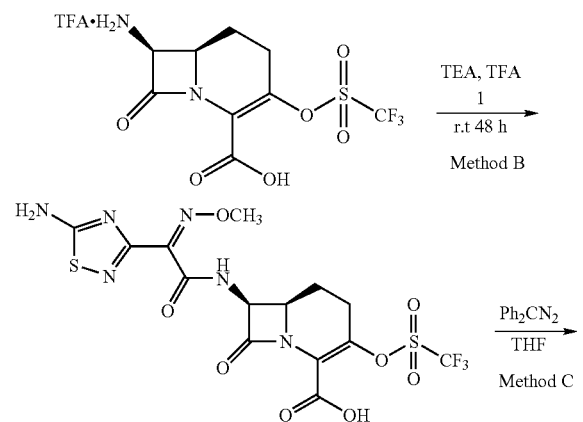

Method A: To a solution of (6R,7S)-tert-butyl-7-(tert-butoxycarbonylamino)-8-oxo-3-(trifluoromethylsulfonyloxy)-1-aza-bicyclo[4.2.0]oct-2-ene-2-carboxylate (see Example 9) (502 mg, 1.04 mmol) in dichloromethane (DCM) (10 mL) was added triethylsilane (TES) (116 mg, 10 mmol). The mixture was cooled down to 0° C. and 2,2,2-trifluoroacetic acid (TFA) (10 mL) was added. Then, the mixture was allowed to warm to room temperature and stirred for 4 hours, concentrated under reduced pressure and washed with petroleum ether to obtain white solid (580 mg crude solid). The resulting product was used without further purification.

Method B: (6R,7S)-7-amino-8-oxo-3-(trifluoromethylsulfonyloxy)-1-aza-bicyclo[4.2.0]oct-2-ene-2-carboxylic acid (1.5 g, 4.3 mmol) was suspended in tetrahydrofuran (THF) (15 mL) and triethylamine (2.1 g, 21 mmol) was added. The suspension was stirred for 0.5 hour at room temperature, and (Z)—S-benzo[d]thiazol-2-yl-2-(5-amino-1,2,4-thiadiazol-3-yl)-2-(methoxyimino)ethanethioate 1 (see Example 10) (1.4 g, 4.3 mmol) was added with stirring at 0° C. The mixture was allowed to warm to room temperature and stirred for 48 hours and concentrated under reduced pressure. The residue was dissolved in ethyl acetate (EA), washed with dilute HCl aqueosu (pH=4), washed with brine, dried with NaSO₄, filtered and then the solvent was removed in vacuo to give 2.6 g slight yellow solid. The resulting product was used without further purification.

Method C: (6R,7S,Z)-7-(2-(5-amino-1,2,4-thiadiazol-3-yl)-2-(methoxyimino)acetamido)-8-oxo-3-(trifluoromethylsulfonyloxy)-1-aza-bicyclo[4.2.0]oct-2-ene-2-carboxylic acid (2.6 g crude solid) was dissolved in THF and (diazomethylene)dibenzene (4.9 g, 25 mmol) was added dropwise. The reaction mixture was stirred for 2 hours at room temperature. Then, the solvent was concentrated in vacuo and petroleum ether (P.E) was added to obtain precipitation. The resulting product was used without further purification.

Method D: A solution of 1,3,4-thiadiazole-2-thiol 2 (47 mg 0.39 mmol) in dry THF was cooled down in ice and treated with NaH (14 mg, 0.36 mmol). After 10 min, the suspension was added by syringe to the solution of (6R,7S,Z)-benzhydryl-7-(2-(5-amino-1,2,4-thiadiazol-3-yl)-2-(methoxyimino)acetamido)-8-oxo-3-(trifluoromethylsulfonyloxy)-1-aza-bicyclo[4.2.0]oct-2-ene-2-carboxylate (226 mg 0.33 mmol) in dry tetrahydrofuran (THF) at –30° C. The temperature was allowed to reach 0° C. over 2 hours. The mixture was washed with cold HCl (aq), brine, dried with $Na_2SO_4$, filtered and concentrated. The residue was purified by gel column chromatography (EA:P.E, 2:1) to give white solid (114 mg, 53%).

Method E: A solution of triethylsilane (TES) (0.5 mL), 2,2,2-trifluoroacetic acid (TFA) (1 mL) and dichloromethane (DCM) (1 mL) was cooled down to 0° C. and (6R,7S,Z)-benzhydryl-3-(1,3,4-thiadiazol-2-ylthio)-7-(2-(5-amino-1,2,4-thiadiazol-3-yl)-2-(methoxyimino)acetamido)-8-oxo-1-aza-bicyclo[4.2.0]oct-2-ene-2-carboxylate (114 mg, 0.17 mmol) was added in portions. The reaction mixture was stirred for 3 h at 0° C. and then evaporated to dryness, washed with diethyl ether to obtain (6R,7S,Z)-3-(1,3,4-thiadiazol-2-ylthio)-7-(2-(5-amino-1,2,4-thiadiazol-3-yl)-2-(methoxyimino)acetamido)-8-oxo-1-aza-bicyclo[4.2.0]oct-2-ene-2-carboxylic acid (82 mg crude solid), purified by Prep-HPLC to give 26 mg white solid, yield: 31%.

Method F

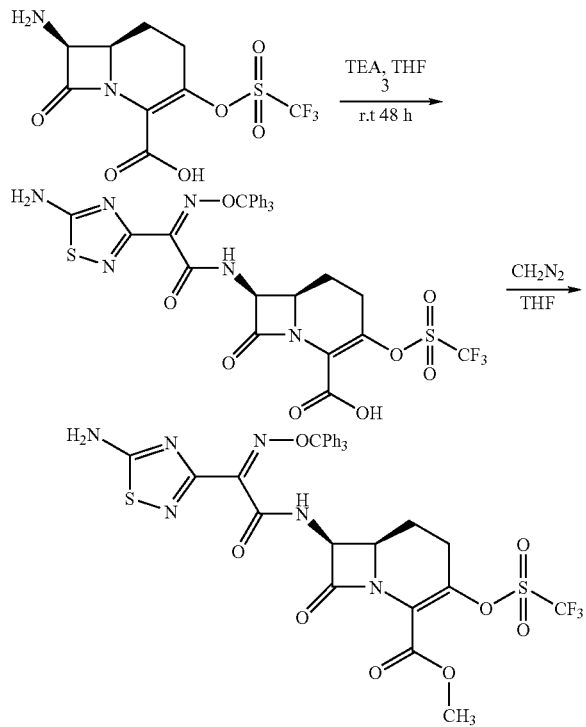

Similar to Method B, (6R,7S)-7-amino-8-oxo-3-(trifluoromethylsulfonyloxy)-1-aza-bicyclo[4.2.0]oct-2-ene-2-carboxylic acid (1.5 g, 4.3 mmol) was suspended in tetrahydrofuran (THF) (15 mL) and triethylamine (2.1 g, 21 mmol) was added. The suspension was stirred for 0.5 hour at room temperature, and (Z)—S-benzo[d]thiazol-2-yl-2-(5-amino-1,2,4-thiadiazol-3-yl)-2-(trityloxyimino)ethanethioate (see Example 10) (2.5 g, 4.3 mmol) was added with stirring at 0° C. The mixture was allowed to warm to room temperature and stirred for 48 hours and concentrated under reduced pressure. The residue was dissolved in ethyl acetate (EA), washed with dilute aqueous HCl (pH=4), washed with brine, dried with $NaSO_4$, filtered and then the solvent was removed in vacuo to give 3.6 g as a slight yellow solid. The resulting product was used without further purification.

To a solution of (6R,7S,Z)-7-(2-(5-amino-1,2,4-thiadiazol-3-yl)-2-(trityloxyimino)acetamido)-8-oxo-3-(trifluoromethylsulfonyloxy)-1-aza-bicyclo[4.2.0]oct-2-ene-2-carboxylic acid (55 mg, 0.074 mmol, 1.0 eq) in THF (1 mL) at 0° C., a solution of $CH_2N_2$ in $Et_2O$ (10 mL, 0.74 mol, 10 eq) was added. The resulted suspension was stirred for 6 hrs. The reaction mixture was concentrated in vacuo to get the crude product. The crude product was purified by column chromatography on silica gel using P.E/EA=4:1 as an eluent to furnish the desired product as a light yellow solid in 18% yield.

Method G

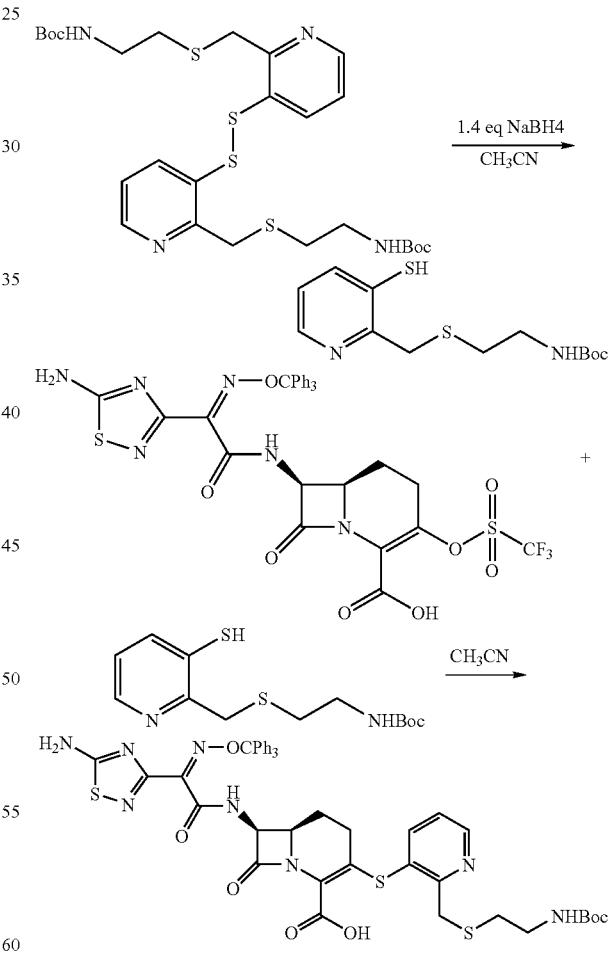

To a solution of di-tert-butyl-2,2'-(3,3'-disulfanediylbis (pyridine-3,2-diyl)bis(methylene)bis(sulfanediyl)bis (ethane-2,1-diyl)dicarbamate 156 mg in acetonitrile (10 mL) was added $NaBH_4$ 14.4 mg. The mixture was stirred at room temperature for 18 h. and was the mixture was used for next step without purification. (6R,7S,Z)-7-(2-(5-amino-1,2,4- thiadiazol-3-yl)-2-(trityloxyimino)acetamido)-8-oxo-3-(trifluoromethylsulfonyloxy)-1-aza-bicyclo[4.2.0]oct-2-ene-2-carboxylic acid (see Method F) was added to the solution and stirred for 3.5 h and evaporated to dryness. The residue was taken to column chromatography (P.E/EA, 2:1) and 270 mg (6R,7S,Z)-7-(2-(5-amino-1,2,4-thiadiazol-3-yl)-2-(trityloxyimino)acetamido)-3-(2-((2-(tert-butoxycarbonylamino)ethylthio)methyl)pyridin-3-ylthio)-8-oxo-1-aza-bicyclo[4.2.0]oct-2-ene-2-carboxylic acid was obtained as a white solid yield: 30%.

Example 9

Preparation of (6R,7S)-tert-butyl-7-(tert-butoxycarbonylamino)-8-oxo-3-(trifluoromethylsulfonyloxy)-1-aza-bicyclo[4.2.0]oct-2-ene-2-carboxylate Step 1: A mixture of (1R,2S)-2-amino-1,2-diphenylethanol (4.28 g, 20.0 mmol), $K_2CO_3$ (0.28 g 2.03 mmol) and diethyl carbonate (20 mL, 166 mmol) was heated under reflux for 16 h. The resulting mixture was washed with water (10 mL) and extracted with $CH_2Cl_2$ (300 mL). The organic phase was dried $MgSO_4$, filtered and concentrated. The residue was recrystallized form toluene to give the desired compound (4S,5R)-4,5-diphenyloxazolidin-2-one as white solid. Yield 88%, ESI-MS: 240.1 [M$^+$]

Step 2: NaH (0.66 g, 60% mineral oil dispersion, 20.8 mmol) was placed in a three necked flask under argon and washed with anhydrous hexane (15 ml). After addition of THF (50 mL) to NaH, a solution of (4S,5R)-4,5-diphenyloxazolidin-2-one in THF was added to the suspension and the mixture was stirred for 2 h at r.t. Then, ethyl bromoacetate was added dropwise in a period of 30 min, and the mixture was stirred for 30 min. The reaction was quenched with water

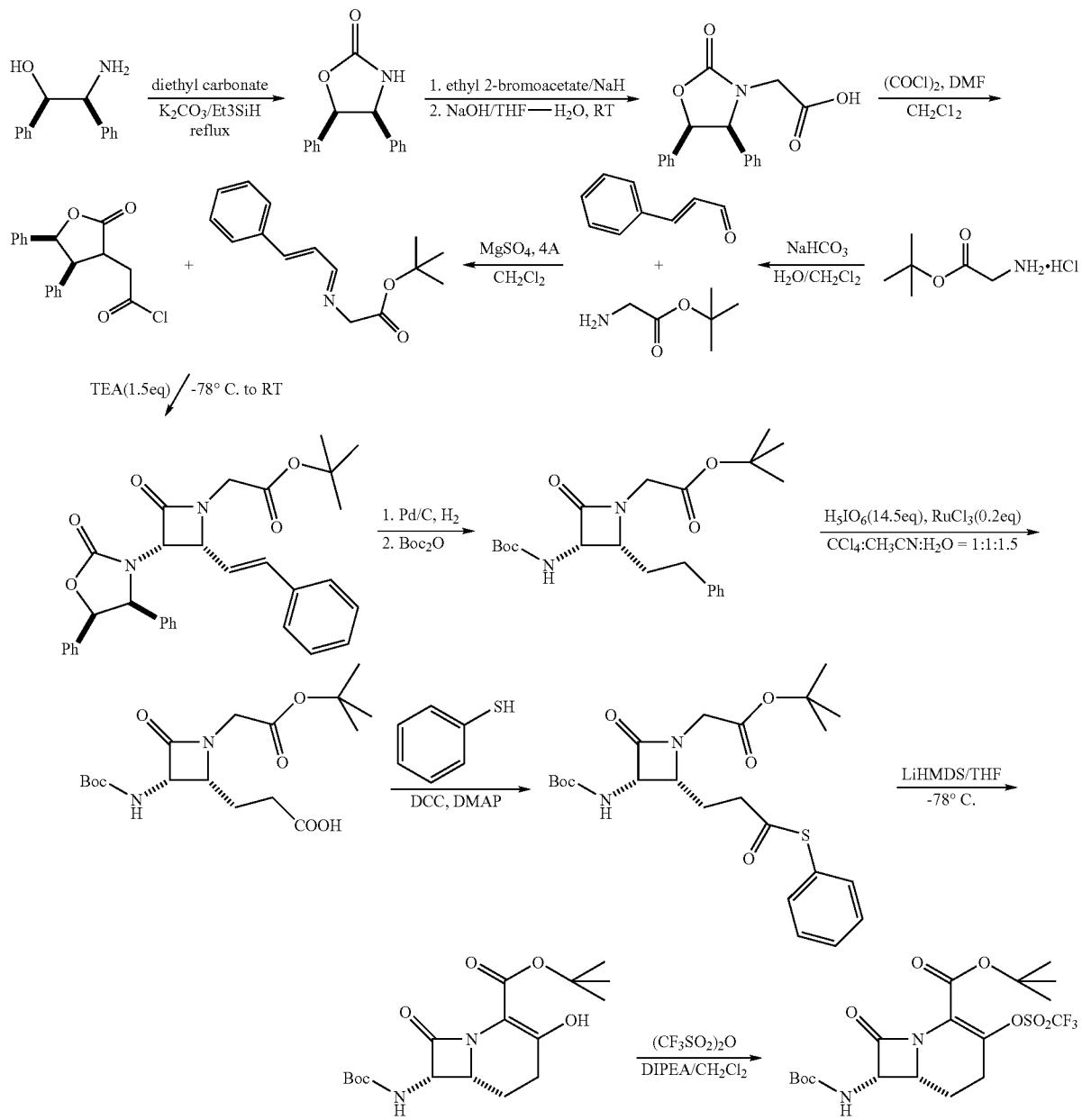

100 mL) and extracted with $CH_2Cl_2$. The combined extracts were washed with water, dried $MgSO_4$, filtered and concentrated. The residue was purified by silica gel column chromatography to give ethyl-2-((4S,5R)-2-oxo-4,5-diphenyloxazolidin-3-yl)acetate.

A THF (20 mL) solution of ethyl 2-((4S,5R)-2-oxo-4,5-diphenyloxazolidin-3-yl) acetate was added to a solution of KOH (2.99 g, 53.3 mmol) in a $H_2O$/MeOH/THF (35 mL, $H_2O$/MeOH/THF=3:3:8) and the mixture was stirred for 2 h at r.t. Then, 1 M aq HCl 100 mL was added to the mixture. The desired product was extracted with $Et_2O$ (3×100 mL) and the combined extracts were washed with sat. aq NaCl 50 mL, dried $MgSO_4$, filtered and concentrated. The residue was recrystallized from toluene to give 2-((4S,5R)-2-oxo-4,5-diphenyloxazolidin-3-yl)acetic acid yield 83%. ESI-MS: 298.1 [M$^+$].

Step 3: Glycine t-butyl ester hydrochloride (125 g, 0.75 mol) was treated with 10 N aqueous sodium hydroxide (180 mL) and extracted with dichloromethane. The dichloromethane solution was back washed with saturated aqueous NaCl, dried by sodium sulfate, filtered and concentrated in vacuum to get the glycine-butyl ester (60 g). The compound tert-butyl-2-aminoacetate (31.5 g, 0.24 mol) in dichloromethane was treated sequentially with 1 equivalent of cinnamaldehyde (26.4 g, 0.2 mol) and a desiccating agent, such as magnesium sulfate 70 g, in the amount of about 2 grams of desiccating agent per gram of starting amino acid ester or amide. The reaction was stirred at ambient temperature until all of the reactants were consumed as measured by thin layer chromatography. The reactions were typically complete after 3 hours. The reaction mixture was then filtered and the filter cake was washed with dichloromethane. The filtrate was concentrated under reduced pressure to provide the desired imine that was used as is in the subsequent step.

Step 4: 2-((4S,5R)-2-oxo-4,5-diphenyloxazolidin-3-yl) acetic acid (5.95 g, 20 mmol) was dissolved in $CH_2Cl_2$. Then, DMF (0.04 mL, 0.6 mmol) was added, followed by $(COCl)_2$ (2.6 mL, 30 mmol). The reaction mixture was stirred for 1.5 h at room temperature and concentrated. The product was used for next step without further purification. Triethylamine (4.18 mL, 30.0 mmol) was added at −78° C. to a solution of the acid chloride (6.32 g, 20.0 mmol) in dry methylene chloride (100 mL). After 20 min, a solution of the imine (4.91 g, 20.0 mmol) in dry $CH_2Cl_2$ 50 mL was added dropwise at the same temperature. The cooling bath was removed and the resulting mixture was stirred under nitrogen atmosphere at 0° C. for 2 hours. Then, the reaction mixture was successively washed with water 100 mL, 1 N HCl (50 mL), saturated aqueous solution of $NaHCO_3$ (100 mL). The organic layer was dried over $MgSO_4$, filtered and concentrated to afford a crude material, which was washed by little $CH_3OH$ to afford a white solid tert-butyl-2-((3S,4R)-2-oxo-3-((4S,5R)-2-oxo-4,5-diphenyloxazolidin-3-yl)-4-((E)-styryl)azetidin-1-yl)acetate. ESI-MS: 525.1 [M$^+$]. $^1$HNMR (300 MHz, DMSO-d$_6$): δ 7.46-6.91 (m, 15H), 6.80 (d, 15.6 Hz, 1H), 6.37 (dd, 8.1/ 15.9 Hz, 1H), 5.93 (d, 8.1 Hz, 1H), 5.28 (d, 8.1 Hz, 1H), 4.60-4.50 (m, 2H), 4.60 (d, 17.7 Hz, 1H), 3.77 (d, 18.0 Hz, 1H), 1.358 (s, 9H).

Step 5: Pearlman's catalyst (2 g) and di-tert-butyl dicarbonate (6.5 g, 30 mmol) were added successively to a solution of the corresponding tert-butyl-2-((3S,4R)-2-oxo-3-((4S, 5R)-2-oxo-4,5-diphenyloxazolidin-3-yl)-4-((E)-styryl)azetidin-1-yl)acetate (1 mmol) in THF (30 mL). The resulting mixture was stirred at room temperature under a hydrogen atmosphere (120 psi) for 48 h. Then, the mixture was filtered through Celite®. After evaporation of the filtrate under reduced pressure, the resulting crude was crystallization by methanol to give 2-((3S,4R)-3-(tert-butoxycarbonylamino)-2-oxo-4-phenethylazetidin-1-yl)acetate (2.63 g, 65%). ESI-MS: 405.2 [M$^+$]

Step 6: To a mixture of the tert-butyl-2-((3S,4R)-3-(tert-butoxycarbonylamino)-2-oxo-4-phenethylazetidin-1-yl)acetate (2.1 g, 5.19 mmol) in carbon tetrachloride (30 mL), acetonitrile (30 mL), and water (45 mL) was added at roomtemperature periodic acid (17.24 g, 75.26 mmol). The biphasic mixture was stirred until both phases became clear, and ruthenium trichloride hydrate (236 mg, 1.05 mmol) was added. Stirring was continued until no starting material was detected by TLC (4 h). The reaction mixture was cooled down to 0° C., and diethyl ether (300 mL) was added with vigorous stirring for 10 min. The organic phase was separated and the aqueous layer extracted with diethyl ether (2×150 mL). The combined organic layers were washed with brine (100 mL), dried, filtered, and concentrated. The resulting crude was purified by chromatography ($CH_2Cl_2$:EA=2:1) to give 3-((2R,3S)-1-(2-tert-butoxy-2-oxoethyl)-3-(tert-butoxycarbonylamino)-4-oxoazetidin-2-yl) propanoic acid (1.2 g, 62%). ESI-MS: 373.2 [M$^+$]

Step 7: To a cold (0° C.) solution of (6.8 g, 16.83 mmol) of 3-((2R,3S)-1-(2-tert-butoxy-2-oxoethyl)-3-(tert-butoxycarbonylamino)-4-oxoazetidin-2-yl)propanoic acid in 300 mL of methylene chloride maintained under nitrogen were added 103.7 mg (0.85 mmol) of dimethylaminopyridine, thiophenol (2.32 g, 21.04 mmol), and dicyclohexylcarbodiimide (DCC) (4.34 g, 21.04 mmol). The mixture was stirred at 0° C. for 10 minutes and at room temperature for 6 hours. The mixture was poured into 400 mL of methylene chloride and the mixture washed with an aqueous sodium bicarbonate solution (50% of saturated), with 1 M hydrochloric acid, and with saturated sodium bicarbonate solution. The organic phase was dried over sodium sulfate, filtered and evaporated to dryness to yield the title compound as partly crystalline oil. The resulting crude was purified by chromatography ($CH_2Cl_2$:EA=4:1) to give tert-butyl-2-((3S,4R)-3-(tert-butoxycarbonylamino)-2-oxo-4-(3-oxo-3-(phenylthio)propyl) azetidin-1-yl)acetate (7.5 g, 89%). ESI-MS: 465.2 [M$^+$]

Step 8: To a solution of 18.12 g (39 mmole) of tert-butyl-2-((3S,4R)-3-(tert-butoxycarbonylamino)-2-oxo-4-(3-oxo-3-(phenylthio)propyl)azetidin-1-yl)acetate in 300 mL of anhydrous THF and maintained under argon at −78° C. was added 156 mL (156 mmol) of lithium hexamethyldisilazane (1M/L) (also maintained under argon at −78° C.). After about 6 hrs, the mixture was poured into 1000 ml of aqueous ammonium chloride (50% of saturation) and the pH was adjusted to 3 with 1 M HCl aqueous. The acidified mixture was extracted three times with 800 ml of portions of methylene chloride. The extracts was combined, washed with brine, dried over sodium sulfate, filtered and concentrated by evaporation. The residue was initially chromatographed over silica using hexane-ethyl acetate (ca 3:1, v/v), followed by a (2:1, v/v). mixture of the same solvents for elution of the product. The desired fraction was evaporated to dryness to provide (6R, 7S)-tert-butyl-7-(tert-butoxycarbonylamino)-3-hydroxy-8-oxo-1-aza-bicyclo[4.2.0]oct-2-ene-2-carboxylate (10.2 g, 74%). ESI-MS: 377.1 [M$^+$]

Step 9: A $CH_2Cl_2$ solution of trifluoromethanesulfonic anhydride (338.4 mg, 1.2 mmol) was rapidly added to a solution of (6R,7S)-tert-butyl-7-(tert-butoxycarbonylamino)-3-hydroxy-8-oxo-1-aza-bicyclo[4.2.0]oct-2-ene-2-carboxylate (354 mg, 1 mmol) and DIPEA (193 mg, 1.5 mmol) in $CH_2Cl_2$ (5 mL) at −40° C. After 15 min, the reaction mixture was poured into a saturated aqueous solution of $NaHCO_3$ (10 mL). The resulting mixture was extracted with $CH_2Cl_2$ (3×20 mL). The extracts were combined, washed with brine (1×5 mL), dried (MgSO$_4$), filtered and concentrated to give 438 mg (91%) of (6R,7S)-tert-butyl-7-(tert-butoxycarbonylamino)-8-oxo-3-(trifluoromethylsulfonyloxy)-1-aza-bicyclo[4.2.0]oct-2-ene-2-carboxylate as a white solid. ESI-MS: 486.2 [M$^+$]. $^1$HNMR (300 MHz, DMSO-d$_6$): δ 7.71 (d, 6.9 Hz, 1H), 5.20 (dd, 4.2/6.9 Hz, 1H), 3.85 (dd, 4.2/8.4 Hz, 1H), 2.62 (d, 2.7 Hz, 2H), 1.90-1.80 (m, 2H), 1.46 (s, 9H), 1.38 (s, 9H)

Example 10

Preparation of (Z)—S-benzo[d]thiazol-2-yl-2-(5-amino-1,2,4-thiadiazol-3-yl)-2-(trityloxyimino)ethanethioate

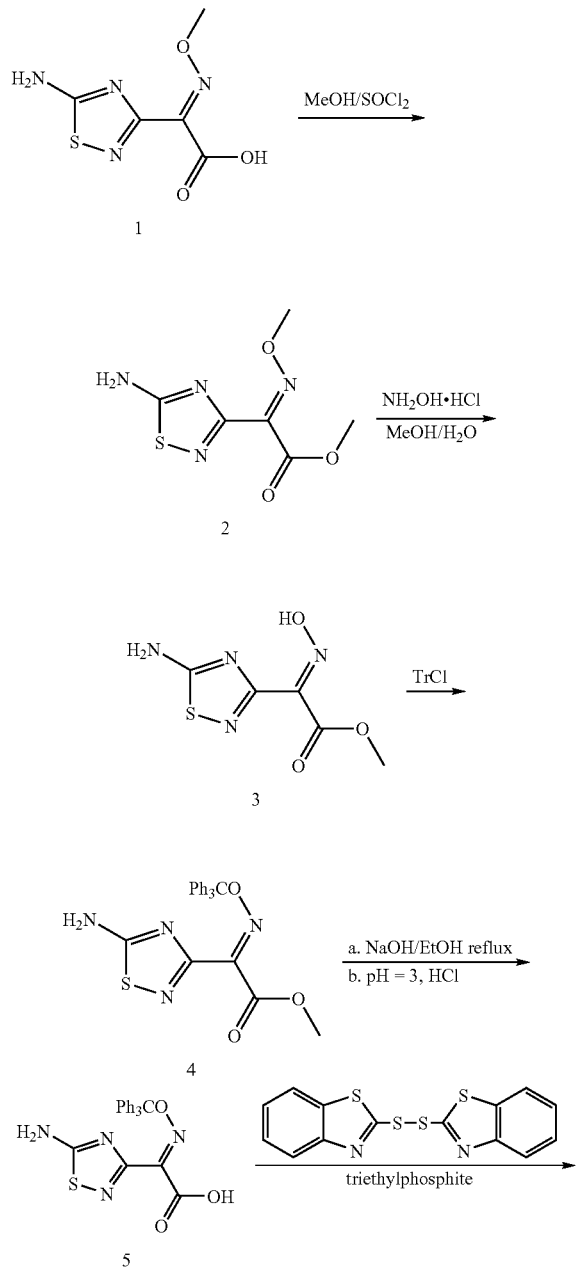

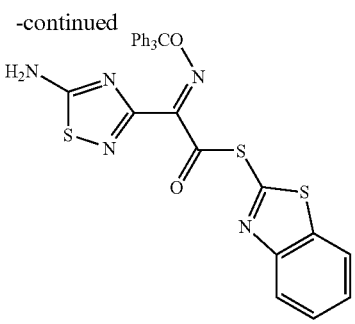

Step 1: The compound SOCl$_2$ (200 mL, 2.74 mol) was slowly added to the methanol (400 mL) during 1.5 hours at 0° C. Then, (Z)-2-(5-amino-1,2,4-thiadiazol-3-yl)-2-(methoxyimino)acetic acid 1 (61 g, 0.30 mol) was added in one portion and the reaction mixture was stirred for 24 h at 70° C. Concentration gave a white solid which was partitioned between ethyl acetate (500 mL×3) and water (200 mL). The organic phase was washed (saturated NaHCO$_3$, water), dried on Na$_2$SO$_4$ and concentrated to give 56 g (Z)-methyl-2-(5-amino-1,2,4-thiadiazol-3-yl)-2-(methoxyimino)acetate 2 as a white solid in 85% yield. This product was used without further purification.

Step 2: A solution of (Z)-methyl-2-(5-amino-1,2,4-thiadiazol-3-yl)-2-(methoxyimino)acetate 2 (60 g, 0.28 mol) and NH$_2$OH·HCl (140 g, 1.98 mol) in methanol (400 mL) and H$_2$O (200 mL) was stirred at 100° C. for 24 h. Concentration gave a yellow syrup which was partitioned between ethyl acetate (1 L) and water (400 mL). The aqueous layer was extracted with ethyl acetate (2×1 L). The organic phase was dried on NaSO$_4$, filtered and concentrated to dry. The crude solid was crystallized from DCM/PE (20:1, 1 L) 5 times, the product was collected and 20 g (Z)-methyl-2-(5-amino-1,2,4-thiadiazol-3-yl)-2-(hydroxyimino)acetate 3 was obtained as a white solid in 45% yield. The product was used without further purification.

Step 3: To a solution of (Z)-methyl-2-(5-amino-1,2,4-thiadiazol-3-yl)-2-(hydroxyimino)acetate 3 (10 g, 0.05 mol) in 50 mL THF at 0° C. was added 5.5 g TEA, stirred 10 minutes. Then, 14 g of trityl chloride was added in at 0° C. and the reaction solution was stirred at this temperature for 2 hours. Concentration gave a white solid which was partitioned between ethyl acetate (500 mL) and water (200 mL). The aqueous layer was extracted with ethyl acetate (2×500 mL). The organic phase was washed with 1% NaOH aqueous solution (200 mL) three times. The organic phase was dried over NaSO$_4$, filtered and concentrated to dry. The solid obtained was crystallized from petroleum ether (1 L). The product was collected and (Z)-methyl-2-(5-amino-1,2,4-thiadiazol-3-yl)-2-(trityloxyimino)acetate 4 15 g was obtained as a white solid in 68% yield. The product was used without further purification.

Step 4: A solution of (Z)-methyl-2-(5-amino-1,2,4-thiadiazol-3-yl)-2-(trityloxyimino)acetate 4 (15 g, 33.8 mmol) in 80 mL 2.5 M NaOH and 40 mL ethanol was heated to gentle reflux for 2 hours. The reaction solution was cooled down and THF (40 mL) was added in. Then, adjusted reaction solution to PH=3 by 5% aq. HCl, The whole reaction solution was extracted with EA (100 mL). The organic phase was dried on Na$_2$SO$_4$, filtered and concentrated. The crude (Z)-2-(5-amino-1,2,4-thiadiazol-3-yl)-2-(trityloxyimino)acetic acid 5 (12 g, 28.0 mmol) was obtained as white solid in 70% yield. The product was used without further purification.

Step 5: To a solution of (Z)-2-(5-amino-1,2,4-thiadiazol-3-yl)-2-(trityloxyimino) acetic acid 5 (5.4 g, 12 mmol) in anhydrous acetonitrile TEA (1.265 g, 12.5 mmol.) was added in at 0° C. The reaction solution was stirred for 10 min. Disulfide (4.9 g, 14.7 mmol.) was added during 30 min to the reaction solution. Then, a solution of triethyphosphite (3.545 g, 21.35 mmol.) in CH$_3$CN (30 mL) was added during 30 min. The reaction was stirred at room temperature for 27 hours and filtered. The solid obtained was washed by CH$_3$CN (50 mL) three times to get (Z)—S-benzo[d]thiazol-2-yl-2-(5-amino-1,2,4-thiadiazol-3-yl)-2-(trityloxyimino)ethanethioate B6 (3.2 g, 46%).

Example 11

Preparation of (Z)—S-benzo[d]thiazol-2-yl-2-(5-amino-1,2,4-thiadiazol-3-yl)-2-(methoxyimino)ethanethioate

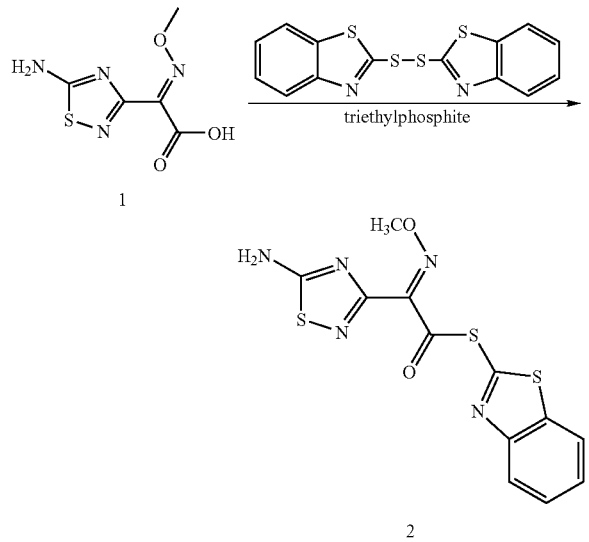

(Z)—S-benzo[d]thiazol-2-yl-2-(5-amino-1,2,4-thiadiazol-3-yl)-2-(methoxyimino)ethanethioate 2 was prepared from (Z)-2-(5-amino-1,2,4-thiadiazol-3-yl)-2-(methoxyimino) acetic acid 1 in 40% yield by Example 10. The product was used without further purification. ESI-MS: 352.4 [M+H]

Example 12

Preparation of (Z)—S-benzo[d]thiazol-2-yl-2-(5-chloro-2-(tritylamino)thiazol-4-yl)-2-(trityloxyimino)ethanethioate

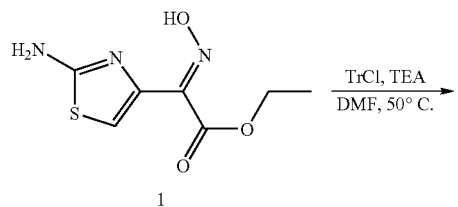

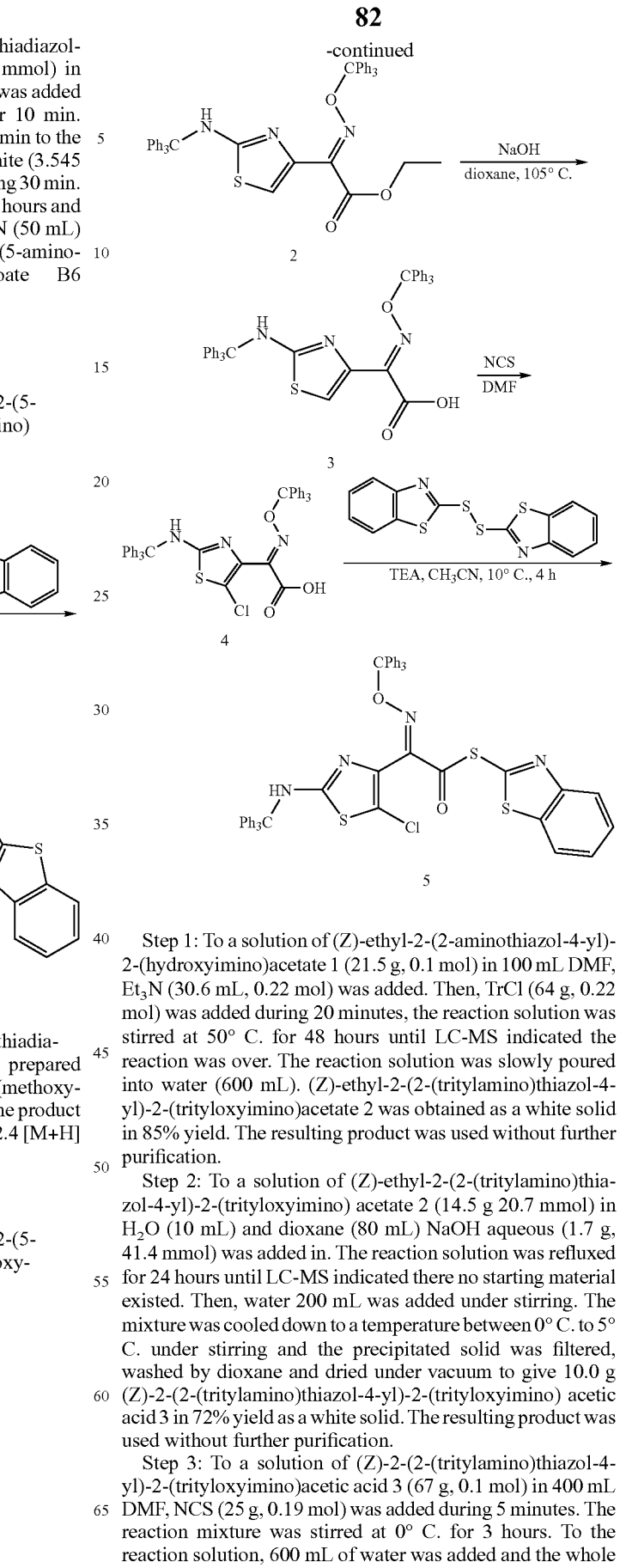

Step 1: To a solution of (Z)-ethyl-2-(2-aminothiazol-4-yl)-2-(hydroxyimino)acetate 1 (21.5 g, 0.1 mol) in 100 mL DMF, Et$_3$N (30.6 mL, 0.22 mol) was added. Then, TrCl (64 g, 0.22 mol) was added during 20 minutes, the reaction solution was stirred at 50° C. for 48 hours until LC-MS indicated the reaction was over. The reaction solution was slowly poured into water (600 mL). (Z)-ethyl-2-(2-(tritylamino)thiazol-4-yl)-2-(trityloxyimino)acetate 2 was obtained as a white solid in 85% yield. The resulting product was used without further purification.

Step 2: To a solution of (Z)-ethyl-2-(2-(tritylamino)thiazol-4-yl)-2-(trityloxyimino) acetate 2 (14.5 g 20.7 mmol) in H$_2$O (10 mL) and dioxane (80 mL) NaOH aqueous (1.7 g, 41.4 mmol) was added in. The reaction solution was refluxed for 24 hours until LC-MS indicated there no starting material existed. Then, water 200 mL was added under stirring. The mixture was cooled down to a temperature between 0° C. to 5° C. under stirring and the precipitated solid was filtered, washed by dioxane and dried under vacuum to give 10.0 g (Z)-2-(2-(tritylamino)thiazol-4-yl)-2-(trityloxyimino) acetic acid 3 in 72% yield as a white solid. The resulting product was used without further purification.

Step 3: To a solution of (Z)-2-(2-(tritylamino)thiazol-4-yl)-2-(trityloxyimino)acetic acid 3 (67 g, 0.1 mol) in 400 mL DMF, NCS (25 g, 0.19 mol) was added during 5 minutes. The reaction mixture was stirred at 0° C. for 3 hours. To the reaction solution, 600 mL of water was added and the whole reaction solution was extracted with 300 mL of ethyl acetate. The organic layer was washed with 200 mL of saturated aqueous sodium chloride solution, dried over anhydrous magnesium sulfate, filtered and concentrated to dry. The residue was crystallized from ethyl acetate to give crude (Z)-2-(5-chloro-2-(tritylamino)thiazol-4-yl)-2-(trityloxyimino) acetic acid as a white solid. The resulting product was purified by column chromatography (50% EtOAc in petroleum ester) to give (Z)-2-(5-chloro-2-(tritylamino)thiazol-4-yl)-2-(trityloxyimino)acetic acid 4 as a white solid (76 g, 80%).

Step 4: (Z)—S-benzo[d]thiazol-2-yl-2-(5-chloro-2-(tritylamino)thiazol-4-yl)-2-(trityloxyimino)ethanethioate 5 was prepared from (Z)-2-(5-chloro-2-(tritylamino) thiazol-4-yl)-2-(trityloxyimino)acetic acid 4 according to Example 10. The resulting product was purified by column chromatography (20% DCM in petroleum ester) in 20% yield as a white solid. ESI-MS: 8653.2 [M+H]. The compound may be used in methods similar to those of Methods A-G.

Example 13

Preparation of (Z)—S-benzo[d]thiazol-2-yl-2-(2-amino-5-chlorothiazol-4-yl)-2-(methoxyimino)ethanethioate

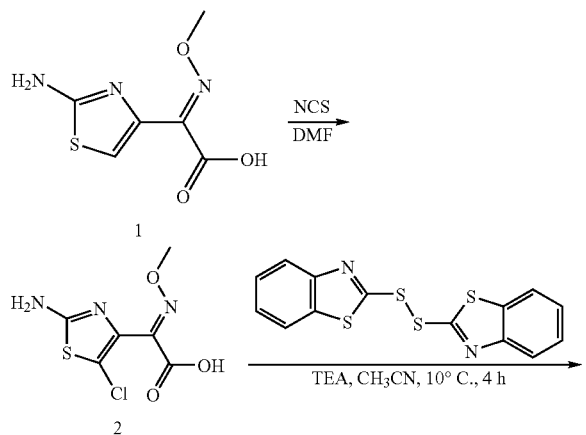

Step 1: (Z)-ethyl-2-(2-amino-5-chlorothiazol-4-yl)-2-(methoxyimino)acetate 2 was prepared from (Z)-ethyl-2-(2-aminothiazol-4-yl)-2-(methoxyimino)acetate 1 as set forth in Example 12. The resulting product was purified by column chromatography (50% EtOAc in petroleum ester) in 80% yield.

Step 2: (Z)—S-benzo[d]thiazol-2-yl-2-(2-amino-5-chlorothiazol-4-yl)-2-(methoxyimino)ethanethioate 3 was prepared from (Z)-ethyl-3-((Z)-amino(methylthio) methyleneamino)-2-(methoxyimino)propanoate by following Example 10. The resulting product (Z)—S-benzo[d]thiazol-2-yl-2-(2-amino-5-chlorothiazol-4-yl)-2-(methoxyimino)ethanethioate 3 was purified by column chromatography (20% DCM in petroleum ester as eluent) in 16% yield as a white solid. ESI-MS: 345.9 [M+H]. The compound may be used in methods similar to those of Methods A-G.

Example 14

Preparation of 1,2-di(pyridine-3-yl)disulfane

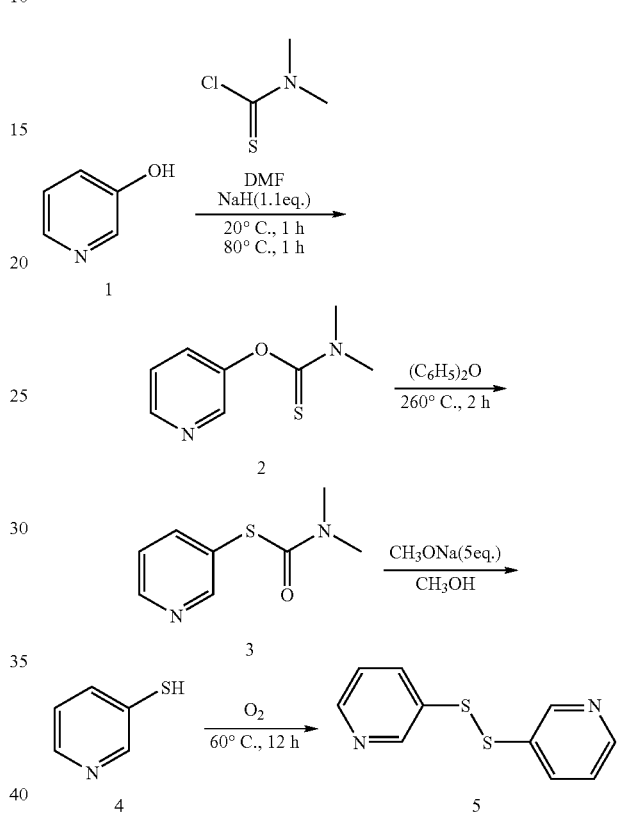

Step 1: NaH (4.0 g, 0.1 mol) was added to 3-hydroxylpyridine 1 (9.5 g, 0.1 mol) in DMF (100 mL) at room temperature. Then, the reaction mixture was stirred for 10 min and dimethylcarbamothioic chloride (12.4 g, 0.1 mol) was added in one portion. The reaction solution was heated to 80° C. for 1 h. The reaction mixture was diluted with water, extracted with EA from water. The combined organic layer was dried ($Na_2SO_4$), filtered and concentrated. The residue was purified by column chromatography to afford O-pyridin-3-yl-dimethylcarbamothioate 2 as a slight yellow oil (16.5 g, 91%). $^1$HNMR (400 MHZ, $CDCl_3$): 8.48 (d, 1H), 8.39 (s, 1H), 7.45 (d, 1H), 7.34 (m, 1H), 3.46 (s, 3H), 3.37 (s, 3H).

Step 2: The solution of O-pyridin-3-yl-dimethylcarbamothioate 2 (3.6 g, 20 mmol) in diphenyl ether (100 mL) was heated to reflux for 2 h. TLC indicated no O-pyridin-3-yl-dimethylcarbamothioate existed and concentrated. The residue was purified by column chromatography to afford S-pyridin-3-yldimethylcarbamothioate 3 as a yellow oil (2.8 g, 77%). $^1$HNMR (400 MHZ, $CDCl_3$): 8.51 (s, 1H), 8.37 (d, 1H), 7.67 (d, 1H), 7.22 (m, 1H), 3.11 (s, 3H), 3.03 (s, 3H).

Step 3: Na (1.8 g, 77 mmol) was added to $CH_3OH$ (10 mL) during 0.5 hour. The mixture was stirred at room temperature until all the metal was dissolved. Then, S-pyridin-3-yldimethylcarbamothioate 3 (2.8 g, 15.4 mmol) was added in and the reaction solution was heated to reflux for 2 hours, cooled to room temperature, diluted with water, adjusted to pH=6 and extracted with EA from water. The organic layer was washed with brine, dried (Na$_2$SO$_4$), filtered and concentrated. 0.9 g pyridine-3-thiol 4 was obtained as yellow oil. $^1$HNMR (400 MHZ, CDCl$_3$): 8.51 (s, 1H), 8.37 (d, 1H), 7.67 (d, 1H), 7.22 (m, 1H), 3.0 (s, 1H).

Step 4: Pyridine-3-thiol 4 was purified by column chromatography, 1,2-di(pyridine-3-yl)disulfane 5 was formed in process of purification. 0.65 g oil was obtained, yield 38.4%. $^1$HNMR (400 MHZ, CDCl$_3$): 8.68 (s, 2H), 8.51 (d, 2H), 7.83 (d, 2H), 7.28 (m, 2H).

Example 15

Preparation of 4,5-dimethylthiazole-2-thiol

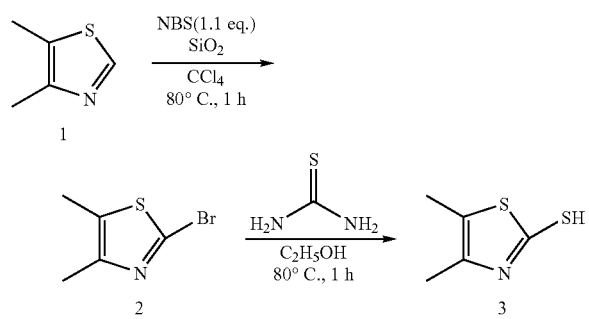

Step 1: Bromine (6.8 mL, 132 mmol) was added to a solution of 4,5-dimethylthiazole 1 (4.7 mL, 44 mmol) at 0° C., dropwise and stirred at room temperature overnight. The reaction was diluted with water and extracted with EA. The organic layer was dried over sodium sulfate, filtered and concentrated. The residue was purified by column chromatography to afford 3.9 g clear oil, yield 47%.

Step 2: The solution of 2-bromo-4,5-dimethylthiazole 2 (3.9 g, 20.3 mmol) in ethanol (10 mL) was added to the solution of thiourea (7.6 g, 100 mmol) in ethanol (100 mL) at 80° C. dropwise. After the addition, the mixture was heated to reflux for another 2 h and concentrated. The residue was purified by column chromatography (P.E/EA 2:1) to afford 1.3 g 4,5-dimethylthiazole-2-thiol 3 as a white solid, yield 44%. ESI-MS: 146.2 [M+H]

Example 16

Preparation of Sodium 1,2,3-thiazole-5-thiolate

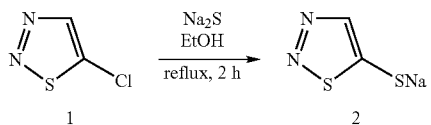

A mixture of 5-chloro-1,2,3-thiadiazole 1 (0.24 g, 1.99 mmol), Na$_2$S.9H$_2$O (0.48 g, 2.0 mmol) and ethanol (10 mL) was heated to reflux for 2 h and concentrated. 500 mg sodium 1,2,3-thiazole-5-thiolate 2 was obtained as a white solid, yield 100%. ESI-MS: 140.1 [M$^+$]

Example 17

Preparation of 1,2-di(thiazol-4-yl)disulfane

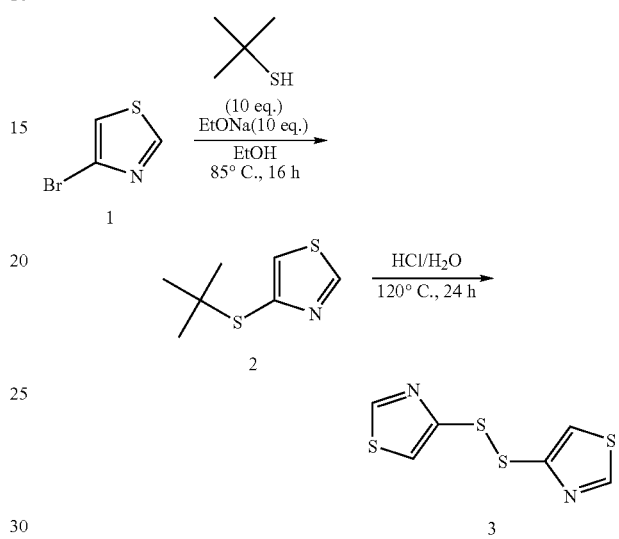

Step 1: Na (0.69 g, 30 mmol) was added to a solution of t-butylthiol (3.38 mL, 30 mmol) at room temperature portion-wise and stirred for 0.5 h. Then, 4-bromothiazole 1 (0.49 g, 3.0 mmol) was added and the mixture was heated to reflux overnight. LC-MS indicate desired product formed and the reaction was concentrated. The residue was dissolved in EA, filtered through silica gel and the filtrate was concentrated again. The residue was used for the next step directly.

Step 2: The residue from last step was dissolved in conc. hydrochloride, the resulting mixture was heated to 120° C. for 24 h until LC-MS indicate no 4-(tert-butylthio)thiazole 2 existed. The reaction solvent was concentrated, ammonia was added to the residue, concentrated again, purified by column chromatography (P.E/EA 1:1) to afford 24 mg 1,2-di(thiazol-4-yl)disulfane 3 as a white solid, yield 6.9%. ESI-MS: 233.2 [M+H]

Example 18

Preparation of tert-butyl 2-((4-mercaptopyridin-3-yl)methylthio)ethylcarbamate

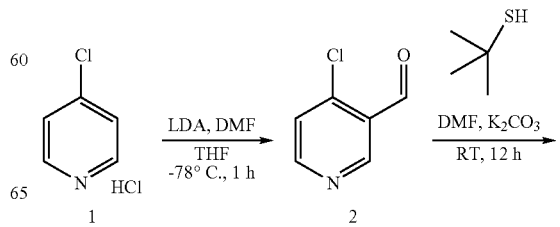

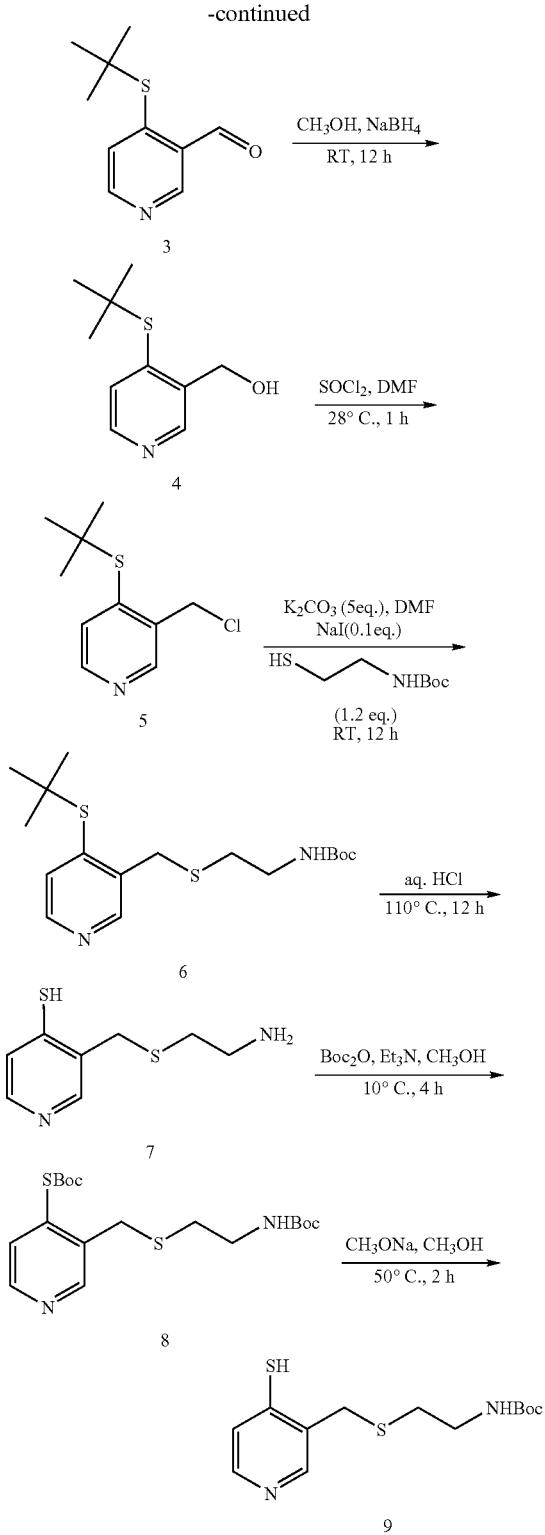

(P.E/EA 10:1) to afford 4.6 g white solid, yield 65%. $^1$HNMR (400 MHz, CDCl$_3$), 10.51 (s, 1H), 9.05 (s, 1H), 8.08 (d, 1H), 7.45 (d, 1H).

Step 2: The mixture of 4-chloronicotinaldehyde 2 (4.6 g, 32.6 mmol), 2-methyl-2-propanethiol (4.4 mL, 32.6 mmol), K$_2$CO$_3$ (9.0 g, 65.2 mmol) and DMF (70 mL) was stirred at 100° C. for 12 h until TLC indicate no 4-chloronicotinaldehyde was existed. The reaction mixture was diluted with water, extracted with EA and the organic layer was concentrated. The residue was purified by column chromatography (P.E/EA 12:1) to afford 6.3 g clear oil, yield 99%. $^1$HNMR (400 MHz, CDCl$_3$): 10.63 (s, 1H), 9.03 (s, 1H), 8.65 (d, 1H), 7.50 (d, 1H), 1.40 (s, 9H).

Step 3: NaBH$_4$ 0.38 g (10.0 mmol) was added to 4-(tert-butylthio)nicotinaldehyde 3 (0.97 g, 5.0 mmol) in CH$_3$OH (10 mL) portionwise. The mixture was stirred overnight at room temperature. The reaction mixture was diluted with water, extracted with EA. The organic layer was concentrated and the residue was purified by column chromatography (P.E/EA 2:1-0:1) to afford 0.9 g yellow oil, yield 91.4%. ESMS: m/z 198.1 (M+H).

Step 4: SOCl$_2$ 0.45 mL (6.15 mmol) was added to the solution of the (4-(tert-butylthio)pyridine-3-yl)methanol 4 (0.8 g, 4.1 mmol) in DMF (15 mL) dropwise at 0° C. and stirred at room temperature for 1 h. The reaction mixture was diluted with water, extracted with EA and the organic layer was concentrated. The residue was purified by column chromatography (P.E/EA 5:1) to afford 0.80 g brown oil, yield 90.5%. ESMS: m/z 216.0 [M+H].

Step 5: The mixture of the 4-(tert-butylthio)-3-(chloromethyl)pyridine 5 (0.8 g, 4.1 mmol), N-Boc-aminoethanethiol 3.46 mL (20.5 mmol), NaI 0.15 g (1.0 mmol) and DMF (15 mL) was stirred at room temperature for 1 h. The reaction mixture was diluted with water and extracted with EA. The organic layer was concentrated and the residue was purified by column chromatography (P.E/EA 2:1) to afford 1.39 g oil, yield 96%. $^1$HNMR (400 MHz, CDCl$_3$): 8.56 (s, 1H), 8.41 (d, 1H), 7.44 (d, 1H), 4.96 (s, 1H), 4.12 (s, 2H), 3.35 (m, 2H), 2.61 (m, 2H), 1.40 (m, 9H), 1.27 (m, 9H).

Step 6: Tert-butyl 2-((4-(tert-butylthio)pyridine-3-yl)methylthio)ethylcarbamate 6 was dissolved in concentrated HCl, heated to reflux for 24 hours until LC-MS indicated no tert-butyl-2-((4-(tert-butylthio)pyridine-3-yl)methylthio)ethylcarbamate was existed. The reaction mixture was concentrated and the residue was used for the next step directly.

Step 7: Boc$_2$O (0.56 g, 3.4 mmol) was added to the solution of Et$_3$N (0.48 mL, 2.55 mmol) and 3-((2-aminoethylthio)methyl)pyridine-4-thiol 7 (0.85 mmol) in CH$_3$OH. The reaction mixture was diluted with water and extracted with EA. The organic layer was concentrated and the residue was purified by column chromatography to afford 0.48 g yellow oil, yield 93%. ESMS:m/z 401.2 (M+H).

Step 8: The mixture of tert-butyl-2-((4-(tert-butoxycarbonylthio)-pyridine-3-yl)methylthio)ethylcarbamate 8 (200 mg, 0.5 mmol), CH$_3$ONa (10 mmol), CH$_3$OH (40 mL) was heated to reflux overnight until TLC indicate no tert-butyl-2-((4-(tert-butoxycarbonylthio)pyridine-3-yl)methylthio)ethylcarbamate existed. The reaction mixture was diluted with water and the water layer was adjusted to pH=6 with concentrated HCl, extracted with EA from water. The organic layer was concentrated and the residue was purified by column chromatography to afford 0.48 g of 9 as a yellow oil, yield Step 1: LDA (0.11 mmol) was added to 4-chloropyridine 1 (15 g, 0.1 mol) in THF (250 mL) dropwise at −60° C. and stirred at this temperature for 1 h. Then, DMF (9.3 mL, 0.12 mol) was added and stirred at room temperature overnight. The product was extracted with EA from water. The combined organic layer was dried (Na$_2$SO$_4$), filtered and concentrated. The residue was purified by column chromatography 73%. ¹HNMR (400 MHz, CDCl₃): 7.85 (s, 1H), 7.52 (m, 1H), 7.46 (m, 1H), 5.26 (s, 1H), 3.97 (s, 2H), 3.35 (m, 2H), 2.65 (m, 2H), 1.44 (s, 9H).

Example 19

Preparation of 1,2-bis(5-methylthiophen-2-yl)disulfane

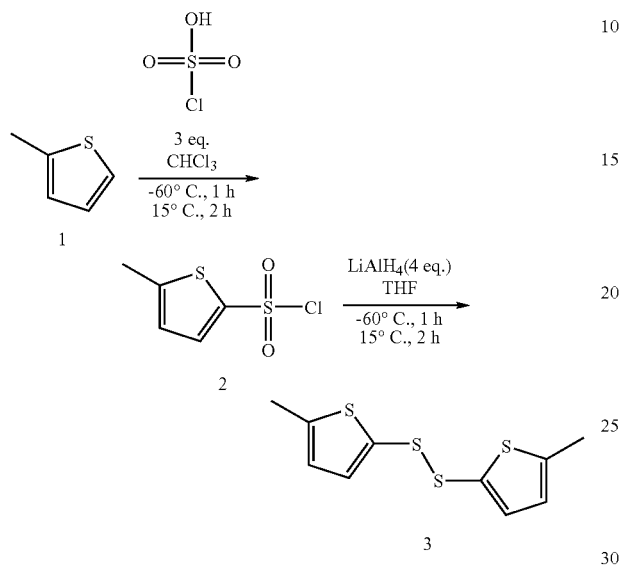

Step 1: Thiophene 1 (4.4 mL, 51 mmol) was added to a solution of ClSO₂OH (10 mL, 155 mmol) in CH₂Cl₂ (100 mL) at 0° C. during 0.5 hour. The reaction solution was stirred at this temperature for another 3 hours. Then, the reaction mixture was poured into ice-water and extracted with CH₂Cl₂ twice. The organic layer was washed with brine, concentrated and 6.0 g 5-methylthiophene-2-sulfonyl chloride 2 was obtained as a light oil, yield 59.5%.

Step 2: The solution of 5-methylthiophene-2-sulfonyl chloride 2 (1.2 g, 6.1 mmol) in THF (10 mL) was added to LiAlH₄ (0.93 g, 24.4 mmol) in THF (50 mL) at −60° C. during 20 minutes. The reaction solution was stirred at room temperature for 1 hour, quenched with Na₂SO₄.10H₂O and filtered. The filtrate was concentrated and the residue was purified by column chromatography (P.E/EA 5:1) to afford 0.6 g 1,2-bis(5-methylthiophen-2-yl)disulfane 3 as a yellow oil, yield 76%. ¹HNMR (400 Hz, CDCl₃): 6.96 (d, 2H), 6.66 (d, 2H), 2.50 (s, 6H).

Example 20

Preparation of Di-tert-butyl 2,2'-(3,3'-disulfanediyl-bis(pyridine-3,2-diyl))bis(ethane-2,1-diyl)dicarbamate

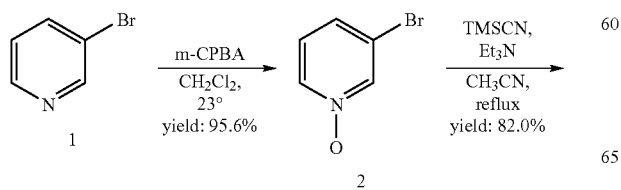

-continued

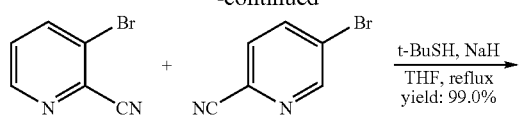

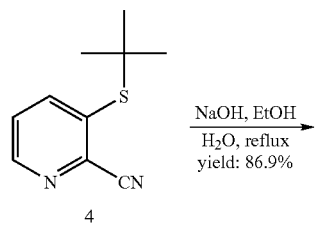

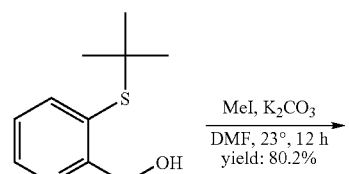

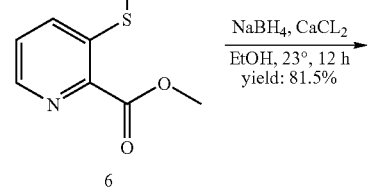

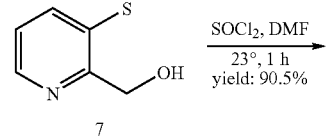

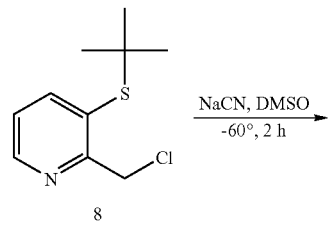

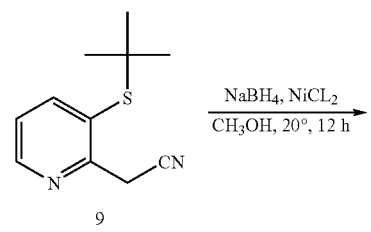

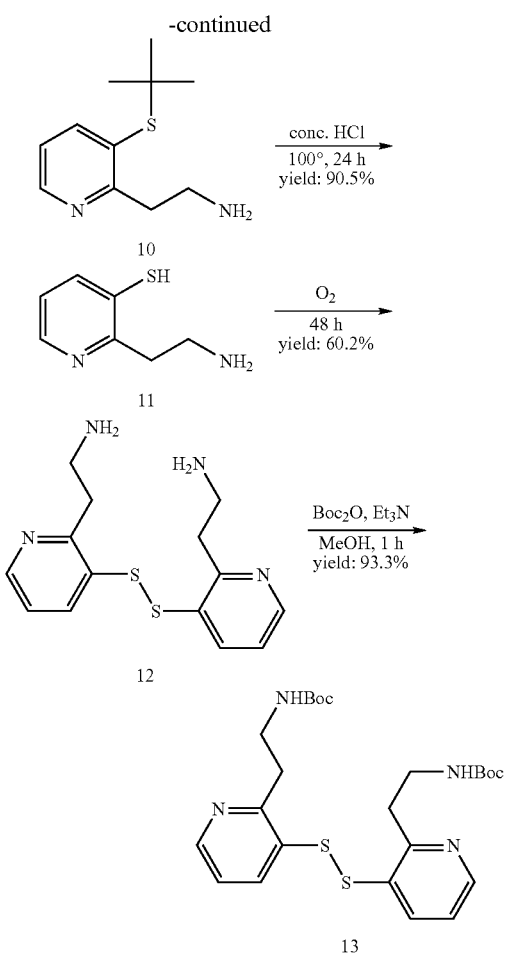

Step 1: m-Chloroperbenzoic acid (10 g, 85%, 49 mmol) was added to a solution of 3-bromopyridine 1 (4.74 g, 30 mmol) in $CH_2Cl_2$ (50 mL) portion-wise. The reaction solution was stirred at room temperature for 1 hour. TLC indicated there was no starting material existed. Then, $Na_2S_2O_3$ (3.0 g, 19 mmol) was added into the reaction mixture. The resulting mixture was filtered. The filtrate was concentrated, purified by column chromatography with EA as eluent and 3-bromopyridine-1-oxide 2 was obtained as a light yellow oil (5.0 g, 96%).

Step 2: The mixture of 3-bromopyridine-1-oxide 2 (3.48 g, 20 mmol), TMSCN (5.94 g, 60 mmol), $Et_3N$ (5.05 mL, 40 mmol) and $CH_3CN$ (30 mL) was heated to reflux for 4 h until TLC indicated no 3-bromopyridine-1-oxide 2 existed. The reaction mixture was concentrated and the residue was purified by column chromatography (P.E:EA=10:1). 0.3 g 5-bromopicolinonitrile/3.0 g 3-bromopicolinonitrile 3 were obtained as a white solid, yield 82.0%

Step 3: NaH (0.9 g, 22.5 mmol) was suspended in dry THF, 2.53 mL t-butylthiol (22.5 mmol) was added to the suspension, the resulting mixture was heated to 50° C. for 1 hour until $H_2$ evolution ceased. To the white suspension 2-cyano-3-bromopyridine (2.74 g, 15 mmol) was added and the reaction was heated to reflux for 1.5 hour under $N_2$. LC-MS indicated no 3-bromopicolinonitrile existed and the reaction was filtered through silica gel. The filtrate was concentrated and the residue was purified by column chromatography (PE:EA=5:1), 2.88 g 3-(tert-butylthio)picolinonitrile 4 was obtained as a light oil in yield 99%.

Step 4: NaOH 5.2 g (130 mmol) was dissolved in 5 mL $H_2O$ and 5 mL ethanol. To this solution 2.5 g 3-(tert-butylthio)picolinonitrile 4 (13 mmol) was added in. The mixture was heated to reflux for 1 hour, at the same time $N_2$ was bubbled into the solution to remove the $NH_3$ evolved. Then, the reaction was cooled down to room temperature, diluted with water and extracted with EA. The aqueous layer was adjusted to pH=2, and extracted with EA from the water. The organic layer was washed with brine, dried over sodium sulfide and concentrated. 2.38 g solid 5 was obtained, yield 87%.

Step 5: To a solution of 3-(tert-butylthio)picolinic acid 5 (0.53 g, 2.5 mmol) in DMF (10 mL), $CH_3I$ (0.23 mL, 3.75 mmol) and $K_2CO_3$ (0.69 g, 5.0 mmol) was added. The mixture was stirred overnight at room temperature and extracted with EA from sat. aq. $Na_2CO_3$. The organic layer was washed with brine and concentrated. The residue was purified by column chromatography (PE:EA=5:1) and 0.45 g methyl-3-(tert-butylthio)picolinate 6 was obtained in yield 80% as a light oil.

Step 6: $NaBH_4$ (0.38 g, 10 mmol) was added to the solution of $CaCl_2$ (0.56 g, 5.0 mmol) and methyl-3-(tert-butylthio)picolinate 6 (0.45 g, 2.5 mmol) in ethanol (10 mL) portion-wise. Then, the reaction mixture was stirred at room temperature overnight and extracted with EA from sat. aq. $Na_2CO_3$. The organic layer was washed with brine, concentrated and the residue was purified by column chromatography (PE:EA=2:1), 0.40 g yellow oil 7 was obtained in yield 82%.

Step 7: $SOCl_2$ (0.45 mL, 6.15 mmol) was added to the solution of the (3-(tert-butylthio)pyridin-2-yl)methanol 7 (0.8 g, 4.1 mmol) in DMF (15 mL) drop-wise at 0° C. The reaction solution was stirred at room temperature for 1 h, extracted with EA from sat. aq. $Na_2CO_3$. The organic layer was washed with brine, concentrated and the residue was purified by column chromatography (PE:EA=10:1). 0.80 g oil 8 was obtained in yield 90.5%

Step 8: The mixture of the 3-(tert-butylthio)-2-(chloromethyl)pyridine 8 (4.4 g, 20.4 mmol), NaCN (2.0 g, 40.8 mmol) and DMSO (40 mL) was heated to 60° C. for 2 hours. Then, the desired product was extracted with EA from water. The organic layer was washed with brine and concentrated. The residue was purified by column chromatography (PE:EA=2:1) and 3.4 g slight yellow oil 9 was obtained in yield 81%.

Step 9: $NaBH_4$ (0.18 g, 4.8 mmol) was added to the suspension of $NiCl_2$ (0.13 g, 0.96 mmol) and 2-(3-(tert-butylthio)pyridin-2-yl)acetonitrile 9 (0.1 g, 0.48 mmol) in $CH_3OH$ (15 mL) portion-wise. The reaction solution was stirred at room temperature overnight. The product was extracted with EA from water. The organic layer was washed with brine and concentrated. 0.05 g oil 10 was obtained yield 51%.

Step 10: 2-(3-(tert-butylthio)pyridin-2-yl)ethanamine 10 was dissolved in concentrated HCl, heated to reflux for 24 hours until LC-MS indicate no starting materials existed. The reaction mixture was concentrated and the residue was used for the next step directly.

Step 11: The crude 2-(2-aminoethyl)pyridine-3-thiol 11 from last step was dissolved in ammonia and air was bubbled into the reaction solution until LC-MS indicated no 2-(2-aminoethyl)pyridine-3-thiol existed. The reaction mixture was concentrated and residue was used for the next step directly.

Step 12: $Boc_2O$ 0.56 g (3.4 mmol) was added to the solution of $Et_3N$ (0.48 mL, 2.55 mmol) and 2,2'-(3,3'-disulfanediylbis(pyridine-3,2-diyl))diethanamine 12 (0.85 mmol) in $CH_3OH$. The mixture was stirred for 1 h at room temperature. Then, the reaction mixture was diluted with water, extracted with EA. The organic layer was washed with brine and concentrated. The residue was purified by column chromatography with EA as eluent and 0.48 g white solid 13 was obtained yield 93%. ESI-MS: 507.7 [M+H]. ¹HNMR (400 MHz, CDCl$_3$): 8.40 (m, 2H), 7.77 (m, 2H), 7.13 (m, 2H), 3.62 (m, 4H), 3.13 (m, 4H), 1.43 (s, 18H).

Example 21

Preparation of Di-tert-butyl 3,3'-(3,3'-disulfanediyl-bis(pyridine-3,2-diyl))bis(propane-3,1-diyl)dicarbamate

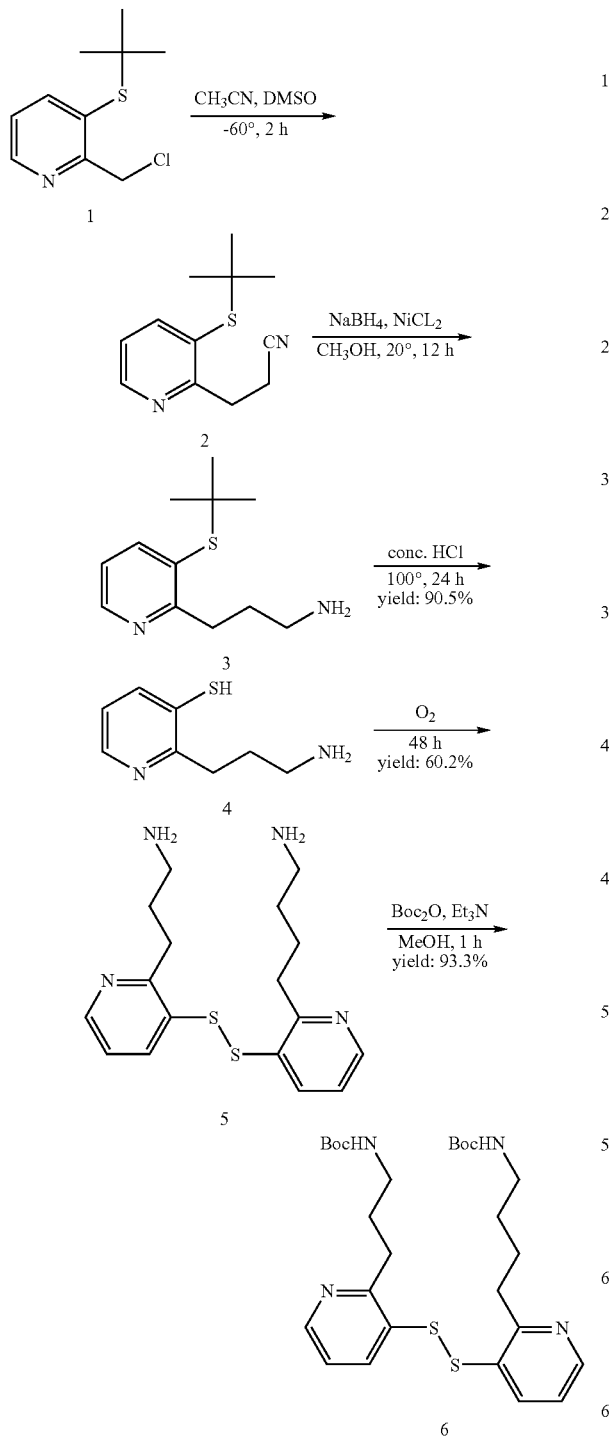

Step 1: n-BuLi (5.6 mL, 13.9 mmol) was added to CH$_3$CN (7.2 mL, 139 mmol) in THF at −60° C., dropwise, The mixture was stirred for 4 hours at this temperature, then 3-(tert-butylthio)-2-(chloromethyl)pyridine 1 (3.0 g, 13.9 mmol) was added, stirred for another 2 hours and quenched with water at this temperature. Then, the reaction mixture was extracted with EA from water. The organic layer was washed with brine, concentrated and the residue was purified by column chromatography with PE:EA=5:1 as eluent, 0.8 g oil was obtained, yield 26%.

Step 2: NaBH$_4$ (0.18 g, 4.8 mmol) was added to the suspension of NiCl$_2$ (0.13 g, 0.96 mmol) and 3-(3-(tert-butylthio)pyridin-2-yl)propanenitrile 2 (0.1 g, 0.48 mmol) in CH$_3$OH (15 mL) portion-wise. Then, the reaction mixture was stirred at room temperature overnight and extracted with EA from water. The organic layer was washed with brine and concentrated. 0.05 g oil was obtained, yield 50.5%

Step 3: 3-(3-(tert-butylthio)pyridin-2-yl)propylamine 3 was dissolved in conc. HCl, heated to reflux for 24 hours until LC-MS indicated no starting material existed. The reaction mixture was concentrated, used for the next step directly.

Step 4: The crude product from last step was dissolved in ammonia, air was bubbled in until LC-MS indicated no 2-(3-aminopropyl)pyridine-3-thiol 4 existed, concentrated, used for the next step directly.

Step 5: Boc$_2$O (0.56 g, 3.4 mmol) was added to the solution of Et$_3$N (0.48 mL, 2.55 mmol) and 4-(3-((2-(3-aminopropyl)pyridin-3-yl)disulfanyl)pyridin-2-yl)butan-1-amine 5 (0.85 mmol) in CH$_3$OH, the mixture was stirred for 1 hour at room temperature. Then, the reaction mixture was diluted with water and extracted with EA. The organic layer was washed with brine, concentrated and the residue was purified by column chromatography with EA as eluent, 0.48 g white solid 6 was obtained, yield 93%. ESI-MS: 579.6 [M+H]. ¹HNMR (400 MHz, CDCl$_3$): 8.40 (m, 2H), 7.78 (m, 2H), 7.14 (m, 2H), 4.86 (s, 2H), 3.19 (m, 4H), 2.98 (m, 4H), 1.94 (m, 4H), 1.47 (s, 18H).

Example 22

Preparation of 3,3'-disulfanediyldipyridin-2-amine

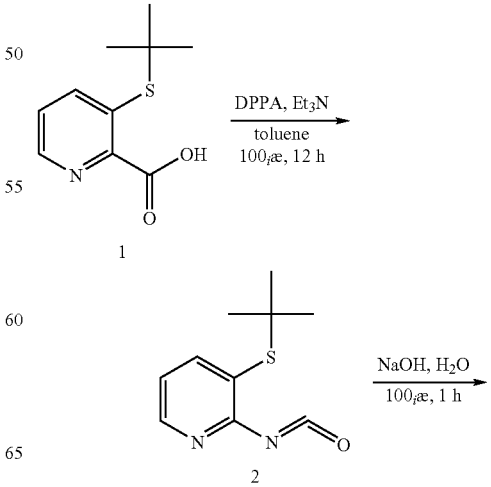

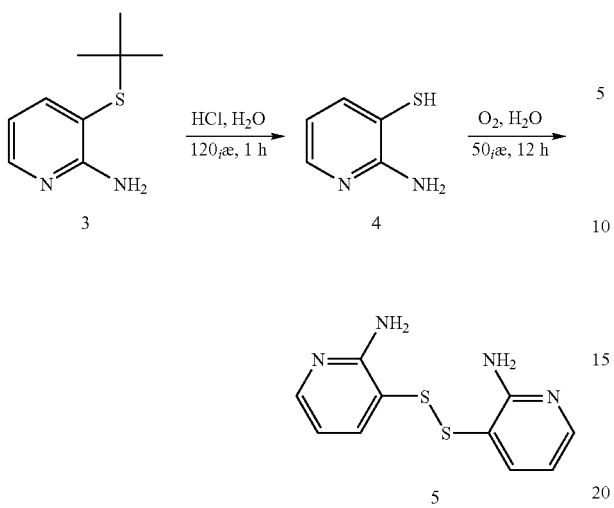

Step 1: A mixture of 3-(tert-butylthio)picolinic acid 1 (10 g, 47 mmol), DPPA (12 mL, 56.4 mmol), Et₃N (7.9 mL, 56.4 mmol) and toluene (300 mL) was stirred overnight at 100° C. TLC indicated no starting material existed and the reaction mixture was used for the next step directly.

Step 2: To the toluene solution from last step, aqueous NaOH was added, the mixture was heated to reflux for 2 hours, cooled to room temperature, extracted with EA from water, the organic layer was washed with brine, concentrated and the residue was purified by column chromatography with PE:EA=5:1 as eluent, 3.8 g solid was obtained, yield 44%.

Step 3: 3-(tert-butylthio)pyridin-2-amine 3 (360 mg, 2 mmol) was dissolved in concentrate HCl, heated to reflux for 24 hours until LC-MS indicated no 3-(tert-butylthio)pyridin-2-amine 3 existed. The reaction mixture was concentrated and the residue was used for the next step directly.

Step 4: The crude product 4 from last step was dissolved in ammonia, air was bubbled in until LC-MS indicated no starting material existed. The solution was filtered, 170 mg 3,3'-disulfanediyldipyridin-2-amine 5 as a slight yellow solid was obtained, yield 68%. ESI-MS: 251.2 [M+H]. ¹HNMR (400 MHz, CDCl₃): 8.08 (m, 2H), 7.34 (m, 2H), 6.53 (m, 2H), 5.23 (s, 6H).

Example 23

Preparation of Di-tert-butyl 2,2'-(3,3'-disulfanediyl-bis(pyridine-3,2-diyl)bis(methylene))bis(sulfanediyl) bis(ethane-2,1-diyl)dicarbamate

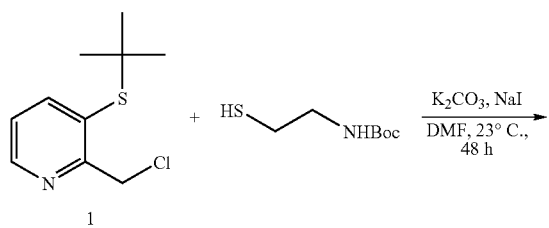

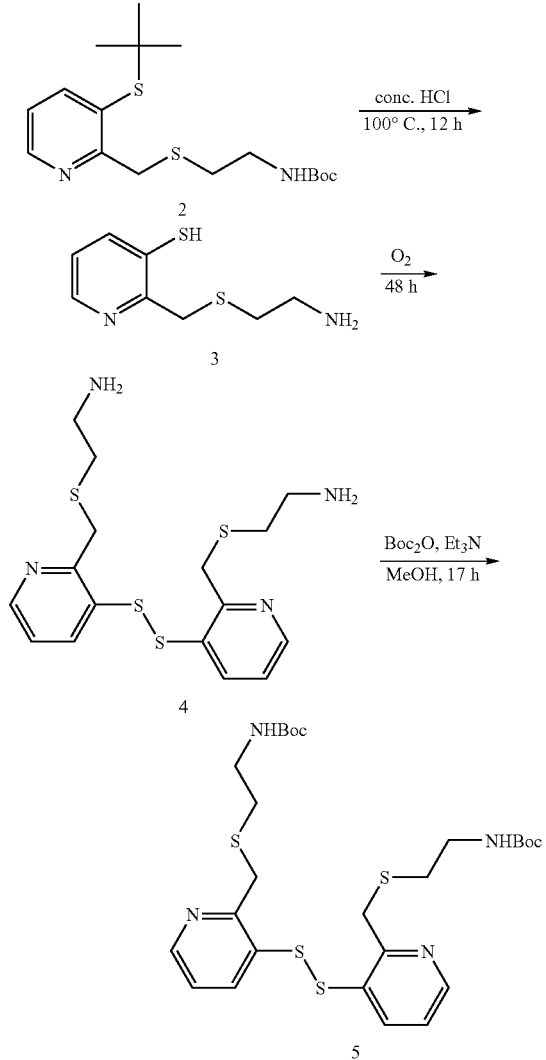

Step 1: A mixture of 3-(tert-butylthio)-2-(chloromethyl)pyridine 1 (0.8 g, 4.1 mmol) (obtained from example 20 step 7), N-Boc-aminoethanethiol (3.46 mL, 20.5 mmol), NaI (0.15 g, 1.0 mmol) and DMF (15 mL) was stirred at room temperature for 1 hour. Then, the reaction mixture was extracted with EA from sat. aq. Na₂CO₃. The organic layer was washed with brine, concentrated and the residue was purified by column chromatography with PE:EA=2:1 as eluent, 1.39 g of tert-butyl 2-((3-(tert-butylthio)pyridin-2-yl)methylthio)ethylcarbamate 2 was obtained as a slight oil, yield 95.5%.

Step 2: tert-butyl-2-((3-(tert-butylthio)pyridin-2-yl)methylthio)ethylcarbamate 2 was dissolved in concentrated HCl, heated to reflux for 24 hours until LC-MS indicated no starting material existed. The reaction mixture was concentrated, and slight yellow solid 2-((2-aminoethylthio)methyl)pyridine-3-thiol 3 was obtained, which was used for the next step directly.

Step 3: The crude 2-((2-aminoethylthio)methyl)pyridine-3-thiol 3 was dissolved in ammonia and air was bubbled in until LC-MS indicated no starting material existed. The reaction mixture was concentrated, and slight yellow solid 2,2'-(3,3'-disulfanediylbis(pyridine-3,2-diyl)bis(methylene))bis(sulfanediyl)diethanamine 4 was obtained, which was used for the next step directly.

Step 4: Boc₂O (0.56 g, 3.4 mmol) was added to the solution of Et₃N (0.48 mL, 2.55 mmol) and 2,2'-(3,3'-disulfanediylbis(pyridine-3,2-diyl)bis(methylene))bis(sulfanediyl) diethanamine 4 (0.85 mmol) in CH₃OH. The mixture was stirred for 1 h at room temperature, diluted with water and extracted with EA. The organic layer was washed with brine, concentrated and the residue was purified by column chromatography with EA as eluent, 0.48 g yellow solid di-tert-butyl 2,2'-(3,3'-disulfanediyl)bis(pyridine-3,2-diyl)bis(methylene))bis(sulfanediyl)bis(ethane-2,1-diyl)dicarbamate 5 was obtained, yield 93%. ESI-MS: 600.06 [M+H]. ¹HNMR (400 MHz, CDCl₃): 8.36 (s, 2H), 7.92 (m, 2H), 7.18 (m, 2H), 5.12 (s, 2H), 3.98 (s, 4H), 3.30 (s, 4H), 2.64 (s, 4H), 1.42 (s, 18H).

Example 24

Preparation of Di-tert-butyl 3,3'-(3,3'-disulfanediyl-bis(pyridine-3,2-diyl)bis(methylene))bis(sulfanediyl)dipyrrolidine-1-carboxylate

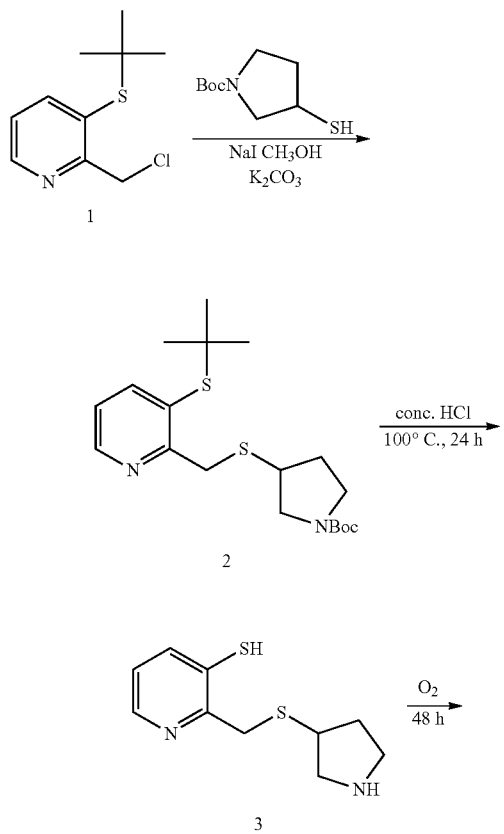

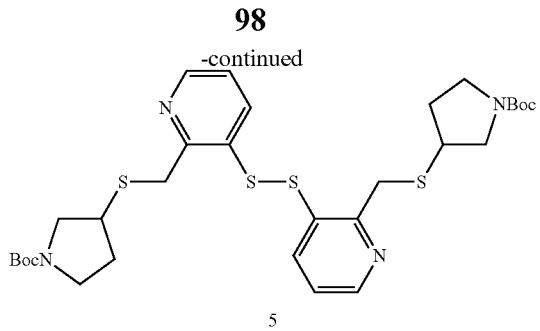

Step 1: A mixture of 3-(tert-butylthio)-2-(chloromethyl)pyridine 1 (0.8 g, 4.1 mmol), N-Boc-aminoethanethiol (3.46 mL, 20.5 mmol), NaI (0.15 g, 1.0 mmol) and DMF (15 mL) was stirred at room temperature for 1 h. Then, the reaction mixture was extracted with EA from sat. aq. Na₂CO₃. The organic layer was washed with brine, concentrated and the residue was purified by column chromatography with PE:EA=2:1 as eluent, 1.39 g oil was obtained, yield 96%.

Step 2: tert-butyl-3-((3-(tert-butylthio)pyridin-2-yl)methylthio)pyrrolidine-1-carboxylate 2 was dissolved in concentrate HCl, heated to reflux for 24 hours until LC-MS indicated no starting material existed. The reaction mixture was concentrated, used for the next step directly.

Step 3: The crude product from last step was dissolved in ammonia, air was bubbled into it, until LC-MS indicated no 2-((pyrrolidin-3-ylthio)methyl)pyridine-3-thiol 3 existed. The reaction mixture was concentrated, used for the next step directly.

Step 4: Boc₂O (0.56 g, 3.4 mmol) was added to the solution of Et₃N (0.48 mL, 2.55 mmol) and 1,2-bis(2-((pyrrolidin-3-ylthio)methyl)pyridin-3-yl)disulfane 4 (0.85 mmol) in CH₃OH and the mixture was stirred for 1 h at room temperature. Then, the reaction mixture was diluted with water, extracted with EA. The organic layer was washed with brine, concentrated and the residue was purified by column chromatography with EA as eluent, 0.48 g of di-tert-butyl-3,3'-(3,3'-disulfanediylbis(pyridine-3,2-diyl)bis(methylene))bis(sulfanediyl)dipyrrolidine-carboxylate 5 was obtained as a white solid, yield 93%. ESI-MS: 652.0 [M+H]. ¹HNMR (400 MHz, CDCl₃): 8.36 (s, 2H), 7.91 (m, 2H), 7.19 (m, 2H), 3.98 (s, 4H), 3.60 (m, 2H), 3.640 (m, 2H), 3.30 (s, 4H), 3.10 (m, 2H), 2.15 (m, 2H), 1.83 (m, 2H), 1.43 (s, 18H).

Example 25

Preparation of di-tert-butyl 2,2'-(3,3'-disulfanediylbis(pyridine-3,2-diyl)bis(methylene))bis(sulfanediyl)bis(ethane-2,1-diyl)bis(methylcarbamate)

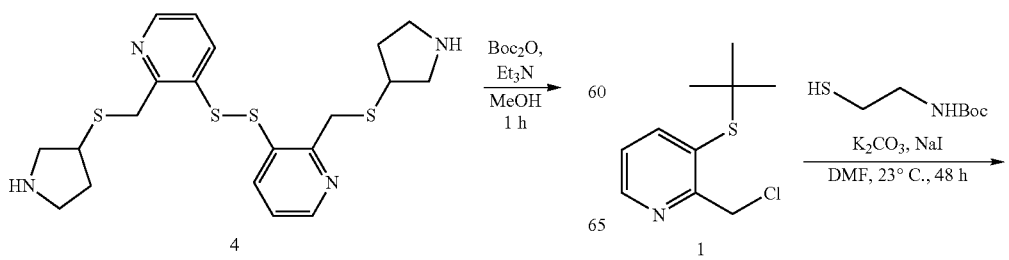

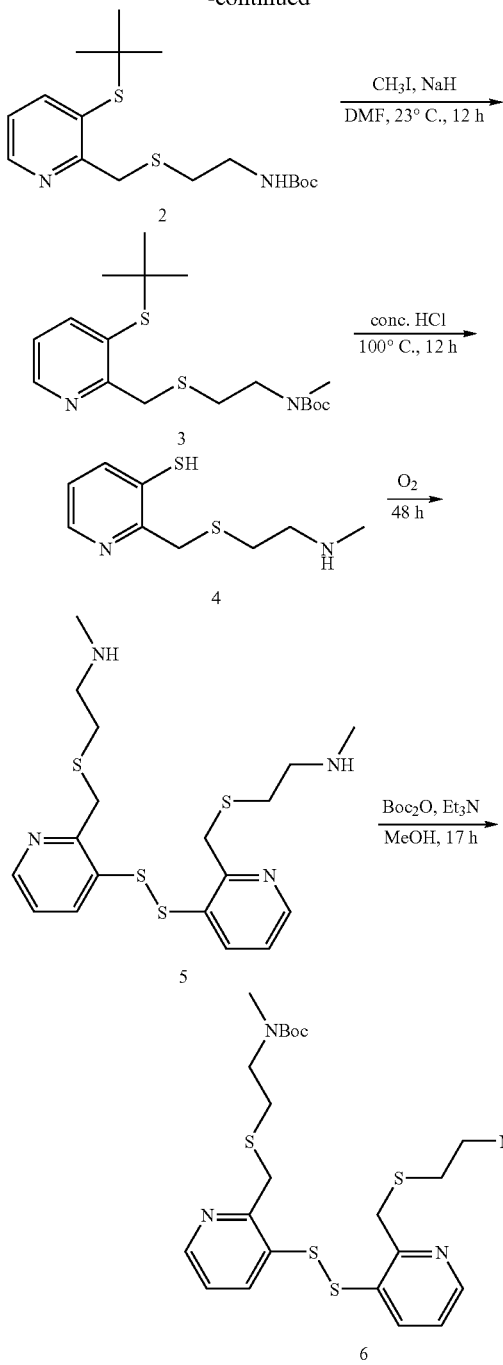

mixture was extracted with EA from water, the organic layer was washed with brine, concentrated and the residue was purified by column chromatography with P.E:EA=2:1 as eluent, 2.27 g of tert-butyl 243-(tert-butylthio)pyridin-2-yl)methylthio)ethyl(methyl)carbamate 3 was obtained as a slight oil, yield 76%.

Step 3: tert-butyl-2-(3-(tert-butylthio)pyridin-2-yl)methylthio)ethyl(methyl)carbamate 3 was dissolved in concentrate HCl, heated to reflux for 24 hours until LC-MS indicated no tert-butyl-2-((3-(tert-butylthio)pyridin-2-yl)methylthio)ethyl(methyl)carbamate 3 existed. The reaction mixture was concentrated and residue was used for the next step directly.

Step 4: The crude product from last step was dissolved in ammonia, air was bubbled into the reaction solution until LC-MS indicated no 2-((2-(methylamino)ethylthio)methyl)pyridine-3-thiol 4 existed. The reaction mixture was concentrated, used for the next step directly.

Step 5: $Boc_2O$ (0.56 g, 3.4 mmol) was added to the solution of $Et_3N$ (0.48 mL, 2.55 mmol) and 2,2'-(3,3'-disulfanediylbis(pyridine-3,2-diyl)bis(methylene))bis(sulfanediyl)bis(N-methylethanamine) 5 (0.85 mmol) in $CH_3OH$, the mixture was stirred for 1 h at room temperature. The reaction mixture was diluted with water, extracted with EA, the organic layer was washed with brine, concentrated and the residue was purified by column chromatography with EA as eluent. 0.48 g of 2,2'-(3,3'-disulfanediylbis(pyridine-3,2-diyl)bis(methylene))bis(sulfanediyl)bis(ethane-2,1-diyl)bis(methylcarbamate) 6 was obtained as a yellow solid, yield 93%. ESI-MS: 628.1 [M+H]. $^1HNMR$. (400 MHz, $CDCl_3$): 8.36 (s, 2H), 7.94 (m, 2H), 7.21 (m, 2H), 4.11 (s, 4H), 3.36 (s, 4H), 2.84 (s, 6H), 2.66 (s, 4H), 1.45 (s, 18H).

Example 26

Preparation of Di-tert-butyl-3,3'-disulfanediylbis(pyridine-3,2-diyl)bis(methylene)dicarbamate

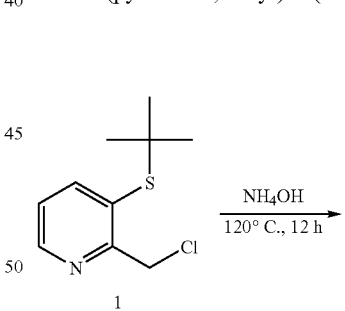

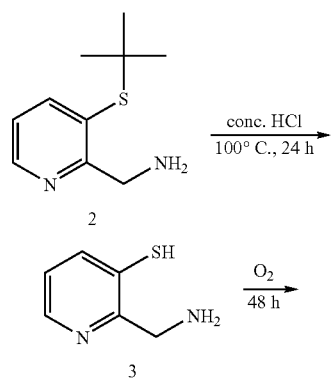

Step 1: A mixture of 3-(tert-butylthio)-2-(chloromethyl)pyridine 1 (0.8 g, 4.1 mmol), N-Boc aminoethanethiol (3.46 mL, 20.5 mmol), NaI (0.15 g, 1.0 mmol) and DMF (15 mL) was stirred at room temperature for 1 h. Then, the reaction mixture was extracted with EA from sat. aq. $Na_2CO_3$. The organic layer was washed with brine, concentrated and the residue was purified by column chromatography with P.E:EA=2:1 as eluent, 1.39 g oil was obtained, yield 96%.

Step 2: NaH (0.65 g, 16.2 mmol) was added to the solution of tert-butyl 2-((3-(tert-butylthio)pyridin-2-yl)methylthio)ethylcarbamate 2 (2.9 g, 8.1 mmol) in THF, stirred for 0.5 hour, then $CH_3I$ (0.56 mL, 8.9 mmol) was added. The mixture was stirred at room temperature overnight. Then, the reaction -continued

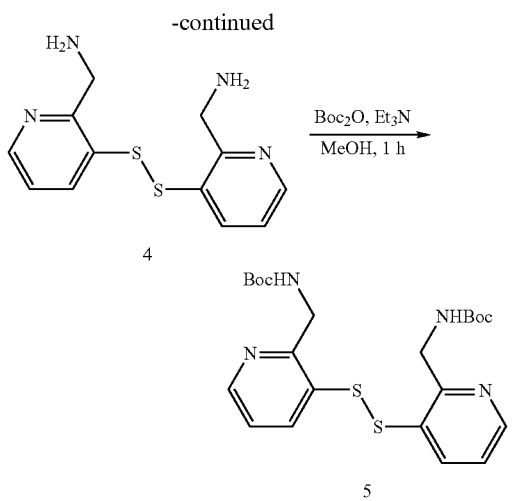

Step 1: A mixture of 3-(tert-butylthio)-2-(chloromethyl) pyridine 1 (0.8 g, 4.1 mmol) and ammonia (410 mmol) was heated to 120° C. in a sealed tube for 2 hours. The reaction mixture was concentrated, used for the next step directly.

Step 2: (3-(tert-butylthio)pyridin-2-yl)methanamine 2 was dissolved in conc. HCl, heated to reflux for 24 hours until LC-MS indicated no starting material existed. The reaction mixture was concentrated, used for the next step directly.

Step 3: The crude product 2-(aminomethyl)pyridine-3-thiol 3 from step 2 was dissolved in ammonia, air was bubbled into it until LC-MS indicated no starting material existed, concentrated, used for next step directly.

Step 4: Boc$_2$O (0.56 g, 3.4 mmol) was added to the solution of Et$_3$N (0.48 mL, 2.55 mmol) and 3,3'-disulfanediyl)bis (pyridine-3,2-diyl)dimethanamine 4 (0.85 mmol) in CH$_3$OH, the mixture was stirred for 1 hour at room temperature. The reaction mixture was diluted with water, extracted with EA. The organic layer was washed with brine, concentrated and the residue was purified by column chromatography with EA as eluent, 0.48 g di-tert-butyl-3,3'-disulfanediyl)bis(pyridine-3,2-diyl)bis(methylene)dicarbamate 5 was obtained as a slight yellow solid, yield 93%. ESI-MS: 479.6 [M+H].
$^1$HNMR (400 MHz, CDCl$_3$): 8.43 (m, 2H), 7.80 (m, 2H), 7.18 (m, 2H), 5.98 (s, 2H), 4.58 (s, 4H), 1.49 (s, 18H).

Example 27

Preparation of (6R,7S,Z)-7-(2-(2-amino-5-chlorothiazol-4-yl)-2-(hydroxyimino)acetamido)-8-oxo-3-(pyridin-4-ylthio)-1-aza-bicyclo[4.2.0]oct-2-ene-2-carboxylic Acid

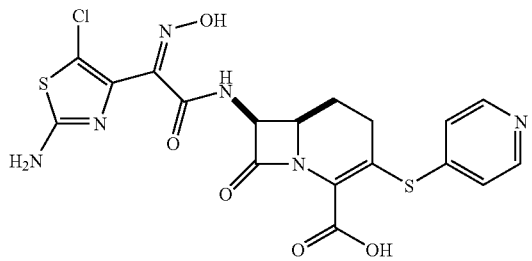

Step 1: (6R,7S,Z)-benzhydryl-7-(2-(5-chloro-2-(tritylamino)thiazol-4-yl)-2-(trityloxyimino)acetamido)-8-oxo-3-(pyridin-4-ylthio)-1-aza-bicyclo[4.2.0]oct-2-ene-2-carboxylate was prepared from (6R,7S,Z)-benzhydryl-7-(2-(5-chloro-2-(tritylamino)thiazol-4-yl)-2-(trityloxyimino) acetamido)-8-oxo-3-(trifluoromethylsulfonyloxy)-1-aza-bicyclo[4.2.0]oct-2-ene-2-carboxylate as a slight yellow solid by following Method D. The resulting product was purified by column chromatography (eluting solvent: PE:EA=3:1) in 91% yield.

Step 2: (6R,7S,Z)-7-(2-(2-amino-5-chlorothiazol-4-yl)-2-(hydroxyimino)acetamido)-8-oxo-3-(pyridin-4-ylthio)-1-aza-bicyclo[4.2.0]oct-2-ene-2-carboxylic acid 1 was prepared from (6R,7S,Z)-benzhydryl-7-(2-(5-chloro-2-(tritylamino)thiazol-4-yl)-2-(trityloxyimino)acetamido)-8-oxo-3-(pyridin-4-ylthio)-1-aza-bicyclo[4.2.0]oct-2-ene-2-carboxylate as a slight yellow solid in 63.5% yield by following Method E. ESI-MS: m/z 495.8 [M+H].

Example 28

Preparation of (6R,7S,Z)-7-(2-(2-amino-5-chlorothiazol-4-yl)-2-(hydroxyimino)acetamido)-3-(2-aminopyridin-3-ylthio)-8-oxo-1-aza-bicyclo[4.2.0] oct-2-ene-2-carboxylic Acid

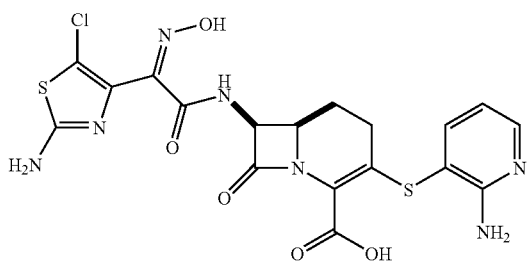

Step 1: (6R,7S,Z)-benzhydryl-3-(2-aminopyridin-3-ylthio)-7-(2-(5-chloro-2-(tritylamino)thiazol-4-yl)-2-(trityloxyimino)acetamido)-8-oxo-1-aza-bicyclo[4.2.0]oct-2-ene-2-carboxylate was prepared from (6R,7S,Z)-benzhydryl-3-(2-aminopyridin-3-ylthio)-7-(2-(5-chloro-2-(tritylamino)thiazol-4-yl)-2-(trityloxyimino)acetamido)-8-oxo-1-aza-bicyclo[4.2.0]oct-2-ene-2-carboxylate by following Method D. The resulting product (slight yellow powder) was purified by column chromatography (eluting solvent: PE:EA=4:1) in 30% yield.

Step 2: (6R,7S,Z)-7-(2-(2-amino-5-chlorothiazol-4-yl)-2-(hydroxyimino)acetamido)-3-(2-aminopyridin-3-ylthio)-8-oxo-1-aza-bicyclo[4.2.0]oct-2-ene-2-carboxylic acid 1 was prepared from (6R,7S,Z)-benzhydryl-3-(2-aminopyridin-3-ylthio)-7-(2-(5-chloro-2-(tritylamino)thiazol-4-yl)-2-(trityloxyimino)acetamido)-8-oxo-1-aza-bicyclo[4.2.0]oct-2- ene-2-carboxylate as a slight yellow solid in 40.5% yield by following Method E. ESI-MS: m/z 511.8 [M+H].

Example 29

Preparation of (6R,7S,Z)-7-(2-(2-amino-5-chlorothiazol-4-yl)-2-(hydroxyimino)acetamido)-3-(2-((2-(methylamino)ethylthio)methyl)pyridin-3-ylthio)-8-oxo-1-aza-bicyclo[4.2.0]oct-2-ene-2-carboxylic acid

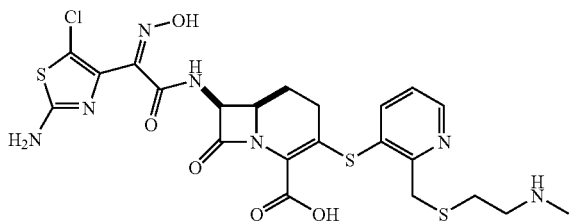

Step 1: (6R,7S,Z)-benzhydryl-7-(2-(5-chloro-2-(tritylamino)thiazol-4-yl)-2-(trityloxyimino)acetamido)-3-(2-((2-(methylamino)ethylthio)methyl)pyridin-3-ylthio)-8-oxo-1-aza-bicyclo[4.2.0]oct-2-ene-2-carboxylate was prepared from (6R,7S,Z)-benzhydryl-7-(2-(5-chloro-2-(tritylamino)thiazol-4-yl)-2-(trityloxyimino)acetamido)-8-oxo-3-(trifluoromethylsulfonyloxy)-1-aza-bicyclo[4.2.0]oct-2-ene-2-carboxylate by following Method D. The resulting product was purified by column chromatography (eluting solvent: PE:EA=4:1) and a white solid was obtained in 64% yield.

Step 2: (6R,7S,Z)-7-(2-(2-amino-5-chlorothiazol-4-yl)-2-(hydroxyimino)acetamido)-3-(2-((2-(methylamino)ethylthio)methyl)pyridin-3-ylthio)-8-oxo-1-aza-bicyclo[4.2.0]oct-2-ene-2-carboxylic acid 1 was prepared from (6R,7S,Z)-benzhydryl-7-(2-(5-chloro-2-(tritylamino)thiazol-4-yl)-2-(trityloxyimino)acetamido)-3-(2-((2-(methylamino)ethylthio)methyl)pyridin-3-ylthio)-8-oxo-1-aza-bicyclo[4.2.0]oct-2-ene-2-carboxylate as a slight yellow solid in 57% yield by following Method E. ESI-MS: m/z 599.9 [M+H].

Example 30

Preparation of (6R,7S,Z)-7-(2-(2-amino-5-chlorothiazol-4-yl)-2-(hydroxyimino)acetamido)-8-oxo-3-(2-((pyrrolidin-3-ylthio)methyl)pyridin-3-ylthio)-1-aza-bicyclo[4.2.0]oct-2-ene-2-carboxylic acid

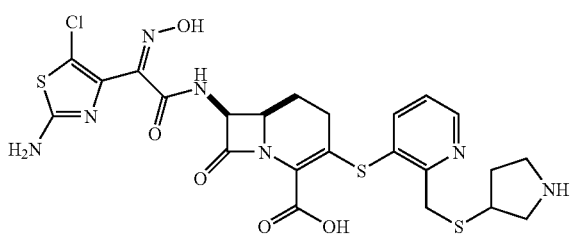

Step 1: (6R,7S,Z)-benzhydryl-7-(2-(5-chloro-2-(tritylamino)thiazol-4-yl)-2-(trityloxyimino)acetamido)-8-oxo-3-(2-((pyrrolidin-3-ylthio)methyl)pyridin-3-ylthio)-1-aza-bicyclo[4.2.0]oct-2-ene-2-carboxylate was prepared from (6R,7S,Z)-benzhydryl-7-(2-(5-chloro-2-(tritylamino)thiazol-4-yl)-2-(trityloxyimino)acetamido)-8-oxo-3-(trifluoromethylsulfonyloxy)-1-aza-bicyclo[4.2.0]oct-2-ene-2-carboxylate by following Method D. The resulting product was purified by column chromatography (eluting solvent: PE:EA=5:2) and a white solid was obtained in 42% yield.

Step 2: (6R,7S,Z)-7-(2-(2-amino-5-chlorothiazol-4-yl)-2-(hydroxyimino)acetamido)-8-oxo-3-(2-((pyrrolidin-3-ylthio)methyl)pyridin-3-ylthio)-1-aza-bicyclo[4.2.0]oct-2-ene-2-carboxylic acid 1 was prepared from (6R,7S,Z)-benzhydryl-7-(2-(5-chloro-2-(tritylamino)thiazol-4-yl)-2-(trityloxyimino)acetamido)-8-oxo-3-(2-((pyrrolidin-3-ylthio)methyl)pyridin-3-ylthio)-1-aza-bicyclo[4.2.0]oct-2-ene-2-carboxylate as a slight yellow solid in 31% yield by following Method E. ESI-MS: m/z 611.8 [M+H].

Example 31

Preparation of (6R,7S,Z)-7-(2-(2-amino-5-chlorothiazol-4-yl)-2-(hydroxyimino)acetamido)-3-(2-(aminomethyl)pyridin-3-ylthio)-8-oxo-1-aza-bicyclo[4.2.0]oct-2-ene-2-carboxylic Acid

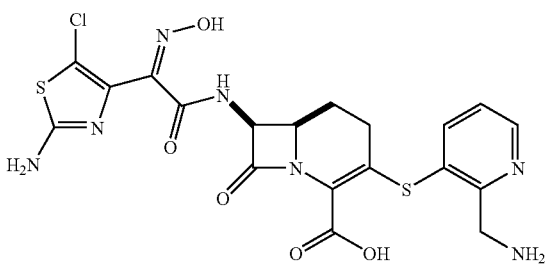

Step 1: (6R,7S,Z)-benzhydryl-3-(2-(aminomethyl)pyridin-3-ylthio)-7-(2-(5-chloro-2-(tritylamino)thiazol-4-yl)-2-(trityloxyimino)acetamido)-8-oxo-1-aza-bicyclo[4.2.0]oct-2-ene-2-carboxylate was prepared from (6R,7S,Z)-benzhydryl-7-(2-(5-chloro-2-(tritylamino)thiazol-4-yl)-2-(trityloxyimino)acetamido)-8-oxo-3-(trifluoromethylsulfonyloxy)-1-aza-bicyclo[4.2.0]oct-2-ene-2-carboxylate by following Method D. The resulting product was purified by column chromatography (eluting solvent: PE:EA=3:1) and a slight yellow solid was obtained in 43% yield.

Step 2: (6R,7S,Z)-7-(2-(2-amino-5-chlorothiazol-4-yl)-2-(hydroxyimino)acetamido)-3-(2-(aminomethyl)pyridin-3-ylthio)-8-oxo-1-aza-bicyclo[4.2.0]oct-2-ene-2-carboxylic acid 1 was prepared from (6R,7S,Z)-benzhydryl-3-(2-(aminomethyl)pyridin-3-ylthio)-7-(2-(5-chloro-2-(tritylamino)thiazol-4-yl)-2-(trityloxyimino)acetamido)-8-oxo-1-aza-bicyclo[4.2.0]oct-2-ene-2-carboxylate as as light yellow solid in 51% yield by following Method E. ESI-MS: m/z 524.8 [M+H].

Example 32

Synthesis of (6R,7S,Z)-7-(2-(2-amino-5-chlorothiazol-4-yl)-2-(hydroxyimino)acetamido)-3-(2-(2-aminoethyl)pyridin-3-ylthio)-8-oxo-1-aza-bicyclo[4.2.0]oct-2-ene-2-carboxylic Acid

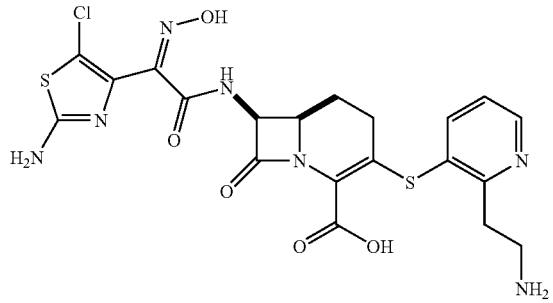

Step 1: (6R,7S,Z)-benzhydryl-3-(2-(2-aminoethyl)pyridin-3-ylthio)-7-(2-(5-chloro-2-(tritylamino)thiazol-4-yl)-2-(trityloxyimino)acetamido)-8-oxo-1-aza-bicyclo[4.2.0]oct-2-ene-2-carboxylate was prepared from (6R,7S,Z)-benzhydryl-7-(2-(5-chloro-2-(tritylamino)thiazol-4-yl)-2-(trityloxyimino)acetamido)-8-oxo-3-(trifluoromethylsulfonyloxy)-1-aza-bicyclo[4.2.0]oct-2-ene-2-carboxylate by following Method D. The resulting product was purified by column chromatography (eluting solvent: PE:EA=3:2) and a slight yellow solid was obtained in 47% yield.

Step 2: (6R,7S,Z)-7-(2-(2-amino-5-chlorothiazol-4-yl)-2-(hydroxyimino)acetamido)-3-(2-(2-aminoethyl)pyridin-3-ylthio)-8-oxo-1-aza-bicyclo[4.2.0]oct-2-ene-2-carboxylic acid 1 was prepared from (6R,7S,Z)-benzhydryl-3-(2-(2-aminoethyl)pyridin-3-ylthio)-7-(2-(5-chloro-2-(tritylamino)thiazol-4-yl)-2-(trityloxyimino)acetamido)-8-oxo-1-aza-bicyclo[4.2.0]oct-2-ene-2-carboxylate as a slight yellow solid in 20% yield by following Method E. ESI-MS: m/z 537.9 [M+H].

Example 33

Synthesis of (6R,7S,Z)-7-(2-(2-amino-5-chlorothiazol-4-yl)-2-(hydroxyimino)acetamido)-3-(4,5-dimethylthiazol-2-ylthio)-8-oxo-1-aza-bicyclo[4.2.0]oct-2-ene-2-carboxylic Acid

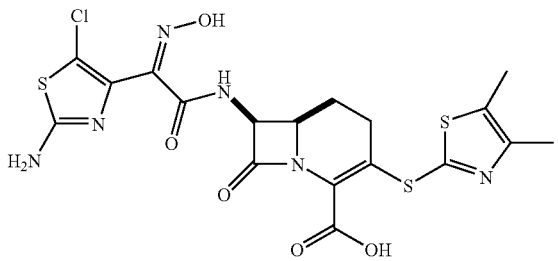

Step 1: (6R,7S,Z)-benzhydryl-7-(2-(5-chloro-2-(tritylamino)thiazol-4-yl)-2-(trityloxyimino)acetamido)-3-(4,5-dimethylthiazol-2-ylthio)-8-oxo-1-aza-bicyclo[4.2.0]oct-2-ene-2-carboxylate was prepared from (6R,7S,Z)-benzhydryl-7-(2-(5-chloro-2-(tritylamino)thiazol-4-yl)-2-(trityloxyimino)acetamido)-8-oxo-3-(trifluoromethylsulfonyloxy)-1-aza-bicyclo[4.2.0]oct-2-ene-2-carboxylate by following Method D. The resulting product was purified by column chromatography (eluting solvent: PE:EA=2:1) and desired compound as a white solid was obtained in 93% yield.

Step 2: (6R,7S,Z)-7-(2-(2-amino-5-chlorothiazol-4-yl)-2-(hydroxyimino)acetamido)-3-(4,5-dimethylthiazol-2-ylthio)-8-oxo-1-aza-bicyclo[4.2.0]oct-2-ene-2-carboxylic acid 1 was prepared from (6R,7S,Z)-benzhydryl-7-(2-(5-chloro-2-(tritylamino)thiazol-4-yl)-2-(trityloxyimino)acetamido)-3-(4,5-dimethylthiazol-2-ylthio)-8-oxo-1-aza-bicyclo[4.2.0]oct-2-ene-2-carboxylate as a slight yellow solid in 20% yield by following Method E. ESI-MS: m/z 530.8 [M+H].

Example 34

Synthesis of (6R,7S,Z)-7-(2-(2-amino-5-chlorothiazol-4-yl)-2-(hydroxyimino)acetamido)-8-oxo-3-(pyridin-3-ylthio)-1-aza-bicyclo[4.2.0]oct-2-ene-2-carboxylic Acid

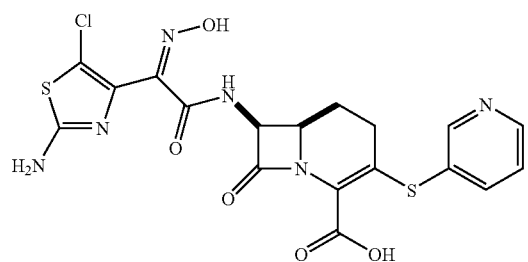

Step 1: (6R,7S,Z)-benzhydryl-7-(2-(5-chloro-2-(tritylamino)thiazol-4-yl)-2-(trityloxyimino)acetamido)-8-oxo-3-(pyridin-3-ylthio)-1-aza-bicyclo[4.2.0]oct-2-ene-2-carboxylate was prepared from (6R,7S,Z)-benzhydryl-7-(2-(5-chloro-2-(tritylamino)thiazol-4-yl)-2-(trityloxyimino)acetamido)-8-oxo-3-(trifluoromethylsulfonyloxy)-1-aza-bicyclo[4.2.0]oct-2-ene-2-carboxylate by following Method D. The resulting product was purified by column chromatography (eluting solvent: PE:EA=3:1) and desired compound as a slight yellow solid was obtained in 46% yield.

Step 2: (6R,7S,Z)-7-(2-(2-amino-5-chlorothiazol-4-yl)-2-(hydroxyimino)acetamido)-8-oxo-3-(pyridin-3-ylthio)-1-aza-bicyclo[4.2.0]oct-2-ene-2-carboxylic acid 1 was prepared from (6R,7S,Z)-benzhydryl-7-(2-(5-chloro-2-(tritylamino)thiazol-4-yl)-2-(trityloxyimino)acetamido)-8-oxo-3-(pyridin-3-ylthio)-1-aza-bicyclo[4.2.0]oct-2-ene-2- carboxylate as a slight yellow solid in 31% yield by following Method E. ESI-MS: m/z 495.9 [M+H].

Example 35

Synthesis of (6R,7S,Z)-7-(2-(2-amino-5-chlorothiazol-4-yl)-2-(hydroxyimino)acetamido)-8-oxo-3-(thiazol-4-ylthio)-1-aza-bicyclo[4.2.0]oct-2-ene-2-carboxylic Acid

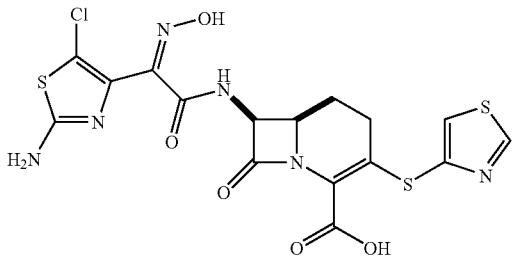

Step 1: (6R,7S,Z)-benzhydryl-7-(2-(5-chloro-2-(tritylamino)thiazol-4-yl)-2-(trityloxyimino)acetamido)-8-oxo-3-(thiazol-4-ylthio)-1-aza-bicyclo[4.2.0]oct-2-ene-2-carboxylate was prepared from (6R,7S,Z)-benzhydryl-7-(2-(5-chloro-2-(tritylamino)thiazol-4-yl)-2-(trityloxyimino)acetamido)-8-oxo-3-(trifluoromethylsulfonyloxy)-1-aza-bicyclo[4.2.0]oct-2-ene-2-carboxylate by following Method D. The resulting product was purified by column chromatography (eluting solvent: PE:EA=5:2) and desired compound as a white solid was obtained in 65% yield.

Step 2: (6R,7S,Z)-7-(2-(2-amino-5-chlorothiazol-4-yl)-2-(hydroxyimino)acetamido)-8-oxo-3-(thiazol-4-ylthio)-1-aza-bicyclo[4.2.0]oct-2-ene-2-carboxylic acid 1 was prepared from (6R,7S,Z)-benzhydryl-7-(2-(5-chloro-2-(tritylamino)thiazol-4-yl)-2-(trityloxyimino)acetamido)-8-oxo-3-(thiazol-4-ylthio)-1-aza-bicyclo[4.2.0]oct-2-ene-2-carboxylate as a white solid in 36% yield by following Method E. ESI-MS: m/z 500.8 [M+H].

Example 36

Preparation of (6R,7S,Z)-methyl 7-(2-(5-amino-1,2,4-thiadiazol-3-yl)-2-(hydroxyimino)acetamido)-3-(3-(3-(2-aminoethylthio)methyl)pyridin-4-ylthio)-8-oxo-1-aza-bicyclo[4.2.0]oct-2-ene-2-carboxylate

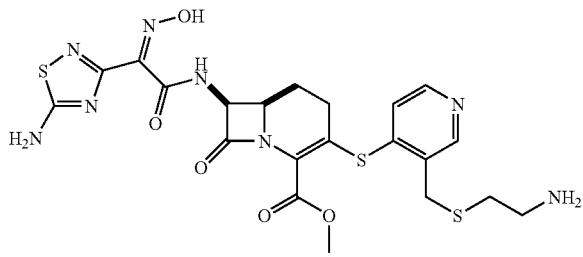

Step 1: (6R,7S,Z)-methyl-7-(2-(5-amino-1,2,4-thiadiazol-3-yl)-2-(trityloxyimino)acetamido)-8-oxo-3-(trifluoromethylsulfonyloxy)-1-aza-bicyclo[4.2.0]oct-2-ene-2-carboxylate was prepared from (6R,7S,Z)-7-(2-(5-amino-1,2,4-thiadiazol-3-yl)-2-(trityloxyimino)acetamido)-8-oxo-3-(trifluoromethylsulfonyloxy)-1-aza-bicyclo[4.2.0]oct-2-ene-2-carboxylic acid by following Method F in 28% yield. A light yellow solid was obtained.

Step 2: (6R,7S,Z)-methyl-7-(2-(5-amino-1,2,4-thiadiazol-3-yl)-2-(trityloxyimino)acetamido)-3-(3-((2-(tert-butoxycarbonylamino)ethylthio)methyl)pyridin-4-ylthio)-8-oxo-1-aza-bicyclo[4.2.0]oct-2-ene-2-carboxylate was prepared from (6R,7S,Z)-methyl-7-(2-(5-amino-1,2,4-thiadiazol-3-yl)-2-(trityloxyimino)acetamido)-8-oxo-3-(trifluoromethylsulfonyloxy)-1-aza-bicyclo[4.2.0]oct-2-ene-2-carboxylate using Method D in 71% yield. A yellow colored solid was obtained.

Step 3: (6R,7S,Z)-methyl-7-(2-(5-amino-1,2,4-thiadiazol-3-yl)-2-(hydroxyimino)acetamido)-3-(3-((2-aminoethylthio)methyl)pyridin-4-ylthio)-8-oxo-1-aza-bicyclo[4.2.0]oct-2-ene-2-carboxylate 1 was prepared from (6R,7S,Z)-methyl-7-(2-(5-amino-1,2,4-thiadiazol-3-yl)-2-(trityloxyimino)acetamido)-3-(3-((2-(tert-butoxycarbonylamino)ethylthio)methyl)pyridin-4-ylthio)-8-oxo-1-aza-bicyclo[4.2.0]oct-2-ene-2-carboxylate using Method E in 21% yield. A yellow colored solid was obtained as the desired product. ESMS: m/z 565.1 [M+H].

Example 37

Preparation of (6R,7S,Z)-7-(2-(2-amino-5-chlorothiazol-4-yl)-2-(methoxyimino)acetamido)-8-oxo-3-(pyridin-4-ylthio)-1-aza-bicyclo[4.2.0]oct-2-ene-2-carboxylic Acid

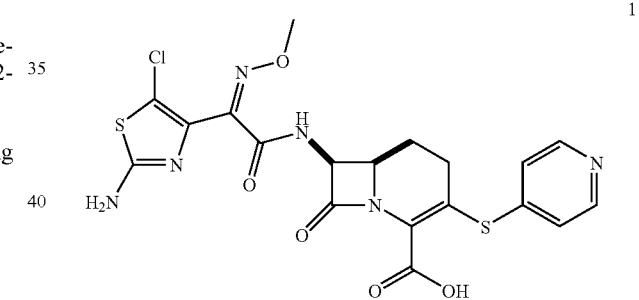

Step 1: (6R,7S,Z)-benzhydryl-7-(2-(2-amino-5-chlorothiazol-4-yl)-2-(methylimino)acetamido)-8-oxo-3-(pyridin-4-ylthio)-1-aza-bicyclo[4.2.0]oct-2-ene-2-carboxylate was prepared from (6R,7S,Z)-benzhydryl-7-(2-(2-amino-5-chlorothiazol-4-yl)-2-(methoxyimino)acetamido)-8-oxo-3-(trifluoromethylsulfonyloxy)-1-aza-bicyclo[4.2.0]oct-2-ene-2-carboxylate with pyridine-4-thiol according to Method D. The resulting product was purified by column chromatography (eluting solvent: PE:EA=3:2) in 35% yield Step 2: (6R,7S,Z)-7-(2-(2-amino-5-chlorothiazol-4-yl)-2-(methoxyimino)acetamido)-8-oxo-3-(pyridin-4-ylthio)-1-aza-bicyclo[4.2.0]oct-2-ene-2-carboxylic acid 1 was prepared from (6R,7S,Z)-benzhydryl-7-(2-(2-amino-5-chlorothiazol-4-yl)-2-(methylimino)acetamido)-8-oxo-3-(pyridin-4-ylthio)-1-aza-bicyclo[4.2.0]oct-2-ene-2-carboxylate by following Method E. The crude product was purified by preparative HPLC to furnish (6R,7S,Z)-7-(2-(2-amino-5-chlorothiazol-4-yl)-2-(methoxyimino)acetamido)-8-oxo-3-(pyridin-4-ylthio)-1-aza-bicyclo[4.2.0]oct-2-ene-2-carboxylic acid (as a light yellow solid) in 28% yield. ESI-MS: m/z 509.9 [M+H].

Example 38

Preparation of (6R,7S,Z)-7-(2-(2-amino-5-chlorothiazol-4-yl)-2-(methoxyimino)acetamido)-3-(4,5-dimethylthiazol-2-ylthio)-8-oxo-1-aza-bicyclo[4.2.0]oct-2-ene-2-carboxylic Acid

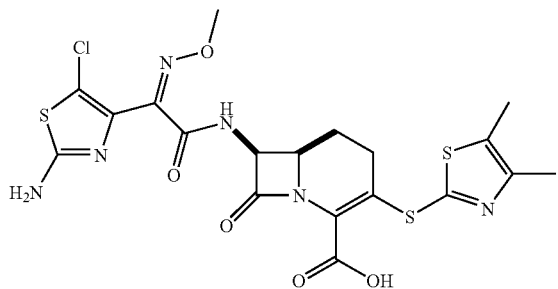

Step 1: (6R,7S,Z)-benzhydryl-7-(2-(2-amino-5-chlorothiazol-4-yl)-2-(methoxyimino)acetamido)-3-(4,5-dimethylthiazol-2-ylthio)-8-oxo-1-aza-bicyclo[4.2.0]oct-2-ene-2-carboxylate was prepared from (6R,7S,Z)-benzhydryl-7-(2-(2-amino-5-chlorothiazol-4-yl)-2-(methoxyimino)acetamido)-8-oxo-3-(trifluoromethylsulfonyloxy)-1-aza-bicyclo[4.2.0]oct-2-ene-2-carboxylate with 4,5-dimethylthiazole-2-thiol according to Method D. The resulting product (white powder) was purified by column chromatography (eluting solvent: PE:EA=3:2) in 39% yield Step 2: (6R,7S,Z)-7-(2-(2-amino-5-chlorothiazol-4-yl)-2-(methoxyimino)acetamido)-3-(4,5-dimethylthiazol-2-ylthio)-8-oxo-1-aza-bicyclo[4.2.0]oct-2-ene-2-carboxylic acid was prepared from (6R,7S,Z)-benzhydryl-7-(2-(2-amino-5-chlorothiazol-4-yl)-2-(methoxyimino)acetamido)-3-(4,5-dimethylthiazol-2-ylthio)-8-oxo-1-aza-bicyclo[4.2.0]oct-2-ene-2-carboxylate by following Method D. The crude product was purified by preparative HPLC to furnish (6R,7S,Z)-7-(2-(2-amino-5-chlorothiazol-4-yl)-2-(methoxyimino)acetamido)-3-(4,5-dimethylthiazol-2-ylthio)-8-oxo-1-aza-bicyclo[4.2.0]oct-2-ene-2-carboxylic acid 1 (white powder) in 25% yield. ESI-MS: m/z 543.2 [M+H].

Example 39

Preparation of (6R,7S,Z)-7-(2-(2-amino-5-chlorothiazol-4-yl)-2-(methoxyimino)acetamido)-3-(2-(2-aminoethyl)pyridin-3-ylthio)-8-oxo-1-aza-bicyclo[4.2.0]oct-2-ene-2-carboxylic Acid

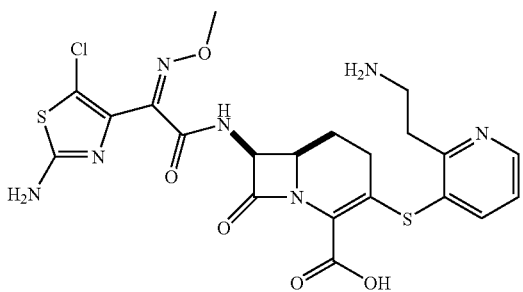

Step 1: Tert-butyl 2-(3-mercaptopyridin-2-yl)ethylcarbamate was prepared from di-tert-butyl-2,2'-(3,3'-disulfanediylbis(pyridine-3,2-diyl))bis(ethane-2,1-diyl)dicarbamate by following Method G. This product was used without further purification.

Step 2: (6R,7S,Z)-benzhydryl-3-(2-(2-(tert-butoxycarbonylamino)ethyl)pyridin-3-ylthio)-7-(2-(5-chloro-2-(tritylamino)thiazol-4-yl)-2-(methoxyimino)acetamido)-8-oxo-1-aza-bicyclo[4.2.0]oct-2-ene-2-carboxylate was prepared from (6R,7S,Z)-benzhydryl-7-(2-(5-chloro-2-(tritylamino)thiazol-4-yl)-2-(trityloxyimino)acetamido)-8-oxo-3-(trifluoromethylsulfonyloxy)-1-aza-bicyclo[4.2.0]oct-2-ene-2-carboxylate with tert-butyl 2-(3-mercaptopyridin-2-yl)ethylcarbamate according to Method G. The resulting product (white powder) was purified by column chromatography (eluting solvent PE:EA=3:2) in 39% yield Step 3: (6R,7S,Z)-7-(2-(2-amino-5-chlorothiazol-4-yl)-2-(methoxyimino)acetamido)-3-(2-(2-aminoethyl)pyridin-3-ylthio)-8-oxo-1-aza-bicyclo[4.2.0]oct-2-ene-2-carboxylic acid was prepared from (6R,7S,Z)-benzhydryl 3-(2-(2-(tert-butoxycarbonylamino)ethyl)pyridin-3-ylthio)-7-(2-(5-chloro-2-(tritylamino)thiazol-4-yl)-2-(methoxyimino)acetamido)-8-oxo-1-aza-bicyclo[4.2.0]oct-2-ene-2-carboxylate according to Method E. The crude product was purified by preparative HPLC to furnish (6R,7S,Z)-7-(2-(2-amino-5-chlorothiazol-4-yl)-2-(methoxyimino)acetamido)-3-(2-(2-aminoethyl)pyridin-3-ylthio)-8-oxo-1-aza-bicyclo[4.2.0]oct-2-ene-2-carboxylic acid 1 (white powder) in 25% yield. ESI-MS: m/z 552.8 [M+H].

Example 40

Preparation of (6R,7S)-7-(2-(2-amino-5-chlorothiazol-4-yl)-2-(methoxyimino)acetamido)-3-(2-aminopyridin-3-ylthio)-8-oxo-1-aza-bicyclo[4.2.0]oct-2-ene-2-carboxylic acid

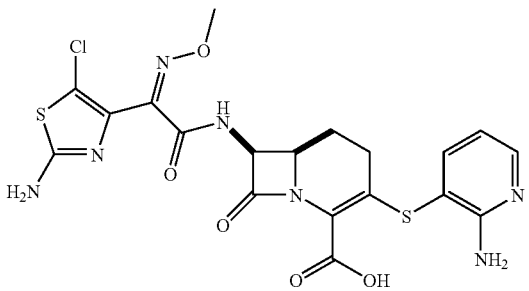

Step 1: 2-aminopyridine-3-thiol was prepared from 3,3'-disulfanediyldipyridin-2-amine by following Method G in 98% yield. This product was used without further purification.

Step 2: (6R,7S)-benzhydryl-7-(2-(2-amino-5-chlorothiazol-4-yl)-2-(methoxyimino)acetamido)-3-(2-aminopyridin-3-ylthio)-8-oxo-1-aza-bicyclo[4.2.0]oct-2-ene-2-carboxylate was prepared from (6R,7S,Z)-benzhydryl-7-(2-(2-amino-5-chlorothiazol-4-yl)-2-(methoxyimino)acetamido)-8-oxo-3-(trifluoromethylsulfonyloxy)-1-aza-bicyclo[4.2.0]oct-2-ene-2-carboxylate with 2-aminopyridine-3-thiol according to Method G. The resulting product (white powder) was purified by column chromatography (eluting solvent: PE:EA=3:2) in 39% yield Step 3: (6R,7S)-7-(2-(2-amino-5-chlorothiazol-4-yl)-2-(methoxyimino)acetamido)-3-(2-aminopyridin-3-ylthio)-8-oxo-1-aza-bicyclo[4.2.0]oct-2-ene-2-carboxylic acid was prepared from (6R,7S)-benzhydryl-7-(2-(2-amino-5-chlorothiazol-4-yl)-2-(methoxyimino)acetamido)-3-(2-aminopyridin-3-ylthio)-8-oxo-1-aza-bicyclo[4.2.0]oct-2-ene-2-carboxylate according to Method G. The crude product was purified by preparative HPLC to furnish (6R,7S)-7-(2-(2- amino-5-chlorothiazol-4-yl)-2-(methoxyimino)acetamido)-3-(2-aminopyridin-3-ylthio)-8-oxo-1-aza-bicyclo[4.2.0]oct-2-ene-2-carboxylic acid 1 (white powder) in 29% yield. ESI-MS: m/z 524.8 [M+H].

[4.2.0]oct-2-ene-2-carboxylic acid 1 (white powder) in 22% yield. ESI-MS: m/z 612.9 [M+H].

Example 41

Preparation of (6R,7S,Z)-7-(2-(2-amino-5-chlorothiazol-4-yl)-2-(methoxyimino)acetamido)-3-(2-((2-(methylamino)ethylthio)methyl)pyridin-3-ylthio)-8-oxo-1-aza-bicyclo[4.2.0]oct-2-ene-2-carboxylic Acid

Example 42

Preparation of (6R,7S,Z)-7-(2-(2-amino-5-chlorothiazol-4-yl)-2-(methoxyimino)acetamido)-8-oxo-3-(2-((pyrrolidin-3-ylthio)methyl)pyridin-3-ylthio)-1-aza-bicyclo[4.2.0]oct-2-ene-2-carboxylic Acid

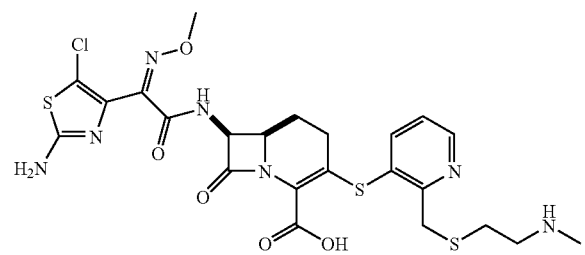

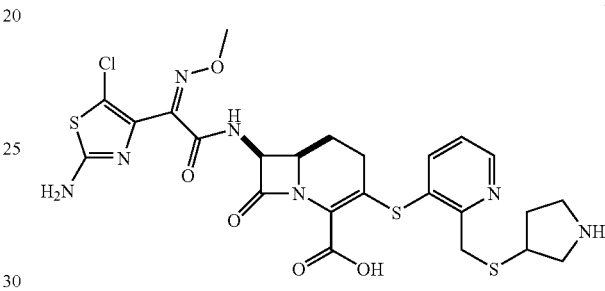

Step 1: tert-butyl-2-((3-mercaptopyridin-2-yl)methylthio)ethyl(methyl)carbamate was prepared from di-tert-butyl-2,2'-(3,3'-disulfanediylbis(pyridine-3,2-diyl)bis(methylene))bis(sulfanediyl)bis(ethane-2,1-diyl)bis(methylcarbamate) by following Method G in 99% yield. This product was used without further purification.

Step 2: (6R,7S,Z)-benzhydryl-7-(2-(2-amino-5-chlorothiazol-4-yl)-2-(methoxyimino)acetamido)-3-(2-((2-(tert-butoxycarbonyl(methyl)amino)ethylthio)methyl)pyridin-3-ylthio)-8-oxo-1-aza-bicyclo[4.2.0]oct-2-ene-2-carboxylate was prepared from (6R,7S,Z)-benzhydryl 7-(2-(2-amino-5-chlorothiazol-4-yl)-2-(methoxyimino)acetamido)-8-oxo-3-(trifluoromethylsulfonyloxy)-1-aza-bicyclo[4.2.0]oct-2-ene-2-carboxylate with tert-butyl 2-((3-mercaptopyridin-2-yl)methylthio)ethyl(methyl)carbamate according to Method G. The resulting product (white powder) was purified by column chromatography (eluting solvent: PE:EA=3:2) in 33% yield Step 3: (6R,7S,Z)-7-(2-(2-amino-5-chlorothiazol-4-yl)-2-(methoxyimino)acetamido)-3-(2-((2-(methylamino)ethylthio)methyl)pyridin-3-ylthio)-8-oxo-1-aza-bicyclo[4.2.0]oct-2-ene-2-carboxylic acid was prepared from (6R,7S,Z)-benzhydryl-7-(2-(2-amino-5-chlorothiazol-4-yl)-2-(methoxyimino)acetamido)-3-(2-((2-(tert-butoxycarbonyl(methyl)amino)ethylthio)methyl)pyridin-3-ylthio)-8-oxo-1-aza-bicyclo[4.2.0]oct-2-ene-2-carboxylate according to Method E. The crude product was purified by preparative HPLC to furnish (6R,7S,Z)-7-(2-(2-amino-5-chlorothiazol-4-yl)-2-(methoxyimino)acetamido)-3-(2-((2-(methylamino)ethylthio)methyl)pyridin-3-ylthio)-8-oxo-1-aza-bicyclo Step 1: tert-butyl-3-((3-mercaptopyridin-2-yl)methylthio)pyrrolidine-1-carboxylate was prepared from di-tert-butyl-3,3'-(3,3'-disulfanediyl)bis(pyridine-3,2-diyl)bis(methylene))bis(sulfanediyl)dipyrrolidine-1-carboxylate by following Method G. This product was used without further purification.

Step 2: (6R,7S,Z)-benzhydryl-7-(2-(2-amino-5-chlorothiazol-4-yl)-2-(methoxyimino)acetamido)-3-(2-((1-(tert-butoxycarbonyl)pyrrolidin-3-ylthio)methyl)pyridin-3-ylthio)-8-oxo-1-aza-bicyclo[4.2.0]oct-2-ene-2-carboxylate was prepared from (6R,7S,Z)-benzhydryl-7-(2-(2-amino-5-chlorothiazol-4-yl)-2-(methoxyimino)acetamido)-8-oxo-3-(trifluoromethylsulfonyloxy)-1-aza-bicyclo[4.2.0]oct-2-ene-2-carboxylate with tert-butyl-3-((3-mercaptopyridin-2-yl)methylthio)pyrrolidine-1-carboxylate according to Method G. The resulting product (white powder) was purified by column chromatography (eluting solvent: PE:EA=3:2) in 36% yield Step 3: (6R,7S,Z)-7-(2-(2-amino-5-chlorothiazol-4-yl)-2-(methoxyimino)acetamido)-8-oxo-3-(2-((pyrrolidin-3-ylthio)methyl)pyridin-3-ylthio)-1-aza-bicyclo[4.2.0]oct-2-ene-2-carboxylic acid was prepared from (6R,7S,Z)-benzhydryl 7-(2-(2-amino-5-chlorothiazol-4-yl)-2-(methoxyimino)acetamido)-3-(2-((1-(tert-butoxycarbonyl)pyrrolidin-3-ylthio)methyl)pyridin-3-ylthio)-8-oxo-1-aza-bicyclo[4.2.0]oct-2-ene-2-carboxylate according to Method E. The crude product was purified by preparative HPLC to furnish (6R,7S,Z)-7-(2-(2-amino-5-chlorothiazol-4-yl)-2-(methoxyimino)acetamido)-8-oxo-3-(2-((pyrrolidin-3- ylthio)methyl)pyridin-3-ylthio)-1-aza-bicyclo[4.2.0]oct-2-ene-2-carboxylic acid 1 (white powder) in 27% yield. ESI-MS: m/z 624.9 [M+H].

Example 43

Preparation of (6R,7S,Z)-7-(2-(2-amino-5-chlorothiazol-4-yl)-2-(methoxyimino)acetamido)-3-(2-(aminomethyl)pyridin-3-ylthio)-8-oxo-1-aza-bicyclo[4.2.0]oct-2-ene-2-carboxylic acid

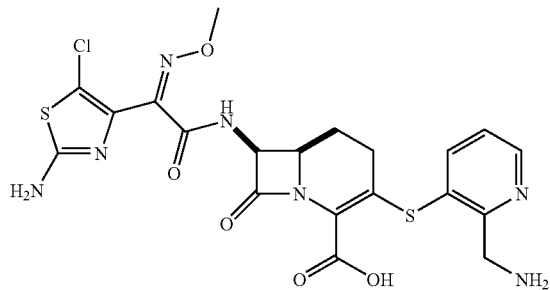

Step 1: tert-butyl-(3-mercaptopyridin-2-yl)methylcarbamate was prepared from di-tert-butyl-3,3'-disulfanediylbis(pyridine-3,2-diyl)bis(methylene)dicarbamate by following Method G. This product was used without further purification.

Step 2: (6R,7S,Z)-benzhydryl-7-(2-(2-amino-5-chlorothiazol-4-yl)-2-(methoxyimino)acetamido)-3-(2-((tert-butoxycarbonylamino)methyl)pyridin-3-ylthio)-8-oxo-1-aza-bicyclo[4.2.0]oct-2-ene-2-carboxylate was prepared from (6R,7S,Z)-benzhydryl 7-(2-(2-amino-5-chlorothiazol-4-yl)-2-(methoxyimino)acetamido)-8-oxo-3-(trifluoromethylsulfonyloxy)-1-aza-bicyclo[4.2.0]oct-2-ene-2-carboxylate with tert-butyl (3-mercaptopyridin-2-yl)methylcarbamate according to Method G. The resulting product (white powder) was purified by column chromatography (eluting solvent: PE:EA=1:1) in 35% yield Step 3: (6R,7S,Z)-7-(2-(2-amino-5-chlorothiazol-4-yl)-2-(methoxyimino)acetamido)-3-(2-(aminomethyl)pyridin-3-ylthio)-8-oxo-1-aza-bicyclo[4.2.0]oct-2-ene-2-carboxylic acid was prepared from (6R,7S,Z)-benzhydryl 7-(2-(2-amino-5-chlorothiazol-4-yl)-2-(methoxyimino)acetamido)-3-(2-((tert-butoxycarbonylamino)methyl)pyridin-3-ylthio)-8-oxo-1-aza-bicyclo[4.2.0]oct-2-ene-2-carboxylate according to Method E. The crude product was purified by preparative HPLC to furnish (6R,7S,Z)-7-(2-(2-amino-5-chlorothiazol-4-yl)-2-(methoxyimino)acetamido)-3-(2-(aminomethyl)pyridin-3-ylthio)-8-oxo-1-aza-bicyclo[4.2.0]oct-2-ene-2-carboxylic acid 1 (white powder) in 25% yield. ESI-MS: m/z 538.8 [M+H].

Example 44

Preparation of (6R,7S,Z)-7-(2-(5-amino-1,2,4-thiadiazol-3-yl)-2-(hydroxyimino)acetamido)-8-oxo-3-(pyridin-4-ylthio)-1-aza-bicyclo[4.2.0]oct-2-ene-2-carboxylic Acid

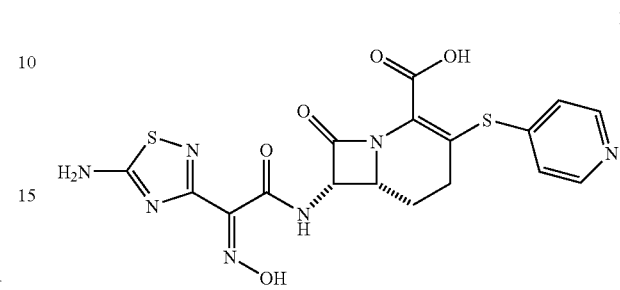

Step 1: (6R,7S,Z)-7-(2-(5-amino-1,2,4-thiadiazol-3-yl)-2-(methoxyimino)acetamido)-8-oxo-3-(trifluoromethylsulfonyloxy)-1-aza-bicyclo[4.2.0]oct-2-ene-2-carboxylic acid was prepared from (6R,7S)-7-amino-8-oxo-3-(trifluoromethylsulfonyloxy)-1-aza-bicyclo[4.2.0]oct-2-ene-2-carboxylic acid TFA salt with (Z)—S-benzo[d]thiazol-2-yl-2-(5-amino-1,2,4-thiadiazol-3-yl)-2-(methoxyimino) ethanethioate according to Method B in 90% yield. This product was used without further purification. A white solid was obtained.

Step 2: (6R,7S,Z)-benzhydryl-7-(2-(5-amino-1,2,4-thiadiazol-3-yl)-2-(methoxyimino)acetamido)-8-oxo-3-(trifluoromethylsulfonyloxy)-1-aza-bicyclo[4.2.0]oct-2-ene-2-carboxylate was prepared from (6R,7S,Z)-7-(2-(5-amino-1,2,4-thiadiazol-3-yl)-2-(methoxyimino)acetamido)-8-oxo-3-(trifluoromethylsulfonyloxy)-1-aza-bicyclo[4.2.0]oct-2-ene-2-carboxylic acid with (diazomethylene)dibenzene according to Method C in 96% yield. A white solid was obtained.

Step 3: (6R,7S,Z)-benzhydryl-7-(2-(5-amino-1,2,4-thiadiazol-3-yl)-2-(methoxyimino)acetamido)-8-oxo-3-(pyridin-4-ylthio)-1-aza-bicyclo[4.2.0]oct-2-ene-2-carboxylate was prepared from (6R,7S,Z)-benzhydryl-7-(2-(5-amino-1,2,4-thiadiazol-3-yl)-2-(methoxyimino)acetamido)-8-oxo-3-(trifluoromethylsulfonyloxy)-1-aza-bicyclo[4.2.0]oct-2-ene-2-carboxylate with pyridine-4-thiol according to Method D. The resulting product (white powder) was purified by column chromatography (eluting solvent: PE:EA=2:1) in 35% yield Step 4: (6R,7S,Z)-7-(2-(5-amino-1,2,4-thiadiazol-3-yl)-2-(methoxyimino)acetamido)-8-oxo-3-(pyridin-4-ylthio)-1-aza-bicyclo[4.2.0]oct-2-ene-2-carboxylic acid was prepared from (6R,7S,Z)-benzhydryl 7-(2-(5-amino-1,2,4-thiadiazol-3-yl)-2-(methoxyimino)acetamido)-8-oxo-3-(pyridin-4-ylthio)-1-aza-bicyclo[4.2.0]oct-2-ene-2-carboxylate by following Method E in 5 h. The crude product was purified by preparative HPLC to furnish (6R,7S,Z)-7-(2-(5-amino-1,2,4-thiadiazol-3-yl)-2-(methoxyimino)acetamido)-8-oxo-3-(pyridin-4-ylthio)-1-aza-bicyclo[4.2.0]oct-2-ene-2-carboxylic acid 1 (as a white solid) in 31% yield. ESI-MS: m/z 461.9 [M+H].

Example 45

Preparation of (6R,7S,Z)-7-(2-(5-amino-1,2,4-thiadiazol-3-yl)-2-(hydroxyimino)acetamido)-3-(5-amino-1,3,4-thiadiazol-2-ylthio)-8-oxo-1-aza-bicyclo[4.2.0]oct-2-ene-2-carboxylic Acid

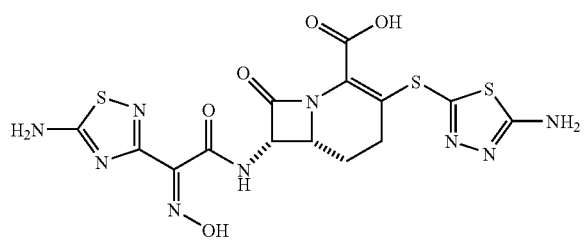

Step 1: (6R,7S,Z)-benzhydryl-7-(2-(5-amino-1,2,4-thiadiazol-3-yl)-2-(trityloxyimino)acetamido)-3-(5-amino-1,3,4-thiadiazol-2-ylthio)-8-oxo-1-aza-bicyclo[4.2.0]oct-2-ene-2-carboxylate was prepared from (6R,7S,Z)-benzhydryl 7-(2-(5-amino-1,2,4-thiadiazol-3-yl)-2-(trityloxyimino)acetamido)-8-oxo-3-(trifluoromethylsulfonyloxy)-1-aza-bicyclo[4.2.0]oct-2-ene-2-carboxylate with 5-amino-1,3,4-thiadiazole-2-thiol according to Method D. The resulting product was purified by column chromatography (eluting solvent: PE:EA=2:1) in 36% yield.

Step 2: (6R,7S,Z)-7-(2-(5-amino-1,2,4-thiadiazol-3-yl)-2-(hydroxyimino)acetamido)-3-(5-amino-1,3,4-thiadiazol-2-ylthio)-8-oxo-1-aza-bicyclo[4.2.0]oct-2-ene-2-carboxylic acid was prepared from (6R,7S,Z)-benzhydryl-7-(2-(5-amino-1,2,4-thiadiazol-3-yl)-2-(trityloxyimino)acetamido)-3-(5-amino-1,3,4-thiadiazol-2-ylthio)-8-oxo-1-aza-bicyclo[4.2.0]oct-2-ene-2-carboxylate by following Method D. The crude product was purified by preparative HPLC to furnish (6R,7S,Z)-7-(2-(5-amino-1,2,4-thiadiazol-3-yl)-2-(hydroxyimino)acetamido)-3-(5-amino-1,3,4-thiadiazol-2-ylthio)-8-oxo-1-aza-bicyclo[4.2.0]oct-2-ene-2-carboxylic acid 1 (as a white solid) in 33% yield. ESI-MS: m/z 483.8 [M+H].

Example 46

Preparation of (6R,7S,Z)-3-(1,3,4-thiadiazol-2-ylthio)-7-(2-(5-amino-1,2,4-thiadiazol-3-yl)-2-(hydroxyimino)acetamido)-8-oxo-1-aza-bicyclo[4.2.0]oct-2-ene-2-carboxylic Acid

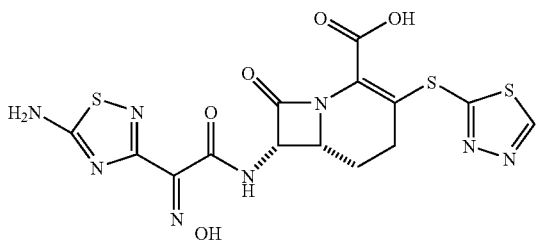

Step 1: (6R,7S,Z)-benzhydryl-3-(1,3,4-thiadiazol-2-ylthio)-7-(2-(5-amino-1,2,4-thiadiazol-3-yl)-2-(trityloxyimino)acetamido)-8-oxo-1-aza-bicyclo[4.2.0]oct-2-ene-2-carboxylate was prepared from (6R,7S,Z)-benzhydryl-7-(2-(5-amino-1,2,4-thiadiazol-3-yl)-2-(trityloxyimino)acetamido)-8-oxo-3-(trifluoromethylsulfonyloxy)-1-aza-bicyclo[4.2.0]oct-2-ene-2-carboxylate with 1,3,4-thiadiazole-2-thiol according to Method D. The resulting product was purified by column chromatography (eluting solvent: PE:EA=3:1) in 40% yield.

Step 2: (6R,7S,Z)-3-(1,3,4-thiadiazol-2-ylthio)-7-(2-(5-amino-1,2,4-thiadiazol-3-yl)-2-(hydroxyimino)acetamido)-8-oxo-1-aza-bicyclo[4.2.0]oct-2-ene-2-carboxylic acid was prepared from (6R,7S,Z)-benzhydryl 3-(1,3,4-thiadiazol-2-ylthio)-7-(2-(5-amino-1,2,4-thiadiazol-3-yl)-2-(trityloxyimino)acetamido)-8-oxo-1-aza-bicyclo[4.2.0]oct-2-ene-2-carboxylate by following Method E. The crude product was purified by preparative HPLC to furnish (6R,7S,Z)-3-(1,3,4-thiadiazol-2-ylthio)-7-(2-(5-amino-1,2,4-thiadiazol-3-yl)-2-(hydroxyimino)acetamido)-8-oxo-1-aza-bicyclo[4.2.0]oct-2-ene-2-carboxylic acid 1 (as a white solid) in 30% yield. ESI-MS: m/z 468.9 [M+H].

Example 47

Preparation of (6R,7S,Z)-7-(2-(5-amino-1,2,4-thiadiazol-3-yl)-2-(hydroxyimino)acetamido)-3-(2-((2-aminoethylthio)methyl)pyridin-3-ylthio)-8-oxo-1-aza-bicyclo[4.2.0]oct-2-ene-2-carboxylic Acid

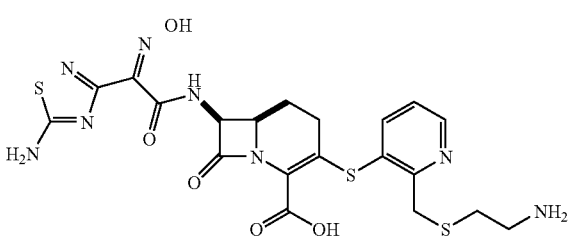

Step 1: tert-butyl-2-((3-mercaptopyridin-2-yl)methylthio) ethylcarbamate was prepared from di-tert-butyl-2,2'-(3,3'-disulfanediylbis(pyridine-3,2-diyl)bis(methylene))bis(sulfanediyl)bis(ethane-2,1-diyl)dicarbamate according to Method G. This product was used without further purification.

Step 2: (6R,7S,Z)-benzhydryl-7-(2-(5-amino-1,2,4-thiadiazol-3-yl)-2-(trityloxyimino)acetamido)-3-(2-((2-(tert-butoxycarbonylamino)ethylthio)methyl)pyridin-3-ylthio)-8-oxo-1-aza-bicyclo[4.2.0]oct-2-ene-2-carboxylate was prepared from (6R,7S,Z)-benzhydryl-7-(2-(5-amino-1,2,4-thiadiazol-3-yl)-2-(trityloxyimino)acetamido)-8-oxo-3-(trifluoromethylsulfonyloxy)-1-aza-bicyclo[4.2.0]oct-2-ene-2-carboxylate with tert-butyl 2-((3-mercaptopyridin-2-yl) methylthio)ethylcarbamate according to Method G. The resulting product was purified by column chromatography (eluting solvent: PE:EA=2:1) in 42% yield.

Step 3: (6R,7S,Z)-7-(2-(5-amino-1,2,4-thiadiazol-3-yl)-2-(hydroxyimino)acetamido)-3-(2-((2-aminoethylthio)methyl)pyridin-3-ylthio)-8-oxo-1-aza-bicyclo[4.2.0]oct-2-ene-2-carboxylic acid was prepared from (6R,7S,Z)-benzhydryl-7-(2-(5-amino-1,2,4-thiadiazol-3-yl)-2-(trityloxyimino)acetamido)-3-(2-((2-(tert-butoxycarbonylamino)ethylthio)methyl)pyridin-3-ylthio)-8-oxo-1-aza-bicyclo[4.2.0]oct-2-ene-2-carboxylate by following Method E. The crude product was purified by preparative HPLC to furnish (6R,7S,Z)-7-(2-(5-amino-1,2,4-thiadiazol-3-yl)-2-(hydroxyimino)acetamido)-3-(2-((2-aminoethylthio)methyl)pyridin-3-ylthio)-8-oxo-1-aza-bicyclo[4.2.0]oct-2-ene-2-carboxylic acid 1 (as a white solid) in 37% yield. ESI-MS: m/z 550.9 [M+H]. $^1$HNMR (400 MHz, DMSO-d6): 11.91 (s, 1H), 9.19 (m, 1H), 8.03 (s, 2H), 7.95 (brs, H), 7.80 (d, 5.6 Hz, 1H), 7.35 (m, 1H), 5.46 (m, 1H), 4.00 (s, 2H), 3.86 (m, 1H), 3.02 (m, 2H), 2.72 (m, 2H), 2.12 (m, 2H), 1.64 (m, 2H).

Example 48

Preparation of (6R,7S,Z)-7-(2-(5-amino-1,2,4-thiadiazol-3-yl)-2-(hydroxyimino)acetamido)-3-(3-((2-aminoethylthio)methyl)pyridin-4-ylthio)-8-oxo-1-aza-bicyclo[4.2.0]oct-2-ene-2-carboxylic Acid 1

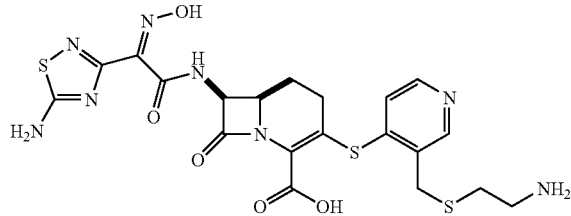

Step 1: (6R,7S,Z)-benzhydryl-7-(2-(5-amino-1,2,4-thiadiazol-3-yl)-2-(trityloxyimino)acetamido)-3-(3-((2-(tert-butoxycarbonylamino)ethylthio)methyl)pyridin-4-ylthio)-8-oxo-1-aza-bicyclo[4.2.0]oct-2-ene-2-carboxylate was prepared from (6R,7S,Z)-benzhydryl-7-(2-(5-amino-1,2,4-thiadiazol-3-yl)-2-(trityloxyimino)acetamido)-8-oxo-3-(trifluoromethyl sulfonyloxy)-1-aza-bicyclo[4.2.0]oct-2-ene-2-carboxylate with tert-butyl 2-((4-mercaptopyridin-3-yl)methylthio)ethylcarbamate according to Method D. The resulting product was purified by column chromatography (eluting solvent: DCM:EA=2:1) in 42% yield.

Step 2: (6R,7S,Z)-7-(2-(5-amino-1,2,4-thiadiazol-3-yl)-2-(hydroxyimino)acetamido)-3-(3-((2-aminoethylthio)methyl)pyridin-4-ylthio)-8-oxo-1-aza-bicyclo[4.2.0]oct-2-ene-2-carboxylic acid was prepared from (6R,7S,Z)-benzhydryl-7-(2-(5-amino-1,2,4-thiadiazol-3-yl)-2-(trityloxyimino)acetamido)-3-(3-((2-(tert-butoxycarbonylamino)ethylthio)methyl)pyridin-4-ylthio)-8-oxo-1-aza-bicyclo[4.2.0]oct-2-ene-2-carboxylate by following Method E. The crude product was purified by preparative HPLC to furnish (6R,7S,Z)-7-(2-(5-amino-1,2,4-thiadiazol-3-yl)-2-(hydroxyimino)acetamido)-3-(3-((2-aminoethylthio)methyl)pyridin-4-ylthio)-8-oxo-1-aza-bicyclo[4.2.0]oct-2-ene-2-carboxylic acid 1 (as a white solid) in 43% yield. ESI-MS: m/z 550.9 [M+H]. $^1$HNMR (400 MHz, DMSO-d6): 11.90 (s, 1H), 9.20 (d, 5.6 Hz, 1H), 8.47 (s, 1H), 8.40 (d, 5.6 Hz, 1H), 8.06 (s, 2H), 7.82 (s, 2H), 7.19 (d, 1.2 Hz, 1H), 5.54 (m, 1H), 4.00 (m, 1H), 3.88 (m, 2H), 3.03 (m, 2H), 2.65 (m, 2H), 2.50 (m, 2H), 2.00 (m, 2H).

Example 49

Preparation of (6R,7S,Z)-7-(2-(5-amino-1,2,4-thiadiazol-3-yl)-2-(methoxyimino)acetamido)-3-(5-amino-1,3,4-thiadiazol-2-ylthio)-8-oxo-1-aza-bicyclo[4.2.0]oct-2-ene-2-carboxylic Acid 1

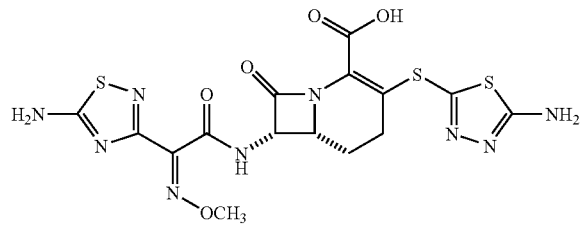

Step 1: (6R,7S,Z)-7-(2-(5-amino-1,2,4-thiadiazol-3-yl)-2-(methoxyimino)acetamido)-8-oxo-3-(trifluoromethylsulfonyloxy)-1-aza-bicyclo[4.2.0]oct-2-ene-2-carboxylic acid was prepared from (Z)—S-benzo[d]thiazol-2-yl 2-(5-amino-1,2,4-thiadiazol-3-yl)-2-(methoxyimino)ethanethioate and (6R,7S)-7-amino-8-oxo-3-(trifluoromethylsulfonyloxy)-1-aza-bicyclo[4.2.0]oct-2-ene-2-carboxylic acid in 100% yield by following Method B. The resulting white solid product was used without further purification.

Step 2: (6R,7S,Z)-benzhydryl-7-(2-(5-amino-1,2,4-thiadiazol-3-yl)-2-(methoxyimino)acetamido)-8-oxo-3-(trifluoromethylsulfonyloxy)-1-aza-bicyclo[4.2.0]oct-2-ene-2-carboxylate was prepared from (6R,7S,Z)-7-(2-(5-amino-1,2,4-thiadiazol-3-yl)-2-(methoxyimino)acetamido)-8-oxo-3-(trifluoromethylsulfonyloxy)-1-aza-bicyclo[4.2.0]oct-2-ene-2-carboxylic acid in 100% yield by following Method C. The resulting white solid product was used without further purification.

Step 3: (6R,7S,Z)-benzhydryl-7-(2-(5-amino-1,2,4-thiadiazol-3-yl)-2-(methoxyimino)acetamido)-3-(5-amino-1,3,4-thiadiazol-2-ylthio)-8-oxo-1-aza-bicyclo[4.2.0]oct-2-ene-2-carboxylate was prepared from (6R,7S,Z)-benzhydryl 7-(2-(5-amino-1,2,4-thiadiazol-3-yl)-2-(methoxyimino)acetamido)-8-oxo-3-(trifluoromethylsulfonyloxy)-1-aza-bicyclo[4.2.0]oct-2-ene-2-carboxylate and 5-amino-1,3,4-thiadiazole-2-thiol in 61% yield by following Method D. The resulting white solid product was purified by gel column chromatography (P.E/EA 2:1 as fluent).

Step 4: (6R,7S,Z)-7-(2-(5-amino-1,2,4-thiadiazol-3-yl)-2-(methoxyimino)acetamido)-3-(5-amino-1,3,4-thiadiazol-2-ylthio)-8-oxo-1-aza-bicyclo[4.2.0]oct-2-ene-2-carboxylic acid 1 was prepared from (6R,7S,Z)-benzhydryl 7-(2-(5-amino-1,2,4-thiadiazol-3-yl)-2-(methoxyimino)acetamido)-3-(5-amino-1,3,4-thiadiazol-2-ylthio)-8-oxo-1-aza-bicyclo[4.2.0]oct-2-ene-2-carboxylate in 33% yield by following Method E. ESI-MS: m/z 497.9 [M+H]

Example 50

Preparation of (6R,7S,Z)-3-(1,3,4-thiadiazol-2-ylthio)-7-(2-(5-amino-1,2,4-thiadiazol-3-yl)-2-(methoxyimino)acetamido)-8-oxo-1-aza-bicyclo[4.2.0]oct-2-ene-2-carboxylic Acid 1

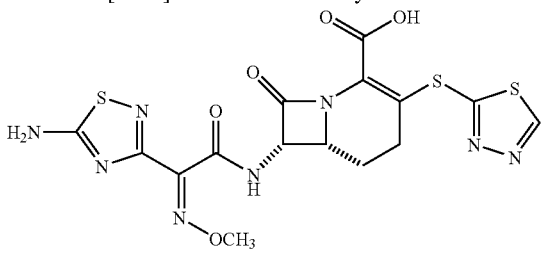

Step 1: (6R,7S,Z)-benzhydryl-3-(1,3,4-thiadiazol-2-ylthio)-7-(2-(5-amino-1,2,4-thiadiazol-3-yl)-2-(methoxyimino)acetamido)-8-oxo-1-aza-bicyclo[4.2.0]oct-2-ene-2-carboxylate was prepared from (6R,7S,Z)-benzhydryl-7-(2-(5-amino-1,2,4-thiadiazol-3-yl)-2-(methoxyimino)acetamido)-8-oxo-3-(trifluoromethylsulfonyloxy)-1-aza-bicyclo[4.2.0]oct-2-ene-2-carboxylate and 1,3,4-thiadiazole-2-thiol in 53% yield by following Method D. The resulting white solid product was purified by gel column chromatography (P.E/EA 4:1 as fluent).

Step 2: (6R,7S,Z)-3-(1,3,4-thiadiazol-2-ylthio)-7-(2-(5-amino-1,2,4-thiadiazol-3-yl)-2-(methoxyimino)acetamido)-8-oxo-1-aza-bicyclo[4.2.0]oct-2-ene-2-carboxylic acid 1 was prepared from (6R,7S,Z)-benzhydryl 3-(1,3,4-thiadiazol-2-ylthio)-7-(2-(5-amino-1,2,4-thiadiazol-3-yl)-2-(methoxyimino)acetamido)-8-oxo-1-aza-bicyclo[4.2.0]oct-2-ene-2-carboxylate in 31% yield by following Method E. The resulting white solid product was purified by Prep-HPLC. ESI-MS: m/z 482.9 [M+H]

Example 51

Preparation of (6R,7S,Z)-7-(2-(5-amino-1,2,4-thiadiazol-3-yl)-2-(methoxyimino)acetamido)-3-(2-((2-aminoethylthio)methyl)pyridin-3-ylthio)-8-oxo-1-aza-bicyclo[4.2.0]oct-2-ene-2-carboxylic Acid

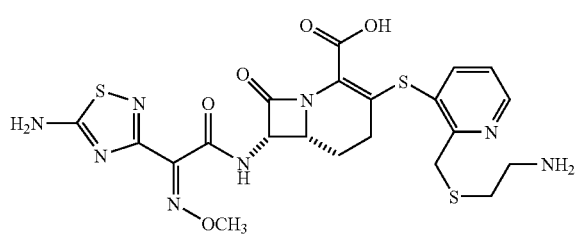

Step 1: tert-butyl-2-((3-mercaptopyridin-2-yl)methylthio)ethylcarbamate was prepared from di-tert-butyl-2,2'-(3,3'-disulfanediylbis(pyridine-3,2-diyl)bis(methylene))bis(sulfanediyl)bis(ethane-2,1-diyl)dicarbamate in 100% yield by following Method G. The slight yellow solution was used without further purification.

Step 2: (6R,7S,Z)-benzhydryl-7-(2-(5-amino-1,2,4-thiadiazol-3-yl)-2-(methoxyimino)acetamido)-3-(2-((2-(tert-butoxycarbonylamino)ethylthio)methyl)pyridin-3-ylthio)-8-oxo-1-aza-bicyclo[4.2.0]oct-2-ene-2-carboxylate was prepared from tert-butyl-2-((3-mercaptopyridin-2-yl)methylthio)ethylcarbamate and (6R,7S,Z)-benzhydryl 7-(2-(5-amino-1,2,4-thiadiazol-3-yl)-2-(methoxyimino)acetamido)-8-oxo-3-(trifluoromethylsulfonyloxy)-1-aza-bicyclo[4.2.0]oct-2-ene-2-carboxylate in 30% yield by following Method G. The resulting white solid product was purified by gel column chromatography (P.E/EA 3:1 as fluent).

Step 3: (6R,7S,Z)-7-(2-(5-amino-1,2,4-thiadiazol-3-yl)-2-(methoxyimino)acetamido)-3-(2-((2-aminoethylthio)methyl)pyridin-3-ylthio)-8-oxo-1-aza-bicyclo[4.2.0]oct-2-ene-2-carboxylic acid 1 was prepared from (6R,7S,Z)-benzhydryl 7-(2-(5-amino-1,2,4-thiadiazol-3-yl)-2-(methoxyimino)acetamido)-3-(2-((2-(tert-butoxycarbonylamino)ethylthio)methyl)pyridin-3-ylthio)-8-oxo-1-aza-bicycle[4.2.0]oct-2-ene-2-carboxylate in 50% yield by following Method E. The resulting white solid product was purified by Prep-HPLC. ESI-MS: m/z 565.0 [M+H]

Example 52

Preparation of (6R,7S,Z)-7-(2-(5-amino-1,2,4-thiadiazol-3-yl)-2-(methoxyimino) acetamido)-3-(3-((2-aminoethylthio)methyl)pyridin-4-ylthio)-8-oxo-1-aza-bicyclo[4.2.0]oct-2-ene-2-carboxylic acid

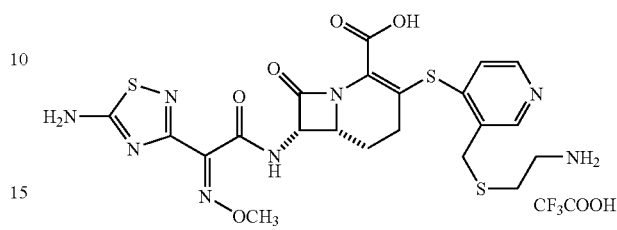

Step 1: (6R,7S,Z)-benzhydryl-7-(2-(5-amino-1,2,4-thiadiazol-3-yl)-2-(methoxyimino)acetamido)-3-(3-((2-(tert-butoxycarbonylamino)ethylthio)methyl)pyridin-4-ylthio)-8-oxo-1-aza-bicyclo[4.2.0]oct-2-ene-2-carboxylate was prepared from (6R,7S,Z)-benzhydryl-7-(2-(5-amino-1,2,4-thiadiazol-3-yl)-2-(methoxyimino)acetamido)-8-oxo-3-(trifluoromethylsulfonyloxy)-1-aza-bicyclo[4.2.0]oct-2-ene-2-carboxylate and tert-butyl-2-((4-mercaptopyridin-3-yl)methylthio)ethylcarbamate in 72% yield by following Method D. The resulting white solid product was purified by gel column chromatography (P.E/EA 2:1 as fluent).

Step 2: (6R,7S,Z)-7-(2-(5-amino-1,2,4-thiadiazol-3-yl)-2-(methoxyimino)acetamido)-3-(3-((2-aminoethylthio)methyl)pyridin-4-ylthio)-8-oxo-1-aza-bicyclo[4.2.0]oct-2-ene-2-carboxylic acid 1 was prepared from (6R,7S,Z)-benzhydryl-7-(2-(5-amino-1,2,4-thiadiazol-3-yl)-2-(methoxyimino)acetamido)-3-(3-((2-(tert-butoxycarbonylamino)ethylthio)methyl)pyridin-4-ylthio)-8-oxo-1-aza-bicyclo[4.2.0]oct-2-ene-2-carboxylate in 49% yield by following Method E. The resulting white solid product was purified by Prep-HPLC. ESI-MS: m/z 564.9 [M+H]

Example 53

Preparation of (6R,7S,Z)-7-(2-(5-amino-1,2,4-thiadiazol-3-yl)-2-(methoxyimino)acetamido)-8-oxo-3-(pyridin-4-ylthio)-1-aza-bicyclo[4.2.0]oct-2-ene-2-carboxylic Acid

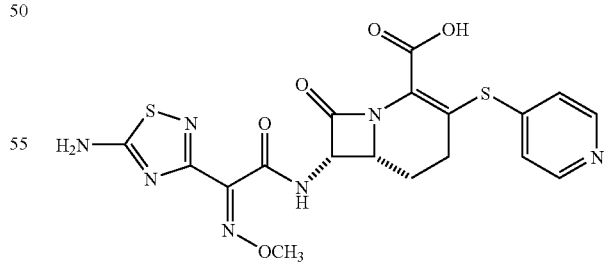

Step 1: (6R,7S,Z)-benzhydryl-7-(2-(5-amino-1,2,4-thiadiazol-3-yl)-2-(methoxyimino)acetamido)-8-oxo-3-(pyridin-4-ylthio)-1-aza-bicyclo[4.2.0]oct-2-ene-2-carboxylate was prepared from (6R,7S,Z)-benzhydryl-7-(2-(5-amino-1,2,4-thiadiazol-3-yl)-2-(methoxyimino)acetamido)-8-oxo-3-(trifluoromethylsulfonyloxy)-1-aza-bicyclo[4.2.0]oct-2- ene-2-carboxylate and pyridine-4-thiol in 60% by following Method D. The resulting white solid product was purified by gel column chromatography.

Step 2: (6R,7S,Z)-7-(2-(5-amino-1,2,4-thiadiazol-3-yl)-2-(methoxyimino)acetamido)-8-oxo-3-(pyridin-4-ylthio)-1-aza-bicyclo[4.2.0]oct-2-ene-2-carboxylic acid 1 was prepared from (6R,7S,Z)-benzhydryl-7-(2-(5-amino-1,2,4-thiadiazol-3-yl)-2-(methoxyimino)acetamido)-8-oxo-3-(pyridin-4-ylthio)-1-aza-bicyclo[4.2.0]oct-2-ene-2-carboxylate in 33% yield by following Method E. The resulting white solid product was purified by Prep-HPLC. ESI-MS: m/z 475.9 [M+H].

Example 54

Method H

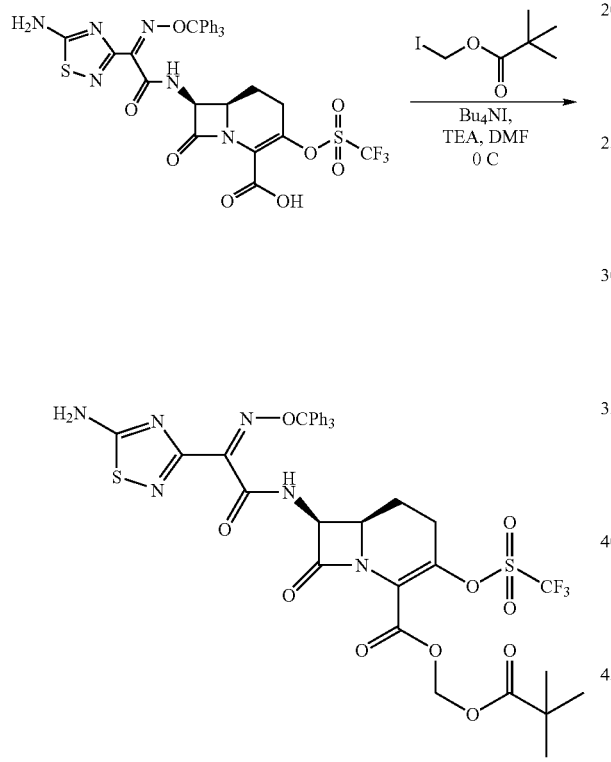

To a solution of (6R,7S,Z)-7-(2-(5-amino-1,2,4-thiadiazol-3-yl)-2-(trityloxyimino)acetamido)-8-oxo-3-(trifluoromethylsulfonyloxy)-1-aza-bicyclo[4.2.0]oct-2-ene-2-carboxylic acid (3.0 g, 4.03 mmol, 1.0 eq) and Bu$_4$NI (148 mg, 0.403 mmol, 0.1 eq) in DMF (60 mL) at 0° C., TEA (1.22 g, 0.0121 mol, 3.0 eq) was added. Then, to the resulting solution I-pivalate (4.0 g, 0.0165 mol, 4.0 eq) was added. The resulting solution was stirred for 50 mins at 0° C. To the reaction mixture cooled H$_2$O (300 mL) was added in. Then the resulting mixture was extracted with EA (300 mL) twice. The EA phase was washed with water (300 mL) twice, brine (300 mL), dried over Na$_2$SO$_4$, filtered and evaporated at room temperature. The residue was dissolved in THF (4 mL), slowly added into vigorously stirred petroleum ether (100 mL), filtered and crude product was got as a light brown solid in 100% yield, which was used without further purification.

Example 55

Preparation of (6R,7S,Z)-pivaloyloxymethyl 7-(2-(5-amino-1,2,4-thiadiazol-3-yl)-2-(hydroxyimino)acetamido)-3-(3-((2-aminoethylthio)methyl)pyridin-4-ylthio)-8-oxo-1-aza-bicyclo[4.2.0]oct-2-ene-2-carboxylate

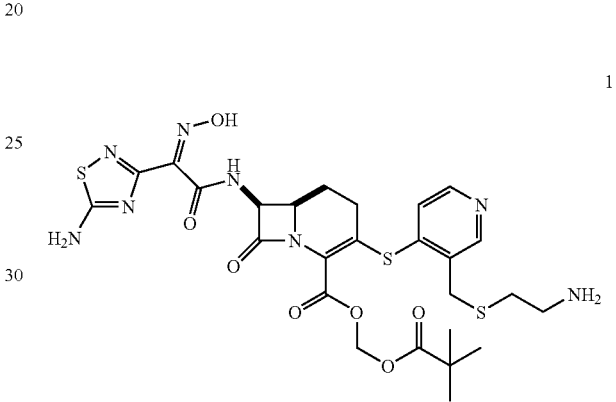

Step 1: (6R,7S,Z)-pivaloyloxymethyl 7-(2-(5-amino-1,2,4-thiadiazol-3-yl)-2-(trityloxyimino)acetamido)-8-oxo-3-(trifluoromethylsulfonyloxy)-1-aza-bicyclo[4.2.0]oct-2-ene-2-carboxylate was prepared from (6R,7S,Z)-7-(2-(5-amino-1,2,4-thiadiazol-3-yl)-2-(trityloxyimino)acetamido)-8-oxo-3-(trifluoromethylsulfonyloxy)-1-aza-bicyclo[4.2.0]oct-2-ene-2-carboxylic acid by following Method H in 100% yield. A light brown crude solid was obtained.

Step 2: (6R,7S,Z)-pivaloyloxymethyl 7-(2-(5-amino-1,2,4-thiadiazol-3-yl)-2-(trityloxyimino)acetamido)-3-(3-((2-(tert-butoxycarbonylamino)ethylthio)methyl)pyridin-4-ylthio)-8-oxo-1-aza-bicyclo[4.2.0]oct-2-ene-2-carboxylate was prepared from (6R,7S,Z)-pivaloyloxymethyl-7-(2-(5-amino-1,2,4-thiadiazol-3-yl)-2-(trityloxyimino)acetamido)-8-oxo-3-(trifluoromethylsulfonyloxy)-1-aza-bicyclo[4.2.0]oct-2-ene-2-carboxylate using Method D. Crude product was purified by prep-TLC (EA:PE=3:1) to get a light yellow colored solid in 20% yield.

Step 3: (6R,7S,Z)-pivaloyloxymethyl 7-(2-(5-amino-1,2,4-thiadiazol-3-yl)-2-(trityloxyimino)acetamido)-3-(3-((2-(tert-butoxycarbonylamino)ethylthio)methyl)pyridin-4-ylthio)-8-oxo-1-aza-bicyclo[4.2.0]oct-2-ene-2-carboxylate (10 mg, 0.01 mmol, 1.0 eq) was dissolved in HCOOH (1.0 mL), stirred at room temperature for 24 hrs, the reaction procedure was detected by LC-MS. The resulting mixture was evaporated at room temperature. The residue was washed by Et$_2$O (2 mL) twice. A light brown colored solid was obtained as the desired product 1 in 60% yield. ESMS: m/z 665.2 [M+H].

Example 56

Preparation of (6R,7S,Z)-methyl 7-(2-(2-amino-5-chlorothiazol-4-yl)-2-(hydroxyimino)acetamido)-8-oxo-3-(pyridin-4-ylthio)-1-aza-bicyclo[4.2.0]oct-2-ene-2-carboxylate

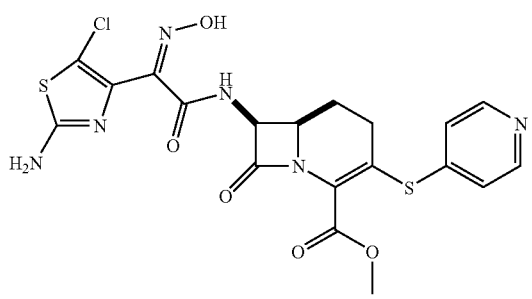

Step 1: (6R,7S,Z)-methyl-7-(2-(5-chloro-2-(tritylamino)thiazol-4-yl)-2-(trityloxyimino)acetamido)-8-oxo-3-(trifluoromethylsulfonyloxy)-1-aza-bicyclo[4.2.0]oct-2-ene-2-carboxylate was prepared from (6R,7S,Z)-7-(2-(5-chloro-2-(tritylamino)thiazol-4-yl)-2-(trityloxyimino)acetamido)-8-oxo-3-(trifluoromethylsulfonyloxy)-1-aza-bicyclo[4.2.0]oct-2-ene-2-carboxylic acid by following Method F. The product was purified by column chromatography on silica gel (EA:PE=1:2) in 35% yield. A light yellow solid was obtained.

Step 2: (6R,7S,Z)-methyl-7-(2-(5-chloro-2-(tritylamino)thiazol-4-yl)-2-(trityloxyimino)acetamido)-8-oxo-3-(pyridin-4-ylthio)-1-aza-bicyclo[4.2.0]oct-2-ene-2-carboxylate was prepared from (6R,7S,Z)-methyl 7-(2-(5-chloro-2-(tritylamino)thiazol-4-yl)-2-(trityloxyimino)acetamido)-8-oxo-3-(trifluoromethylsulfonyloxy)-1-aza-bicyclo[4.2.0]oct-2-ene-2-carboxylate using Method D. The product was purified by column chromatography on silica gel (EA:PE=2:1) in 31% yield. A white solid was obtained.

Step 3: (6R,7S,Z)-methyl-7-(2-(2-amino-5-chlorothiazol-4-yl)-2-(hydroxyimino)acetamido)-8-oxo-3-(pyridin-4-ylthio)-1-aza-bicyclo[4.2.0]oct-2-ene-2-carboxylate 1 was prepared from (6R,7S,Z)-methyl 7-(2-(5-chloro-2-(tritylamino)thiazol-4-yl)-2-(trityloxyimino)acetamido)-8-oxo-3-(pyridin-4-ylthio)-1-aza-bicyclo[4.2.0]oct-2-ene-2-carboxylate using Method E. The product was purified by Prep-HPLC in 20% yield. A yellow colored solid was obtained as the desired product. ESMS: m/z 509 [M+H].

Example 57

Preparation of (6R,7S,Z)-pivaloyloxymethyl 7-(2-(2-amino-5-chlorothiazol-4-yl)-2-(hydroxyimino)acetamido)-8-oxo-3-(pyridin-4-ylthio)-1-aza-bicyclo[4.2.0]oct-2-ene-2-carboxylate 1

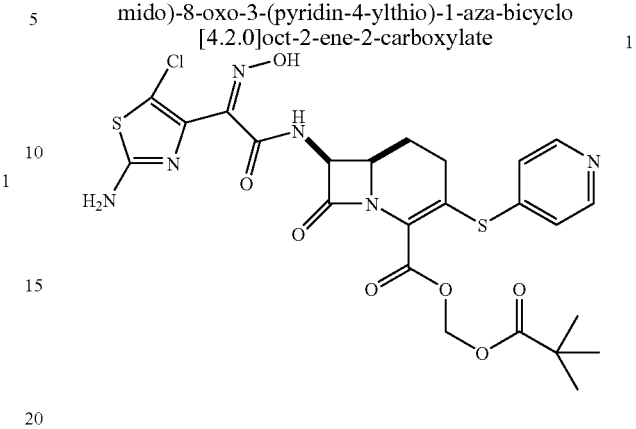

Step 1: (6R,7S,Z)-pivaloyloxymethyl-7-(2-(5-chloro-2-(tritylamino)thiazol-4-yl)-2-(trityloxyimino)acetamido)-8-oxo-3-(trifluoromethylsulfonyloxy)-1-aza-bicyclo[4.2.0]oct-2-ene-2-carboxylate was prepared from (6R,7S,Z)-7-(2-(5-chloro-2-(tritylamino)thiazol-4-yl)-2-(trityloxyimino)acetamido)-8-oxo-3-(trifluoromethylsulfonyloxy)-1-aza-bicyclo[4.2.0]oct-2-ene-2-carboxylic acid by following Method H in 66.6% yield. A light yellow solid was obtained.

Step 2: (6R,7S,Z)-pivaloyloxymethyl-7-(2-(5-chloro-2-(tritylamino)thiazol-4-yl)-2-(trityloxyimino)acetamido)-8-oxo-3-(pyridin-4-ylthio)-1-aza-bicyclo[4.2.0]oct-2-ene-2-carboxylate was prepared from (6R,7S,Z)-pivaloyloxymethyl-7-(2-(5-chloro-2-(tritylamino)thiazol-4-yl)-2-(trityloxyimino)acetamido)-8-oxo-3-(trifluoromethylsulfonyloxy)-1-aza-bicyclo[4.2.0]oct-2-ene-2-carboxylate using Method D. The resulting product was purified by column chromatography (eluting solvent PE:AE=1:1) in 24% yield. A yellow colored solid was obtained.

Step 3: (6R,7S,Z)-pivaloyloxymethyl-7-(2-(2-amino-5-chlorothiazol-4-yl)-2-(hydroxyimino)acetamido)-8-oxo-3-(pyridin-4-ylthio)-1-aza-bicyclo[4.2.0]oct-2-ene-2-carboxylate 1 was prepared from ((6R,7S,Z)-pivaloyloxymethyl-7-(2-(5-chloro-2-(tritylamino)thiazol-4-yl)-2-(trityloxyimino)acetamido)-8-oxo-3-(pyridin-4-ylthio)-1-aza-bicyclo[4.2.0]oct-2-ene-2-carboxylate using Method E in 22% yield. A yellow colored solid was obtained as the desired product. ES-MS: m/z 609.1 [M+H].

Example 58

The following compounds were prepared according to the synthetic routes described in the examples above.

TABLE 1

| Compound # | Structure | MW |
|---|---|---|
| 1 | 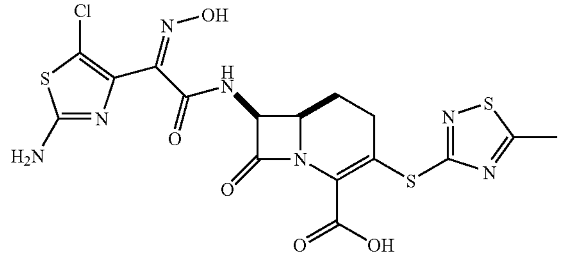 | 515.97 |

TABLE 1-continued

| Compound # | Structure | MW |
|---|---|---|
| 2 | 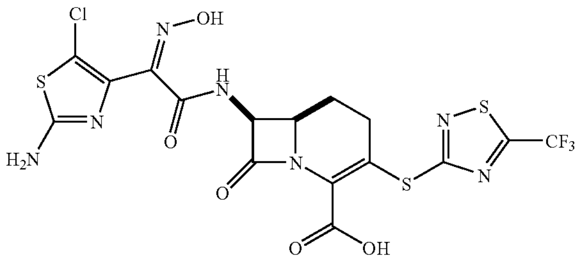 | 569.95 |
| 3 | 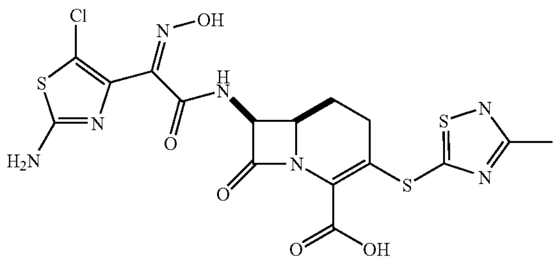 | 515.97 |
| 4 | 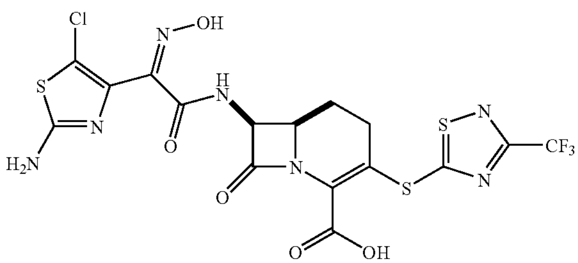 | 569.95 |
| 5 | 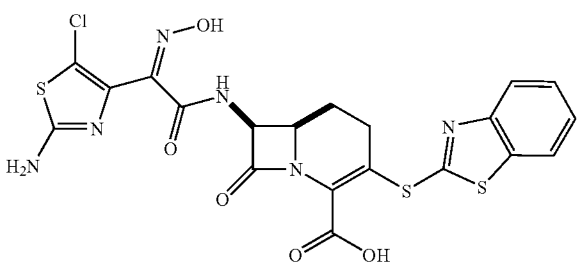 | 551.02 |
| 6 | 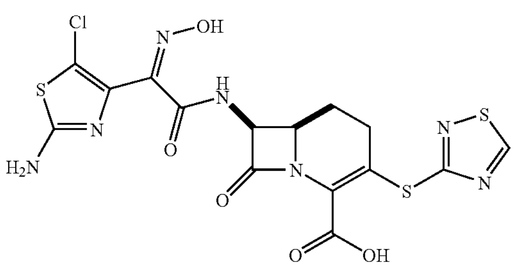 | 501.95 |
| 7 | 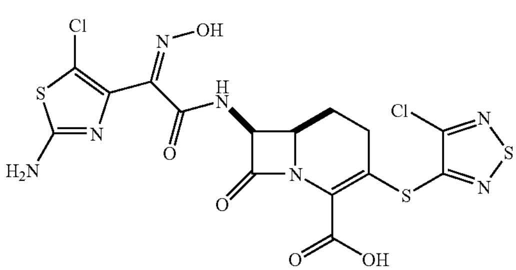 | 536.39 |

TABLE 1-continued

| Compound # | Structure | MW |
|---|---|---|
| 8 | 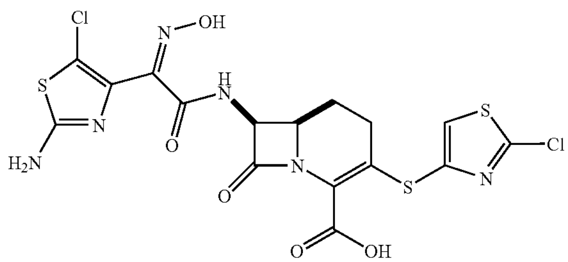 | 535.40 |
| 9 | 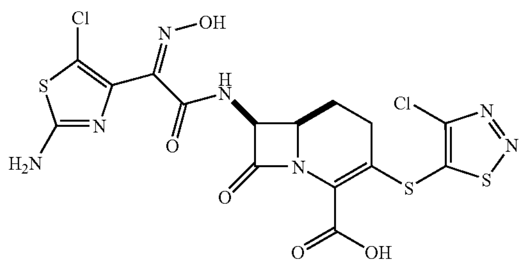 | 536.39 |
| 10 | 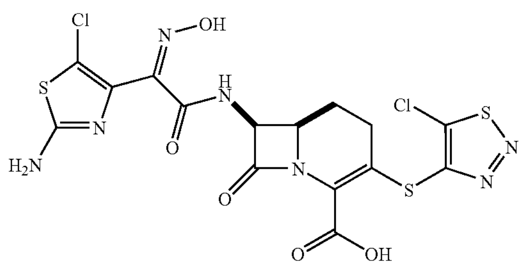 | 536.39 |
| 11 | 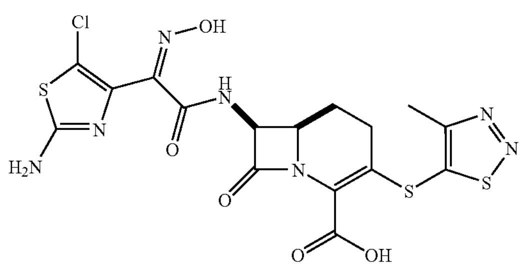 | 515.97 |
| 12 | 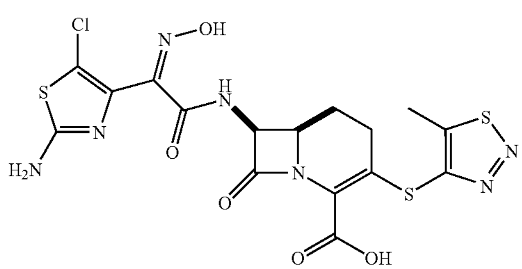 | 515.97 |

TABLE 1-continued

| Compound # | Structure | MW |
|---|---|---|
| 13 | 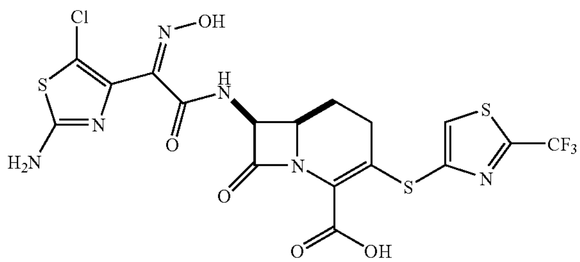 | 568.96 |
| 14 | 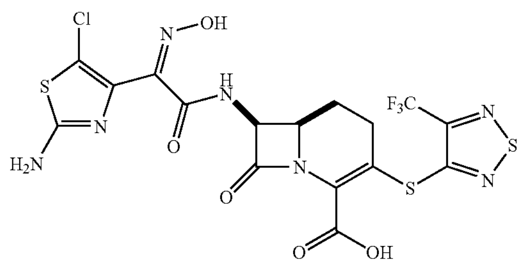 | 569.95 |
| 15 | 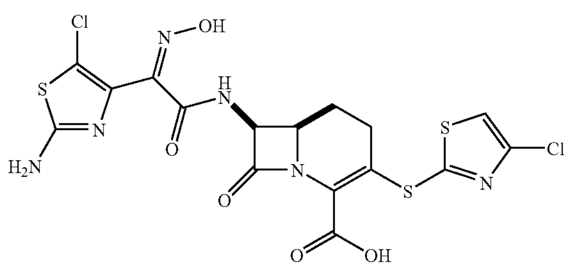 | 535.40 |
| 16 | 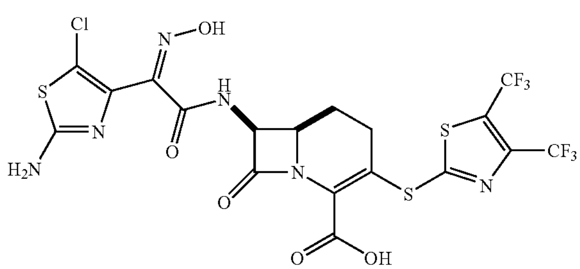 | 636.96 |
| 17 | 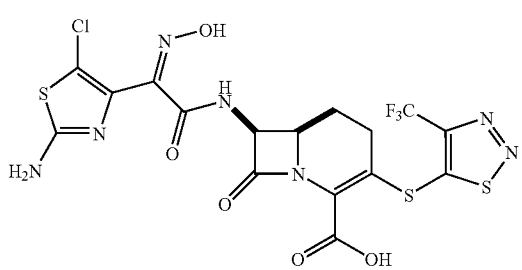 | 569.95 |
| 18 | 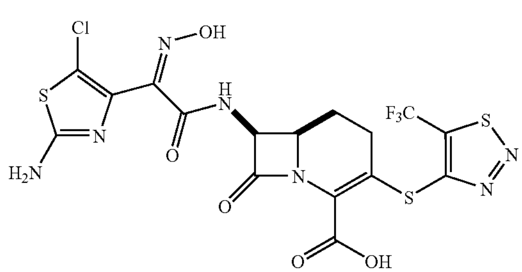 | 569.95 |

TABLE 1-continued

| Compound # | Structure | MW |
|---|---|---|
| 19 | 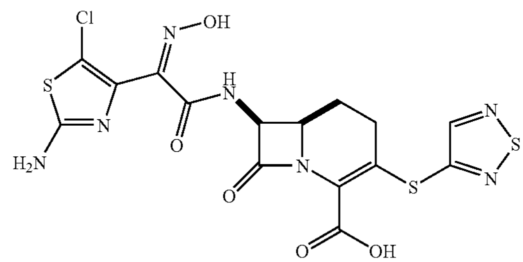 | 501.95 |
| 20 | 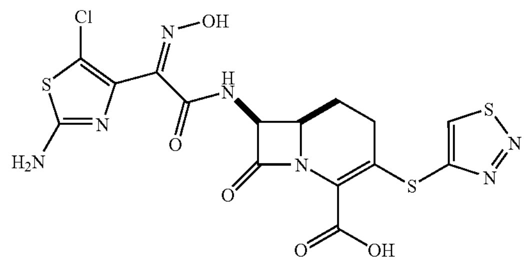 | 501.95 |
| 21 | 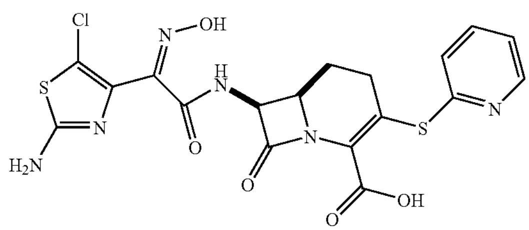 | 494.93 |
| 22 | 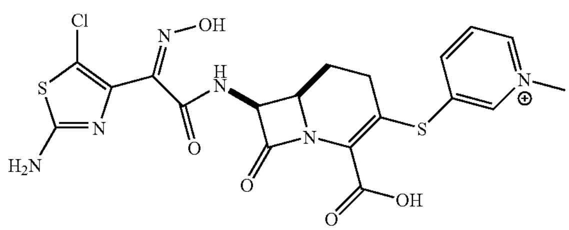 | 509.97 |
| 23 | 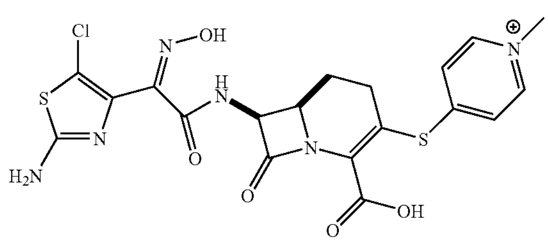 | 509.97 |
| 24 | 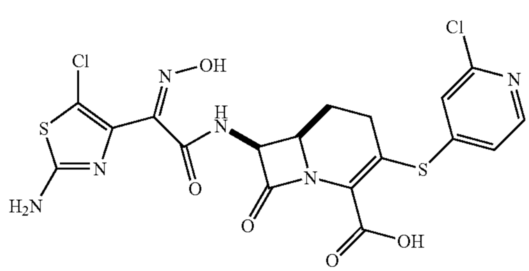 | 529.38 |

TABLE 1-continued

| Compound # | Structure | MW |
|---|---|---|
| 25 | (structure) | 562.93 |
| 26 | (structure) | 529.38 |
| 27 | (structure) | 529.38 |
| 28 | (structure) | 529.38 |
| 29 | (structure) | 563.82 |
| 30 | (structure) | 510.93 |

TABLE 1-continued

| Compound # | Structure | MW |
|---|---|---|
| 31 | 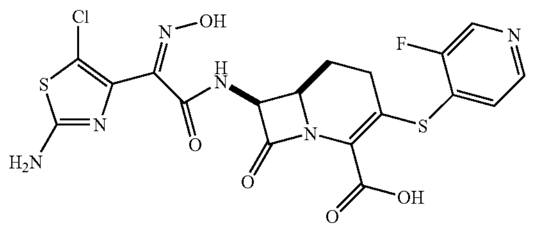 | 512.92 |
| 32 | 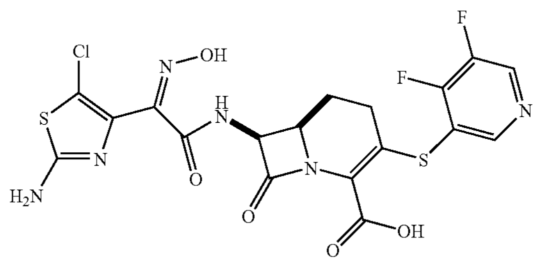 | 530.91 |
| 33 | 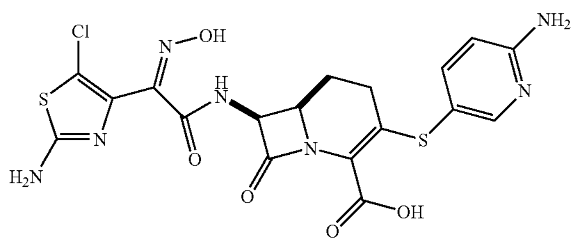 | 509.95 |
| 34 | 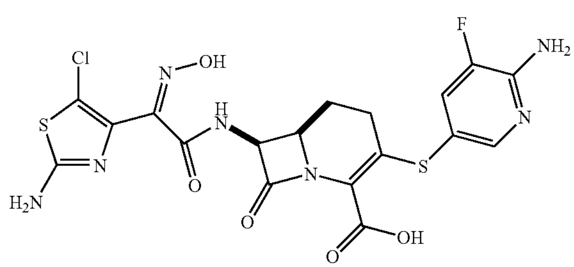 | 527.94 |
| 35 | 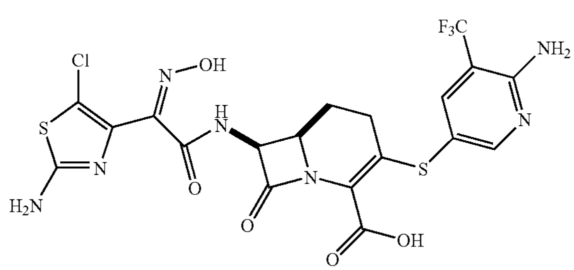 | 577.94 |
| 36 | 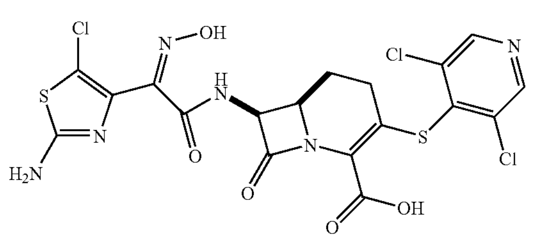 | 563.82 |

TABLE 1-continued
| Compound # | Structure | MW |
|---|---|---|
| 37 | 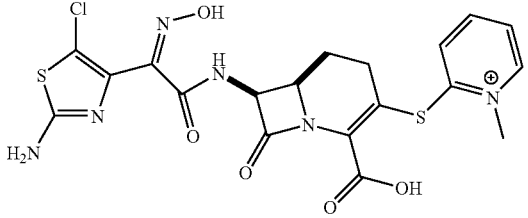 | 509.97 |
| 38 | 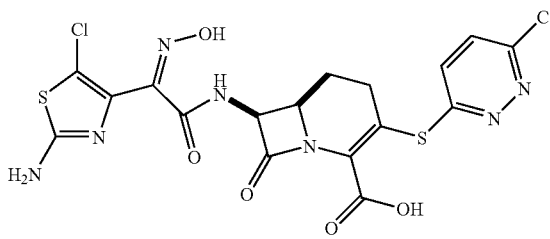 | 530.37 |
| 39 | 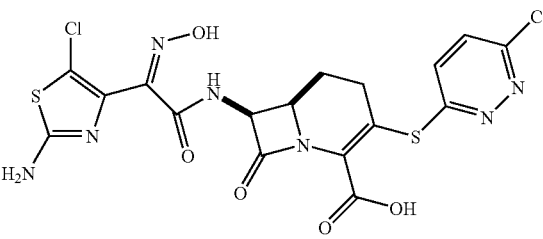 | 563.92 |
| 40 | 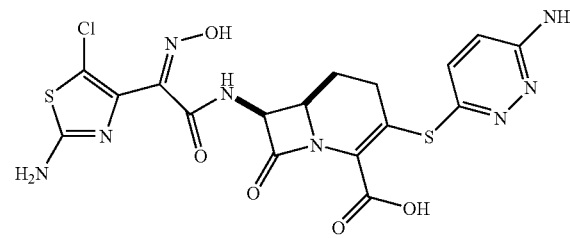 | 510.93 |
| 41 | 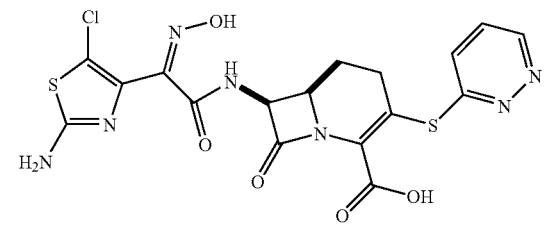 | 495.92 |
| 42 | 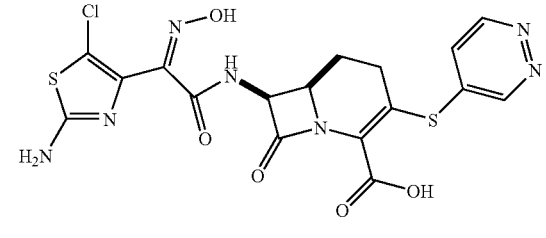 | 495.92 |

TABLE 1-continued

| Compound # | Structure | MW |
|---|---|---|
| 43 | 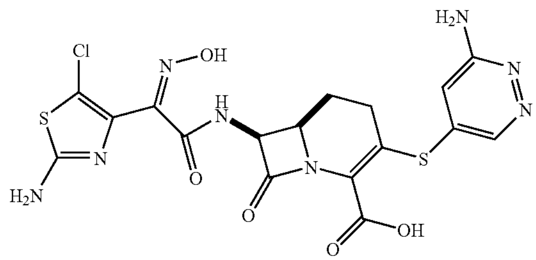 | 510.93 |
| 44 | 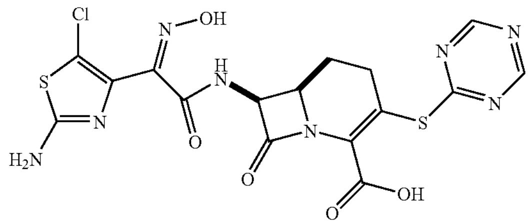 | 496.91 |
| 45 | 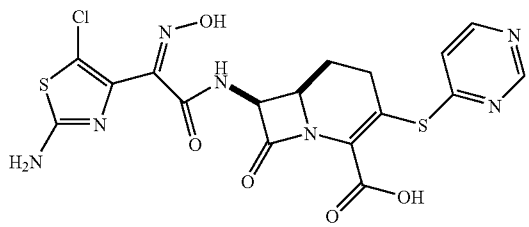 | 495.92 |
| 46 | 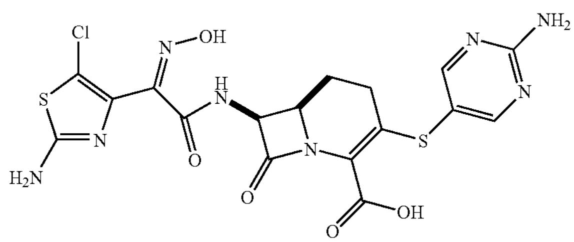 | 510.93 |
| 47 | 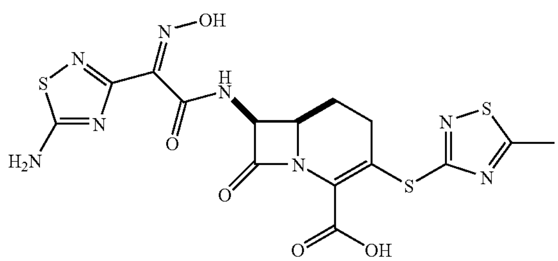 | 482.52 |
| 48 | 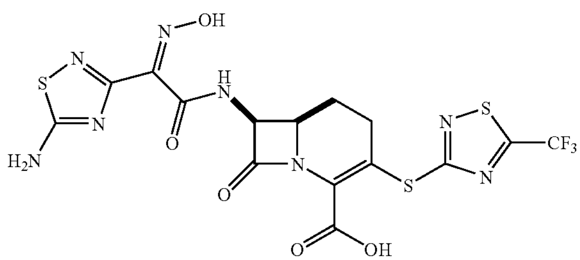 | 536.49 |

TABLE 1-continued

| Compound # | Structure | MW |
|---|---|---|
| 49 | 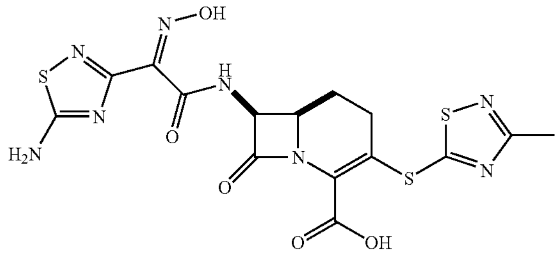 | 482.52 |
| 50 | 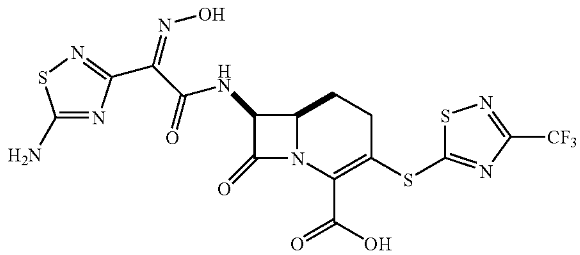 | 536.49 |
| 51 | 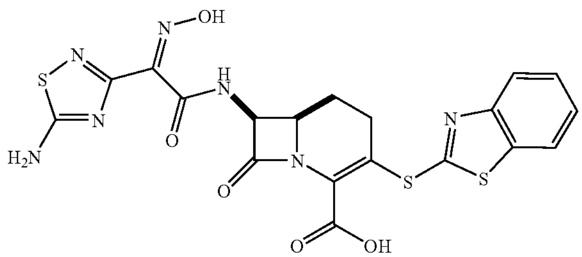 | 517.56 |
| 52 | 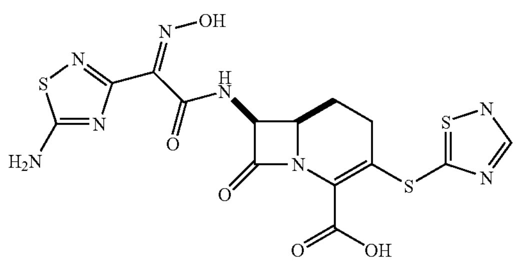 | 468.49 |
| 53 | 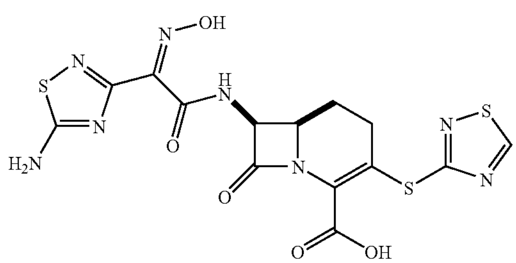 | 468.49 |
| 54 | 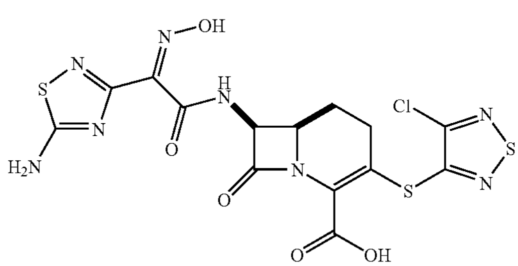 | 502.94 |

TABLE 1-continued

| Compound # | Structure | MW |
|---|---|---|
| 55 | 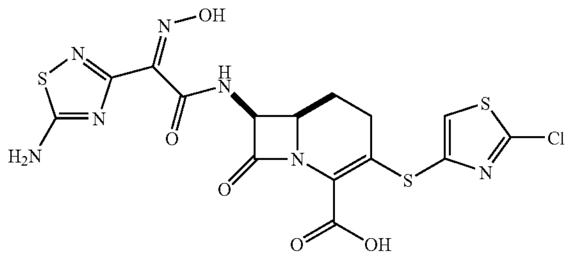 | 501.95 |
| 56 | 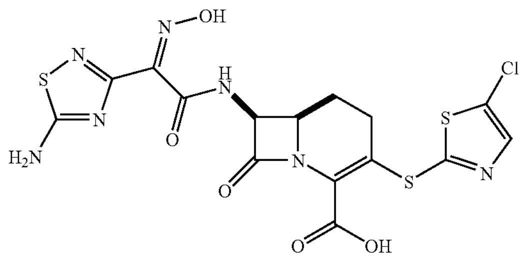 | 501.95 |
| 57 | 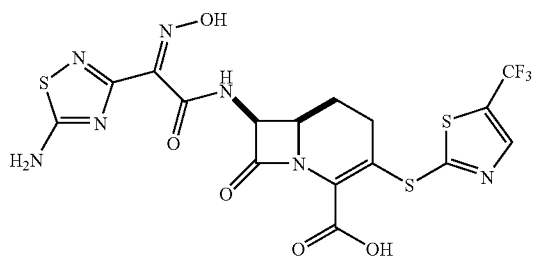 | 535.50 |
| 58 | 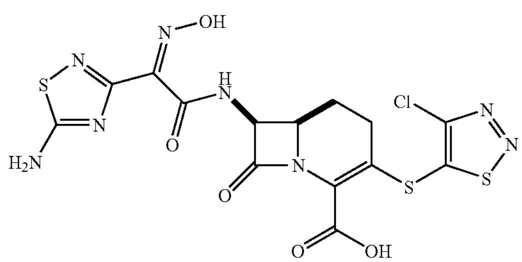 | 502.94 |
| 59 | 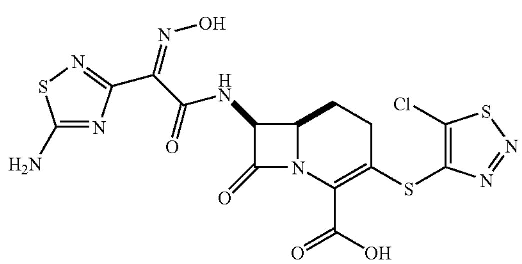 | 502.94 |
| 60 | 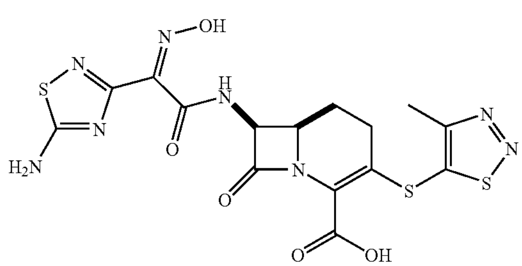 | 482.52 |

TABLE 1-continued

| Compound # | Structure | MW |
|---|---|---|
| 61 | 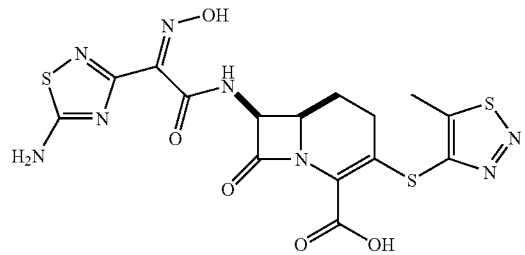 | 482.52 |
| 62 | 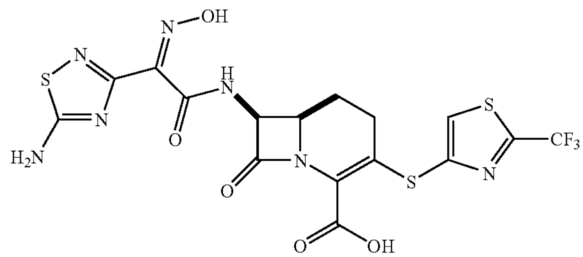 | 535.50 |
| 63 | 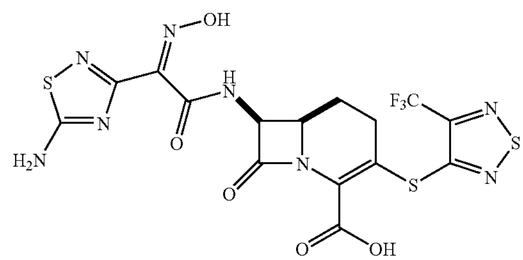 | 536.49 |
| 64 | 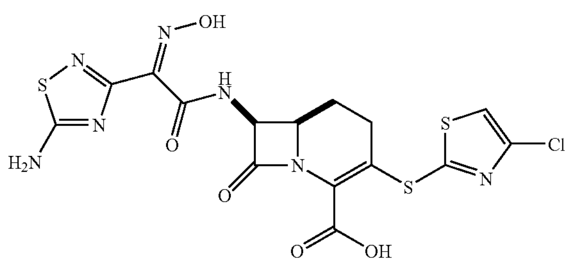 | 501.95 |
| 65 | 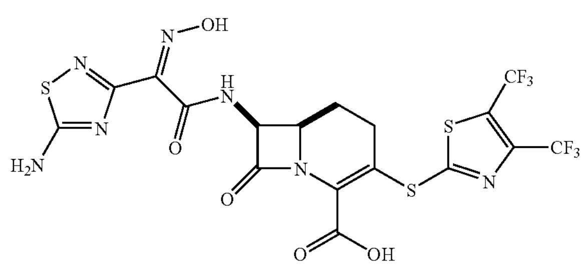 | 603.50 |
| 66 | 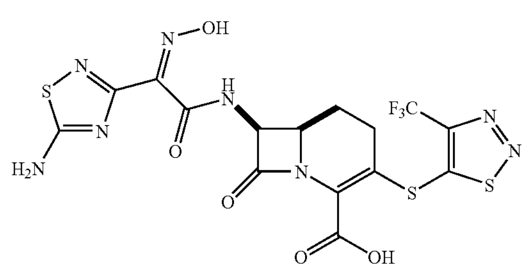 | 536.49 |

TABLE 1-continued

| Compound # | Structure | MW |
|---|---|---|
| 67 | 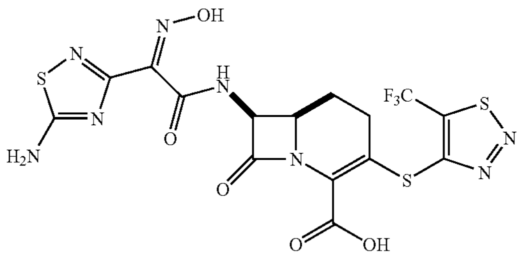 | 536.49 |
| 68 | 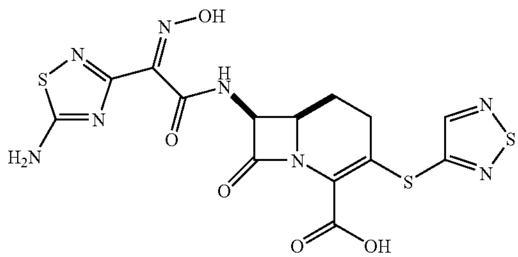 | 468.49 |
| 69 | 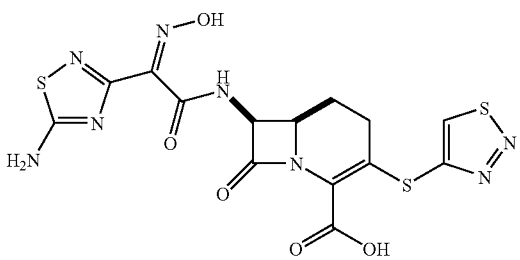 | 468.49 |
| 70 | 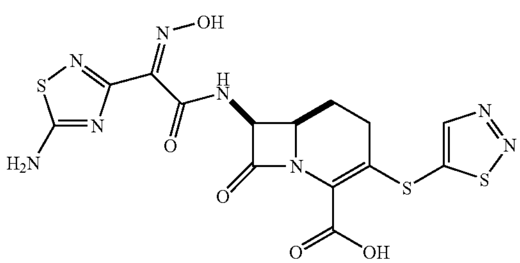 | 468.49 |
| 71 | 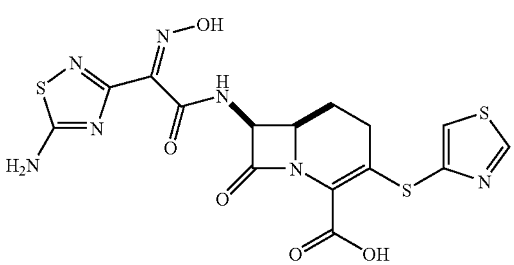 | 467.50 |
| 72 | 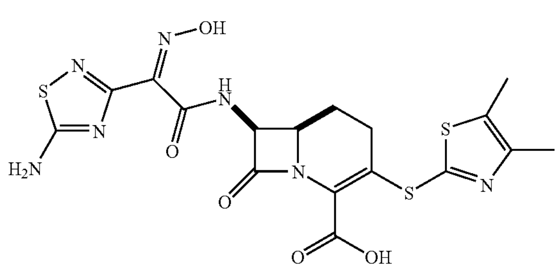 | 495.56 |

TABLE 1-continued

| Compound # | Structure | MW |
|---|---|---|
| 73 | 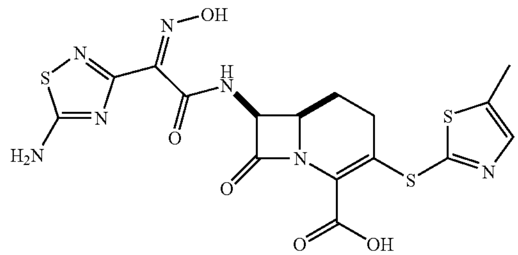 | 481.53 |
| 74 | 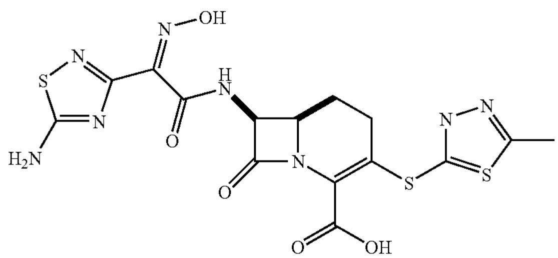 | 482.52 |
| 75 | 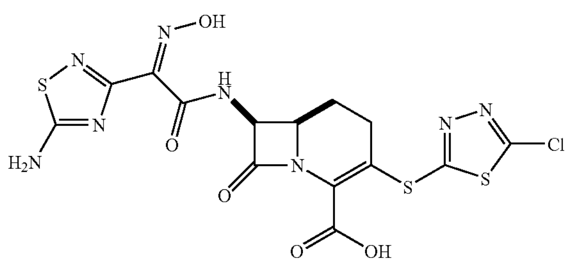 | 502.94 |
| 76 | 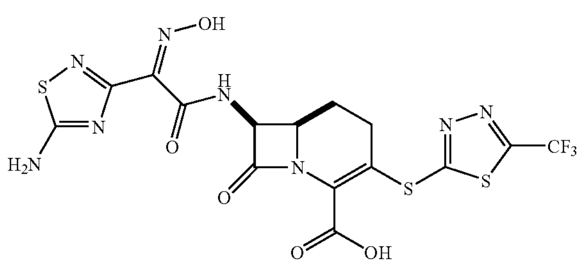 | 536.49 |
| 77 | 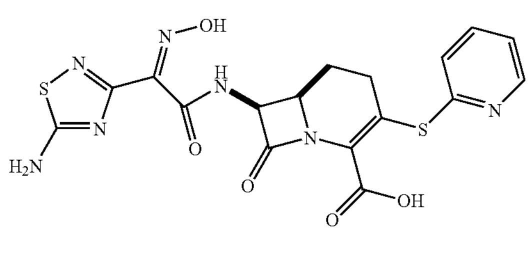 | 461.47 |
| 78 | 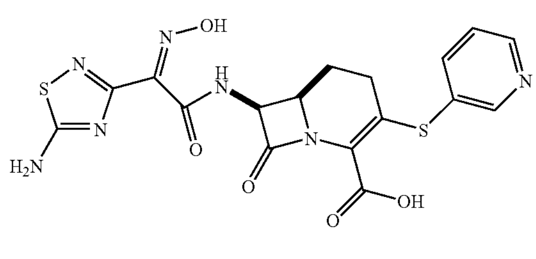 | 461.47 |

TABLE 1-continued

| Compound # | Structure | MW |
|---|---|---|
| 79 | 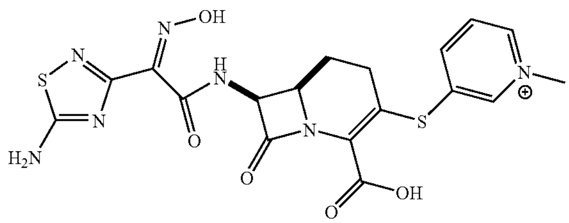 | 476.51 |
| 80 | 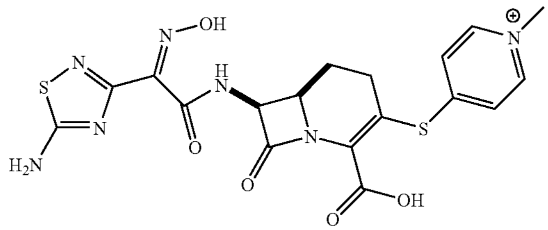 | 476.51 |
| 81 | 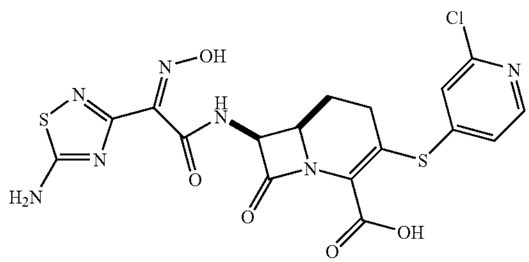 | 495.92 |
| 82 | 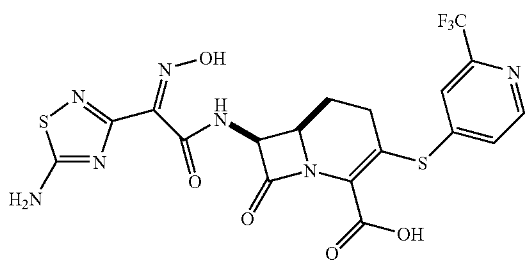 | 529.47 |
| 83 | 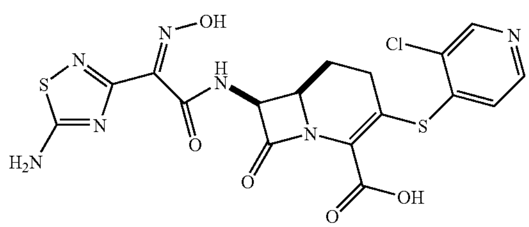 | 495.92 |
| 84 | 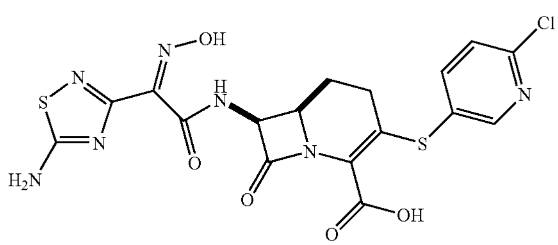 | 495.92 |

TABLE 1-continued
| Compound # | Structure | MW |
|---|---|---|
| 85 | 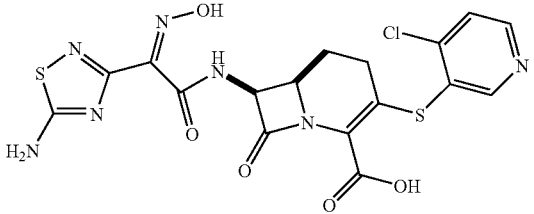 | 495.92 |
| 86 | 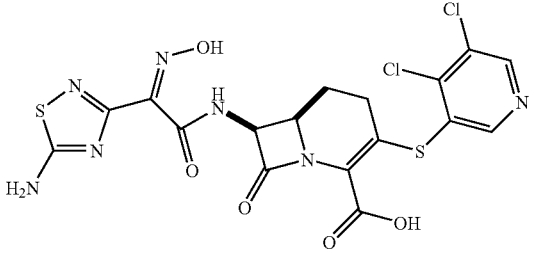 | 530.37 |
| 87 | 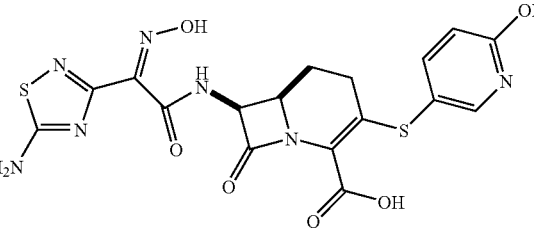 | 477.47 |
| 88 | 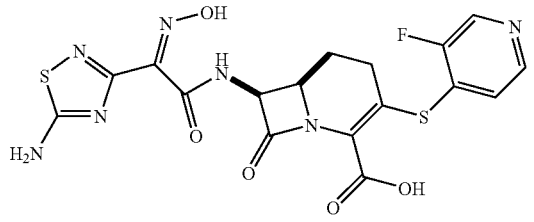 | 479.47 |
| 89 | 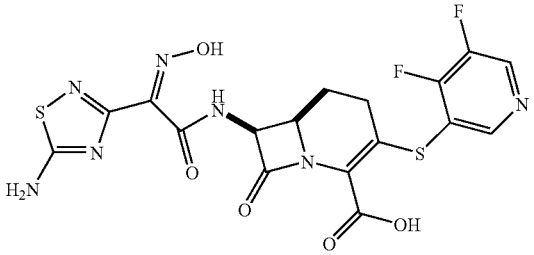 | 497.46 |
| 90 | 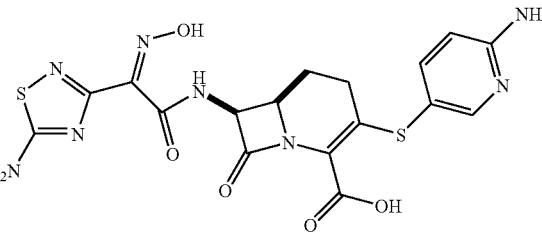 | 476.49 |

TABLE 1-continued
| Compound # | Structure | MW |
|---|---|---|
| 91 | 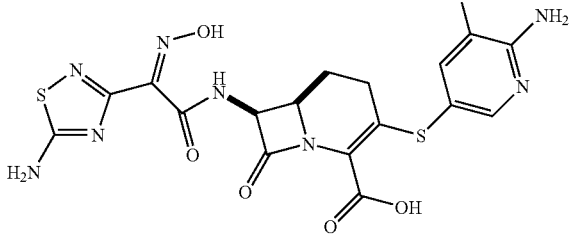 | 494.48 |
| 92 | 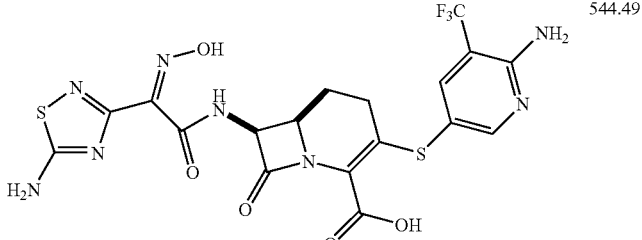 | 544.49 |
| 93 | 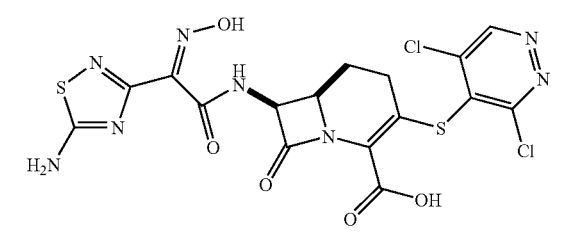 | 530.37 |
| 94 | 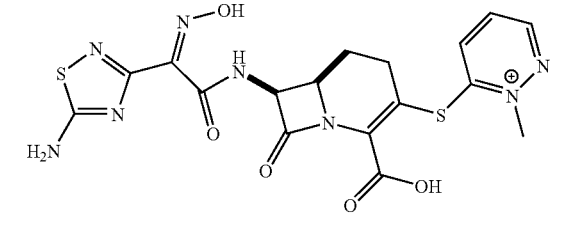 | 476.51 |
| 95 | 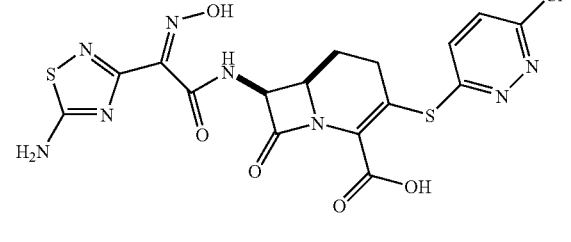 | 496.91 |
| 96 | 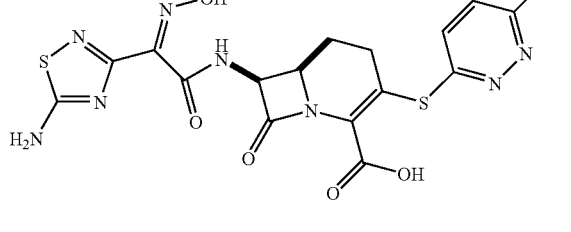 | 530.46 |

TABLE 1-continued
| Compound # | Structure | MW |
|---|---|---|
| 97 | 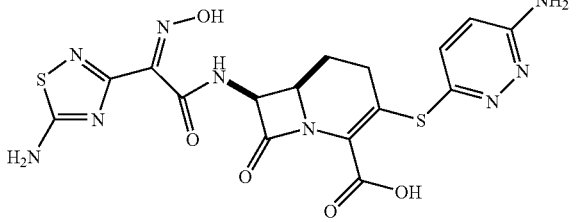 | 477.48 |
| 98 | 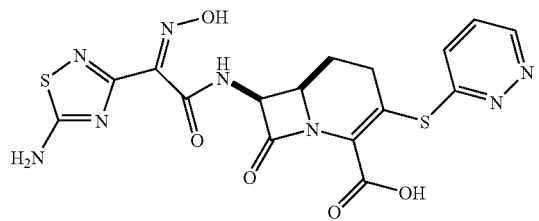 | 462.46 |
| 99 | 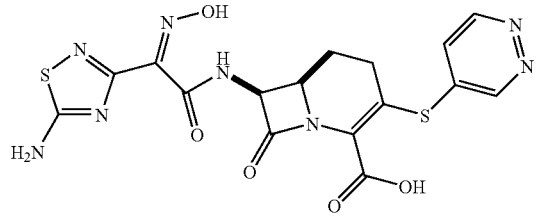 | 462.46 |
| 100 | 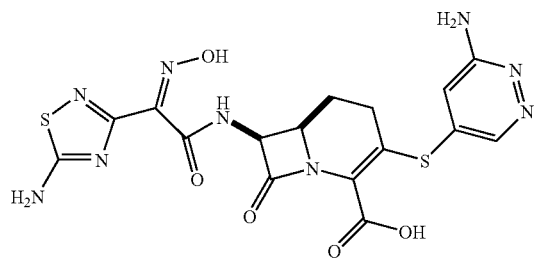 | 477.48 |
| 101 | 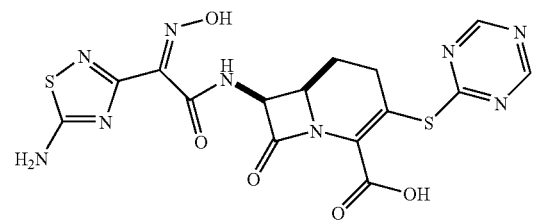 | 463.45 |
| 102 | 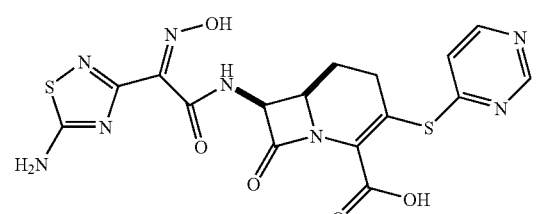 | 462.46 |

TABLE 1-continued

| Compound # | Structure | MW |
|---|---|---|
| 103 | 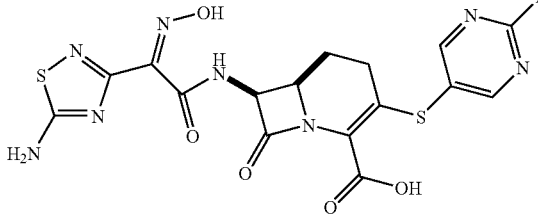 | 477.48 |

Example 59

MIC Assay Protocol

It is well-established that the effectiveness of β-lactam antibiotics is correlated to the amount of time that the concentration of free (unbound) drug exceeds the MIC. A serum protein binding value of >97% is considered too high for a sufficient free drug concentration to be established in a patient using any practical dosing regime. Furthermore, a compound displaying human serum binding of 70% has ten times the amount of free drug as a compound with 97% serum binding (30% vs 3%).

It will be appreciated that, in any given series of compounds, a spectrum of biological activity will be observed. In its most preferred embodiment, a compound of this invention will demonstrate activity superior to vancomycin or cefotaxime against bacterial infections resistant to conventional β-lactam antibiotics such as methicillin and ampicillin. The following procedures may, without limitation, be used to evaluate the compounds of this invention.

The in vitro MIC for bacterial isolates may be obtained in the following manner: a test compound is incorporated into a series of two-fold dilutions in cation adjusted Mueller-Hinton broth (CAMHB). Different bacterial strains diluted to provide a uniform inoculum are added to the CAMHB containing test compounds. A well without test compound is included for each strain as a growth control. The MIC is defined as the concentration of compound that completely inhibits growth as observed by the naked eye. The procedures used in these experiments are generally those standardized by the Clinical and Laboratory Standards Institute (CLSI), as set forth in the CLSI publication entitled "M7-A7. Methods for dilution antimicrobial susceptibility tests for bacteria that grow aerobically; approved standard-seventh edition." (2006), which is incorporated by reference as if fully set forth herein. The following exemplifies such a procedure although it is to be understood that modifications of the procedure may be implemented as required.

Two-fold dilutions of the test compounds are prepared in CAMHB at 2× the concentration range to be tested if the compounds are soluble in aqueous solution. Alternately, dimethylsulfoxide (DMSO) is used to prepare two-fold dilutions at 10× the concentration range to be tested. Reference drugs such as cefotaxime, vancomycin or imipenem are used as positive controls. A few isolated colonies are retrieved from a pure culture prepared on an agar plate and suspended in PBS until the turbidity of the suspension matches a 0.5 McFarland standard which is equal to approximately $10^8$ sCFU/mL. This solution is further diluted in CAMHB to $10^6$ CFU/mL if compounds are diluted in CAMHB and $5 \times 10^5$ CFU/mL if compounds are diluted in DMSO. The CAMHB plates containing the compound dilutions are combined in equal volumes with the higher density inoculum, or 10 μL of the DMSO dilutions are added to the lower density inoculum. When S. aureus is the organism being tested and the compound is oxacillin, a beta-lactam or a carbacephem compound of the present invention, 2% NaCl is added to the growth media. The plates are then incubated for 16-20 hours at 35° C. The plates are then observed to determine which concentration of the test compound is the MIC.

Data for certain representative compounds is shown in Table 2 below.

TABLE 2

| Ex #/ Cpd # | ASAU 001 | ASAU 1028 | ASAU 1029 | ASAU 002 | ASAU 1043 | ASAU 1033 |
|---|---|---|---|---|---|---|
| Comparative Compound 1 | A | B | A | B | B | B |
| Comparative Compound 2 | A | — | — | A | — | — |
| 27/1 | A | A | A | B | B | B |
| 28/1 | A | A | B | — | C | C |
| 29/1 | A | A | A | — | B | B |
| 30/1 | A | A | A | — | B | B |
| 31/1 | A | A | A | — | B | B |
| 32/1 | A | — | C | — | C | B |
| 33/1 | A | B | A | B | B | B |
| 34/1 | A | B | C | — | C | C |
| 35/1 | A | B | B | C | C | C |
| 37/1 | A | B | C | — | C | B |
| 38/1 | A | A | A | — | C | B |
| 39/1 | A | B | B | — | C | C |
| 40/1 | A | B | C | — | C | C |
| 41/1 | A | B | — | — | C | C |
| 42/1 | A | B | B | B | C | B |
| 43/1 | A | C | C | — | C | C |
| 44/1 | A | B | A | — | C | C |
| 45/1 | A | B | A | — | C | C |
| 46/1 | A | B | A | — | C | C |
| 47/1 | A | B | A | — | B | B |
| 48/1 | A | A | A | A | B | B |
| 49/1 | A | C | B | — | C | C |
| 50/1 | A | B | B | — | C | C |
| 51/1 | A | B | B | — | C | C |
| 52/1 | A | B | B | — | C | B |
| 53/1 | A | B | B | — | C | C |

*Key:

| Strain | ACH Code | Phenotype |
|---|---|---|
| S. aureus | ASAU001 | Susceptible Organism ATCC 29213 |
| | ASAU1028 | CA-MRSA, USA400 |
| | ASAU1029 | CA-MRSA, USA300 |
| | ASAU002 | MRSA ATCC 33591 |
| | ASAU1043 | MRSA, CIP, ERY, CLI, GEN resistant |
| | ASAU1033 | MRSA, CIP, ERY, CLIN, TET, GEN resistant |

**MIC Key:
MIC's of 1.0 μg/mL or less = A
MIC's of greater than 1.0 μg/mL to 8.0 μg/mL = B
MIC's of greater than 8.0 μg/mL = C TABLE 2-continued

| Ex #/ Cpd # | ASAU 001 | ASAU 1028 | ASAU 1029 | ASAU 002 | ASAU 1043 | ASAU 1033 |
|---|---|---|---|---|---|---|

***Comparative Compounds:
Comparative Compound 1 is:

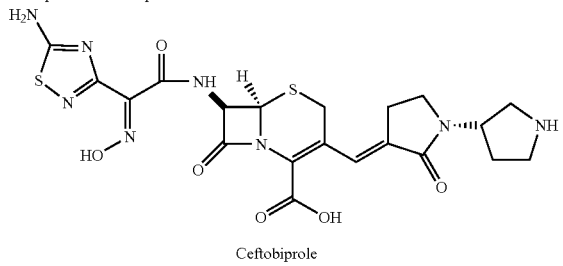

Ceftobiprole

Comparative Compound 2 is:

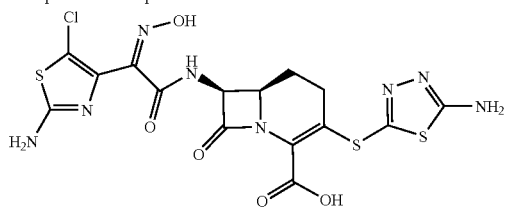

Example 60

*Staphylococcus Aureus*, Methicillin Resistant (ATCC 33591), Infected Thigh Model Groups of 6 male specific-pathogen-free CD-1 mice weighing 22±2 g are used. Animals are rendered immunosuppressedion by two intraperitoneal injections of cyclophosphamide, the first at 150 mg/kg 4 days before infection (day −4) and the second at 100 mg/kg 1 day before infection (day −1). On day 0, animals are inoculated intramuscularly (0.1 ml/thigh) with 1×105 CFU/mouse of *Staphylococcus aureus* Methicillin Resistance (MRSA) (ATCC 33591) into right thigh. Vehicle and/or test substances are then administered (IV, SC, or PO) 2 hours later. At 26 hours after inoculation, muscle of the right thigh is harvested from each of the survival test animals. The removed muscle tissues are then homogenized in 3 to 4 ml of PBS, pH 7.4 with a ceramic mortar. Homogenates of 0.1 ml are used for serial 10-fold dilutions and plated on Muller Hinton Broth in 1.5% Bacto® Agar for CFU determination. Decrease of the CFU/g muscle of right thigh in 99 percent or more (≧99) of the animals indicates significant activity. See, e.g., Andes, D. et al., *Antimicrobial Agents and Chemotherapy*, 46: 1665-1670 (2002); and Griffith, D. C., et al., *Antimicrobial Agents and Chemotherapy*, 50: 1628-1632 (2006).

Figure 2:
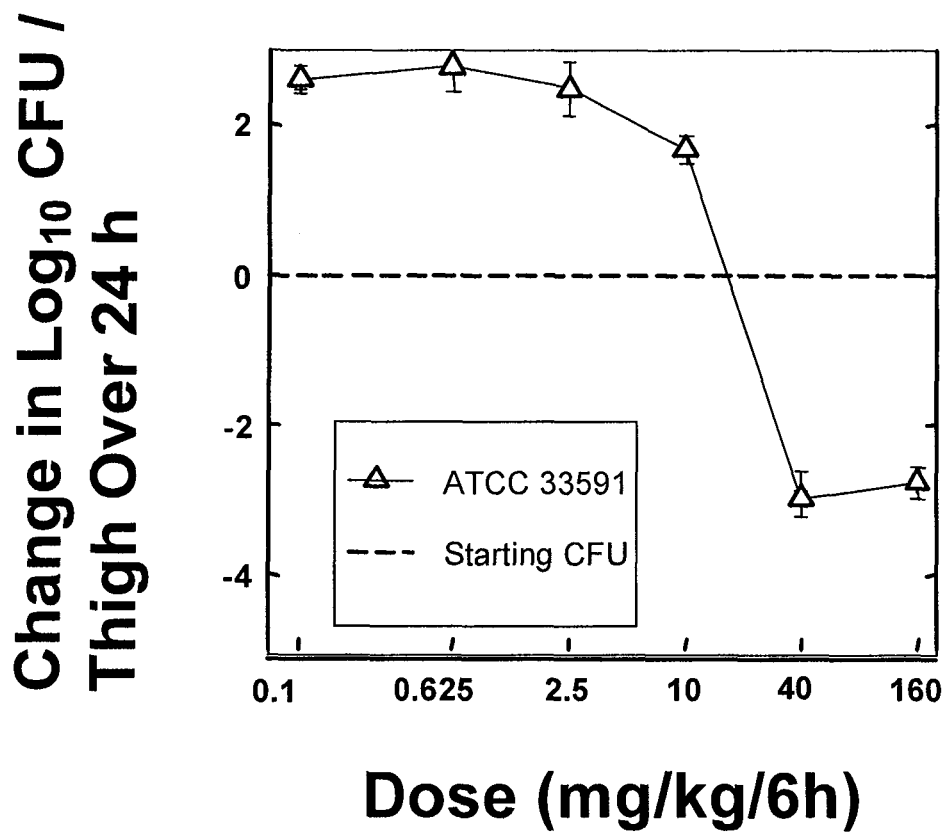
FIG. 2 shows the efficacy of Comparative Compound 2 of Example 60 in a neutropenic mouse thigh infection model with MRSA strain (ATCC 33591).

Data for a representative compound, namely, Compound 1 of Example 48, is shown in FIG. 1. Test compounds were dosed s.c. at 60, 120 or 240 mg/kg/day, except vancomycin at a single dose level of 220 mg/kg/day. In this model, Compound 1 of Example 48 showed high efficacy, generating a 1 log kill at the lowest dose of 60 mg/kg/day (dosed TID 20 mg/kg/8 h), and was more effective than vancomycin dosed every 12 hours at the human equivalent dose of 220 mg/kg/day (dosed BID 110 mg/kg/12 h). Furthermore, the efficacy of Compound 1 of Example 48 is superior to the results shown in FIG. 2 previously reported for Comparative Compound 2 of Example 60 (see Craig, W., et al, "In Vivo Activity of BP-102, a New Carbacephem, Against Methicillin-Susceptible and —Resistant Strains of *Staphylococcus aureus* (MSSA and MRSA) in the Thighs of Neutropenic Mice", F 1166, *Interscience Conference on Antimicrobial Agents and Chemotherapy*, Washington, D.C. (2005)). Comparatice Compound 2 of Example 60 showed efficacy (3-log kill in CFU count) at a much higher dose of 160 mg/kg/day (dosed 4 times per day g/kg/6 h) for MRSA (ATCC 33591, MIC 1 μg/mL).

*Staphylococcus Aureus*, Methicillin Resistant (ATCC 33591) $LD_{90\text{-}100}$ Septicemia Model Groups of 9 male CD-1 (Crl.) derived male mice weighing 24±2 g are used. Each animal is inoculated with an intraperitoneally administered $LD_{90\text{-}100}$ dose ($0.8\text{-}1.5\times10^7$ CFU/mouse) of Methicillin Resistant *Staphylococcus aureus* (MRSA) (ATCC 33591) suspended in 0.5 ml brain-heart infusion broth containing 5% mucin. Test substance and vehicle are administered intravenously, subcutaneously or orally 1, 9 and 17 hours later and mortality is recorded daily during the following 7 days. Prevention of mortality in 50 percent or more (≧50) after the bacterial inoculation, relative to vehicle control, of the animals indicates significant antimicrobial activity. The MED (ED50) was determined by non-linear regression using Graph-Pad Prism (Graph Pad Software, USA). See, e.g., Goldstein, B. P., et al., *Antimicrobial Agents and Chemotherapy*, 39: 1580-1588 (1995); and Misiek, M., et al., *Antimicrobial Agents Chemotherapy* 3: 40-48 (1973).

Pharmacokinetic Study

Male cannulated Sprague-Dawley rats (~250 g) are administered test compounds by IV, PO, or SC routes. All animals are weighed prior to dose administration. Blood (~0.25 mL) is collected by cannula transferred into microtainer tubes containing EDTA at time points 2 (I.V. animals only), 5, 15, 30, 60, 120, 240, 360, 480, 1440 minutes. After collection, the blood samples are centrifuged at approximately 1000×g at 2-8° C. for approximately 10 minutes. Each plasma specimen is collected, aliquoted into cluster tubes, and stored at ~−20° C. until analysis.

Figure 3:
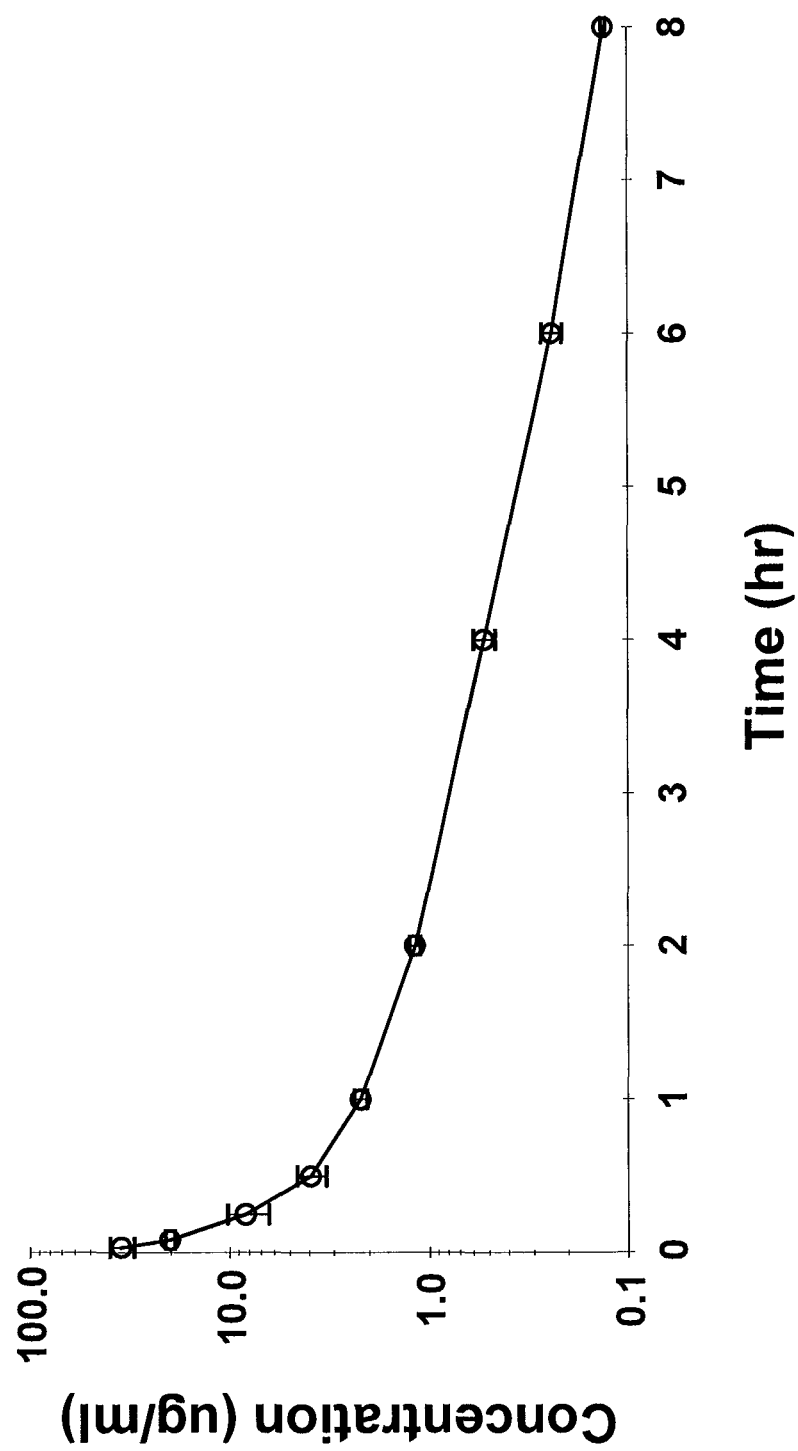
FIG. 3 shows serum concentrations vs. time curve for Compound 1 of Example 48 dosed at 10 mg/kg to rats (n=3) by bolus IV.

Data for a representative compound, namely, Compound 1 of Example 48, is shown in FIG. 1. As shown in FIG. 3, Compound 1 of Example 48 showed a 1.8 hour half-life in rats dosed at 10 mg/kg IV. Using an MIC of 1 μg/ml which corresponds to the strain used in the *Staphylococcus aureus*, Methicillin Resistant (ATCC 33591), Infected Thigh Model above, uncorrected plasma concentrations of compound are above the MIC for 2 h at 10 mg/kg. The large volume of distribution (Vss=1.08 L/kg) indicates that Compound 1 of Example 48 has good tissue distribution and is available in high concentration at the site of infection.

Furthermore, the long plasma circulation time ($T_{in}$=1.8 hour) and tissue distribution characteristics (Vss=1.08 L/kg) of Compound 1 of Example 48 are are superior to the results previously reported for Comparative Compound 2 of Example 60 ($T_{1/2}$=1.47 hour, Vss=0.91 L/kg) (see Griffith, D. et al., "Preclinical Pharmacokinetics and Serum Protein Binding of BP-102 and Other Members of a Novel Series of Carbacephems Active Against Resistant Gram-positive Bacteria", F 1458, *Interscience Conference on Antimicrobial Agents and Chemotherapy*, Washington, D.C. (2005)).

All of the U.S. patents, U.S. patent application publications, U.S. patent applications, foreign patents, foreign patent applications and non-patent publications referred to in this specification are incorporated herein by reference in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the following structure (II):

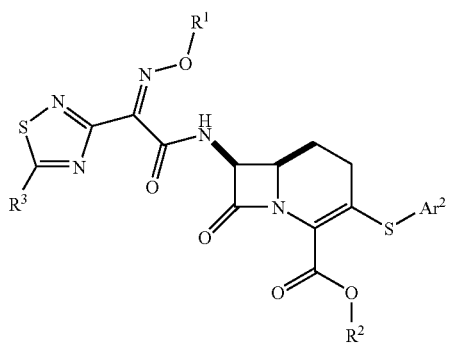

or a stereoisomer, pharmaceutically acceptable salt, ester, or prodrug thereof,
wherein:
R$^1$ is selected from hydrogen, optionally substituted alkyl, optionally substituted alkenyl, optionally substituted alkynyl, optionally substituted alkoxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl and —C(=O)R$^{1a}$, wherein:
R$^{1a}$ is selected from hydrogen, optionally substituted alkyl, optionally substituted alkenyl, optionally substituted alkynyl, optionally substituted alkoxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl and optionally substituted heteroarylalkyl;
R$^2$ is selected from hydrogen, optionally substituted alkyl, optionally substituted alkenyl, optionally substituted alkynyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl and optionally substituted heteroarylalkyl;
R$^3$ is selected from hydrogen, chloro, bromo, fluoro, iodo, cyano, optionally substituted alkyl, optionally substituted alkenyl, optionally substituted alkynyl, optionally substituted cycloalkyl, optionally substituted aryl, optionally substituted heterocyclyl, optionally substituted heteroaryl, —SO$_2$R$^{3a}$, —SOR$^{3a}$, —SR$^{3a}$, —C(=O)R$^{3a}$, —C(=O)NR$^{3a}$R$^{3b}$, —NR$^{3a}$R$^{3b}$ and —OR$^{3a}$, wherein:
R$^{3a}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl; and R$^{3b}$ is selected from hydrogen, optionally substituted alkyl, optionally substituted alkenyl, optionally substituted alkynyl, optionally substituted cycloalkyl, optionally substituted aryl, optionally substituted heterocyclyl, optionally substituted heteroaryl and an amino acid,
or R$^{3a}$ and R$^{3b}$, together with the N atom to which they are attached, form an optionally substituted heterocyclyl or an optionally substituted heteroaryl; and
Ar$^2$ is optionally substituted monocyclic aryl or optionally substituted monocyclic heteroaryl, wherein Ar$^2$ is not substituted with optionally substituted aryl or optionally substituted heteroaryl.

2. A compound of claim 1 wherein R$^1$ is hydrogen.

3. A compound of claim 1 wherein R$^1$ is alkyl and is selected from methyl, ethyl, n-propyl, iso-propyl, n-butyl, tert-butyl, iso-butyl and sec-butyl.

4. A compound of claim 1 wherein R$^1$ is substituted alkyl and is optionally substituted haloalkyl.

5. A compound of claim 1 wherein R$^1$ is alkenyl and is —CH$_2$CH=CH$_2$.

6. A compound of claim 1 wherein R$^1$ is cycloalkyl and is selected from cyclopropyl, cyclobutyl, cyclopentyl, cyclopentenyl, cyclohexyl, and cyclohexenyl.

7. A compound of claim 1 wherein R$^2$ is hydrogen.

8. A compound of claim 1 wherein R$^2$ is alkyl and is selected from methyl, ethyl, n-propyl, iso-propyl, n-butyl, tert-butyl, iso-butyl and sec-butyl.

9. A compound of claim 1 wherein R$^2$ is cycloalkyl and is selected from cyclopropyl, cyclobutyl, cyclopentyl and cyclohexyl.

10. A compound of claim 1 wherein the compound is a prodrug of structure (II) having the following structure (II-B):

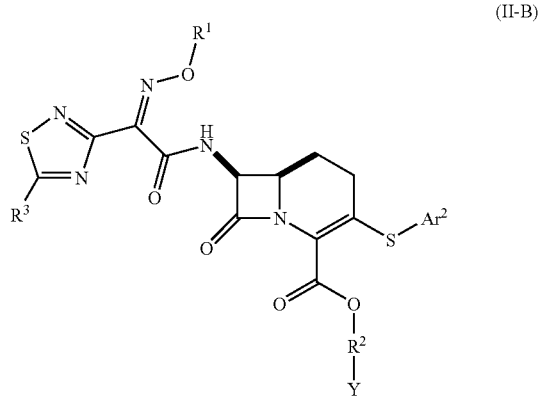

wherein R$^2$ and Y, taken together, are selected from:

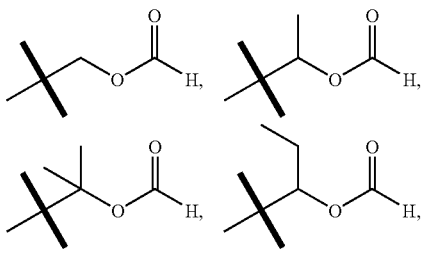

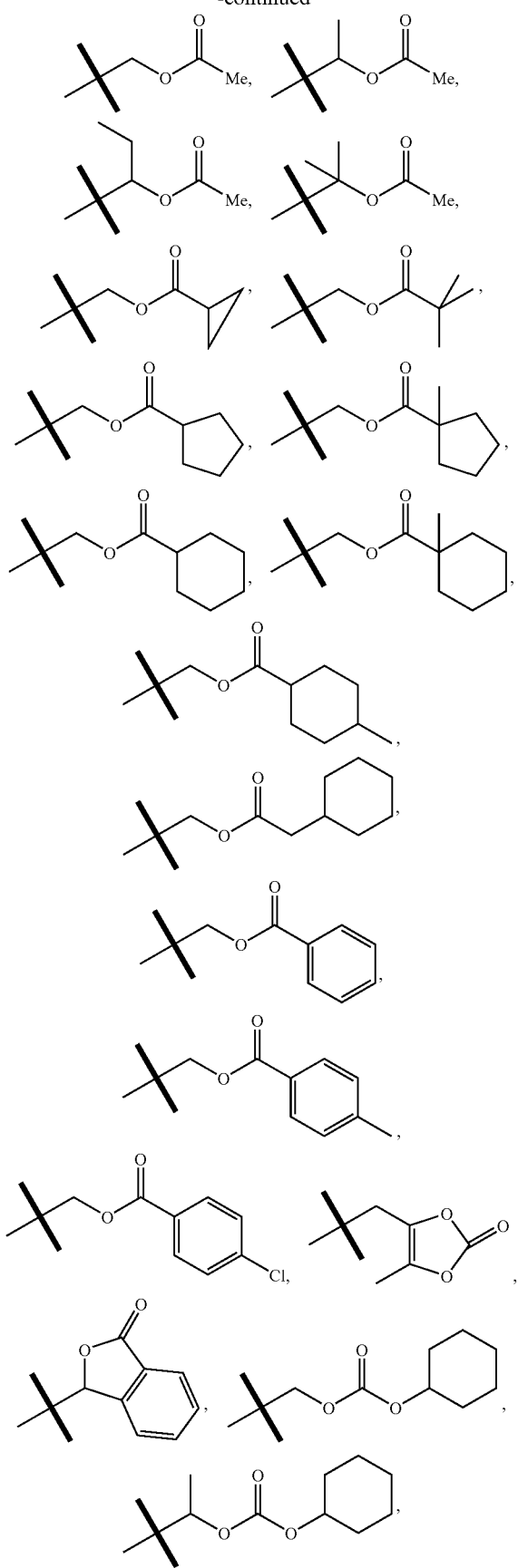
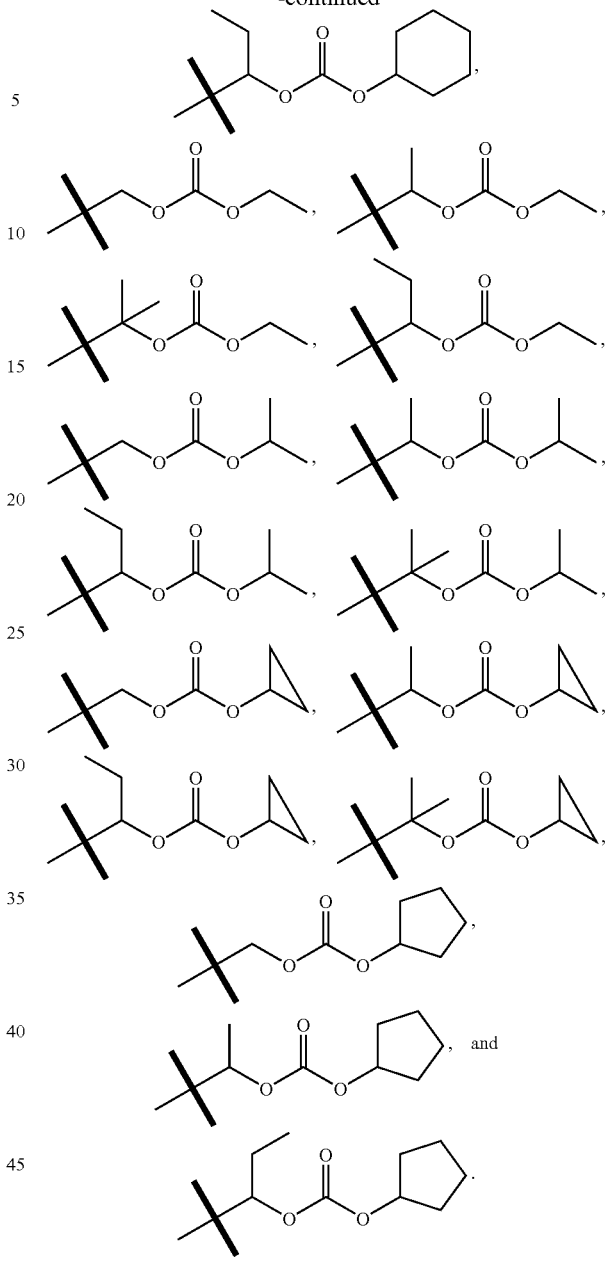
11. A compound of claim 1 wherein $R^3$ is hydrogen.
12. A compound of claim 1 wherein $R^3$ is $-NR^{3a}R^{3b}$.
13. A compound of claim 1 wherein $Ar^2$ is selected from:
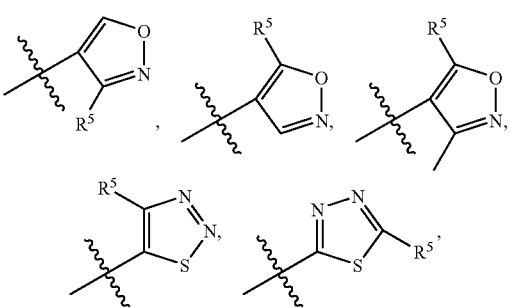

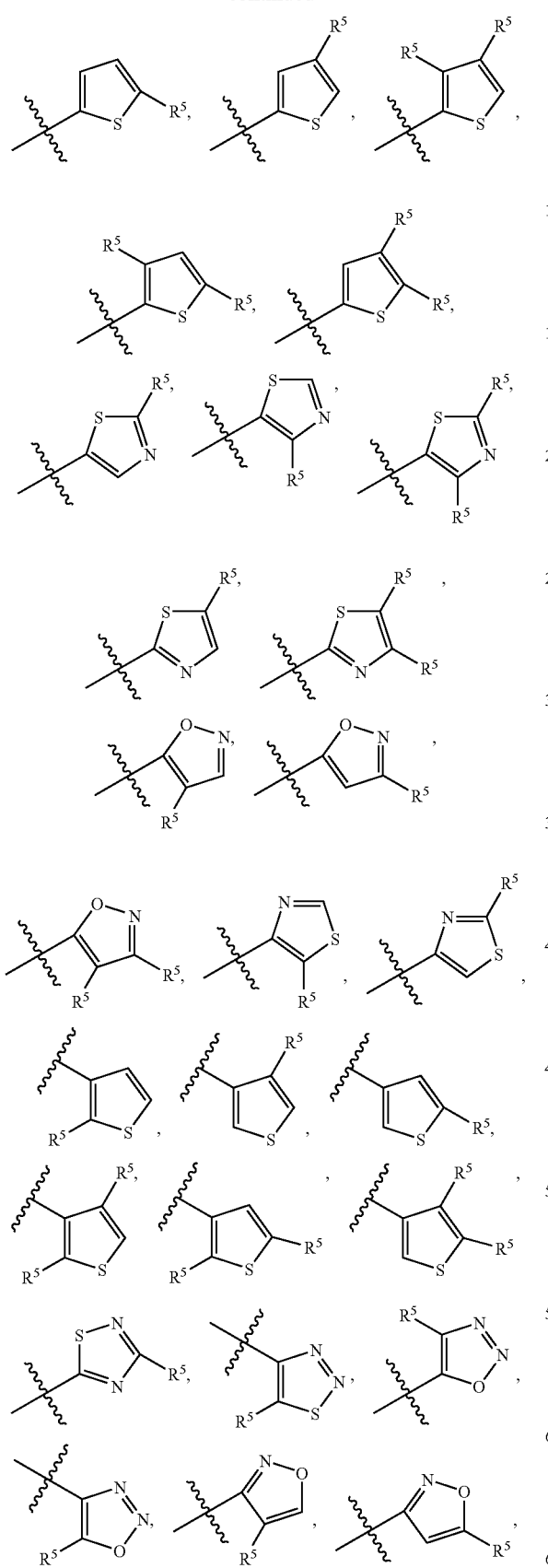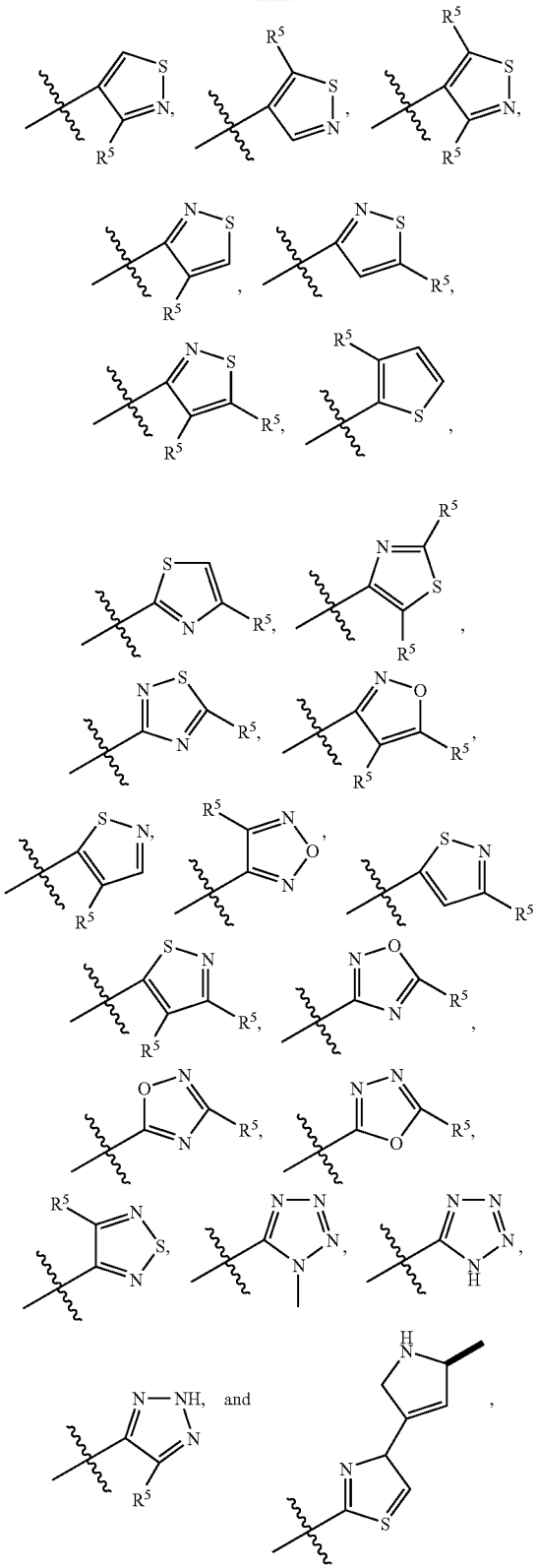
wherein $R^5$ is selected from hydrogen, chloro, bromo, fluoro, iodo, cyano, optionally substituted alkyl, optionally substituted alkenyl, optionally substituted alkynyl, optionally substituted cycloalkyl, optionally substituted heterocyclyl, —SO$_2$R$^{5a}$, —SR$^{5a}$, —C(=O)R$^{5a}$, —C(=O)NR$^{5a}$R$^{5b}$, —NR$^{5a}$R$^{5b}$ and —OR$^{5a}$,
wherein:
- R$^{5a}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl; and
- R$^{5b}$ is selected from hydrogen, optionally substituted alkyl, optionally substituted alkenyl, optionally substituted alkynyl, optionally substituted cycloalkyl, optionally substituted aryl, optionally substituted heterocyclyl and optionally substituted heteroaryl,
- or R$^{5a}$ and R$^{5b}$, together with the N atom to which they are attached, form an optionally substituted heterocyclyl or an optionally substituted heteroaryl.

14. A pharmaceutical composition comprising a compound of claim 1, or a stereoisomer, pharmaceutically acceptable salt or prodrug thereof, and a pharmaceutically acceptable carrier, diluent or excipient.

15. A method of treating a bacterial infection in a mammal in need thereof, comprising administering to the mammal an effective amount of a compound of claim 1.

16. The method of claim 15 wherein the bacterial infection is caused by a β-lactam antibiotic-resistant bacterium.

17. A compound of claim 1, wherein said compound is:

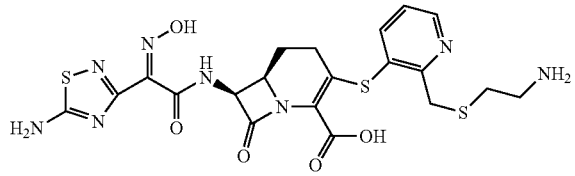 [SMILES: NCCSCc1ncccc1SC1=C(C(=O)O)N2C(=O)[C@@H](NC(=O)/C(=N\O)c3nsc(N)n3)[C@H]2CC1]

or a stereoisomer or pharmaceutically acceptable salt or ester thereof.

18. A pharmaceutical composition comprising a compound of claim 17, or a stereoisomer or pharmaceutically acceptable salt or ester thereof, and a pharmaceutically acceptable carrier, diluent or excipient.

19. A method of treating a bacterial infection in a mammal in need thereof, comprising administering to the mammal an effective amount of a compound of claim 17.

20. The method of claim 19 wherein the bacterial infection is caused by a β-lactam antibiotic-resistant bacterium.

* * * * *